US 8,466,186 B2

(12) United States Patent
Priepke et al.

(10) Patent No.: US 8,466,186 B2
(45) Date of Patent: Jun. 18, 2013

(54) COMPOUNDS

(75) Inventors: Henning Priepke, Warthausen (DE); Raimund Kuelzer, Mittelbiberach (DE); Juergen Mack, Biberach an der Riss (DE); Roland Pfau, Biberach an der Riss (DE); Dirk Stenkamp, Biberach an der Riss (DE); Benjamin Pelcman, Stockholm (SE); Robert Roenn, Uppsala (SE); Dimitrijs Lubriks, Riga (LV); Edgars Suna, Riga (LV)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 14 days.

(21) Appl. No.: 13/314,565

(22) Filed: Dec. 8, 2011

(65) Prior Publication Data
US 2012/0309738 A1 Dec. 6, 2012

(30) Foreign Application Priority Data
Dec. 10, 2010 (EP) .................................. 10 194 456

(51) Int. Cl.
*A01N 43/52* (2006.01)
*A01N 33/02* (2006.01)
*A01N 33/18* (2006.01)
*A61K 31/135* (2006.01)
*A61K 31/04* (2006.01)

(52) U.S. Cl.
USPC ............................. 514/395; 514/646; 514/741

(58) Field of Classification Search
None
See application file for complete search history.

(56) References Cited

U.S. PATENT DOCUMENTS

| | | | |
|---|---|---|---|
| 6,608,084 B1 | 8/2003 | Bourzat et al. | |
| 2004/0198768 A1 | 10/2004 | Park Choo et al. | |
| 2006/0287344 A1 | 12/2006 | Albers et al. | |
| 2007/0060598 A1 | 3/2007 | Albers et al. | |
| 2010/0004301 A1 | 1/2010 | Pelcman et al. | |
| 2010/0256188 A1* | 10/2010 | Pfau et al. | 514/322 |
| 2011/0275656 A1 | 11/2011 | Pfau et al. | |
| 2011/0312935 A1 | 12/2011 | Pfau et al. | |
| 2012/0115902 A1 | 5/2012 | Pfau et al. | |
| 2012/0122930 A1 | 5/2012 | Pfau et al. | |
| 2012/0149676 A1 | 6/2012 | Priepke et al. | |
| 2012/0196897 A1 | 8/2012 | Pfau et al. | |
| 2012/0208839 A1 | 8/2012 | Priepke et al. | |
| 2012/0214786 A1 | 8/2012 | Priepke et al. | |
| 2012/0309738 A1 | 12/2012 | Priepke et al. | |
| 2012/0309755 A1 | 12/2012 | Priepke et al. | |

FOREIGN PATENT DOCUMENTS

| | | |
|---|---|---|
| EP | 0034743 A1 | 9/1981 |
| EP | 0295656 A1 | 12/1988 |
| EP | 0419210 A1 | 3/1991 |
| EP | 1069124 A1 | 1/2001 |
| FR | 2851563 A1 | 8/2004 |
| FR | 2852957 A1 | 10/2004 |
| WO | 0015612 A1 | 3/2000 |
| WO | 0049005 A1 | 8/2000 |
| WO | 0061580 A1 | 10/2000 |
| WO | 0068213 A1 | 11/2000 |
| WO | 0125238 A2 | 4/2001 |
| WO | 03053939 A1 | 7/2003 |
| WO | 03074515 A1 | 9/2003 |
| WO | 03082272 A1 | 10/2003 |
| WO | 2004005323 A2 | 1/2004 |
| WO | 2004035740 A2 | 4/2004 |
| WO | 2004072068 A1 | 8/2004 |
| WO | 2004085425 A1 | 10/2004 |
| WO | 2004089951 A1 | 10/2004 |
| WO | 2005044793 A2 | 5/2005 |
| WO | 2005070906 A1 | 8/2005 |
| WO | 2005070920 A1 | 8/2005 |
| WO | 2005123674 A1 | 12/2005 |
| WO | 2006077366 A1 | 7/2006 |
| WO | 2006090167 A2 | 8/2006 |
| WO | 2007095124 A2 | 8/2007 |
| WO | 2007127382 A1 | 11/2007 |
| WO | 2008009924 A2 | 1/2008 |
| WO | 2008035956 A1 | 3/2008 |
| WO | 2008071944 A1 | 6/2008 |
| WO | 2008129276 A1 | 10/2008 |
| WO | 2010034796 A1 | 4/2010 |
| WO | 2010034797 A1 | 4/2010 |

(Continued)

OTHER PUBLICATIONS

Cancer and Metastasis reviews (1998), 17 (1), 91-106.

(Continued)

*Primary Examiner* — Jeffrey S. Lundgren
*Assistant Examiner* — Michael Schmitt
(74) *Attorney, Agent, or Firm* — Michael P. Morris; Philip I. Datlow

(57) ABSTRACT

This invention relates to compounds of formula I their use as inhibitors of the microsomal prostaglandin $E_2$ synthase-1 (mPGES-1), to pharmaceutical compositions containing them, and their use as medicaments for the treatment and/or prevention of inflammatory diseases and associated conditions. A, M, W, $R^1$, $R^2$, $R^3$, $R^4$, $R^6$, $R^2$, $R^7$, $R^8$, $R^9$, $R^a$, $R^b$ have meanings given in the description.

14 Claims, No Drawings

FOREIGN PATENT DOCUMENTS

| WO | 2010034798 A1 | 4/2010 |
| WO | 2010034799 A1 | 4/2010 |
| WO | 2010100249 A1 | 9/2010 |
| WO | WO 2010100249 A1 * | 9/2010 |

OTHER PUBLICATIONS

Science (1999), vol. 286, 531-537.
Cancer [online], [retrieved on Jul. 6, 2007]. Retrieved from the internet, URL http://www.nlm.nih.gov/medlineplus/cancer.html>.
Cancer [online], [retrieved on Jul. 6, 2007]. Retrieved from the internet, URL http://en.wikipedia.orglwikilCancer.
R.D. Carpenter et al., Carbodiimide-based benzinidazole library method, Journal of Combinatorial Chemistry, Oct. 27, 2006, pp. 907-914, vol. 8, No. 6.
International Search Report Form PCT/ISA/210 and Written Opinion Form PCT/ISA/237 for corresponding PCT/EP2011/072256; date of mailing: Jan. 19, 2012.
D.J. Gale et al., The Amidomethylation of Some N,N-Dialkylanilines; Aust.J. Chem.; pp. 2447-2458; vol. 28; 1975.

* cited by examiner

COMPOUNDS

FIELD OF THE INVENTION

This invention relates to novel compounds, which are inhibitors of the microsomal prostaglandin $E_2$ synthase-1 (mPGES-1), pharmaceutical compositions containing them, and their use as medicaments for the treatment and/or prevention of inflammatory diseases and associated conditions such as inflammatory/nociceptive pain.

BACKGROUND OF THE INVENTION

There are many acute and chronic diseases/disorders that are inflammatory in their nature including but not limited to rheumatoid diseases e.g. rheumatoid arthritis, osteoarthritis, diseases of the visceral system e.g. inflammatory bowel syndrome, autoimmune diseases, e.g. lupus erythematodes, lung diseases like asthma and COPD. Current treatment with non-steroidal anti-inflammatory drugs (NSAIDs) and cyclooxygenase (COX)-2 inhibitors are efficacious, but show a prevalence for gastrointestinal and cardiovascular side effects. There is a high need for new treatment options showing equivalent efficacy with an improved side effect profile.

mPGES inhibitors may show such an improved side effect profile because they block the generation of $PGE_2$ in a more specific manner as described below.

NSAIDs and COX-2 inhibitors reduce inflammation and pain through inhibition of one or both isoformes of COX enzymes. The cyclooxygenase (COX) enzyme exists in two forms, one that is constitutively expressed in many cells and tissues (COX-1), and one that in most cells and tissues is induced by pro-inflammatory stimuli, such as cytokines, during an inflammatory response (COX-2). COXs metabolise arachidonic acid to the unstable intermediate prostaglandin $H_2$ ($PGH_2$). $PGH_2$ is further metabolized to other prostaglandins including $PGE_2$, $PGF_{2\alpha}$, $PGD_2$, prostacyclin and thromboxane $A_2$. These arachidonic acid metabolites are known to have pronounced physiological and pathophysiological activity including pro-inflammatory effects. $PGE_2$ in particular is known to be a strong pro-inflammatory mediator, and is also known to induce fever, inflammation and pain. Consequently, numerous drugs were developed with a view to inhibiting the formation of $PGE_2$, including "NSAIDs" (non-steroidal antiinflammatory drugs) and "coxibs" (selective COX-2 inhibitors). These drugs act predominantly by inhibition of COX-1 and/or COX-2, thereby reducing the formation of $PGE_2$. However, the inhibition of COXs has the disadvantage that it results in the reduction of the formation of all metabolites downstream of $PGH_2$, some of which are known to have beneficial properties. In view of this, drugs which act by inhibition of COXs are therefore known/suspected to cause adverse biological effects.

For example, the non-selective inhibition of COXs by NSAIDs may give rise to gastrointestinal side-effects and affect platelet and renal function. Even the selective inhibition of COX-2 by coxibs, whilst reducing such gastrointestinal side-effects, is believed to give rise to cardiovascular problems.

An alternative treatment of inflammatory diseases that does not give rise to the above-mentioned side effects would thus be of real benefit in the clinic. In particular, a drug that preferably inhibits the transformation of $PGH_2$ to the pro-inflammatory mediator $PGE_2$ selectively might be expected to reduce the inflammatory response in the absence of a corresponding reduction of the formation of other, beneficial arachidonic acid metabolites. Such inhibition would accordingly be expected to alleviate the undesirable side-effects mentioned above.

$PGH_2$ may be transformed to $PGE_2$ by prostaglandin E synthases (PGES). Two microsomal prostaglandin E synthases (mPGES-1 and mPGES-2), and one cytosolic prostaglandin E synthase (cPGES) have been described. mPGES-1 is proposed to be closely linked to COX-2 and both enzyme's are upregulated during e.g. inflammation. Thus agents that are capable of inhibiting the action of m PGES-1 and thereby reducing the formation of $PGE_2$ are likely to be of benefit for the treatment of inflammation and more general acute and chronic pain conditions Benzimidazole and imidazopyridine derivatives with m PGES-1 inhibitory activity are disclosed in WO 2010/034796, WO 2010/034797, WO 2010/034798, WO 2010/034799. WO2010/100249 describes a broad class of different 2-arylamino benzimidazoles in which the aryl group bears a particular side chain.

DETAILED DESCRIPTION OF THE INVENTION

The present invention provides a compound of formula I,

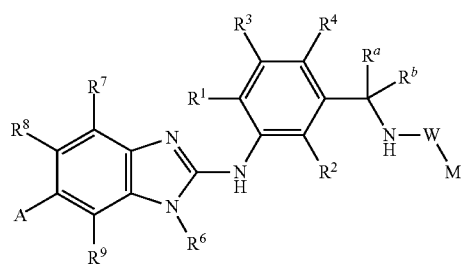

in which
$R^1$ represents halo, —OH, —CN, $C_{1-3}$ alkyl, $C_{2-6}$ alkynyl, —$OC_{1-3}$ alkyl which latter three groups are optionally substituted by one or more substituents selected from fluoro, —CN, =O, —OH, —$OCH_3$, —$OCF_3$;
$R^2$, $R^3$ and $R^4$ independently represent hydrogen, halo, —CN, $C_{1-3}$ alkyl, —$OC_{1-3}$ alkyl which latter two alkyl groups are optionally substituted by one or more substituents selected from fluoro, —CN, =O, —OH, —$OCH_3$, —$OCF_3$;
$R^a$ and $R^b$ independently represent hydrogen, $C_{1-3}$ alkyl which is optionally substituted by one or more fluorine atoms, or both together with the carbon atom which they are bound to, form a $C_{3-7}$ cycloalkyl ring, or a 4-6 membered heterocycloalkyl ring which latter two groups are optionally substituted by one or more fluorine atoms;
W represents —C(O)—, —S(O)—, —S(O)$_2$—, —C(O)O—, —C(O)$NR^d$— which groups are bound to the nitrogen of the —NH— moiety via carbon or sulfur atom;
$R^d$ represents hydrogen, $C_{1-3}$ alkyl;
M represents $C_{1-8}$ alkyl, $C_{2-8}$ alkynyl, $C_{3-8}$ cycloalkyl-$C_{0-4}$ alkyl-,
4-10 membered heterocycloalkyl-$C_{0-4}$ alkyl- which latter four groups are optionally substituted by one or more groups selected from
fluoro, —OH, =O, —CN, —$NH_2$, $C_{1-3}$ alkyl, —NH ($C_{1-3}$ alkyl), —N($C_{1-3}$ alkyl)$_2$, azetidinyl, pyrrolidinyl, piperidinyl,
—$OC_{1-3}$ alkyl, [which latter seven alkyl groups can be substituted by one or more substituents selected from fluoro, —OH, —CN, —OC$_{1-2}$ alkyl (which latter alkyl group is optionally substituted by one or more fluorine atoms)], aryl, heteroaryl [which latter two groups are optionally substituted by one or more substituents selected from halo, —OH, —CN, C$_{1-3}$ alkyl, —OC$_{1-3}$ alkyl (which latter two alkyl groups are optionally substituted by one or more fluorine atoms)], or aryl, heteroaryl which latter two groups are optionally substituted by one or more substituents selected from halo, —OH, —CN, —NH$_2$, aryl, heteroaryl [which latter two groups are optionally substituted by one or more substituents selected from halo, —OH, —CN, C$_{1-3}$ alkyl, —OC$_{1-3}$ alkyl (which latter two alkyl groups are optionally substituted by one or more fluorine atoms)], C$_{1-7}$ alkyl, C$_{2-7}$ alkynyl, C$_{3-7}$ cycloalkyl, 4-7 membered heterocycloalkyl, —NH$_2$, —NH(C$_{1-3}$ alkyl), —N(C$_{1-3}$ alkyl)$_2$, —OC$_{1-3}$ alkyl, —O—C$_{0-2}$alkyl-aryl, —SC$_{1-3}$ alkyl, (which latter alkyl, alkynyl, heterocycloalkyl, aryl or cycloalkyl groups are optionally substituted by one or more substituents selected from fluoro, —CN, =O, —NH$_2$, —NH(C$_{1-3}$ alkyl), —N(C$_{1-3}$ alkyl)$_2$, —OH, —OC$_{1-3}$alkyl)];

R$^6$ represents hydrogen, C$_{1-5}$ alkyl, C$_{3-6}$ alkynyl, 4-7 membered hetero-cycloalkyl-C$_{0-2}$alkyl or C$_{3-7}$cycloalkyl-C$_{0-2}$ alkyl (which latter four groups are optionally substituted by one or more substituents selected from fluoro, —CN, =O, C$_{1-3}$ alkyl, —OH, —NH$_2$, —OC$_{1-3}$ alkyl, —NH(C$_{1-3}$ alkyl), —N(C$_{1-3}$ alkyl)$_2$);

R$^7$, R$^8$ and R$^9$ independently represent hydrogen, halo, —CN, C$_{1-5}$ alkyl, C$_{3-5}$ cycloalkyl-C$_{0-2}$ alkyl-, C$_{1-5}$ alkyl-O—, C$_{3-5}$ cycloalkyl-C$_{0-2}$ alkyl-O— (in which latter four groups the alkyl and cycloalkyl fragments are optionally substituted by one or more substituents selected from fluoro, —CN, —OH, —OC$_{1-3}$ alkyl or by one or more C$_{1-3}$ alkyl groups which are optionally substituted by one or more fluorine atoms);

A represents —NHR$^{10}$, —NR$^{10}$R$^{11}$, or a 4-10-membered heterocycloalkyl group which is bound to the benzimidazole through a nitrogen atom, and which is optionally substituted by one or more substituents R$^{12}$;

R$^{10}$ and R$^{11}$ independently represent C$_{1-7}$ alkyl, C$_{3-7}$ cycloalkyl-C$_{0-4}$ alkyl- or C$_{4-7}$ heterocycloalkyl-C$_{0-4}$ alkyl- [which latter three groups are optionally substituted by one or more groups selected from fluoro, —OH, NH$_2$, —CN, C$_{1-3}$ alkyl, —NH(C$_{1-3}$ alkyl), —N(C$_{1-3}$ alkyl)$_2$, —OC$_{1-5}$ alkyl, —OC$_{3-6}$ cycloalkyl, —OC$_{4-6}$ heterocycloalkyl (which latter six groups are optionally substituted by one or more substituents selected from fluoro, —CF$_3$, —CHF$_2$, —CH$_2$F, —CH$_3$)], or aryl-C$_{0-4}$ alkyl-, heteroaryl-C$_{0-4}$ alkyl- [which latter two groups are optionally substituted by one or more substituents selected from halo, —OH, —CN, C$_{1-3}$ alkyl, C$_{3-5}$ cycloalkyl, C$_{1-3}$ alkyl-O—, C$_{3-5}$ cycloalkyl-O— (which latter four groups are optionally substituted by one or more fluorine atoms)];

each R$^{12}$ independently represents halo, —OH, —NH$_2$, =O, —CN, C$_{1-4}$ alkyl, C$_{3-5}$ cycloalkyl-C$_{0-2}$ alkyl-, C$_{4-5}$ heterocycloalkyl-C$_{0-2}$ alkyl-, C$_{1-4}$ alkyl-O—, C$_{1-3}$ alkyl-C(=O)—, —C(=O)—NH(C$_{1-3}$ alkyl), —C(=O)—N(C$_{1-3}$ alkyl)$_2$ [which latter six groups are optionally substituted by one or more groups selected from fluoro, —OH, oxo, —NH$_2$, —CN, C$_{1-3}$ alkyl, —NH(C$_{1-3}$ alkyl), —N(C$_{1-3}$ alkyl)$_2$, —OC$_{1-3}$ alkyl, —OC$_{3-5}$ cycloalkyl [which latter five groups are optionally substituted by one or more substituents selected from fluoro, —CF$_3$, —CHF$_2$, —CH$_2$F], or aryl-C$_{0-4}$ alkyl-, heteroaryl-C$_{0-4}$ alkyl- [which latter two groups are optionally substituted by one or more substituents selected from halo, —OH, —CN, C$_{1-3}$ alkyl, C$_{3-5}$ cycloalkyl, C$_{1-3}$ alkyl-O—, C$_{3-5}$ cycloalkyl-O— (which latter four groups are optionally substituted by one or more fluorine atoms)];

or a salt thereof, particularly a physiologically acceptable salt thereof.

In a second embodiment, in the general formula I, A, M, W, R$^2$, R$^3$, R$^4$, R$^6$, R$^7$, R$^8$, R$^9$, R$^a$, R$^b$ have the same meaning as defined in any of the preceding embodiments, and R$^1$ represents halo, C$_{1-3}$ alkyl, —OC$_{1-3}$ alkyl which latter two groups are optionally substituted by one or more fluorine atoms.

In another embodiment, in the general formula I, A, M, W, R$^1$, R$^3$, R$^4$, R$^6$, R$^7$, R$^8$, R$^9$, R$^a$, R$^b$ have the same meaning as defined in any of the preceding embodiments, and R$^2$ represents hydrogen, halo, C$_{1-3}$ alkyl optionally substituted by one or more fluorine atoms.

In another embodiment, in the general formula I, A, M, W, R$^1$, R$^2$, R$^6$, R$^7$, R$^8$, R$^9$, R$^a$, R$^b$ have the same meaning as defined in any of the preceding embodiments, and R$^3$ and R$^4$ independently represent hydrogen, halo.

In another embodiment, in the general formula I, A, M, W, R$^1$, R$^2$, R$^3$, R$^4$, R$^6$, R$^7$, R$^8$, R$^9$ have the same meaning as defined in any of the preceding embodiments, and R$^a$, R$^b$ independently represent hydrogen.

In another embodiment, in the general formula I, A, M, R$^1$, R$^2$, R$^3$, R$^4$, R$^6$, R$^7$, R$^8$, R$^9$, R$^a$, R$^b$ have the same meaning as defined in any of the preceding embodiments, and W represents —C(O)—, —S(O)$_2$—, —C(O)O— which groups are bound to the nitrogen of the —NH— moiety via carbon or sulfur atom.

In another embodiment, in the general formula I, A, W, R$^1$, R$^2$, R$^3$, R$^4$, R$^6$, R$^7$, R$^8$, R$^9$, R$^a$, R$^b$ have the same meaning as defined in any of the preceding embodiments, and M represents C$_{1-6}$ alkyl, C$_{2-6}$ alkynyl, C$_{3-8}$ cycloalkyl-C$_{0-1}$ alkyl-, oxetanyl-, tetrahydrofuranyl-, azetidinyl-, pyrrolidinyl-, piperidinyl- or one of the following heterocyclic groups

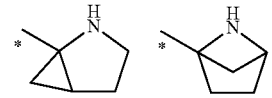

all of which groups are optionally substituted by one or more groups selected from fluoro, —OH, —CN, —NH$_2$, C$_{1-3}$ alkyl, —NH(C$_{1-2}$ alkyl), —N(C$_{1-2}$ alkyl)$_2$, —OC$_{1-2}$ alkyl [which latter four alkyl groups are optionally substituted by one or more substituents selected from fluoro], phenyl, imidazolyl-[which latter two groups are optionally substituted by one or more substituents selected from halo, C$_{1-2}$ alkyl, OC$_{1-2}$alkyl (which latter two alkyl groups are optionally substituted by one or more fluorine atoms)], or phenyl, naphthyl, furanyl, thienyl, oxazolyl, isoxazolyl, thiazolyl, pyrrolyl, pyrazolyl, pyridinyl, pyrazinyl, quinolynyl which latter twelve groups are optionally substituted by one or more substituents selected from halo, aryl, heteroaryl [which latter two groups are optionally substituted by one or more substituents selected from halo, —CH$_3$, —CH$_2$F, —CHF$_2$, —CF$_3$], $C_{1-2}$ alkyl, —OC$_{1-2}$ alkyl [which latter two groups are optionally substituted by one or more fluorine atoms], $C_{2-3}$ alkynyl, —O—C$_{0-2}$alkyl-phenyl [in which latter group the phenyl is optionally substituted by one or more substituents selected from halo, —CH$_3$, —CH$_2$F, —CHF$_2$, —CF$_3$].

In another embodiment, in the general formula I, A, M, W, $R^1$, $R^2$, $R^3$, $R^4$, $R^7$, $R^8$, $R^9$, $R^a$, $R^b$ have the same meaning as defined in any of the preceding embodiments, and $R^6$ represents hydrogen, $C_{1-5}$ alkyl or $C_{3-7}$cycloalkyl-$C_{0-2}$alkyl [which latter two groups are optionally substituted by one or more substituents selected from fluoro, $C_{1-3}$ alkyl, —OC$_{1-3}$ alkyl, —NH(C$_{1-3}$ alkyl), —N(C$_{1-3}$ alkyl)$_2$].

In another embodiment, in the general formula I, A, M, W, $R^1$, $R^2$, $R^3$, $R^4$, $R^6$, $R^8$, $R^a$, $R^b$ have the same meaning as defined in any of the preceding embodiments, and $R^7$ and $R^9$ independently represent hydrogen, halo, —CN, $C_{1-3}$ alkyl optionally substituted by one or more fluorine atoms.

In another embodiment, in the general formula I, A, M, W, $R^1$, $R^2$, $R^3$, $R^4$, $R^6$, $R^7$, $R^9$, $R^a$, $R^b$ have the same meaning as defined in any of the preceding embodiments, and $R^8$ represents hydrogen, halo, —CN, $C_{1-5}$ alkyl, $C_{3-5}$ cycloalkyl-$C_{0-2}$ alkyl- (in which latter two groups the alkyl and cycloalkyl fragments are optionally substituted by one or more fluorine atoms, or by one or more $C_{1-3}$ alkyl groups which are optionally substituted by one or more fluorine atoms).

In another embodiment, in the general formula I, M, W, $R^1$, $R^2$, $R^3$, $R^4$, $R^6$, $R^7$, $R^8$, $R^9$, $R^a$, $R^b$ have the same meaning as defined in any of the preceding embodiments, and A represents —NHR$^{10}$, —NR$^{10}$R$^{11}$, or
azetidinyl-, pyrrolidinyl-, piperidinyl-, morpholinyl-, piperazinyl- or

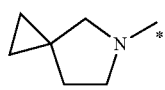

all of which heterocyclic groups are optionally substituted by one or more substituents $R^{12}$ and optionally annulated to a phenyl or a 5- or 6-membered heteroaryl ring, while the above mentioned groups are bonded to the benzimidazole core through a nitrogen atom;

$R^{10}$ and $R^{11}$ independently represent $C_{1-5}$ alkyl, $C_{3-6}$ cycloalkyl-$C_{0-1}$ alkyl-[which latter two groups are optionally substituted by one or more groups selected from fluoro, —OH, $C_{1-3}$ alkyl],
or
aryl-$C_{0-1}$ alkyl- optionally substituted by one or more substituents selected from halo, —OH, —CN, $C_{1-3}$ alkyl, $C_{1-3}$ alkyl-O—[which latter two groups are optionally substituted by one or more fluorine atoms];

each $R^{12}$ independently represents halo, —OH, —CN, $C_{1-4}$ alkyl, $C_{1-2}$ alkyl-O—, $C_{1-2}$ alkyl-C(=O)—, —C(=O)—NH(C$_{1-2}$ alkyl), —C(=O)—N(C$_{1-2}$ alkyl)$_2$ [which latter five groups are optionally substituted by one or more groups selected from fluoro, —OH, $C_{1-3}$ alkyl, —NH(C$_{1-2}$ alkyl), —N(C$_{1-2}$ alkyl)$_2$, —OC$_{1-2}$ alkyl (which latter four groups are optionally substituted by one or more substituents selected from fluoro, CF$_3$, CHF$_2$ or CH$_2$F)], or
phenyl optionally substituted by one or more substituents selected from halo or $C_{1-3}$ alkyl which is optionally substituted by one or more fluorine atoms.

A further embodiment of the present invention comprises compounds of formula Ia

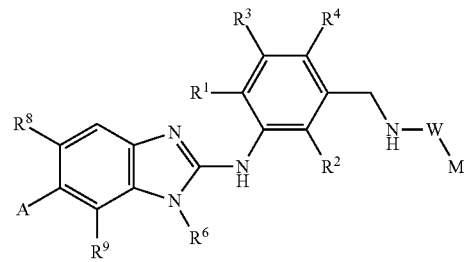

in which
$R^1$ represents halo, $C_{1-3}$ alkyl, —OC$_{1-3}$ alkyl which latter two groups are optionally substituted by one or more fluorine atoms;

$R^2$ represents hydrogen, halo, $C_{1-3}$ alkyl optionally substituted by one or more fluorine atoms;

$R^3$ and $R^4$ independently represent hydrogen, halo;

W represents —C(O)—, —S(O)$_2$—, —C(O)O— which groups are bound to the nitrogen of the —NH— moiety via carbon or sulfur atom;

M represents $C_{1-6}$ alkyl, $C_{2-6}$ alkynyl, $C_{3-8}$ cycloalkyl-$C_{0-1}$ alkyl-, oxetanyl-, tetrahydrofuranyl-, azetidinyl-, pyrrolidinyl-, piperidinyl- or one of the following heterocyclic groups

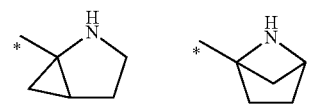

all of which groups are optionally substituted by one or more groups selected from
fluoro, —OH, —CN, —NH$_2$, $C_{1-3}$ alkyl, —NH(C$_{1-2}$ alkyl), —N(C$_{1-2}$ alkyl)$_2$, —OC$_{1-2}$ alkyl, [which latter four alkyl groups are optionally substituted by one or more fluorine atoms], phenyl, imidazolyl-[which latter two groups are optionally substituted by one or more substituents selected from halo, $C_{1-2}$ alkyl, OC$_{1-2}$alkyl (which latter two alkyl groups are optionally substituted by one or more fluorine atoms)],
or
phenyl, naphthyl, furanyl, thienyl, oxazolyl, isoxazolyl, thiazolyl, pyrrolyl, pyrazolyl, pyridinyl, pyrazinyl, quinolynyl which latter twelve groups are optionally substituted by one or more substituents selected from
halo, aryl, heteroaryl [which latter two groups are optionally substituted by one or more substituents selected from halo, —CH$_3$, —CH$_2$F, —CHF$_2$, —CF$_3$],
$C_{1-2}$ alkyl, —OC$_{1-2}$ alkyl [which latter two groups are optionally substituted by one or more fluorine atoms],
$C_{2-3}$ alkynyl, —O—C$_{0-2}$alkyl-phenyl [in which latter group the phenyl is optionally substituted by one or more substituents selected from halo, —CH$_3$, —CH$_2$F, —CHF$_2$, —CF$_3$];

$R^6$ represents hydrogen, $C_{1-5}$ alkyl or $C_{3-7}$cycloalkyl-$C_{0-2}$alkyl [which latter two groups are optionally substituted by one or more substituents selected from fluoro, $C_{1-3}$ alkyl, —$OC_{1-3}$ alkyl, —$NH(C_{1-3}$ alkyl), —$N(C_{1-3}$ alkyl)$_2$];

$R^8$ represents hydrogen, halo, —CN, $C_{1-5}$ alkyl, $C_{3-5}$ cycloalkyl-$C_{0-2}$alkyl- (in which latter two groups the alkyl and cycloalkyl fragments are optionally substituted by one or more fluorine atoms, or by one or more $C_{1-3}$ alkyl groups which are optionally substituted by one or more fluorine atoms).

$R^9$ represents hydrogen, halo, —CN, $C_{1-3}$ alkyl optionally substituted by one or more substituents selected from fluorine atoms;

A represents —$NHR^{10}$, —$NR^{10}R^{11}$, or azetidinyl-, pyrrolidinyl-, piperidinyl-, morpholinyl-, piperazinyl- or

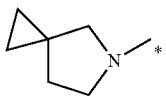

all of which heterocyclic groups can optionally be substituted by one or more substituents $R^{12}$ and optionally annulated to a phenyl or a 5- or 6-membered heteroaryl ring, whereby the above mentioned groups are bonded to the benzimidazole core through a nitrogen atom;

$R^{10}$ and $R^{11}$ independently represent $C_{1-5}$ alkyl or $C_{3-6}$ cycloalkyl-$C_{0-1}$ alkyl-[which latter two groups are optionally substituted by one or more groups selected from: fluoro, —OH, $C_{1-3}$ alkyl], or aryl-$C_{0-1}$ alkyl- which can be substituted by one or more substituents selected from halo, —OH, —CN, $C_{1-3}$ alkyl, $C_{1-3}$ alkyl-O—[which latter two groups are optionally substituted by one or more fluorine atoms];

each $R^{12}$ independently represents halo, —OH, —CN, $C_{1-4}$ alkyl, $C_{1-2}$ alkyl-O—, $C_{1-2}$ alkyl-C(=O)—, —C(=O)—NH($C_{1-2}$ alkyl), —C(=O)—N($C_{1-2}$ alkyl)$_2$ [which latter five groups are optionally substituted by one or more groups selected from fluoro, —OH, $C_{1-3}$ alkyl, —NH($C_{1-2}$ alkyl), —N($C_{1-2}$ alkyl)$_2$, —$OC_{1-2}$ alkyl, (which latter four groups are optionally substituted by one or more substituents selected from fluoro, $CF_3$, $CHF_2$ or $CH_2F$)], or phenyl optionally substituted by one or more substituents selected from halo or $C_{1-3}$ alkyl which is optionally substituted by one or more fluorine atoms.

In another embodiment, in the general formula I or Ia, A, M, W, $R^1$, $R^2$, $R^3$, $R^4$, $R^6$, $R^7$, $R^9$, $R^a$, $R^b$ have the same meaning as defined in any of the preceding embodiments, and $R^8$ represents hydrogen, fluoro, chloro, $CF_3$, —CN.

In another embodiment, in the general formula I or Ia, M, W, $R^1$, $R^2$, $R^3$, $R^4$, $R^6$, $R^7$, $R^8$, $R^9$, $R^a$, $R^b$ have the same meaning as defined in any of the preceding embodiments, and A represents a group selected from

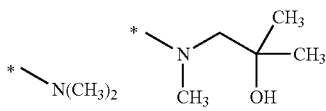

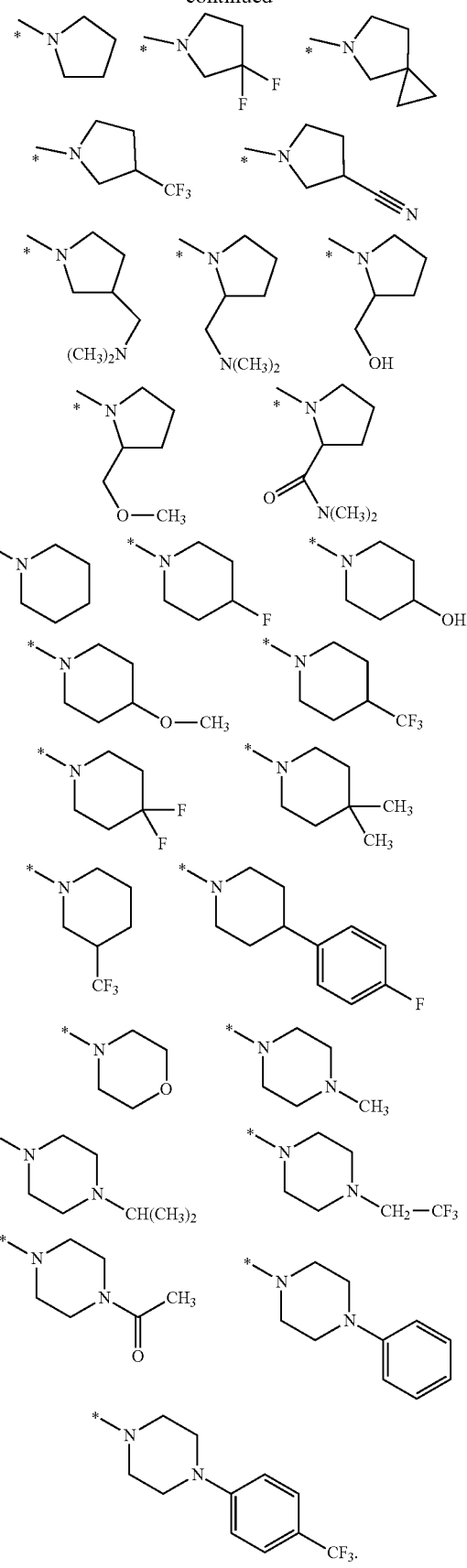

In another embodiment, in the general formula I or Ia, A, W, R¹, R², R³, R⁴, R⁶, R⁷, R⁸, R⁹, R$^a$, R$^b$ have the same meaning as defined in any of the preceding embodiments, and M represents a group selected from
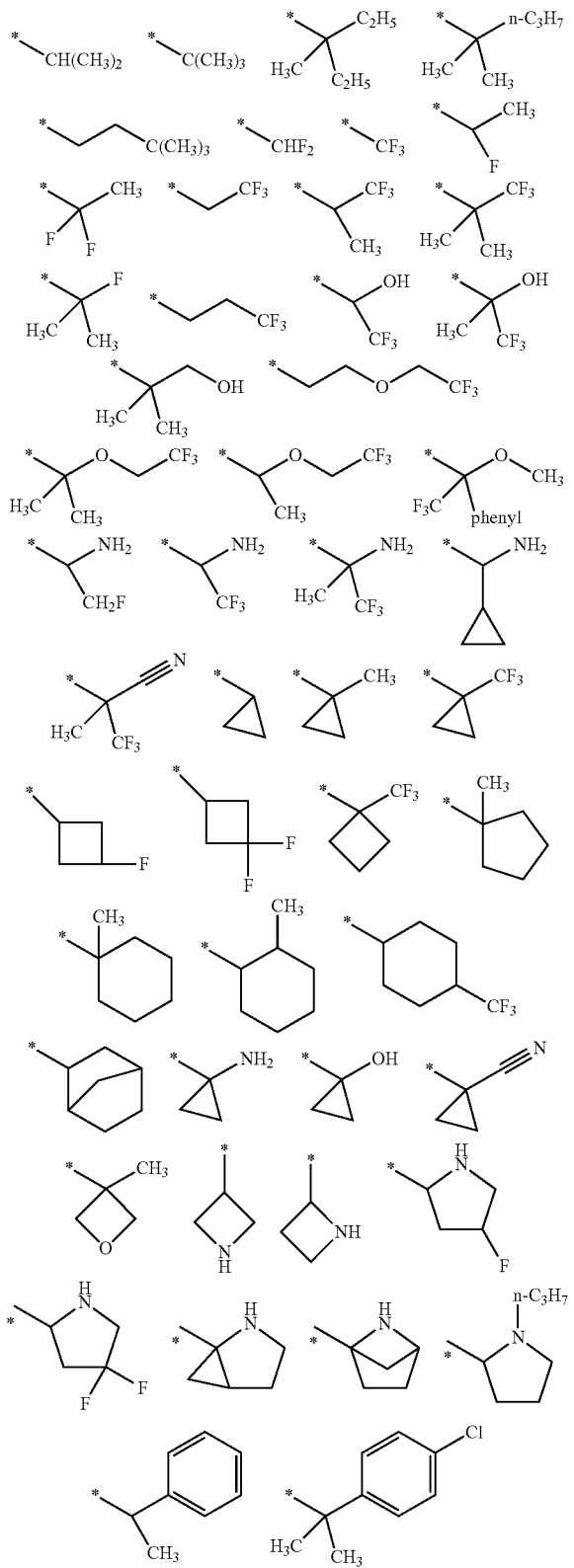
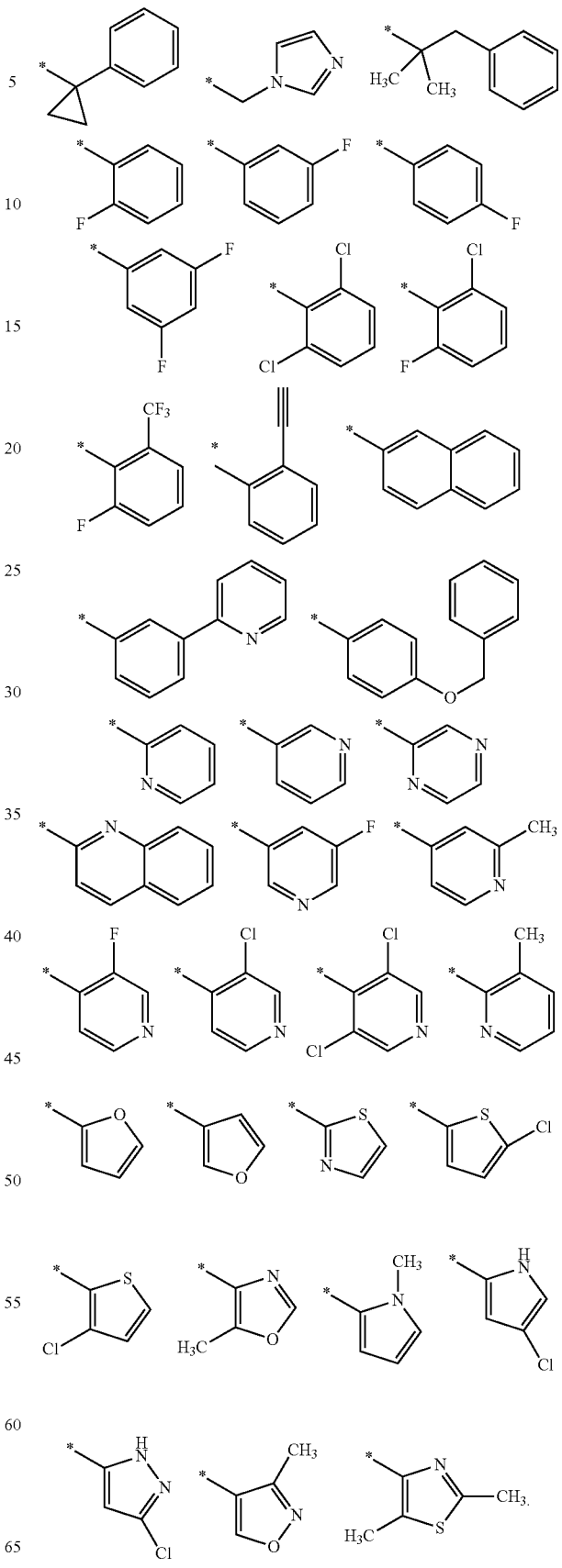

A further embodiment of the present invention comprises compounds of formula Ia

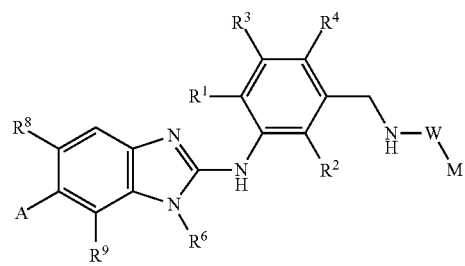

in which

R¹ represents fluoro, chloro, CH₃, CHF₂, CH₂F, CF₃ or —OCF₃;

R² represents hydrogen, fluoro or chloro;

R³ and R⁴ independently represent hydrogen, fluoro;

R⁶ represents hydrogen, —CH₃, —CH₂CF₃, cyclopropylmethyl-, —CH₂CH₂—O—CH₃, —CH₂CH₂—N(CH₃)₂;

R⁸ represents hydrogen, fluoro, chloro, CF₃, —CN;

R⁹ represents hydrogen, fluoro;

A represents a group selected from

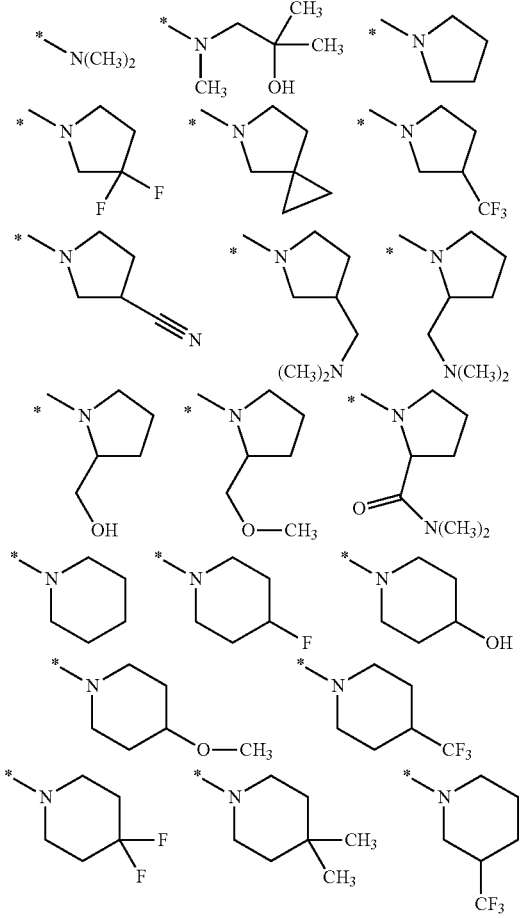

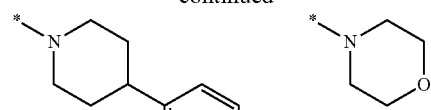

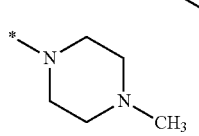

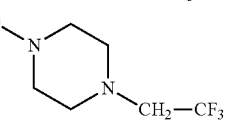

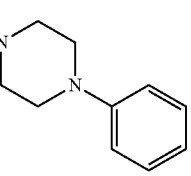

W represents —C(O)—, —S(O)₂— which groups are bound to the nitrogen of the —NH— moiety via carbon or sulfur atom;

M represents a group selected from

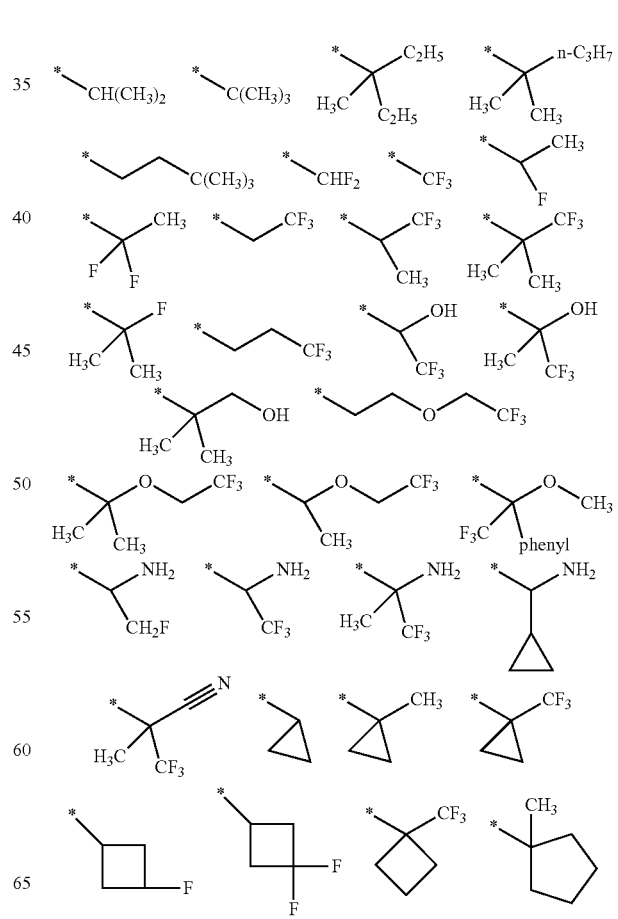

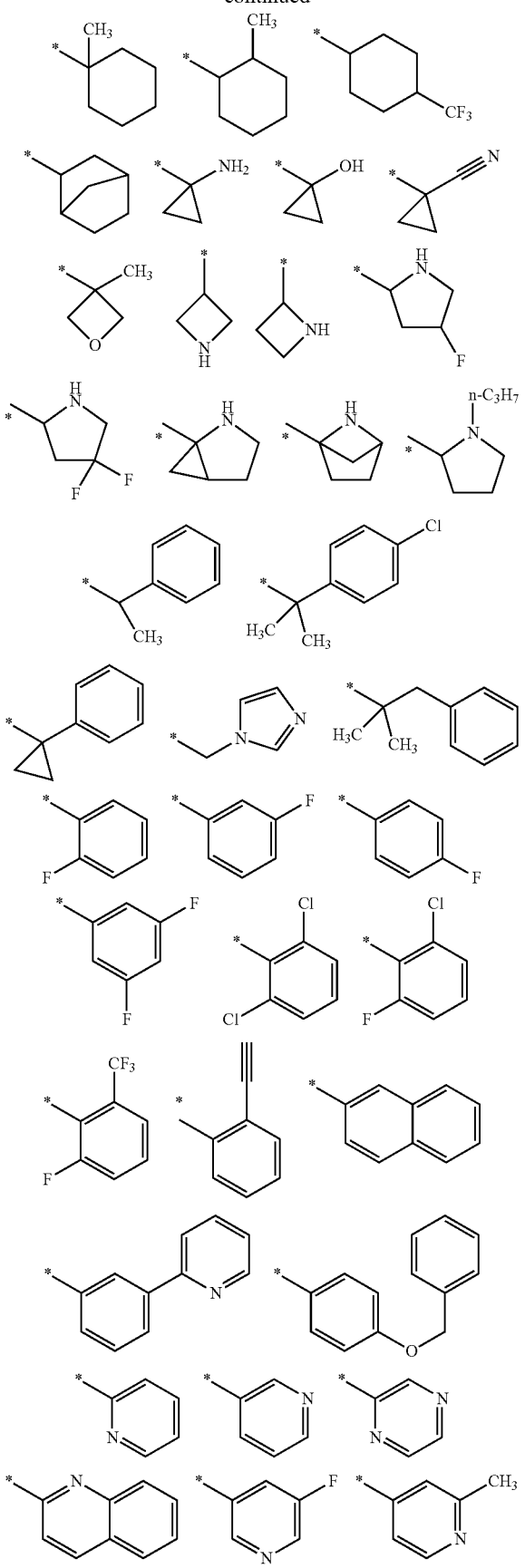
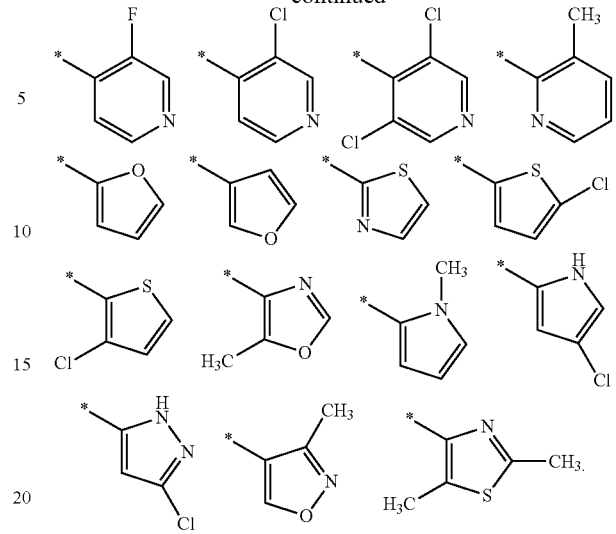

TERMS AND DEFINITIONS USED

General Definitions:

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk is may be used in sub-formulas to indicate the bond which is connected to the core molecule as defined, for example a cyclopropylmethyl-group would be represented by the following drawing:

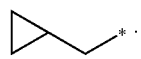

Tautomers/Stereochemistry/Solvates/Hydrates:

Unless specifically indicated, throughout the specification and the appended claims, a given chemical formula or name shall encompass tautomers (e.g. 1H-benzimidazole may be considered to be identical to a corresponding compound containing a 3H-benzimidazole) and all stereo, optical and geometrical isomers (e.g. enantiomers, diastereomers, E/Z isomers etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

Salts:

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanol-amine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxy-ethyl)-pyrrolidine, sodium hydroxide, triethanolamine (2,2',2''-nitrilotris(ethanol)), trometh-amine, zinc hydroxide, acetic acid, 2.2-dichloro-acetic acid, adipic acid, alginic acid, ascorbic acid, L-aspartic acid, benzenesulfonic acid, benzoic acid, 2,5-dihydroxybenzoic acid, 4-acet-amido-benzoic acid, (+)-camphoric acid, (+)-camphor-10-sulfonic acid, carbonic acid, cinna-mic acid, citric acid, cyclamic acid, decanoic acid, dodecylsulfuric acid, ethane-1,2-disulfonic acid, ethanesulfonic acid, 2-hydroxy-ethanesulfonic acid, ethylenediamonotetraacetic acid, formic acid, fumaric acid, galacaric acid, gentisic acid, D-glucoheptonic acid, D-gluconic acid, D-glucuronic acid, glutamic acid, glutantic acid, glutaric acid, 2-oxo-glutaric acid, glycero-phosphoric acid, glycine, glycolic acid, hexanoic acid, hippuric acid, hydrobromic acid, hydrochloric acid isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like. (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

Halogen:

The term halogen generally denotes fluorine, chlorine, bromine and iodine.

Alkyl:

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals H$_3$C—, H$_3$C—CH$_2$—, H$_3$C—CH$_2$—CH$_2$—, H$_3$C—CH(CH$_3$)—, H$_3$C—CH$_2$—CH$_2$—CH$_2$—, H$_3$C—CH$_2$—CH(CH$_3$)—, H$_3$C—CH(CH$_3$)—CH$_2$—, H$_3$C—C(CH$_3$)$_2$—, H$_3$C—CH$_2$—CH$_2$—CH$_2$—CH$_2$—, H$_3$C—CH$_2$—CH$_2$—CH(CH$_3$)—, H$_3$C—CH$_2$—CH(CH$_3$)—CH$_2$—, H$_3$C—CH(CH$_3$)—CH$_2$—CH$_2$—, H$_3$C—CH$_2$—C(CH$_3$)$_2$—, H$_3$C—C(CH$_3$)$_2$—CH$_2$—, H$_3$C—CH(CH$_3$)—CH(CH$_3$)— and H$_3$C—CH$_2$—CH(CH$_2$CH$_3$)—.

Alkynyl:

The term "$C_{2-n}$-alkynyl", wherein n is an integer from 3 to n, is used for a group as defined in the definition for "$C_{1-n}$-alkyl" with at least two carbon atoms, if at least two of those carbon atoms of said group are bonded to each other by a triple bond.

Cycloalkyl:

The term "$C_{3-n}$-cycloalkyl", wherein n is an integer >3, either alone or in combination with another radical denotes a mono-, bi-, tri- or tetracyclic, saturated, hydrocarbon radical with 3 to n C atoms. For example the term $C_{3-7}$-cycloalkyl includes cyclopropyl, cyclobutyl, cyclopentyl, cyclohexyl and cycloheptyl.

The term "cycloalkyl" encompasses fused, bridged and spirocyclic systems. The cycloalkyl radical may further be fused to a phenyl ring or to a 5-6-membered heteroaryl ring, e.g. a thienyl-, pyrrolyl-, thiazolyl-, oxazolyl-, isoxazolyl-, imidazolyl-, pyrazolyl-, triazolyl-, tetrazolyl-, pyridinyl-, pyrimidinyl- pyrazinyl- or pyridazinyl-ring.

Furthermore, the term "cycloalkyl" includes the following exemplary structures, which are not depicted as radicals as they may be attached through a covalent bond to any atom of the cycloalkyl ring fragment but not to an atom of the aryl or heteroaryl fragment:

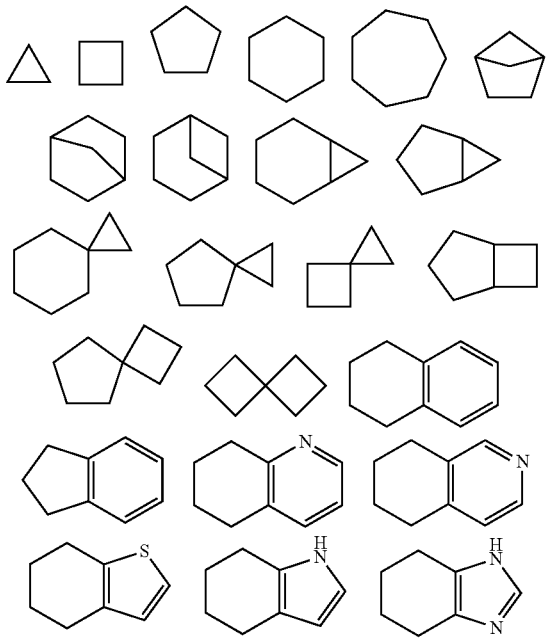

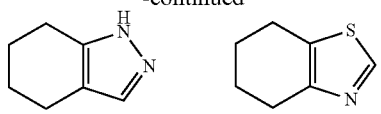

Heterocycloalkyl:

The term "4-n-membered heterocycloalkyl", wherein n is an integer >4, means a saturated or partially unsaturated mono- or polycyclic ring system containing one or more heteroatoms selected from N, O or S(O)$_r$, wherein r=0, 1 or 2, consisting of 4 to n ring atoms. The heterocycloalkyl ring system may further be fused to a phenyl- or 5-6-membered heteroaryl ring such as a thienyl-, pyrrolyl-, thiazolyl-, oxazolyl-, isoxazolyl-, imidazolyl-, pyrazolyl-, triazolyl-, tetrazolyl-, pyridinyl-, pyrimidinyl- pyrazinyl- or pyridazinyl-ring. The term "heterocycloalkyl" is intended to include all the possible isomeric forms. The term "heterocycloalkyl" includes the following exemplary structures, which are not depicted as radicals as they may be attached through a covalent bond to any atom of the heterocycloalkyl or cycloalkyl ring fragment but not to an atom of the aryl or heteroaryl fragment:

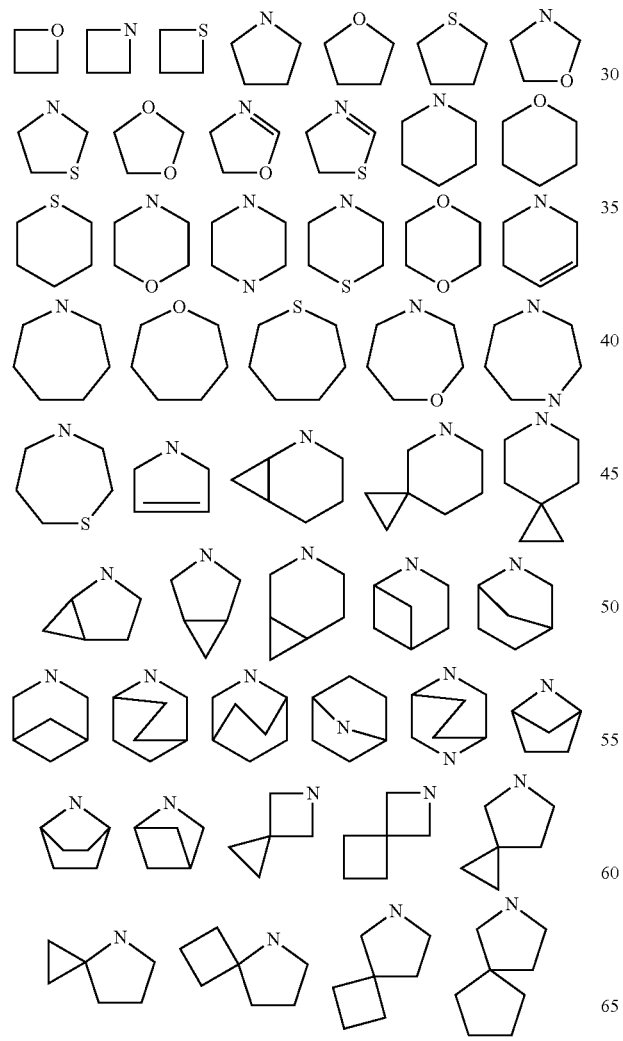

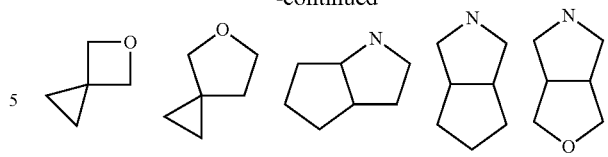

Aryl:

The term "aryl" as used herein, either alone or in combination with another radical, denotes a carbocyclic aromatic monocyclic group containing 6 carbon atoms which may further be fused to a second 5- or 6-membered aromatic, saturated or unsaturated carbocyclic group. The term "aryl" includes phenyl, indanyl, indenyl, naphthyl, anthracenyl, phenanthrenyl, tetrahydronaphthyl and dihydronaphthyl which may be attached through a covalent bond to any atom of the aromatic fragment.

Heteroaryl:

The term "heteroaryl" means a mono- or polycyclic ring system containing one or more heteroatoms selected from N, O or S(O)$_r$, wherein r=0, 1 or 2, consisting of 5 to 14 ring atoms wherein at least one of the heteroatoms is part of the aromatic ring which may further be fused to a second 5- or 7-membered aromatic, saturated or unsaturated cycloalkyl or heterocycloalkyl group. The term "heteroaryl" is intended to include all the possible isomeric forms.

The term "heteroaryl" includes the following exemplary structures, which are not depicted as radicals as they may be attached through a covalent bond to any atom of the mono or bicyclic heteroaryl ring but not to an atom of the cycloalkyl or heterocycloalkyl fragment:

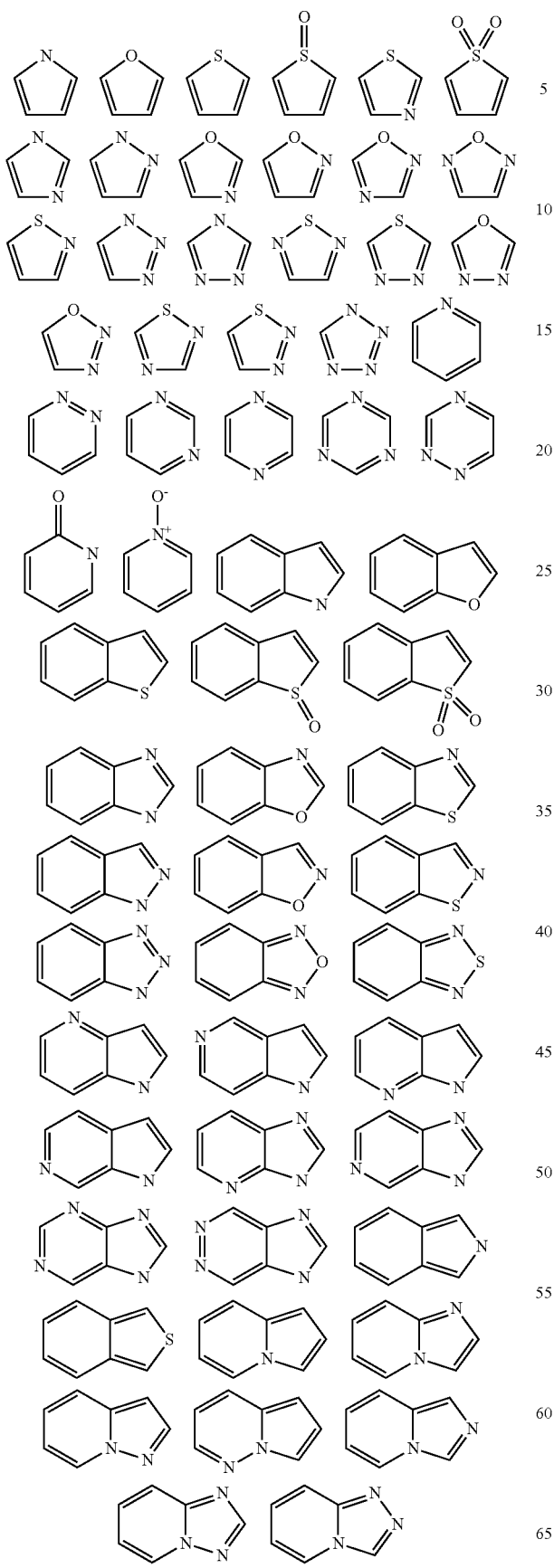
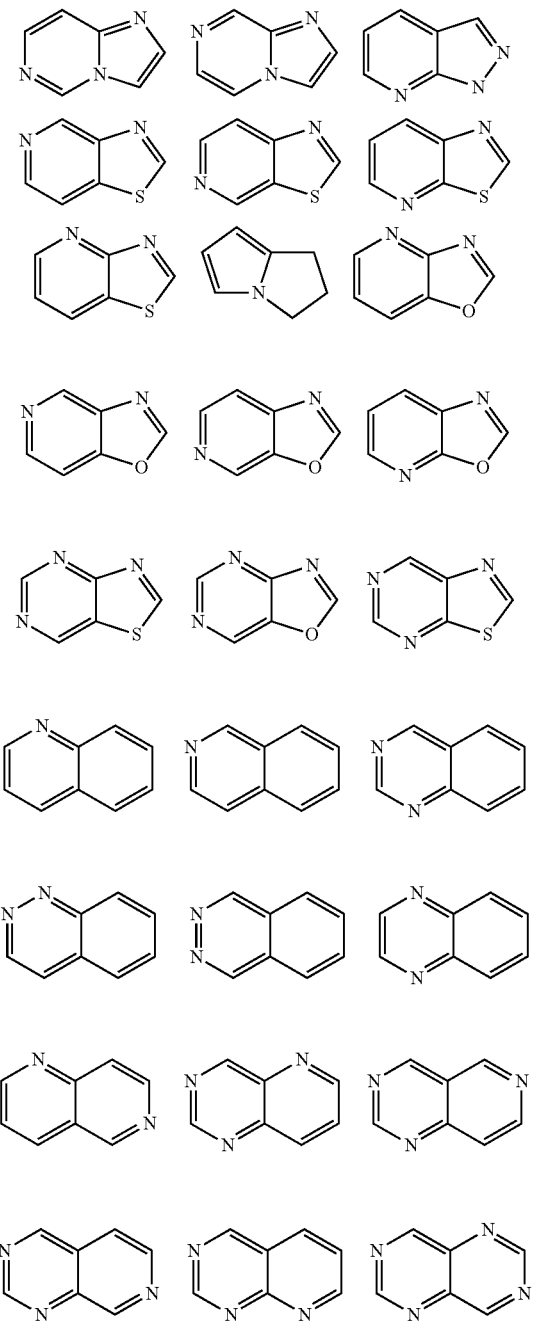

Methods of Preparation

Compounds of the present invention can be prepared in accordance with techniques that are well known to those skilled in the art, for example as described hereinafter and in the experimental section or in analogy to methods described in WO2010/034796 and WO2010/100249. According to a further aspect of the invention there is provided a process for the preparation of a compound of formula I, which process can be performed for example according to the following schemes A-B.

Scheme A (all variable groups are as defined in claim 1):

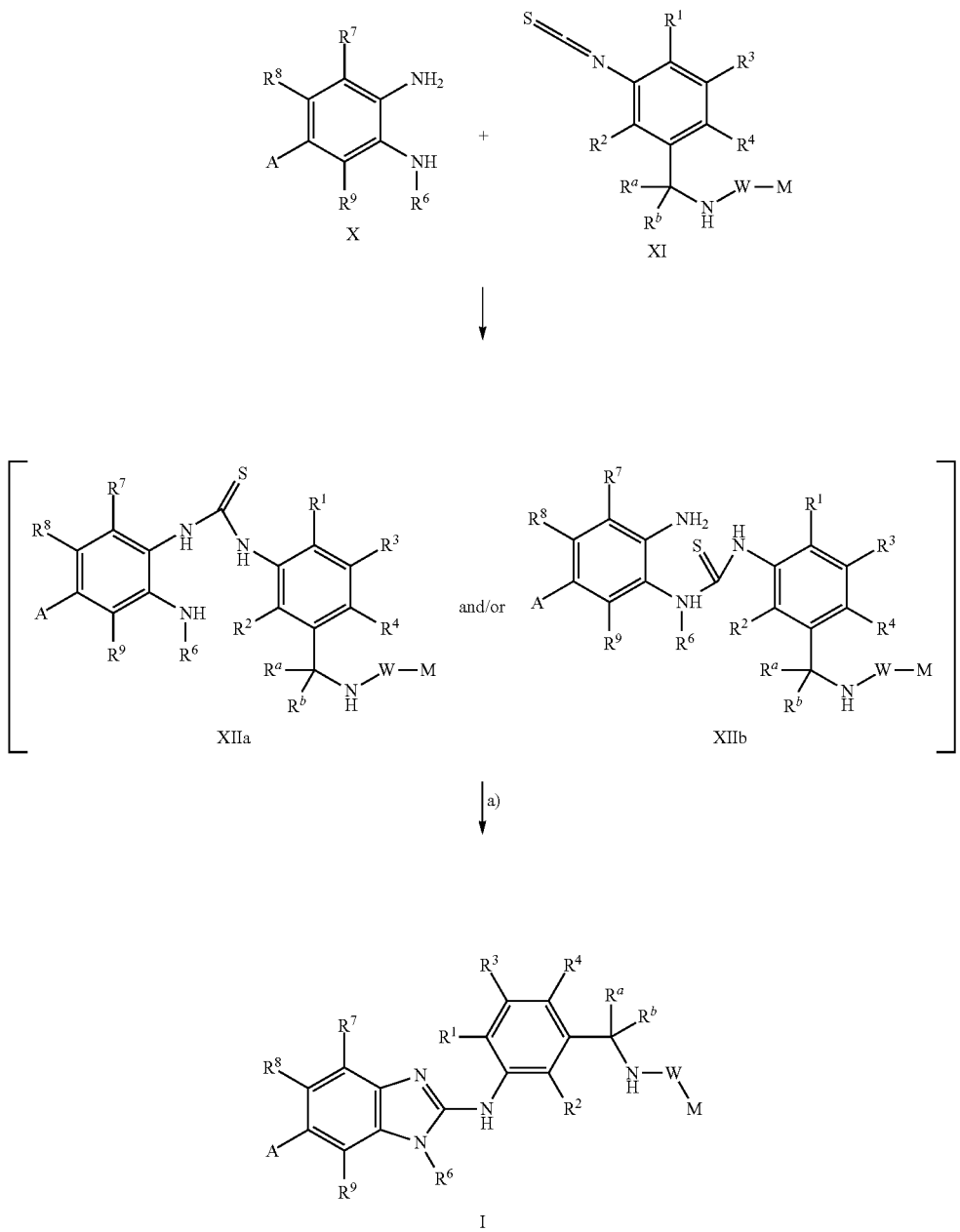

The reaction between phenylenediamine X and the thioisocyanate XI (Step a) can be performed under standard conditions known to those skilled in the art—for example in analogy to the process described in WO2010/034796 and WO2010/100249—in presence of a suitable solvent such as diethyl ether (Et$_2$O), dimethylformamide (DMF), dichloromethane (DCM), acetonitrile (MeCN) and/or tetrahydrofuran (THF). The reaction is preferably performed in the presence of a suitable reagent which enhances the cyclisation step as for instance CH$_3$—I or a carbodiimide based compound such as N,N'-dicyclohexylcarbodiimide (DCC), 1-ethyl-3-(3-dimethylaminopropyl) carbodiimide (EDCI, or its salt, e.g. hydrochloride) or N,N'-diisopropylcarbodiimide (DIC) or in presence of an amine base e.g. triethylamine (TEA) or diisopropyl ethyl amine (DIPEA). The reaction may proceed at any suitable temperature between 0° C. to 200° C., preferably between room temperature and 100° C. Step a can be performed in a step-wise reaction including isolation of the thiourea intermediates XIIa and/or XIIb or in a one-pot procedure.

Alternatively, the compounds of formula I can be synthesized according to scheme B.

Scheme B (all variable groups are as defined in claim 1 and PG$^{amino}$ is a protecting group of the benzylic amino group):

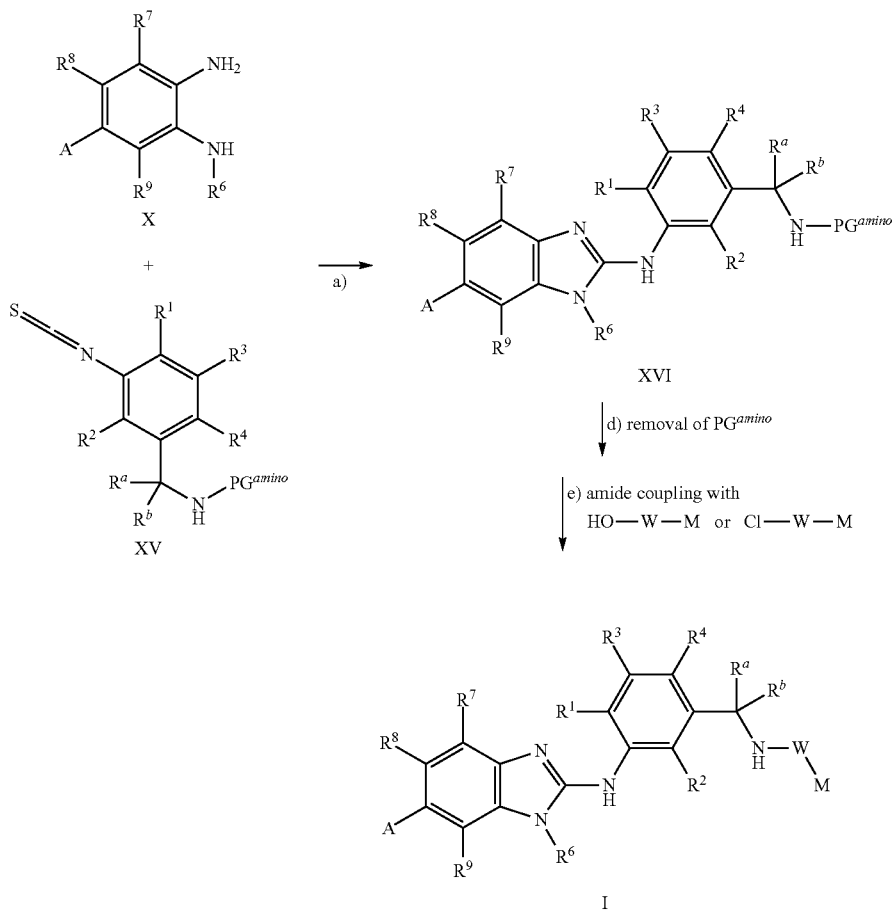

The protecting group PG$^{amino}$ in XV is a literature known protecting group of an amino group well known to those skilled in the art as for example described in "*Protective Groups in Organic Synthesis*", 3$^{rd}$ edition, T. W. Greene & P. G. M. Wutz, Wiley-Interscience (1999), for example a tert-butoxycarbonyl-, benzyloxycarbonyl-, ethoxycarbonyl-, methoxycarbonyl-, allyloxycarbonyl- or trifluormethylcarbonyl group.

Step a) can be performed as described in Scheme 1.

Step d) PG$^{amino}$ in XVI can be removed in accordance with techniques that are well known to those skilled in the art and which are exemplified hereinafter. For example XVI can be deprotected using an appropriate agent (depending on the protecting group) such as for example trifluoro acetic acid, HCl or H$_2$SO$_4$ solutions, KOH; Ba(OH)$_2$, Pd on carbon (Pd/C), trimethylsilyl iodide or other conditions as described in "*Protective Groups in Organic Synthesis*", 3$^{rd}$ edition, T. W. Greene & P. G. M. Wutz, Wiley-Interscience (1999). Appropriate co-solvent for this step is for example DCM, THF, MeCN, DMF, DMA, NMP or mixtures of the above mentioned solvents at any suitable temperature between 0° C. to 100° C.

The amide formation in step e) can be performed with the acids HO—W-M and an additional in-situ activating agent like 1-propylphosphonic acid cyclic anhydride (PPA), O-(benzo¬ triazol-1-yl)-N,N,N',N'-tetra-methyl-uronium tetrafluoroborate (TBTU), O-(benzo¬ triazol-1-yl)-N,N,N', N'-tetramethyl-uro-nium hexafluorophosphate (HBTU), O-(7-azabenzotriazol-1-yl)-N,N,N',N'-tetramethyl-uro-nium-hexafluorophosphate (HATU), DCC, EDCI, carbonyl¬ di¬ imidazole (CDI), carbonylditriazole (CDT), 1-chloro-2-methyl-propenyl-dimethylamine, oxalyl chloride or other activating agents of the state of the art. Alternatively, the amide formation can be performed directly with the corresponding acid chloride Cl-W-M under analogous conditions without an additional in situ activating agent. The coupling reaction is preferably performed in the presence of a base such as NaOH, KOH, NaHCO$_3$, TEA, DIPEA, pyridine, N,N-dimethylaminopyridine (DMAP) or other appropriate bases of the state of the art and for example described in Houben-Weyl, "Methods in Organic Synthesis", Vol. E22a, p 425ff. The coupling reactions are performed in an appropriate solvent for example DCM, dioxane, THF, MeCN, DMF, dimethylacetamide (DMA), N-methylpyrrolidone (NMP) or in mixtures of the above mentioned solvents at any suitable temperature between 0° C. to 100° C.

The synthesis of the building blocks X can be performed in a procedure described in scheme C—wherein all variable groups in XIII and XIV are as defined in claim 1 and LG is a leaving group on the aromatic ring (for example a fluoro, chloro, bromo, iodo or trifluormethylsulfonyl group)—using standard reaction conditions known to those skilled in the art which are exemplified in the experimental part in detail.

Scheme C [all variable groups are as defined in claim 1 and LG is a leaving group as for example Fluoro, Chloro, Bromo, Iodo, or CF$_3$(SO$_3$)]

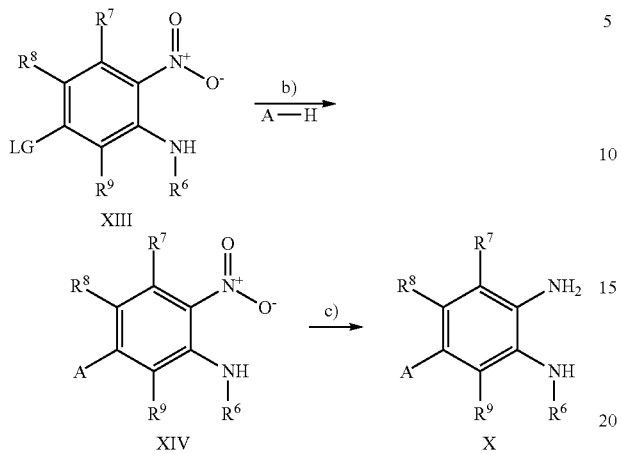

Step b can be performed by an aromatic substitution reaction of the building block XIII with the amine A-H or an appropriate salt thereof and using literature known reaction conditions. For example the reaction can be performed employing a building block XIII wherein LG is preferably a fluoro or chloro substituent in presence of a suitable base like K$_2$CO$_3$, Na$_2$CO$_3$, Cs$_2$CO$_3$, TEA, DIPEA in an appropriate solvent for example DMF, DMSO, DMA, NMP or mixtures of the above mentioned solvents at any suitable temperature between 0° C. to 180° C. Alternatively the reaction can also be performed in presence of a Pd-catalyst, in this case the preferred groups LG are bromo, iodo or trifluormethylsulfonyl. For example Pd(PPh$_3$)$_4$ can be used in presence of a suitable base for example K$_2$CO$_3$, Na$_2$CO$_3$, Cs$_2$CO$_3$, TEA, DIPEA in an appropriate solvent for example THF, MeCN, DMF or mixtures of the mentioned solvents preferably at a temperature between 0° C. to 120° C.

The nitro group in precursor XIV can be reduced to the amino group in step c) under literature known reduction conditions for example via hydrogenation (preferably at 1-5 bar) in presence of Pt/C, Pd/C or Raney-Nickel (Ra/Ni) in MeOH, EtOH or THF or mixtures thereof, optionally under acidic conditions in presence of HCl, or by using SnCl$_2$/HCl, Na$_2$S$_2$O$_4$, Zn/HCl, Fe/HCl, Fe-powder/aqueous NH$_4$Cl solution or according to procedures described in the literature for example R. Larock, *Comprehensive Organic Transformations*, VCH Verlagsgemeinschaft, Weinheim (1989). Appropriate solvent for this step is for example DCM, THF, MeCN, DMF, DMA, NMP, EtOH, MeOH or mixtures of the above mentioned solvents at any suitable temperature between 0° C. to 100° C.

XI

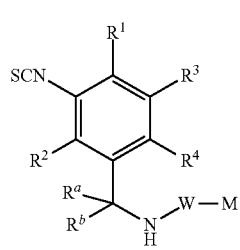

XV

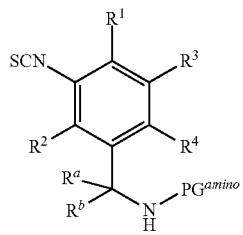

The synthesis of the building blocks XI and XV—wherein all variable groups are as defined in claim 1 and PG$^{amino}$ is a protecting group of the benzylic amino group—is employing standard reaction conditions according to scheme D known to those skilled in the art which are exemplified in the experimental part in detail or in WO2010/100249.

Scheme D (all variable groups are as defined in claim 1 and PG$^{amino}$ is a protecting group of the benzylic amino group):

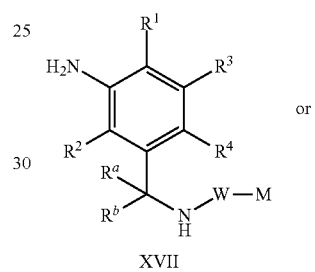

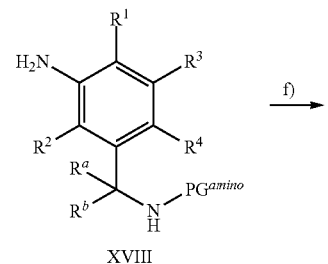

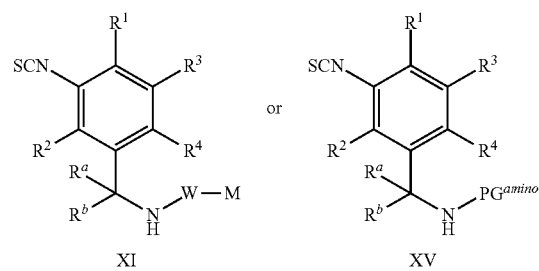

Step f) can be performed according to standard literature procedures for example with reagents such as 1,1'-thiocarbonyldi-2-pyridone, O,O'-di-2-pyridylthiocarbonate, 1,1'-thiocarbonyldiimidazole or with thiophosgene in a solvent as for example DCM, dioxane or DMF at temperatures between 0-150° C. and optionally under addition of a base like DMAP or TEA.

The building blocks XVII and XVIII can be prepared according to scheme E:

Scheme E (all variable groups are as defined in claim 1 and PG$^{amino}$ and is a protecting group of the benzylic amino group):

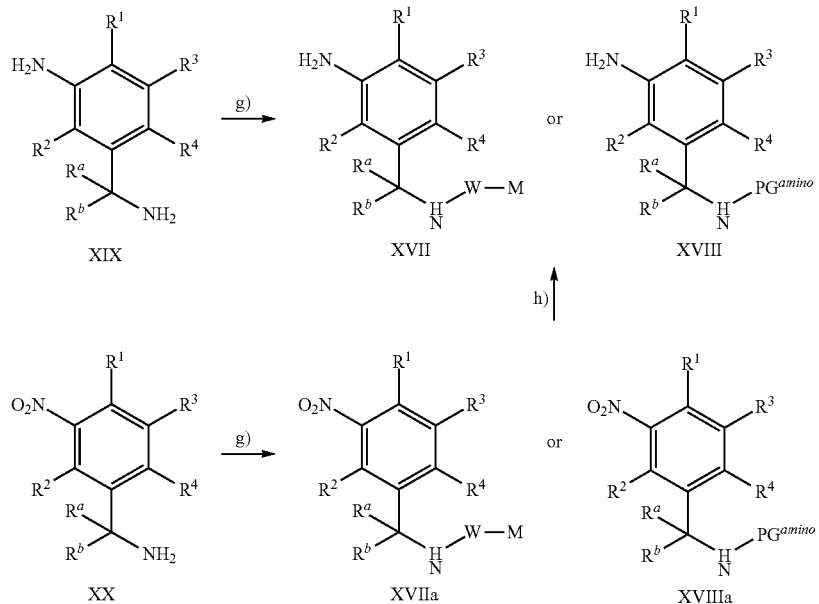

The amide formation in step g) can be performed in analogy to step c) or step e) to synthesize compound XVII or by using common reagents for amino group protection for example di-tert-butyl-dicarbonate, methyl-, ethyl-, benzyl or allyl-chloroformate under standard reaction conditions as described in "Protective Groups in Organic Synthesis", 3$^{rd}$ edition, T. W. Greene & P. G. M. Wutz, Wiley-Interscience (1999) to synthesize compounds XVIII.

The nitro group in precursor XVIIa or XVIIIa can be reduced to the amino group in step h) under literature known reduction conditions for example via hydrogenation (preferably at 1-5 bar) in presence of Pd/C, Pt/C or RaNi in MeOH, EtOH or THF optionally under acidic conditions in presence of HCl, or by using SnCl$_2$/HCl, Na$_2$S$_2$O$_4$, Zn/HCl, Fe/HCl, Fe-powder/aqueous NH$_4$Cl solution or according to procedures described in the literature for example R. Larock, *Comprehensive Organic Transformations*, VCH Verlagsgemeinschaft, Weinheim (1989). Appropriate solvent for this step is for example DCM, THF, MeCN, DMF, DMA, NMP, EtOH, MeOH or mixtures of the above mentioned solvents at any suitable temperature between 0° C. to 100° C.

The building blocks XIX and XX can be prepared according to scheme F-H:

Scheme F (R$^a$ amd R$^b$ are hydrogen atoms, all other variable groups are as defined in claim 1):

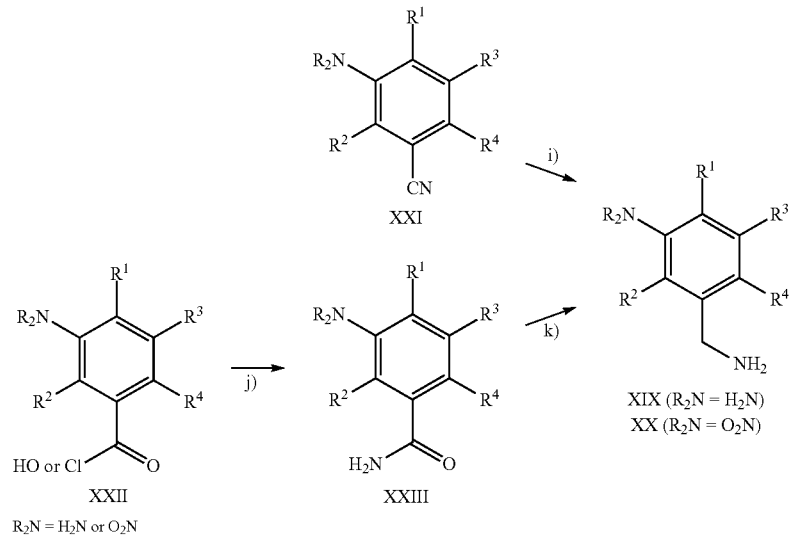

Step i) can be performed via hydrogenation (1-5 bar) with a catalyst like Pd/C, PtO$_2$ or RaNi in a suitable solvent like MeOH or EtOH optionally using HCl or NH$_3$ as additive at temperatures between 0-60° C. or via reduction with LiAlH$_4$ or BH$_3$-containing reagents in a suitable solvent like THF, MeOH or EtOH under literature-known conditions.

Step j) can be performed under the amide coupling conditions described for step e) and using NH$_3$ as coupling partner, for example 1-chloro-2-methyl-propenyl-dimethylamine in THF can be used as activating agent.

Step k) can be performed using LiAlH$_4$ or BH$_3$-containing reagents under literature known conditions as for example compiled in R. C. Larock, Comprehensive Organic Transformations, VCH, 1989, p. 432-433, preferably with LiAlH$_4$ in THF at 0-80° C.

Alternatively compounds XIX and XX can be prepared as described in WO2010/100249 or according to scheme G Scheme G (all variable groups are as defined in claim 1):

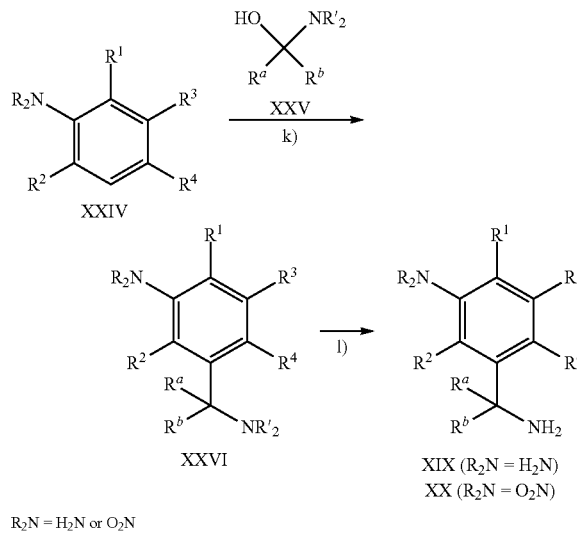

Step k) can be performed mixing XXIV with reagent XXV in concentrated H$_2$SO$_4$ or F$_3$C—SO$_3$H at temperatures between 0-150° C., preferably between 20-80° C.

Step l) can be performed using literature known deprotection procedures for the corresponding nitrogen protecting groups for example treatment of the phthalimide with hydrazine or cleavage of the amide bond using bases like NaOH in MeOH or EtOH at temperatures between 20-80° C. or under acidic conditions using aqueous HCl solution or HCl in dioxane at temperatures between 20-80° C.

Alternatively compounds XIX and XX can be prepared according to scheme H

Scheme H (R$^b$ = H, all variable groups are as defined in claim 1):

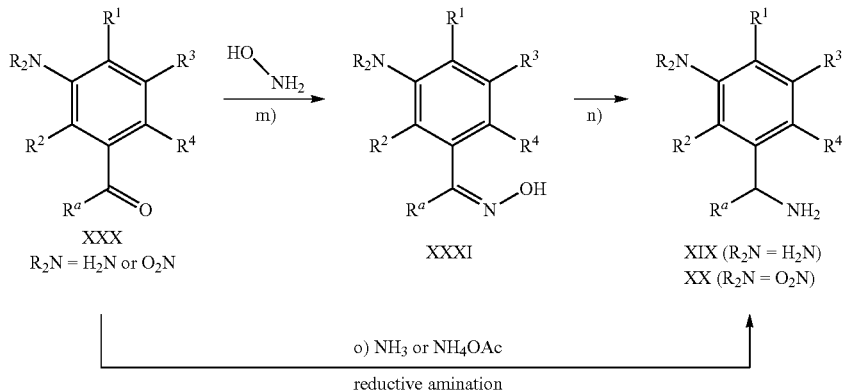

Step m) can be performed mixing XXX with HO—NH$_2$ in an appropriate solvent for example MeCN, DCM, THF, optionally using HCl as additive at temperatures between 0-60° C.

Step n) can be performed applying literature known reduction conditions for example via hydrogenation preferably at 1-5 bar H$_2$ pressure in presence of Pd/C or Ra—Ni in MeOH, EtOH or THF optionally using HCl or HOAc as catalyst, or by using SnCl$_2$/HCl, Zn/HCl, Fe/HCl, Fe-powder/aqueous NH$_4$Cl solution or according to procedures described in the literature for example R. Larock, Comprehensive Organic Transformations, VCH Verlagsgemeinschaft, Weinheim (1989).

Step o) can be performed applying literature known reduction conditions e.g. using ammonia or ammonium salts (e.g. ammonium acetate) and Borane reagents, for example NaBH$_3$CN, BH$_3$-THF-complex or BH$_3$-SMe$_2$-complex in water, MeOH, EtOH, THF or mixtures thereof, under buffered conditions preferably at a pH between 5-9 or employing hydrogenations using Pd/C or Ra—Ni as catalysts in MeOH, EtOH or THF optionally using HCl or HOAc as co-catalyst or according to procedures described in the literature for example in WO2010/100249 or R. Larock, *Comprehensive Organic Transformations*, VCH Verlagsgemeinschaft, Weinheim (1989).

Biological Assays

The aim of this assay is to determine the affinity of a test compound for the mPGES-1 enzyme.

Similar assays to measure inhibition of mPGES-1 have previously been described in the literature [1, 2].

LITERATURE REFERENCES

1. Riendeau, D., R. Aspiotis, D. Ethier, Y. Gareau, E. Grimm, J. Guay, S. Guiral, H. Juteau, J. Mancini, N. Methot, J. Rubin, and R. Friesen, *Inhibitors of the inducible microso-*

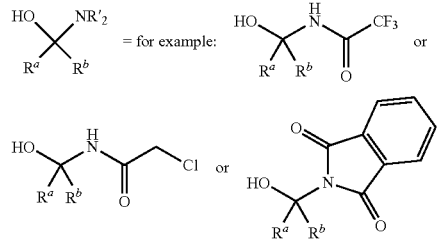

mal prostaglandin E2 synthase (*mPGES*-1) derived from MK-886. Bioorg Med Chem Lett, 2005. 15(14): p. 3352-3355.
2. Cote, B., L. Boulet, C. Brideau, D. Claveau, D. Ethier, R. Frenette, M. Gagnon, A. Giroux, J. Guay, S. Guiral, J. Mancini, E. Martins, F. Masse, N. Methot, D. Riendeau, J. Rubin, D. Xu, H. Yu, Y. Ducharme, and R. Friesen, *Substituted phenanthrene imidazoles as potent, selective, and orally active mPGES-1 inhibitors*. Bioorg Med Chem Lett, 2007. 17(24): p. 6816-6820.

Assay A: mPGES-1 Enzyme Assay
List of Reagents Used:
  Glutathione (Sigma, G-4251)
  Freeze culture in Rosetta *E coli* expression strain.
  LB growth media with Ampillicillin (Amp) final concentration in culture 50 μg/mL
  Chloroamphenicol stock 34 mg/mL (chloro) final concentration in culture 34 μg/mL
  Sterile growth flasks for 500 mL-1 liter cultures
  0.1 M KP, buffer pH 7.4
  9.25% HCl
  $PGH_2$ (0.25 mM)
  Fe (II) $Cl_2$ tetrahydrate, 99% (Sigma, 220229)
  384-well plate with compounds
  96-well plate, polypropylene (Thermo fast 96 skirted VWR)
  384-well plate polypropylene PCR plate (Greiner 785201)
  Greiner 384-well plate pp (In vitro cat. no. 781280)
  Adhesive sealing film for 96-well plates (Sigma-Aldrich)
  Aluminium foil (PCR foil, 310-0030-127-471 from Labora)
  PBS (GIBCO 14040)
  Prostaglandin $E_2$ Assay (Cisbio, cat. no. 62P2APEC)
  Biomek FX robot (Beckman Coulter)
  Biomek NX robot (Beckman Coulter)
  Multidrop; micro or combi (ThermoLabsystems)
  Plate reader: Safire2 (Tecan)

Microsomes from Rosetta *E. coli* bacteria expressing recombinant human mPGES-1 can be derived as described below:

Inoculate 5 mL LB with Amp and Chloro with bacteria from freeze culture. Incubate overnight at 37° C. with 200 rpm. Thereafter, inoculate 500-800 mL LB containing Amp and Chloro with the 5 mL on culture and grow to OD640 of 0.6-0.8. Chill the culture to +4° C. before induction. Induce the culture with IPTG at a final concentration of 400 μM. Express the protein at room temp 18-23° C. with 200 rpm shaking overnight.

The following steps can be performed on the following day:
1. Spin down the cells in 250 mL centrifuge flasks for 15 min at 7000 rpm
2. Dissolve the pellet from 250 mL culture in 12.5 mL homogenization buffer
3. Disintegrate the cells by sonication, 4×10 seconds at 35% amplitude
4. Add 2.5 mL $MgCl_2$ (100 mM) and DNase 12.5 μL (0.8 mg/mL) and incubate on ice for 30 min
5. Spin down the bacteria debris and save the supernatant, 7000 rpm for 15 min
6. Isolate the protein containing membranes in the supernatant by ultracentrifugation 45000×g for 1 hour.
7. Discard the supernatant and dissolve the pellet in 20 mM KPi buffer and aliquot the enzyme and store aliquots at −80° C.

Before each experiment is performed an aliquot of the enzyme is thawed and it can then be dissolved in 0.1 M KP, pH 7.4 buffer containing 2.5 mM GSH. 50 μL of this enzyme solution is subsequently dispensed in a 384-well plate at room temperature. 0.5 μL of the inhibitor dissolved in DMSO is thereafter added to each well and incubated for 25 minutes at room temperature. Subsequently, 2 μL of $PGH_2$ dissolved in an appropriate solvent is added to each well and after one minute at room temperature, the acidified stop solution containing $FeCl_2$ is added. 4 μL of the total volume is transferred to a separate plate and diluted 750-fold in two separate steps before quantification of $PGE_2$.

In order to quantitate the amount of $PGE_2$ that has been formed, a homogenous time resolved fluorescent (HTRF) detection of $PGE_2$ can be performed by the use of a commercially available kit from CisBio essentially according to the manufacturer's protocol. Briefly, 10 μL of the diluted sample is transferred to a white 384-well plate and the following steps can be performed in a sequential manner at room temperature or as indicated.

5 μL reconstitution buffer as supplied by the manufacturer is added to the negative control (NC) wells.
  The plate is covered with adhesive sealing film.
  The plate can now be centrifuged at 1200 rpm for 1 minute.
  The NC samples are covered with sealing film.
  250 μL d2 labeled $PGE_2$ (d2-$PGE_2$) can be diluted in 4750 μL reconstitution buffer as supplied by the manufacturer
  250 μL Eu3+-cryptate can be diluted in 4750 μL reconstitution buffer as supplied by the manufacturer
  5 μL d2-$PGE_2$ can now be added to rows 1 to 24, by using a multidrop. The sealing film is thereafter removed from the NC wells.
  5 μL Eu3+-cryptate labeled anti-$PGE_2$ can now be added to rows 1 to 24 by using a Multidrop.
  The plate can now be covered with sealing film.
  The plate can now be centrifuge at 1200 rpm for 1 minute and place at 4° C. overnight.

After the overnight incubation the fluorescence is measured by the use of an appropriate microplate reader. The fluorescence of Eu3+-cryptate and d2-$PGE_2$ are measured using the following excitation and emission wavelength, europium cryptate: $\lambda_{max}^{ex}$=307 nm, $\lambda_{max}^{em}$=620 nm and d2: $\lambda_{max}^{ex}$=620 nm, $\lambda_{max}^{em}$=665 nm), respectively. The extent of the specific HTRF is measured as a ratio of the emission intensity at 665 nm vs. that at 620 nm. A standard curve using synthetic $PGE_2$ is used to quantify the amount of $PGE_2$ in unknown samples. The degree of inhibition can be calculated as percent inhibition by dividing the amount of $PGE_2$ formed in unknown samples by the amount of $PGE_2$ formed in control samples.

Assay B: mPGES-1 Enzyme Assay (Modified)
mPGES Protein Production

Microsomes from Rosetta *E. coli* bacteria expressing recombinant human mPGES-1 can be derived as described below:

Inoculate 5 ml LB with Ampicilin (50 μg/ml) and Chloramphenicol (34 μg/ml) with bacteria from freeze culture. Incubate 8 h at 37° C. with 200 rpm. Thereafter, inoculate 500-1000 ml LB containing Ampicilin and Chloramphenicol with the 5 ml on culture and grow to OD640 of 0.8-1.0. Chill the culture to +4° C. before induction. Induce the culture with IPTG at a final concentration of 400 μM. Express the protein at room temp 18-23° C. with 200 rpm shaking overnight.

The following steps can be performed on the following day:
1. Spin down the cells in 250 ml centrifuge flasks for 15 min at 7000 rpm (Beckmann Coulte Avanti J-E centrifuge)
2. Dissolve the pellet from 250 ml culture in 12.5 ml homogenization buffer
3. (15 mM Tris-HCL pH8, 1 mM EDTA pH8, 0.25 mM Sucrose, 2.5 mM GSH, 1 Tablet Protease inhibitor per 50 ml buffer)
4. Disintegrate the cells by sonication, 5×10 seconds at 48% amplitude of a 750 W sonifier
5. Add 2.5 ml $MgCl_2$ (100 mM) and DNase 12.5 µl (0.8 mg/ml) and incubate on ice for 30 min
6. Spin down the bacteria debris and save the supernatant, 7000 rpm for 15 min
7. Isolate the protein containing membranes in the supernatant by ultracentrifugation 120000×g for 2 hour at 4° C. (Sorvall T880 rotor).
8. Discard the supernatant and dissolve the pellet in 20 mM Potassium phosphate buffer pH7.4 ($KH_2PO_4$ and $K_2HPO_4$) buffer by sonication (5×10 s, 30% of a 50 W sonifier) and aliquot the enzyme and store aliquots at −80° C.

Before each experiment is performed an aliquot of the enzyme is thawed and it can then be dissolved in 0.1 M Potassium phosphate buffer pH7.4 ($KH_2PO_4$ and $K_2HPO_4$) buffer containing 2.5 mM GSH.

mPGES-1 Enzyme Assay

The aim of this assay is to determine the affinity of a test compound for the mPGES-1 enzyme.

47 µl of recombinant human mPGES-1 (~0.5 µg protein/well) containing microsomal suspension in a buffer containing GSH, (2.5 mmol/L L-Glutathione reduced, dissolved in 0.1 mol/L Phosphat Buffer pH 7.4) is dispensed in a 384-well plate and thereafter 1 µl of the test compound(s) is/are added and incubated for 25 minutes at room temperature. The enzyme reaction is started by the addition of 2 ul PGH2 (final conc. 2 µM) dissolved in water-free Diglyme. After 60 seconds the reaction is terminated by addition of a stop solution containing $FeCl_2$ (10 µL 0.074 mol/l $FeCl_2$). The samples are diluted between 1:25 in PBS (Phosphate Buffered Saline). 10 µl of the diluted samples are transferred to 384-well low volume plate. In order to quantify the amount of $PGE_2$ that has been formed, a homogenous time resolved fluorescent (HTRF) detecting of $PGE_2$ has been performed using a commercially available kit from Cisbio according to the manufactures recommendation. This HTRF-based assay has been described in detail (see: Goedken et al., J Biomol Screen, 2008, 13(7), 619-625). Briefly, the diluted samples are mixed with 5 µl $PGE_2$-d2 conjungate and 5 µl anti-$PGE_2$ cryptate conjungate. After an incubation period of the plates overnight, the fluorescence is measured by the use of an appropriate microplate reader.

The fluorescence of Europium cryptate (maxex=307 nm, maxem=620 nm) and d2-$PGE_2$ (maxex=620 nm, maxem=665 nm) are measured.

The extent of the specific HTRF is measured as a ratio of the emission intensity at 665 nm vs. that at 620 nm at an excitation puls of 320 nm. The quantification plate contains also wells with different concentrations of $PGE_2$ as calibration curve for the calculation of the $PGE_2$ concentrations from the HTRF ratio values.

From all mPGES enzyme assay the background is subtracted and the $IC_{50}$ is calculated over a nonlinear regression with conventional software.

TABLE 1-A mPGES-1 inhibitory effect ($IC_{50}$ values in nM) of compounds of the invention in the biological assays A

| example | IC50 [nM] | example | IC50 [nM] | example | IC50 [nM] | example | IC50 [nM] |
|---|---|---|---|---|---|---|---|
| 1 | 2.5 | 11 | 140 | 28 | 24 | 72 | 11 |
| 2 | 19 | 13 | 2.6 | 29 | 105 | 73 | 61 |
| 3 | 715 | 14 | 4.8 | 30 | 300 | 74 | 144 |
| 4 | 24 | 15 | 3 | 34 | 100 | 75 | 8.7 |
| 5 | 3.8 | 16 | 15 | 54 | 6.6 | 76 | 3.1 |
| 6 | 215 | 17 | 24 | 65 | 15 | 77 | 10 |
| 7 | 74 | 18 | 79 | 66 | 10 | 78 | 1.7 |
| 8 | 106 | 19 | 52 | 68 | 4 | 79 | 2.4 |
| 9 | 143 | 20 | >100 | 69 | 9 | 80 | 54 |
| 10 | 31 | 21 | 30 | 71 | 2.5 | 81 | 6.7 |
| 82 | 1.7 | 83 | 1.3 | 84 | 7.3 | 85 | 20 |
| 86 | 7.1 | 87 | 14 | 88 | 5.3 | 89 | 6.1 |
| 90 | 2.2 | 91 | 3.6 | 93 | 17 | 94 | 3.5 |
| 95 | 2.1 | 96 | 4.1 | 99 | 4.0 | 100 | 7.7 |
| 101 | 2.8 | 102 | 2.4 | 103 | 2.0 | 104 | 2.4 |
| 105 | 3.9 | 106 | 5.7 | 107 | 13 | 108 | 5.8 |
| 109 | 5.2 | 110 | 1.5 | 111 | 19 | 112 | 22 |
| 113 | 11 | 114 | 4.8 | 115 | 9.2 | 116 | 5.9 |
| 117 | 120 | 118 | 53 | 119 | >100 | 120 | 266 |
| 121 | 60 | 122 | 7.9 | 123 | 29 | 124 | 2.6 |
| 125 | 32 | 126 | 6.7 | 127 | 26 | 128 | 172 |
| 129 | 634 | 130 | 15 | 132 | 124 | 133 | 25 |

TABLE 1-B mPGES-1 inhibitory effect ($IC_{50}$ values in nM) of compounds of the invention in the biological assays B

| example | IC50 [nM] | example | IC50 [nM] | example | IC50 [nM] | example | IC50 [nM] |
|---|---|---|---|---|---|---|---|
| 12 | 174 | 33 | 3 | 37 | 7.8 | 40 | 5.7 |
| 48 | 9 | 51 | 23 | 52 | 2.2 | 53 | 3.5 |
| 59 | 2 | 61 | 5 | 70 | 6.5 | 92 | 39 |
| 97 | 3.1 | 98 | 6.5 | 131 | 5 | | |

Method of Treatment

The present invention relates to compounds of formula I which are useful in the prevention and/or treatment of a disease and/or condition in which the inhibition of prostaglandin E synthases, in particular that of the microsomal prostaglandin $E_2$ synthase-1 (mPGES-1) is of therapeutic benefit, including but not limited to the treatment and/or prevention of inflammatory diseases and/or associated conditions.

The term "inflammation" will be understood to include any inflammatory disease, disorder or condition per se, any condition that has an inflammatory component associated with it, and/or any condition characterised by inflammation as a symptom, including inter alia acute, chronic, ulcerative, specific, allergic and necrotic inflammation, and other forms of inflammation known to those skilled in the art. The term thus also includes, for the purposes of this invention, inflammatory pain, pain generally and/or fever.

Where a condition has an inflammatory component associated with it, or a condition characterised by inflammation as a symptom, the skilled person will appreciate that compounds of the invention may be useful in the treatment of the inflammatory symptoms and/or the inflammation associated with the condition.

Compounds of the invention may also have effects that are not linked to inflammatory mechanisms, such as in the reduction of bone loss in a subject. Such conditions include osteoporosis, osteoarthritis, Paget's disease and/or periodontal diseases.

A further aspect of the present invention relates to a compound of formula I as a medicament. Another aspect of the present invention is the use of compounds of formula I for the treatment and/or prevention of a disease and/or condition in which the inhibition of the mPGES-1 is of therapeutic benefit.

A further aspect of the present invention is the use of a compound of formula I for the treatment and/or prevention of inflammatory diseases and/or associated conditions.

The present invention also relates to the use of compounds of formula I for the treatment and/or prevention of the following diseases and conditions:

1. Rheumatic diseases or autoimmune diseases or muscoskeletal diseases: all forms of rheumatic diseases including e.g. soft tissue rheumatism, rheumatoid arthritis, polymyalgia rheumatica, reactive arthritis, tenosynovitis, gout or metabolic arthritis, bursitis, tendonitis, juvenile arthritis, spondyloarthropathies like e.g. spondylitis, ankylosing spondylitis, psoriatric arthropathy; sarcoidosis, fibromyalgia, myositis, polymyositis, osteoarthritis, traumatic arthritis, collagenoses of any origin e.g. systemic lupus erythematosus, scleroderma, dermatomyositis, Still's Disease, Sjögren syndrome, Felty syndrome; rheumatic fever and rheumatic heart disease, diseases of blood vessels like vasculitis, polyarthritis nodosa, Behcet's syndrome, giant cell arthritis, Wegener's granulomatosis, Henoch-Schönlein purpura; psoriatic arthritis, fungal arthritis, in particular including pain associated with any of the aforementioned conditions;
2. Headaches such as migraines with and without aura, tension-type headaches, cluster headaches and headaches with different origins;
3. Sympathetically maintained pain like complex regional pain syndrome Type I and II;
4. Neuropathic pain such as low back pain, hip pain, leg pain, non-herpetic neuralgia, post herpetic neuralgia, diabetic neuropathy, nerve injury-induced pain, acquired immune deficiency syndrome (AIDS) related neuropathic pain, head trauma, toxin and chemotherapy caused nerve injuries, phantom limb pain, multiple sclerosis, root avulsions, painful traumatic mononeuropathy, painful polyneuropathy, thalamic pain syndrome, post-stroke pain, central nervous system injury, post surgical pain, carpal tunnel syndrome, trigeminal neuralgia, post mastectomy syndrome, postthoracotomy syndrome, stump pain, repetitive motion pain, neuropathic pain associated hyperalgesia and allodynia, alcoholism and other drug-induced pain;
5. Cancer pain induced by or associated with tumors such as bone tumors, lymphatic leukemia; Hodgkin's disease, malignant lymphoma; lymphogranulomatoses; lymphosarcoma; solid malignant tumors; extensive metastases;
6. Visceral disorders such as chronic pelvic pain, pancreatitis, peptic ulcer, interstitial cystitis, cystitis, renal colic, angina, dysmenorrhoea, menstruation, gynaecological pain, irritable bowel disease (IBS), inflammatory bowel disease, Crohn's disease and ulcerative colitis, nephritis, prostatitis, vulvodynia, non-ulcer dyspepsia, non-cardiac chest pain, myocardial ischemia;
7. Inflammation associated diseases of ear, nose, mouth and throat like influenza and viral/bacterial infections such as the common cold, allergic rhinitis (seasonal and perennial), pharyngitis, tonsillitis, gingivitis, larhyngitis, sinusitis, and vasomotor rhinitis, fever, hay fever, thyroiditis, otitis, dental conditions like toothache, perioperative and post-operative conditions, trigeminal neuralgia, uveitis; iritis, allergic keratitis, conjunctivitis, blepharitis, neuritis nervi optici, choroiditis, glaucoma and sympathetic opthalmia, as well as pain thereof;
8. Neurological diseases such as cerebral oedema and angioedema, cerebral dementia like e.g. Parkinson's and Alzheimers disease, senile dementia; multiple sclerosis, epilepsy, drug resistant epilepsy, stroke, myasthenia gravis, brain and meningeal infections like encephalomyelitis, meningitis, including HIV as well as schizophrenia, delusional disorders, autism, affective disorders and tic disorders;
9. Work-related diseases like pneumoconiosis, including aluminosis, anthracosis, asbestosis, chalicosis, ptilosis, siderosis, silicosis, tabacosis and byssinosis;
10. Lung diseases such as asthma including allergic asthma (atopic or non-atopic) as well as exercise-induced bronchoconstriction, occupational asthma, viral- or bacterial exacerbation of asthma, other non-allergic asthmas and "wheezy-infant syndrome", Chronic obstructive pulmonary disease (COPD) including emphysema, adult respiratory distress syndrome, bronchitis, pneumonia, adult respiratory distress syndrome (ARDS), pigeon fancier's disease, farmers lung;
11. Skin diseases such as psoriasis and eczema, dermatitis, sunburn, burns as well as aprains and strains and tissue trauma;
12. Vascular and heart diseases which are inflammation-related like artheriosclerosis including cardiac transplant atherosclerosis, panarteritis nodosa, periarteritis nodosa, arteritis temporalis, Wegner granulomatosis, giant cell arthritis, reperfusion injury and erythema nodosum, thrombosis (e.g. deep vein thrombosis, renal, hepathic, portal vein thrombosis); coronary artery disease, aneurysm, vascular rejection, myocardial infarction, embolism, stroke, thrombosis including venous thrombosis, angina including unstable angina, coronary plaque inflammation, bacterial-induced inflammation including *Chlamydia*-induced inflammation, viral induced inflammation, and inflammation associated with surgical procedures such as vascular grafting including coronary artery bypass surgery, revascularization procedures including angioplasty, stent placement, endarterectomy, or other invasive procedures involving arteries, veins and capillaries, artery restenosis;
13. Diabetes-associated symptoms such as diabetic vasculopathy, diabetic neuropathy, diabetic retinopathy, post capillary resistance or diabetic symptoms associated with insulitis (e.g. hyperglycemia, diuresis, proteinuria and increased nitrite and kallikrein urinary excretion);
14. Benign and malignant tumors and neoplasia including cancer, such as colorectal cancer, brain cancer, bone cancer, epithelial cell-derived neoplasia (epithelial carcinoma) such as basal cell carcinoma, adenocarcinoma, gastrointestinal cancer such as lip cancer, mouth cancer, esophageal cancer, small bowel cancer, stomach cancer, colon cancer, liver cancer, bladder cancer, pancreas cancer, ovary cancer, cervical cancer, lung cancer, breast cancer, skin cancer such as squamous cell and basal cell cancers, prostate cancer, renal cell carcinoma, and other known cancers effecting epithelial cells throughout the body; neoplasias like gastrointestinal cancer, Barrett's esophagus, liver cancer, bladder cancer, pancreatic cancer, ovarian cancer, prostate cancer, cervical cancer, lung cancer, breast cancer and skin cancer; adenomatous polyps, including familial adenomatous polyposis (FAP) as well preventing polyps from forming in patients at risk of FAP.
15. Various other disease states and conditions like epilepsy, septic shock e.g. as antihypovolemic and/or antihypotensive agents, sepsis, osteoporosis, benign prostatic hyperplasia and hyperactive bladder, nephritis, pruritis, vitiligo, disturbances of visceral motility at respiratory, genitourinary, gastrointestinal or vascular regions, wounds, allergic skin reactions, mixed-vascular and non-vascular syndromes, septic shock associated with bacterial infections or with trauma, central nervous system injury, tissue damage and postoperative fever, syndromes associated with itching.

Preferred according to the present invention is the use of a compound of formula I for the treatment and/or prevention of pain; in particular pain that is associated with any one of the diseases or conditions listed above.

Another aspect of the present invention is a method for the treatment and/or prevention of above mentioned diseases and conditions, which method comprises the administration of an effective amount of a compound of formula I to a human being.

Dosage

The dose range of the compounds of formula I applicable per day is usually from 0.01 to 5000 mg, preferably from 1 to 2000 mg, more preferably from 5 to 500 mg, most preferably 10 to 250 mg. Each dosage unit may conveniently contain from 2 to 500 mg, preferably 5 to 250 mg.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

Pharmaceutical Formulations

Suitable preparations for administering the compounds of formula will be apparent to those with ordinary skill in the art and include for example tablets, pills, capsules, suppositories, lozenges, troches, solutions, syrups, elixirs, sachets, injectables, inhalatives and powders etc. The content of the pharmaceutically active compound(s) should be in the range from 1 to 99 wt.-%, preferably 10 to 90 wt.-%, more preferably 20 to 70 wt.-%, of the composition as a whole.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers. A further aspect of the invention is a pharmaceutical formulation including a compound of formula I in admixture with a pharmaceutically acceptable adjuvant, diluent or carrier.

Combination Therapy

The compounds according to the present invention can be combined with other treatment options known to be used in the art in connection with a treatment of any of the indications the treatment of which is in the focus of the present invention.

Among such treatment options that are considered suitable for combination with the treatment according to the present inventions are:

- non-steroidal antiinflammatory drugs (NSAIDs) including COX-2 inhibitors;
- opiate receptor agonists;
- Cannabionoid agonists or inhibitors of the endocannabinoid pathway
- Sodium channel blockers;
- N-type calcium channel blockers;
- serotonergic and noradrenergic modulators;
- corticosteroids;
- histamine H1 receptor antagonists;
- histamine H2 receptor antagonists;
- proton pump inhibitors;
- leukotriene antagonists and 5-lipoxygenase inhibitors;
- local anesthetics;
- VR1 agonists and antagonists;
- Nicotinic acetylcholine receptor agonists;
- P2X3 receptor antagonists;
- NGF agonists and antagonists or anti-NGF antibodies;
- NK1 and NK2 antagonists;
- Bradykinin B1 antagonists
- CCR2 antagonists
- NOS or nNOS or eNOS inhibitors
- NMDA antagonist;
- potassium channel modulators;
- GABA modulators;
- serotonergic and noradrenergic modulators;
- anti-migraine drugs;
- neuropathic pain drugs such as pregabaline or duloxetine.

Said list is not considered to have a limiting character.

In the Following Representative Examples of Such Treatment Options Shall be Given.

Non-steroidal antiinflammatory drugs (NSAIDs) including COX-2 inhibitors: propionic acid derivatives (alminoprofen, benoxaprofen, bucloxic acid, carprofen, fenhufen, fenoprofen, flubiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (meclofenamic acid, mefenamic acid, and tolfenamic acid), biphenylcarboxylic acid derivatives, oxicams (isoxicam, meloxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone), and the coxibs (celecoxib, valecoxib, rofecoxib and etoricoxib) and the like;

Antiviral drugs like acyclovir, tenovir, pleconaril, peramivir, pocosanol and the like.

Antibiotic drugs like gentamicin, streptomycin, geldanamycin, doripenem, cephalexin, cefaclor, ceftazichine, cefepime, erythromycin, vancomycin, aztreonam, amoxicillin, bacitracin, enoxacin, mafenide, doxycycline, chloramphenicol and the like;

Opiate receptor agonists: morphine, propoxyphene (Darvon), tramadol, buprenorphin and the like;

Glucocorticosteroids such as bethamethasone, budesonide, dexamethasone, hydrocortisone, methylprednisolone, prednisolone, prednisone, triamcinolone and deflazacort; immunosuppressive, immunomodulatory, or cytsostatic drugs inlcuding but not limited to hydroxychlorquine, D-penicillamine, sulfasalizine, auranofin, gold mercaptopurine, tacrolimus, sirolimus, mycophenolate mofetil, cyclosporine, leflunomide, methotrexate, azathioprine, cyclophosphamide and glatiramer acetate and novantrone, fingolimod (FTY720), minocycline and thalidomide and the like;

anti-TNF antibodies or TNF-receptor antagonists such as but not limited to Etanercept, Infliximab, Adalimumab (D2E7), CDP 571, and Ro 45-2081 (Lenercept), or biologic agents directed against targets such as but not limited to CD-4, CTLA-4, LFA-1, IL-6, ICAM-1, C5 and Natalizumab and the like;

IL-1 receptor antagonists such as but not limited to Kineret;

Sodium channel blockers: carbamazepine, mexiletine, lamotrigine, tectin, lacosamide and the like.

N-type calcium channel blockers: Ziconotide and the like.

Serotonergic and noradrenergic modulators: paroxetine, duloxetine, clonidine, amitriptyline, citalopram;

Histamine H1 receptor antagonists: bromophtniramint, chlorpheniramine, dexchlorpheniramine, triprolidine, clemastine, diphenhydramine, diphenylpyraline, tripelennamine, hydroxyzine, methdiJazine, promethazine, trimeprazine, azatadine, cyproheptadine, antazoline, pheniramine pyrilamine, astemizole, terfenadine, loratadine, cetirizine, deslo-ratadine, fexofenadine and levocetirizine and the like;

Histamine H2 receptor antagonists: cimetidine, famotidine and ranitidine and the like;

Proton pump inhibitors: omeprazole, pantoprazole and esomeprazole and the like;

Leukotriene antagonists and 5-lipoxygenase inhibitors: zafirlukast, mon-telukast, pranlukast and zileuton and the like;

Local anesthetics such as ambroxol, lidocaine and the like;

Potassium channel modulators: like retigabine;

GABA modulators: lacosamide, pregabalin, gabapentin and the like;

Anti-migraine drugs: sumatriptan, zolmitriptan, naratriptan, eletriptan, telcegepant and the like;

NGF antibodies such as RI-724 and the like.

Combination therapy is also possible with new principles for the treatment of pain e.g. P2X3 antagonists, VR1 antagonists, NK1 and NK2 antagonists, NMDA antagonists, mGluR antagonists and the like.

The combination of compounds is preferably a synergistic combination. Synergy, as described for example by Chou and Talalay, Adv. Enzyme Regul. 22:27-55 (1984), occurs when the effect of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased pharmacological effect, or some other beneficial effect of the combination compared with the individual components.

EXPERIMENTAL SECTION

Preparation of Examples for Compounds of the General Formula I

Unless otherwise stated, one or more tautomeric forms of compounds of the examples described hereinafter may be prepared in situ and/or isolated. All tautomeric forms of compounds of the examples described hereinafter should be considered to be disclosed.

The invention is illustrated by way of the following examples, in which the following abbreviations may be employed:

ABBREVIATIONS

AcOH acetic acid
ALOX B aluminium oxide
aq aqueous
Boc tert.-butoxycarbonyl
CE chromatography equipment
CH cyclohexane
conc concentrated
DCM dichloromethane
DIC N,N'-diisopropylcarbodiimide
DIPEA N-ethyldiisopropylamine
DMAP N,N-dimethylaminopyridine
DMSO dimethylsulphoxide
DMF N,N-dimethylformamide
EDC 1-(3-dimethylaminopropyl)-3-ethylcarbodiimide hydrochloride
eq. equivalent
EtOAc ethyl acetate
$Et_2O$ diethyl ether
EtOH ethanol
FA formic acid
HBTU O-(benzotriazol-1-yl)-N,N,N',N'-tetramethyluronium hexafluorophospate
HPLC high performance liquid chromatography
i-PrOH isopropanol
MeCN acetonitrile
MeOH methanol
MS mass spectrometry
MTBE methyl-tert-butyl ether
NMP N-Methylpyrrolidinon
NMR nuclear magnetic resonance
PE petrol ether
PPA 1-propylphosphonic-acid cyclic anhydride
Pd/C 10% Palladium on carbon
Pt/C Platinum on carbon
Ra—Ni Raney-Nickel
RP reversed phase
rt room temperature
$R_f$ retention factor
$R_t$ retention time
sat saturated
TBTU O-(benzotriazol-1-yl)-N,N,N',N'-tetramethyluronium tetrafluoroborate
TCDI thiocarbonyl diimidazole
TEA triethylamine
THF tetrahydrofuran
TFA trifluoroacetic acid
TLC thin layer chromatography Analytical Methods The HPLC/MS data, where specified, were obtained under the following conditions:

Chromatography Equipment (CE):
CE1:
Agilent 1100 with quarternary pump, Gilson G215 Autosampler, HP diode array detector.
The diode array detection took place in a wavelength range from 210-550 nm
Range of mass-spectrometric detection: m/z 120 to m/z 1000
CE 2:
Waters ZQ2000 MS, Alliance 2695, PDA 2996, 210-500 nm, waters 2700 AS.
Range of mass-spectrometric detection: m/z 120 to m/z 820
CE 3:
Waters ZQ2000 MS, Agilent HP 100, binary pump, waters 2700 AS.
The diode array detection took place in a wavelength range from 210-500 nm
Range of mass-spectrometric detection: m/z 120 to m/z 820
CE 4:
Agilent 1200 with binary pump, Agilent MS 6140, HiPALS1367C
The diode array detection took place in a wavelength range from 190-400 nm
Range of mass-spectrometric detection: m/z 100 to m/z 1000
CE 5:
Waters ZQ2000 MS, Agilent HP 100, binary pump, Gilson 215 AS.
The diode array detection took place in a wavelength range from 210-500 nm
Range of mass-spectrometric detection: m/z 120 to m/z 820
CE 6:
Waters SQD MS, Acquity HPLC.
The diode array detection took place in a wavelength range from 210-500 nm Range of mass-spectrometric detection: m/z 120 to m/z 820
CE 7:
Waters Alliance 2695 Separations Module.
Waters 2487 Dual X Absorbance Detector (detection at 254 nm and 280 nm).
Waters 3100 Mass Detector. Range of mass-spectrometric detection: m/z 150 to m/z 1200.
CE 8:
Waters Acquity HPLC system, Waters Acquity TUV Detector (detection at 210 nm), Waters Acquity Binary Solvent Manager and Micromas Quattro micro API Mass Spectrometer.
The following methods were used:
Method A:
CE 4 was used.
Mobile phase: E1: water with 0.15% formic acid; E2: acetonitrile
Eluent gradient:

| time in min | % E1 | % E2 | flow rate in mL/min |
|---|---|---|---|
| 0.0 | 95 | 5 | 1.6 |
| 2.25 | 10 | 90 | 1.6 |
| 2.50 | 10 | 90 | 1.6 |
| 2.75 | 90 | 10 | 1.6 |

Chromatography column: (column temperature: constant at 25° C.): XBridge C18, 2.5 μm, 3.0×30 mm
Method B:
CE 4 was used.
Mobile phase and eluent gradient: As described in method A.
Chromatography column: (column temperature: constant at 25° C.): Sunfire C18, 2.5 μm, 3.0×30 mm
Method C:
CE 2 was used.
Mobile phase: E1: water with 0.1% TFA; E2: acetonitrile with 0.08% TFA
Eluent gradient:

| time in min | % E1 | % E2 | flow rate in mL/min |
|---|---|---|---|
| 0.0 | 95 | 5 | 1.5 |
| 2.00 | 0 | 100 | 1.5 |
| 3.00 | 0 | 100 | 1.5 |
| 3.40 | 95 | 5 | 1.5 |

Chromatography column: (column temperature: constant at 40° C.): Waters sunfire C18, 3.5 μm, 4.6×50 mm
Method D:
CE 3 was used.
Mobile phase: E1: water with 0.032% NH$_3$, E2: MeOH
Eluent gradient:

| time in min | % E1 | % E2 | flow rate in mL/min |
|---|---|---|---|
| 0.0 | 95 | 5 | 1.5 |
| 2.00 | 0 | 100 | 1.5 |

Chromatography column: (column temperature: constant at 40° C.): Waters XBridge C18, 3.5 μm, 4.6×50 mm
Method E:
CE 4 was used.
Mobile phase: E1: water with 0.15% formic acid; E2: acetonitrile
Eluent gradient:

| time in min | % E1 | % E2 | flow rate in mL/min |
|---|---|---|---|
| 0.00 | 95 | 5 | 1.6 |
| 2.00 | 50 | 50 | 1.6 |
| 2.25 | 10 | 90 | 1.6 |
| 2.50 | 10 | 90 | 1.6 |
| 2.75 | 95 | 5 | 1.6 |

Chromatography column: (column temperature: constant at 25° C.): Sunfire C18, 2.5 μm, 3.0×30 mm
Method F:
CE 4 was used.
Mobile phase: E1: water with 0.15% formic acid; E2: acetonitrile
Eluent gradient:

| time in min | % E1 | % E2 | flow rate in mL/min |
|---|---|---|---|
| 0.00 | 95 | 5 | 1.6 |
| 1.00 | 10 | 90 | 1.6 |
| 2.50 | 10 | 90 | 1.6 |
| 2.75 | 95 | 5 | 1.6 |

Chromatography column: (column temperature: constant at 25° C.): Sunfire C18, 2.5 μm, 3.0×30 mm
Method G:
CE 4 was used.
Mobile phase and eluent gradient: as described in Method E.
Chromatography column: (column temperature: constant at 25° C.): Zorbax Stable Bond C18, 1.8 μm, 3.0×30 mm
Method H:
CE 4 was used.
Mobile phase and eluent gradient: As described in Method A.
Chromatography column: (column temperature: constant at 25° C.): Zorbax Stable Bond C18, 1.8 μm, 3.0×30 mm
Method I:
CE 4 was used.
Mobile phase: E1: water with 0.15% formic acid; E2: acetonitrile
Eluent gradient:

| time in min | % E1 | % E2 | flow rate in mL/min |
|---|---|---|---|
| 0.0 | 95 | 5 | 1.6 |
| 2.00 | 10 | 90 | 1.6 |
| 5.00 | 10 | 90 | 1.6 |
| 5.50 | 90 | 10 | 1.6 |

Chromatography column: (column temperature: constant at 25° C.): Zorbax Stable Bond C18, 3.5 μm, 4.6×75 mm
Method J:
CE 3 was used.
Mobile phase: E1: water with 0.1% TFA; E2: acetonitrile with 0.08% TFA
Eluent gradient:

| time in min | % E1 | % E2 | flow rate in mL/min |
|---|---|---|---|
| 0.0 | 95 | 5 | 1.5 |
| 2.00 | 0 | 100 | 1.5 |

-continued

| time in min | % E1 | % E2 | flow rate in mL/min |
|---|---|---|---|
| 2.50 | 0 | 100 | 1.5 |
| 2.60 | 95 | 5 | 1.5 |

Chromatography column: (column temperature: constant at 40° C.): Waters sunfire C18, 3.5 μm, 4.6×50 mm
Method K:
CE 3 was used.
Mobile phase: E1: water with 0.15% HCOOH, E2: MeOH
Eluent gradient and column as in method D:
Method L:
CE 5 was used.
Mobile phase: E1: water with 0.1% TFA; E2: acetonitrile with 0.1% TFA
Eluent gradient:

| time in min | % E1 | % E2 | flow rate in mL/min |
|---|---|---|---|
| 0.0 | 95 | 5 | 1.5 |
| 2.00 | 0 | 100 | 1.5 |
| 2.49 | 0 | 100 | 1.5 |
| 2.50 | 95 | 5 | 1.5 |

Chromatography column: (column temperature: constant at 40° C.): Waters sunfire C18, 3.5 μm, 4.6×50 mm
Method M:
CE 5 was used.
Mobile phase: E1: water with 0.032% NH$_3$; E2: acetonitrile
Eluent gradient:

| time in min | % E1 | % E2 | flow rate in mL/min |
|---|---|---|---|
| 0.0 | 95 | 5 | 1.3 |
| 2.00 | 0 | 100 | 1.3 |
| 2.50 | 0 | 100 | 1.3 |
| 2.60 | 95 | 5 | 1.3 |

Chromatography column: (column temperature: constant at 60° C.): Waters XBridge C18, 1.7 μm, 2.1×50 mm
Method N:
CE 7 was used.
Mobile phase: E1: water with 0.01% TFA; E2: acetonitrile with 0.01% TFA
Eluent gradient:

| time in min | % E1 | % E2 | flow rate in mL/min |
|---|---|---|---|
| 0.00 | 90 | 10 | 0.2 |
| 15.00 | 5 | 95 | 0.2 |
| 25.00 | 5 | 95 | 0.2 |
| 25.10 | 90 | 10 | 0.2 |

Chromatography column: (column temperature: constant at 30° C.): Atlantis dC18, 5 μm, 2.1×50 mm
Method O:
CE 7 was used.
E1: water with 0.01% TFA; E2: acetonitrile with 0.01% TFA
Eluent gradient:

| time in min | % E1 | % E2 | flow rate in mL/min |
|---|---|---|---|
| 0.00 | 90 | 10 | 0.2 |
| 15.00 | 5 | 95 | 0.2 |
| 20.00 | 5 | 95 | 0.2 |
| 20.10 | 90 | 10 | 0.2 |
| 25.00 | 90 | 10 | 0.2 |

Chromatography column: (column temperature: constant at 30° C.): XBridge C18, 3.5 μm, 2.1×50 mm
Method P:
CE 8 was used.
Mobile phase: E1: water with 0.1% HCOOH; E2: acetonitrile with 0.1% HCOOH
Eluent gradient:

| time in min | % E1 | % E2 | flow rate in mL/min |
|---|---|---|---|
| 0.00 | 95 | 5 | 0.2 |
| 10.00 | 2 | 98 | 0.2 |
| 15.00 | 2 | 98 | 0.2 |
| 15.50 | 95 | 5 | 0.2 |
| 20.00 | 95 | 5 | 0.2 |

Chromatography column: (column temperature: constant at 30° C.): Acquity HPLC BEH C18, 1.7 μm, 2.1×50 mm
Method O:
CE 5 was used.
Mobile phase: E1: water with 0.1% TFA; E2: MeOH
Eluent gradient:

| time in min | % E1 | % E2 | flow rate in mL/min |
|---|---|---|---|
| 0.0 | 80 | 20 | 2.0 |
| 1.70 | 0 | 100 | 2.0 |
| 2.50 | 0 | 100 | 2.0 |
| 2.60 | 80 | 20 | 2.0 |

Chromatography column: (column temperature: constant at 60° C.): Waters sunfire C18, 3.5 μm, 4.6×50 mm In the mass spectra in general only the m/z-peak of the main isotope is cited. For all compounds where mass spectra data is given, the isotope patterns are in analogy to the natural occurrence of the elements which are present in the given compound.

Example 1

2-Amino-N-{4-chloro-3-[5-chloro-1-methyl-6-(3-(trifluoromethyl)piperidin-1-yl)-1H-benzo[d]imidazol-2-ylamino]benzyl}-3,3,3-trifluoro-2-methylpropanamide

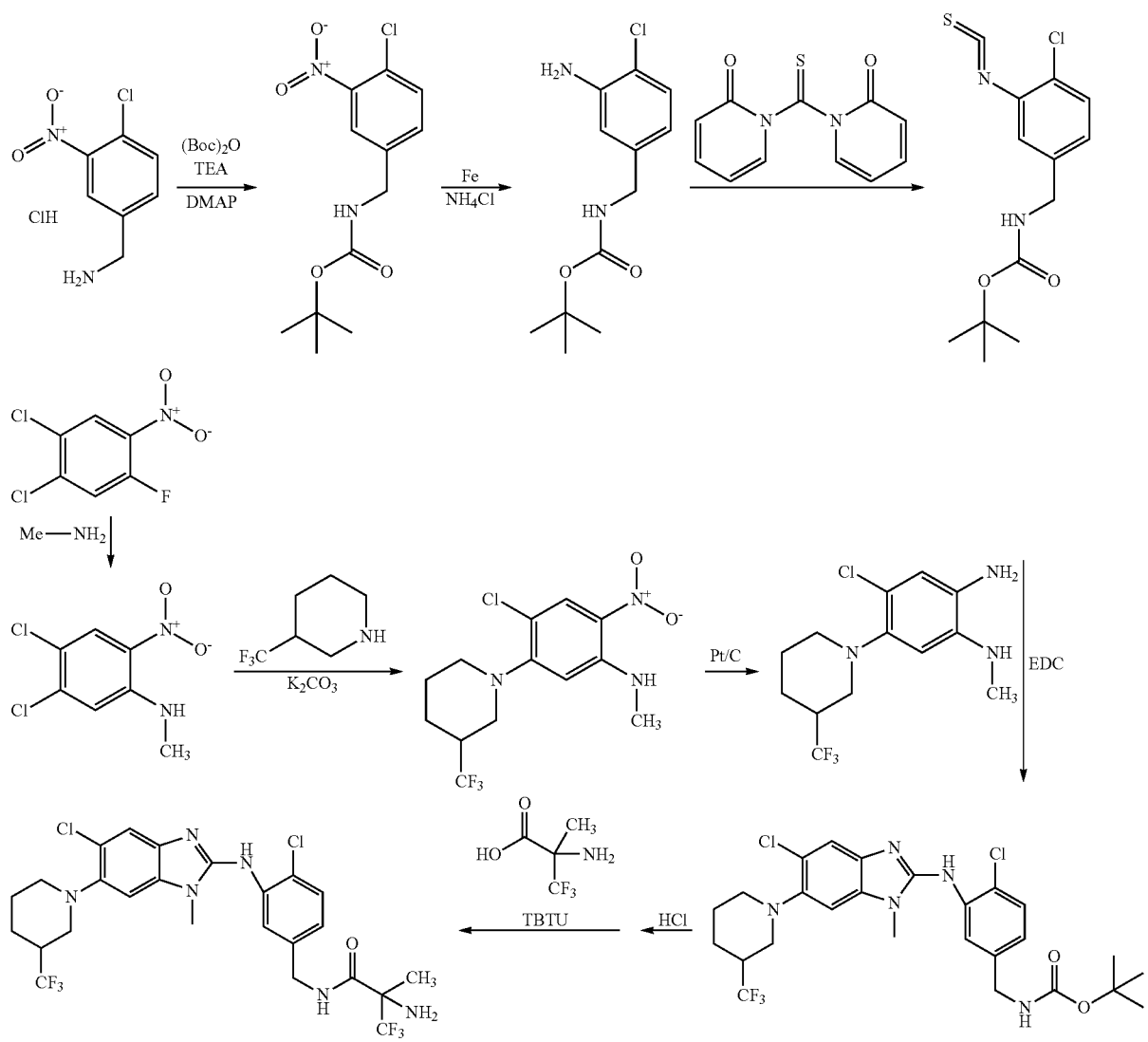

(a) Tert-butyl 4-chloro-3-nitrobenzylcarbamate

TEA (3.12 mL, 22.4 mmol) followed by DMAP (0.14 g, 1.1 mmol) were added to (4-chloro-3-nitrophenyl)methanamine hydrochloride (5.00 g, 22.4 mmol) in DCM (30 mL). The mixture was cooled to 0° C. and BOC-anhydride (5.87 g, 26.9 mmol) in DCM (15 mL) was added. After stirring at 0° C. for 30 min and further 18 h at rt the reaction mixture was poured into ammonia (10%). The mixture was extracted with DCM. The combined extracts were washed with brine, dried over $Na_2SO_4$ and concentrated to give the sub-title compound.

Yield: 5.66 g (88%). $R_f$(TLC): 0.75 (silica gel, DCM:EtOH 98:2)

(b) Tert-butyl 3-amino-4-chlorobenzylcarbamate

Sat. aq. $NH_4Cl$ (50 mL) followed by iron powder (5.51 g, 98.7 mmol) were added at rt to a mixture of tert-butyl 4-chloro-3-nitrobenzylcarbamate (5.66 g, 19.7 mmol) and EtOH (50 mL). After stirring for 4 h at 80° C., 4 h at 90° C. and at rt overnight the reaction mixture was filtered through celite and washed with EtOAc. The aq. layer was extracted with EtOAc. The combined extracts were washed with brine, dried over $Na_2SO_4$ and concentrated to give the sub-title compound.

Yield: 5.02 g (99%). $R_f$(TLC): 0.33 (silica gel, DCM:EtOH 98:2). MS m/z: 257 [M+H]$^+$.

(c) Tert-butyl 4-chloro-3-isothiocyanatobenzylcarbamate

Tert-butyl 3-amino-4-chlorobenzylcarbamate (2.57 g, 10.0 mmol) was added to a mixture of 1,1'-thiocarbonyldi-2-pyridone (2.55 g, 11.0 mmol) and DCM (90 mL) and it was stirred at rt for 4 h. The mixture was diluted with DCM and filtered over silica gel. The organic layer was concentrated to give the sub-title compound.

Yield: 2.73 g (91%). $R_f$(TLC): 0.88 (silica gel, PE:EtOAc 1:1). MS m/z: 297 [M–H]$^-$.

(d) 4,5-Dichloro-N-methyl-2-nitroaniline 1,2-Dichloro-4-fluoro-5-nitrobenzene (5.00 g, 23.8 mmol) in DMF (5.0 mL) was added to methylamine (10% in toluene, 80.0 g, 258 mmol) and stirred at rt overnight. The reaction mixture was filtered through a pad of ALOX B, washed with DMF/MeOH and concentrated to give the sub-title compound.

Yield: 5.22 g (99%). HPLC-method C: $R_t$=2.70 min. MS m/z: 221 [m]$^+$.

(e) 4-Chloro-N-methyl-2-nitro-5-(3-(trifluoromethyl)piperidin-1-yl)aniline 3-(Trifluoromethyl)piperidine (0.69 g, 4.5 mmol) followed by potassium carbonate (1.25 g, 9.1 mmol) were added to 4,5-dichloro-N-methyl-2-nitroaniline (1.00 g, 4.5 mmol) in DMF (15 mL). The reaction mixture was stirred 5 h at 80° C. and overnight at 70° C. After addition of further 1.5 eq of potassium carbonate the mixture was stirred 2 h at rt and 2 days at 100° C. The reaction mixture was filtered through a pad of ALOX B and concentrated. The crude was purified by chromatography to give the sub-title compound.

Yield: 1.01 g (66%). $R_f$(TLC): 0.36 (silica gel, CH:EtOAc 5:1). HPLC-method C: $R_t$=2.94 min.
MS m/z: 336 [M–H]$^-$.

(f) 5-Chloro-2-methylamino-4-(3-(trifluoromethyl)piperidin-1-yl)aniline

A mixture of 4-chloro-N-methyl-2-nitro-5-(3-(trifluoromethyl)piperidin-1-yl)aniline (250 mg, 0.7 mmol), THF (6 mL), MeOH (6 mL) and Pt/C (50 mg) was stirred for 4 h at 35° C. under a hydrogen atmosphere (3.2 bar). The catalyst was removed by filtration and the mixture was concentrated to give the sub-title compound.

Yield: 205 mg (90%). HPLC-method C: $R_t$=2.05 min. MS m/z: 308 [M+H]$^+$.

(g) Tert-butyl N-{4-chloro-3-[5-chloro-1-methyl-6-(3-(trifluoromethyl)piperidin-1-yl)-1H-benzo[d]imidazol-2-ylamino]benzyl}-carbamate Tert-butyl 4-chloro-3-isothiocyanatobenzylcarbamate (938 mg, 3.1 mmol) was added to 5-chloro-2-methylamino-4-(3-(trifluoromethyl)piperidin-1-yl)aniline (920 mg, 3.0 mmol) in MeCN (20 mL). The mixture was stirred for 4 h at rt, then EDC (582 µL, 3.3 mmol) was added and it was stirred overnight. The reaction mixture was purified by chromatography to give the sub-title compound.

Yield: 700 mg (41%). HPLC-method C: $R_t$=2.34 min. MS m/z: 572 [m]$^+$.

(h) 4-Chloro-3-[5-chloro-1-methyl-6-(3-(trifluoromethyl)piperidin-1-yl)-1H-benzo[d]imidazol-2-ylamino]benzylamine 4 M HCl in dioxane (20 mL) was added to tert-butyl N-{4-chloro-3-[5-chloro-1-methyl-6-(3-(trifluoromethyl)piperidin-1-yl)-1H-benzo[d]imidazol-2-ylamino]benzyl}-carbamate (700 mg, 1.2 mmol) in dioxane (20 mL). The reaction mixture was stirred at rt for 2 h then diluted with water and aq. $K_2CO_3$-solution and stirred for 1 h at rt. The mixture was concentrated, filtered and the filtercake was washed with water and dried to give the sub-title compound.

Yield: 570 mg (99%). HPLC-method C: $R_t$=1.83 min. MS m/z: 472 [M+H]$^+$.

(i) 2-Amino-N-{4-chloro-3-[5-chloro-1-methyl-6-(3-(trifluoromethyl)piperidin-1-yl)-1H-benzo[d]imidazol-2-ylamino]benzyl}-3,3,3-trifluoro-2-methylpropanamide TBTU (106 mg, 0.3 mmol) followed by TEA (126 µL, 0.9 mmol) were added to 2-amino-3,3,3-trifluoro-2-methylpropanoic acid (57 mg, 0.4 mmol) in DMF (2 mL). After 5 min at rt a mixture of 4-chloro-3-[5-chloro-1-methyl-6-(3-(trifluoromethyl)piperidin-1-yl)-1H-benzo[d]imidazol-2-ylamino]benzylamine (142 mg, 0.3 mmol) and DMF (2 mL) was added to the reaction mixture and stirred at rt overnight. The reaction mixture was purified by chromatography to give the title compound.

Yield: 104 mg (57%). HPLC-method D: $R_t$=2.77 min. MS m/z: 611 [M+H]$^+$.

Example 2

N-{4-Chloro-3-[6-chloro-5-(3,3-difluoropyrrolidin-1-yl)-1H-benzo[d]imidazol-2-ylamino]benzyl}-2,2-dimethyl-propionamide

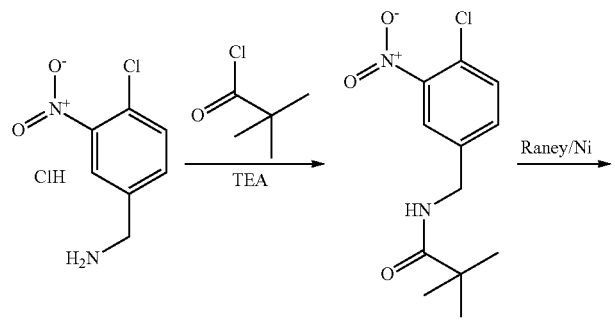
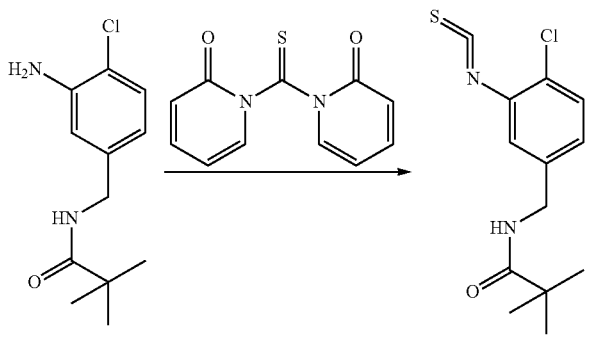

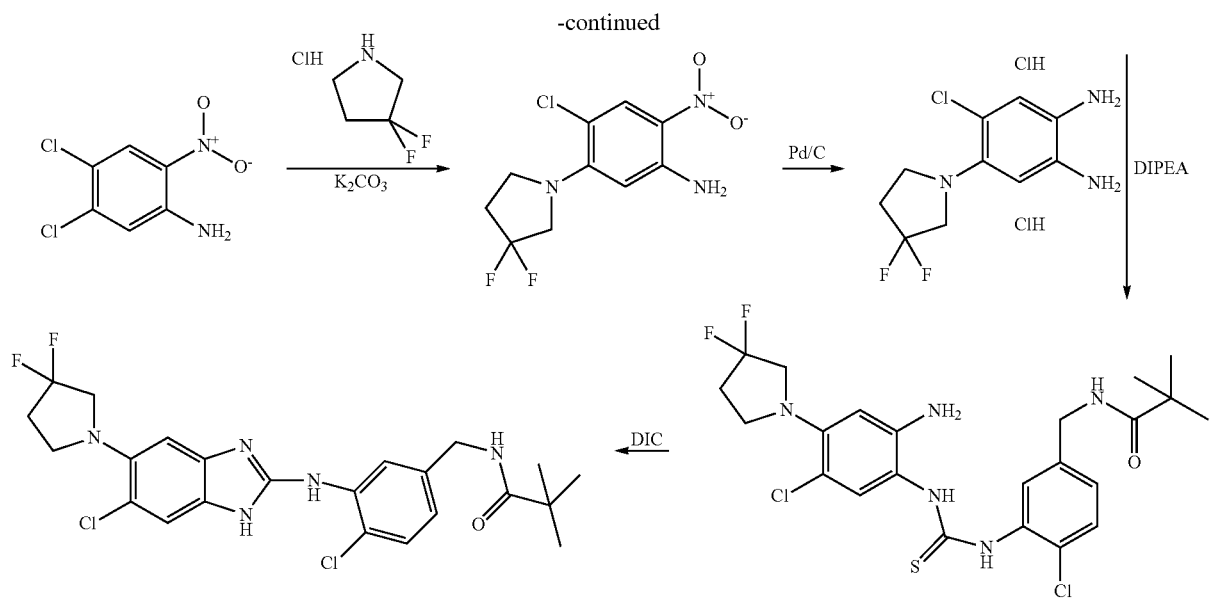

-continued

(a) N-(4-Chloro-3-nitrobenzyl)-2,2-dimethyl-propionamide

TEA (8.00 mL, 57.5 mmol) followed by pivaloyl chloride (2.80 mL, 22.8 mmol) in THF (25 mL) were added to 4-chloro-3-nitrobenzylamine hydrochloride (5.00 g, 22.4 mmol) in THF (100 mL). The reaction mixture was diluted with THF and stirred at rt for 1.5 h. The mixture was filtered and washed. The filtrate was concentrated to give the sub-title compound.

Yield: 5.92 g (98%). HPLC-method A: $R_t$=1.911 min. MS m/z: 271 [M+H]$^+$.

(b) N-(3-Amino-4-chlorobenzyl)-2,2-dimethyl-propionamide

A mixture of N-(4-chloro-3-nitrobenzyl)-2,2-dimethyl-propionamide (5.92 g, 21.9 mmol), THF (150 mL) and Ra—Ni (1.50 g) was stirred for 2 days at RT under a hydrogen atmosphere (3.0 bar). The catalyst was removed by filtration and the mixture was concentrated. The crude was purified by chromatography to give the sub-title compound.

Yield: 4.31 g (82%). $R_f$(TLC): 0.68 (silica gel, DCM:EtOH 9:1). MS m/z: 241 [M+H]$^+$.

(c) N-(4-Chloro-3-isothiocyanatobenzyl)-2,2-dimethyl-propionamide 1,1'-Thiocarbonyldi-2-pyridone (2.12 g, 9.1 mmol) was added to a mixture of N-(3-amino-4-chlorobenzyl)-2,2-dimethyl-propionamide (2.00 g, 8.3 mmol) and DCM (60 mL) and stirred at rt for 1.5 h. The mixture was filtered over silica gel. The organic layer was concentrated to give the sub-title compound.

Yield: 1.48 g (63%). $R_f$(TLC): 0.73 (silica gel, DCM:EtOH 9:1).

(d) 4-Chloro-5-(3,3-difluoropyrrolidin-1-yl)-2-nitroaniline 3,3-Difluoropyrrolidine hydrochloride (3.12 g, 21.7 mmol) followed by potassium carbonate (4.00 g, 29.0 mmol) were added to 4,5-dichloro-2-nitroaniline (3.00 g, 14.5 mmol) in DMF (60 mL). The reaction mixture was stirred at 130° C. over the weekend. After cooling the reaction mixture was poured into ice-water and extracted with EtOAc. The combined organic layers were washed with water, dried, concentrated and the crude was purified by chromatography to give the sub-title compound.

Yield: 1.73 g (31%). $R_f$(TLC): 0.33 (silica gel, PE:EtOAc 7:3). MS m/z: 278 [M+H]$^+$.

(e) 4-Chloro-5-(3,3-difluoropyrrolidin-1-yl)benzene-1,2-diamine dihydrochloride A mixture of 4-chloro-5-(3,3-difluoropyrrolidin-1-yl)-2-nitroaniline (300 mg, 1.1 mmol), THF (10 mL) and Pd/C (20 mg) was stirred for 1.5 days at RT under a hydrogen atmosphere (3.0 bar). The catalyst was removed by filtration. To the filtrate was added 4 M HCl in dioxane (10 mL). The mixture was concentrated and used in the next step without further purification.

Yield: 340 mg (98%). MS m/z: 248 [M+H]$^+$. HPLC-method A: $R_t$=1.40 min

(f) N-{4-Chloro-3-[2-amino-5-chloro-4-(3,3-difluoropyrrolidin-1-yl)phenyl)thioureido]-benzyl}-2,2-dimethyl-propionamide 4-Chloro-5-(3,3-difluoropyrrolidin-1-yl)benzene-1,2-diamine dihydrochloride (340 mg, 1.1 mmol) was added to N-(4-chloro-3-isothiocyanatobenzyl)-2,2-dimethyl-propionamide (300 mg, 1.1 mmol) in MeCN (10 mL) and stirred at rt overnight. After addition of DIPEA (0.41 µL, 2.3 mmol) the reaction mixture was stirred at rt for 4.5 h. The mixture was concentrated. The crude was purified by chromatography to give the sub-title compound.

Yield: 140 mg (25%). $R_f$(TLC): 0.47 (silica gel, DCM:EtOH 9:1).

(g) N-{4-Chloro-3-[6-chloro-5-(3,3-difluoropyrrolidin-1-yl)-1H-benzo[d]imidazol-2-ylamino]benzyl}-2,2-dimethyl-propionamide DIC (50 µL, 0.3 mmol) was added to a mixture of N-{4-chloro-3-[2-amino-5-chloro-4-(3,3-difluoropyrrolidin-1-yl)phenyl)thioureido]-benzyl}-2,2-dimethyl-propionamide (140 mg, 0.3 mmol) and MeCN (4 mL). After 1.5 h at 60° C.

the reaction mixture was allowed to cool and was concentrated. The crude was purified by chromatography to give the title compound.

Yield: 22 mg (17%). $R_f$(TLC): 0.33 (silica gel, DCM:EtOH 9:1). MS m/z: 496 [M+H]$^+$.

Example 3

N-{4-Chloro-3-[5-chloro-6-(3-dimethylaminomethyl-pyrrolidin-1-yl)-1H-benzimidazol-2-ylamino]-benzyl}-2,2-dimethyl-propionamide hydrogen atmosphere (3.0 bar). The catalyst was removed by filtration and the filtrate was concentrated. The crude was purified by chromatography to give the sub-title compound.

Yield: 480 mg (85%). $R_f$(TLC): 0.50 (silica gel, DCM:EtOH:NH$_4$OH 80:20:2). HPLC-method E: $R_t$=0.11 min. MS m/z: 269 [M+H]$^+$.

(c) N-{4-Chloro-3-[5-chloro-6-(3-dimethylaminomethyl-pyrrolidin-1-yl)-1H-benzimidazol-2-ylamino]-benzyl}-carbamic acid tert-butyl ester (4-Chloro-3-isothiocyanato-benzyl)-carbamic acid tert-butyl ester (111 mg, 0.4 mmol) was added to 4-chloro-5-(3-

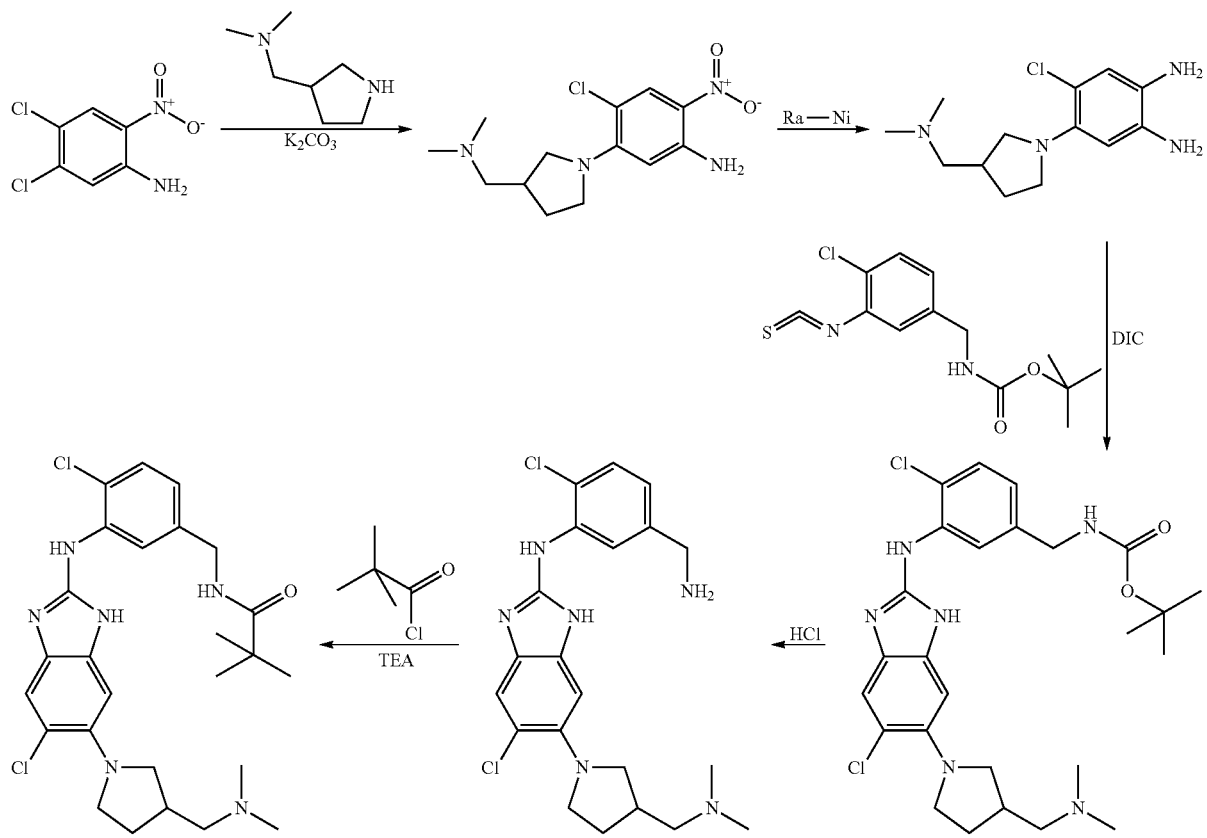

(a) 4-Chloro-5-(3-dimethylaminomethyl-pyrrolidin-1-yl)-2-nitroaniline

Potassium carbonate (500 mg, 3.6 mmol) was added to a mixture of 3-dimethylaminomethyl-pyrrolidine (450 mg, 3.5 mmol) and 4,5-dichloro-2-nitroaniline (500 mg, 2.4 mmol) in DMSO (5 mL). The reaction mixture was stirred at 120° C. overnight, diluted with EtOAc and washed with water and brine. The organic layer was dried over Na$_2$SO$_4$ and concentrated.

Yield: 630 mg (87%). $R_f$(TLC): 0.15 (silica gel, DCM:EtOH 95:5). HPLC-method B: $R_t$=1.28 min. MS m/z: 299 [M+H]$^+$.

(b) 4-Chloro-5-(3-dimethylaminomethyl-pyrrolidin-1-yl)-benzene-1,2-diamine

A mixture of 4-chloro-5-(3-dimethylaminomethyl-pyrrolidin-1-yl)-2-nitroaniline (630 mg, 2.1 mmol), EtOAc (20 mL) and Ra—Ni (150 mg) was stirred for 2 days at rt under a dimethylaminomethyl-pyrrolidin-1-yl)-benzene-1,2-diamine (100 mg, 0.4 mmol) in DMF (3 mL). The mixture was stirred at rt overnight, DIC (62.4 µL, 0.4 mmol) was added and stirring was continued at 80° C. for 3 h. The mixture was concentrated and the crude was purified by chromatography to give the sub-title compound.

Yield: 150 mg (76%). $R_f$(TLC): 0.30 (silica gel, DCM:EtOH:NH$_4$OH 90:10:1). HPLC-method F: $R_t$=1.01 min. MS m/z: 533 [M+H]$^+$.

(d) 4-Chloro-3-[5-chloro-6-(3-dimethylaminomethyl-pyrrolidin-1-yl)-1H-benzimidazol-2-ylamino]-benzylamine 6 M aq. HCl-solution (1.0 ml) was added to N-{4-chloro-3-[5-chloro-6-(3-dimethylaminomethyl-pyrrolidin-1-yl)-1H-benzimidazol-2-ylamino]-benzyl}-carbamic acid tert-butyl ester (130 mg, 0.2 mmol) in THF (2 mL) and stirred at 50° C. for 1 h. The reaction mixture was concentrated to give the sub-title compound.

Yield: 160 mg. $R_f$(TLC): 0.35 (silica gel, DCM:EtOH:NH$_4$OH 80:20:2). HPLC-method E: $R_t$=0.20 min. MS m/z: 433 [M+H]$^+$.

(e) N-{4-Chloro-3-[5-chloro-6-(3-dimethylaminomethyl-pyrrolidin-1-yl)-1H-benzimidazol-2-ylamino]-benzyl}-2,2-dimethyl-propionamide Pivaloyl chloride (10 µL, 0.1 mmol) was added to a mixture of 4-chloro-3-[5-chloro-6-(3-dimethylaminomethyl-pyrrolidin-1-yl)-1H-benzimidazol-2-ylamino]lpenzylamine (60 mg) and TEA (150 µL, 1.1 mmol) in THF (5 mL) and stirred at rt overnight. The reaction mixture was diluted with EtOAc and washed with sat.aq. NaHCO$_3$. The organic layer was dried over Na$_2$SO$_4$ and concentrated. The crude was purified by chromatography to give the title compound.

Yield: 30 mg (56%). $R_f$(TLC): 0.85 (silica gel, DCM:EtOH:NH$_4$OH 80:20:2). HPLC-method E: $R_t$=0.45 min. MS m/z: 517 [M+H]$^+$.

Example 4

N-{3-[6-(5-Aza-spiro[2.4]hept-5-yl)-5-chloro-1H-benzimidazol-2-ylamino]-4-chloro-benzyl}-2,2-dimethyl-propionamide

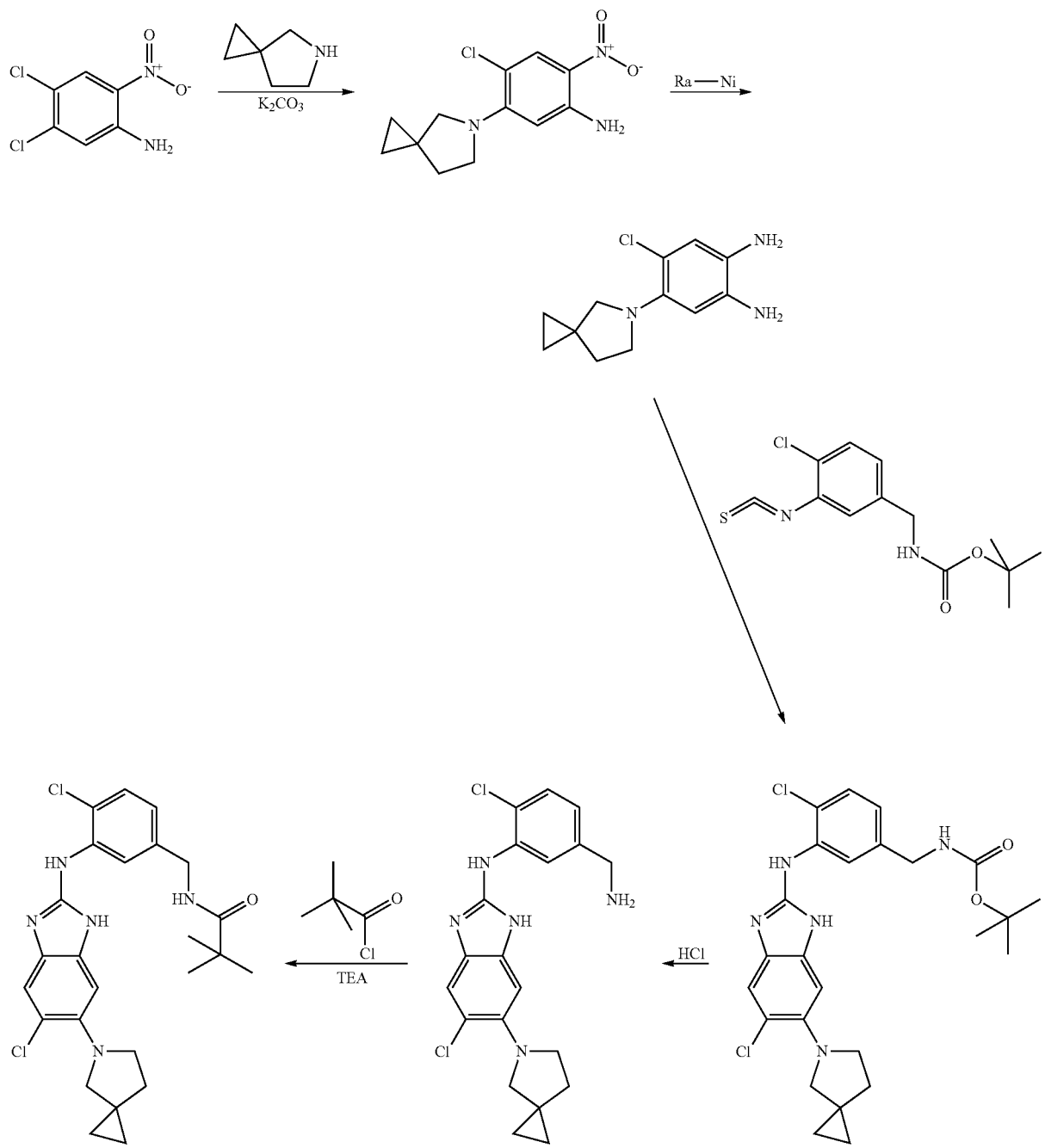

(a) 5-(5-Aza-spiro[2.4]hept-5-yl)-4-chloro-2-nitro-phenylamine

The sub-title compound was prepared from 4,5-dichloro-2-nitroaniline (470 mg, 2.3 mmol), 5-aza-spiro[2.4]heptane (320 mg, 3.3 mmol) and potassium carbonate (470 mg, 3.4 mmol) in DMSO (5 mL) in analogy to example 3, step (a). Yield: 550 mg (91%). $R_f$(TLC): 0.85 (silica gel, DCM:EtOH 99:1). HPLC-method F: $R_t$=1.01 min. MS m/z: 533 [2M+H]$^+$.

(b) 4-(5-Aza-spiro[2.4]hept-5-yl)-5-chloro-benzene-1,2-diamine

A mixture of 5-(5-aza-spiro[2.4]hept-5-yl)-4-chloro-2-nitro-phenylamine (550 mg, 2.1 mmol), EtOAc (20 mL) and Ra—Ni (150 mg) was stirred for 21 h at RT under a hydrogen atmosphere (3 bar). After addition of further catalyst the hydrogenation was continued at rt for 7 h. The catalyst was removed by filtration. The filtrate was acidified with 1.25 M HCl in EtOH (6 mL) and concentrated to give the sub-title compound.
Yield: 620 mg. $R_f$(TLC): 0.05 (silica gel, DCM:EtOH 99:1). HPLC-method F: $R_t$=0.77 min. MS m/z: 238 [M+H]$^+$.

(c) {3-[6-(5-Aza-spiro[2.4]hept-5-yl)-5-chloro-1H-benzimidazol-2-ylamino]-4-chloro-benzyl}-carbamic acid tert-butyl ester TEA (130 µL, 0.9 mmol) followed by 4-(5-aza-spiro[2.4]hept-5-yl)-5-chloro-benzene-1,2-diamine (80 mg) were added to (4-chloro-3-isothiocyanato-benzyl)-carbamic acid tert-butyl ester (example 1, step (c), 69 mg, 0.2 mmol) in DMF (3 mL). The reaction mixture was stirred at rt overnight, then concentrated and purified by chromatography to give the sub-title compound.
Yield: 60 mg (52%). $R_f$(TLC): 0.40 (silica gel, DCM:EtOH 95:5). HPLC-method F: $R_t$=1.25 min. MS m/z: 502 [M+H]$^+$.

(d) 3-[6-(5-Aza-spiro[2.4]hept-5-yl)-5-chloro-1H-benzimidazol-2-ylamino]-4-chloro-benzylamine The sub-title compound was prepared in analogy to example 3, step (d) from {3-[6-(5-aza-spiro[2.4]hept-5-yl)-5-chloro-1H-benzimidazol-2-ylamino]-4-chloro-benzyl}-carbamic acid tert-butyl ester (50 mg, 0.1 mmol) and 6 M aq. HCl (0.40 mL) in THF (2 mL).
Yield: 60 mg. $R_f$(TLC): 0.25 (silica gel, DCM:EtOH: NH$_4$OH 90:10:1).

(e) N-{3-[6-(5-Aza-spiro[2.4]hept-5-yl)-5-chloro-1H-benzimidazol-2-ylamino]-4-chloro-benzyl}-2,2-dimethyl-propionamide The sub-title compound was prepared from 3-[6-(5-aza-spiro[2.4]hept-5-yl)-5-chloro-1H-benzimidazol-2-ylamino]-4-chloro-benzylamine (60 mg, 0.1), pivaloyl chloride (20 µL, 0.1 mmol) and TEA (160 µL, 1.1 mmol) in THF (5 mL) in analogy to example 3, step (e).
Yield: 40 mg. $R_f$(TLC): 0.80 (silica gel, DCM:EtOH: NH$_4$OH 90:10:1). HPLC-method G: $R_t$=1.36 min. MS m/z: 486 [M+H]$^+$.

Example 5

N-{2,4-Dichloro-3-[5-chloro-1-methyl-6-(4-trifluoromethyl-piperidin-1-yl)-1H-benzimidazol-2-ylamino]-benzyl}-2,2-dimethyl-propionamide

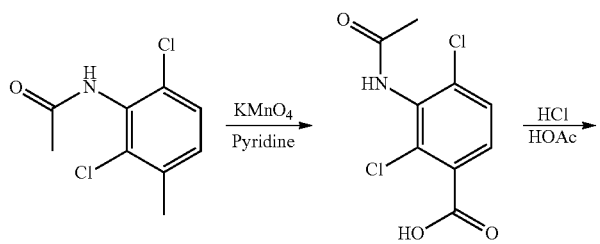

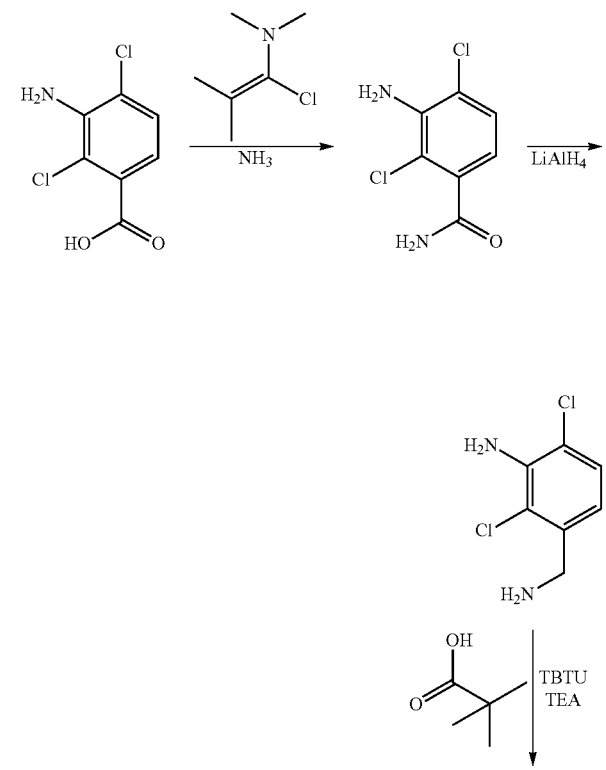

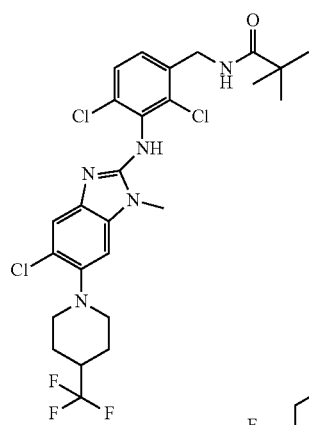
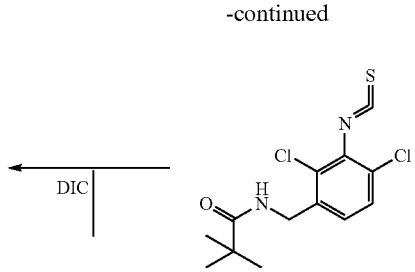
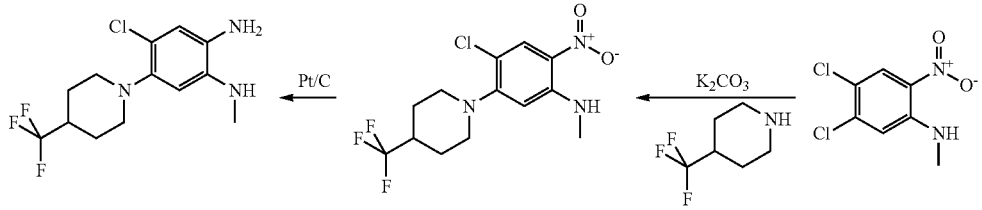

(a) 3-Acetylamino-2,4-dichloro-benzoic acid

Water (110 mL) was added to N-(2,6-dichloro-3-methyl-phenyl)-acetamide (13 g, 59 mmol) in pyridine (30 mL). The mixture was heated to 70° C. and KMnO$_4$ (47 g, 298 mmol) was cautiously added portionwise. After 6 h at reflux the reaction mixture was filtered through a pad of celite and washed with hot water. The filtrate was cooled to rt, concentrated and slowly acidified with 6 M aq. HCl solution. The mixture was cooled in an ice bath, filtered and the filtercake was washed with cold water and dried to give the sub-title compound.

Yield: 11.6 g (78%). $R_f$=0.1 (silica gel, DCM:EtOH 9:1). MS m/z: 248 [M+H]$^+$.

(b) 3-Amino-2,4-dichloro-benzoic acid

3-Acetylamino-2,4-dichloro-benzoic acid (21.0 g, 84.6 mmol) was stirred in 6 M aq. HCl-solution (120 mL) and acetic acid (250 mL) at reflux for 24 h. The reaction mixture was cooled, concentrated, diluted with water and concentrated again. The residue was diluted with water, stirred under cooling and filtered. The filtercake was washed and dried to give the sub-title compound.

Yield: 16.8 g (96%). MS m/z: 204 [M−H]$^-$. HPLC-method C: $R_t$=1.46 min.

(c) 3-Amino-2,4-dichloro-benzamide (1-Chloro-2-methyl-propenyl)-dimethyl-amine (16.1 mL, 116 mmol) was added to 3-amino-2,4-dichloro-benzoic acid (20.0 g, 97.1 mmol) in THF (320 mL). After 4 h at rt the mixture was added dropwise to conc. NH$_3$ (320 mL) and stirred at rt overnight. The reaction mixture was concentrated, cooled and filtered. The filtercake was dried to give the sub-title compound.

Yield: 17.4 g (87%). MS m/z: 205 [M+H]$^+$. HPLC-method C: $R_t$=1.19 min.

(d) 3-Amino-2,4-dichloro-benzylamine

3-Amino-2,4-dichloro-benzamide (2.00 g, 9.8 mmol) in THF (45 mL) was added dropwise to LiAlH$_4$ (1 M in THF, 24.4 mL) in THF (45 mL). The reaction mixture was stirred for 1 h at rt and 10 h at reflux. Excess LiAlH$_4$ was carefully destroyed under cooling as described by L. F. Fieser & M. Fieser Vol 1, p 584 Wiley 1967. After 30 min the mixture was filtered and the filtrate was concentrated to give the sub-title compound.

Yield: 1.85 g (99%). $R_f$=0.12 (silica gel, DCM:EtOH 95:5). MS m/z: 191 [M+H]$^+$.

(e) N-(3-Amino-2,4-dichloro-benzyl)-2,2-dimethyl-propionamide

3-Amino-2,4-dichloro-benzylamine (2.28 g, 11.9 mmol) was added to a mixture of 2,2-dimethyl-propionic acid chloride (1.47 mL, 11.9 mmol) and TEA (4.14 mL, 29.8 mmol) in THF (90 mL) and it was stirred for 3 h. The reaction mixture was concentrated, diluted with EtOAc, washed with 5% aq. NaHCO$_3$ solution and water, dried with Na$_2$SO$_4$ filtered and concentrated to give the sub-title compound.

Yield: 3.1 g (94%). $R_f$=0.61 (silica gel, DCM:EtOH 95:5).

(f) N-(2,4-Dichloro-3-isothiocyanato-benzyl)-2,2-dimethyl-propionamide 1,1'-Thiocarbonyldi-2-pyridone (4.87 g, 21 mmol) was added to a mixture of N-(3-amino-2,4-dichloro-benzyl)-2,2-dimethyl-propionamide (5.50 g, 20 mmol) and dioxane (200 mL) and stirred at rt for 2 h and at reflux for 8 h. The mixture was concentrated, diluted with DCM and filtered over silica gel. The filtrate was concentrated to give the sub-title compound.

Yield: 6.00 g (95%). HPLC-method B: $R_t$=1.58 min. MS m/z: 318 [M+H]$^+$.

(g) 4-Chloro-N-methyl-2-nitro-5-(4-trifluoromethyl-piperidin-1-yl)aniline

The sub-title compound was prepared from 4,5-dichloro-2-nitro-N-methyl-aniline (820 mg, 3.7 mmol), 4-trifluoromethyl-piperidine (680 mg, 4.5 mmol) and potassium carbonate (770 mg, 5.6 mmol) in DMSO (10 mL) in analogy to example 3, step (a).

Yield: 1.07 g (85%). $R_f$(TLC): 0.15 (silica gel, PE:EtOAc 9:1). MS m/z: 338 [M+H]$^+$.

HPLC-method G: $R_t$=1.70 min

(h) 5-Chloro-2-methylamino-4-(4-trifluoromethyl-piperidin-1-yl)aniline

A mixture of 4-chloro-N-methyl-2-nitro-5-(4-trifluoromethyl-piperidin-1-yl)aniline (1.07 g, 3.2 mmol), THF (20 mL), MeOH (30 mL) and Pt/C (100 mg) was stirred for 6 h at rt under a hydrogen atmosphere (3 bar). The catalyst was removed by filtration and the mixture was concentrated to give the sub-title compound.

Yield: 1.00 g. $R_f$(TLC): 0.25 (silica gel, DCM). HPLC-method G: $R_t$=1.30 min. MS m/z: 308 [M+H]$^+$.

(i) N-{2,4-Dichloro-3-[5-chloro-1-methyl-6-(4-trifluoromethyl-piperidin-1-yl)-1H-benzimidazol-2-ylamino]-benzyl}-2,2-dimethyl-propionamide N-(2,4-Dichloro-3-isothiocyanato-benzyl)-2,2-dimethyl-propionamide (120 mg, 0.4 mmol) was added to (4-chloro-2-methylamino-5-(4-trifluoromethyl-piperidin-1-yl)aniline (110 mg, 0.4 mmol) in DMF (2 mL). After 3 h at rt DIC (74 μL, 0.5 mmol) was added to the reaction mixture and it was stirred at 80° C. for 5.5 h. Additional DIC (40 μL, 0.3 mmol) was added and stirring was continued at 100° C. overnight. The reaction mixture was concentrated and the crude was purified by chromatography to give the title compound.

Yield: 140 mg (65%). $R_f$(TLC): 0.35 (silica gel, DCM:EtOH 95:5). MS m/z: 590 [M+H]$^+$.

HPLC-method G: $R_t$=1.44 min.

Example 6

N-{4-Chloro-3-[5-chloro-6-(2-dimethylcarbamoyl-pyrrolidin-1-yl)-1H-benzimidazol-2-ylamino]-benzyl}-2,2-dimethyl-propionamide

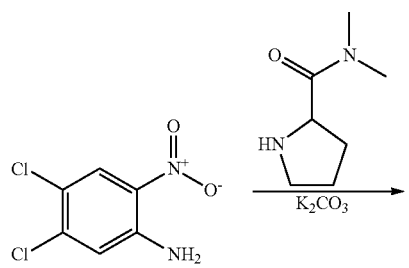

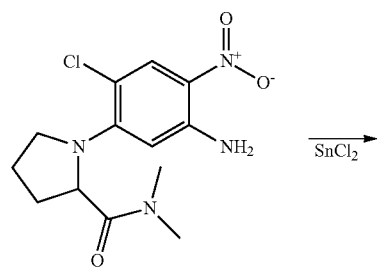

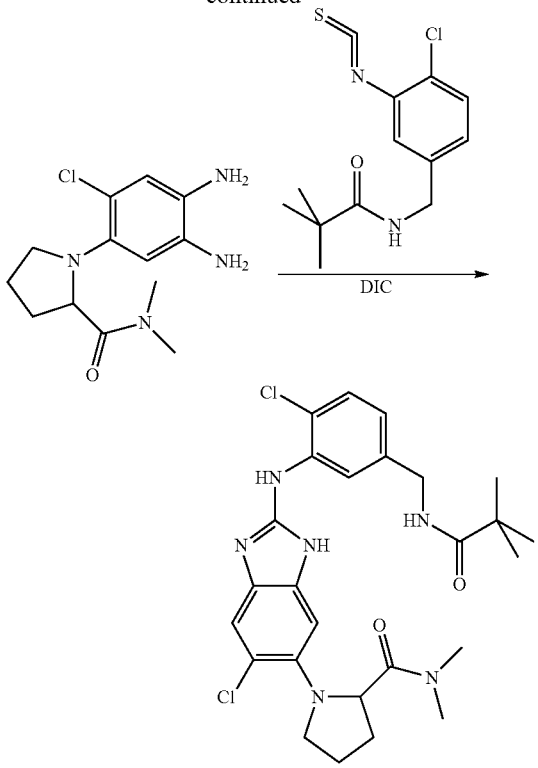

(a) 4-Chloro-5-(2-dimethylcarbamoyl-pyrrolidin-1-yl)-2-nitroaniline

Potassium carbonate (1.00 g, 7.3 mmol) was added to a mixture of pyrrolidine-2-carboxylic acid dimethylamide (1.00 g, 7.0 mmol) and 4,5-dichloro-2-nitroaniline (1.00 g, 4.8 mmol) in DMSO (6 mL). The reaction mixture was stirred at 120° C. for 2.5 h, diluted with EtOAc and washed with water and sat.aq. NaCl. The organic layer was dried over Na$_2$SO$_4$, concentrated and the crude was purified by chromatography to give the sub-title compound.

Yield: 1.18 g (78%). $R_f$(TLC): 0.15 (silica gel, DCM:EtOH 98:2). MS m/z: 313 [M+H]$^+$.

(b) 1-(4,5-Diamino-2-chloro-phenyl)-pyrrolidine-2-carboxylic acid dimethylamide Tin dichloride dihydrate (710 mg, 3.1 mmol) was added to 4-chloro-5-(2-dimethylcarbamoyl-pyrrolidin-1-yl)-2-nitroaniline (200 mg, 0.6 mmol) in EtOAc (5 mL). The reaction mixture was stirred at reflux for 3 h, cooled and poured into sat.aq. NaHCO$_3$-solution. The mixture was filtered through a pad of celite. The organic layer was dried over Na$_2$SO$_4$ and concentrated to give the sub-title compound.

Yield: 75 mg (42%). $R_f$(TLC): 0.40 (silica gel, DCM:EtOH:NH$_4$OH 90:10:1). MS m/z: 283 [M+H]$^+$. HPLC-method F: $R_t$=0.84 min.

(c) N-{4-Chloro-3-[5-chloro-6-(2-dimethylcarbamoyl-pyrrolidin-1-yl)-1H-benzimidazol-2-ylamino]-benzyl}-2,2-dimethyl-propionamide N-(4-Chloro-3-isothiocyanatobenzyl)-2,2-dimethyl-propionamide (75 mg, 0.3 mmol), which was prepared as described in example 2 step (c), was added to 1-(4,5-diamino- 2-chloro-phenyl)-pyrrolidine-2-carboxylic acid dimethylamide (75 mg, 0.3 mmol) in DMF (2 mL) and stirred at rt overnight. DIC (45 µL, 0.3 mmol) was added to the reaction mixture and stirring was continued for 5 h at 80° C. The mixture was concentrated and the crude was purified by chromatography to give the title compound.

Yield: 60 mg (43%). $R_f$(TLC): 0.20 (silica gel, DCM:EtOH 95:5). MS m/z: 531 [M+H]$^+$. HPLC-method F: $R_t$=1.09 min.

Example 7

N-{4-Chloro-3-[5-chloro-6-(2-dimethylaminomethyl-pyrrolidin-1-yl)-1H-benzimidazol-2-ylamino]-benzyl}-2,2-dimethyl-propionamide and the hydrogenation was continued for 6 h at 40° C. The catalyst was removed by filtration, the filtrate was acidified with 1.25 M HCl in EtOH and concentrated to give the sub-title compound.

Yield: 180 mg. $R_f$(TLC): 0.15 (silica gel, DCM:EtOH:NH$_4$OH 90:10:1). MS m/z: 269 [M+H]$^+$.

(c) {4-Chloro-3-[5-chloro-6-(2-dimethylaminomethyl-pyrrolidin-1-yl)-1H-benzimidazol-2-ylamino]-benzyl}-carbamic acid tert-butyl ester (4-Chloro-3-isothiocyanato-benzyl)-carbamic acid tert-butyl ester (68 mg, 0.2 mmol) followed by TEA (160 µL, 1.2 mmol) were added to 4-chloro-5-(2-dimethylaminomethyl-pyrrolidin-1-yl)-benzene-1,2-diamine (95 mg) in DMF (3

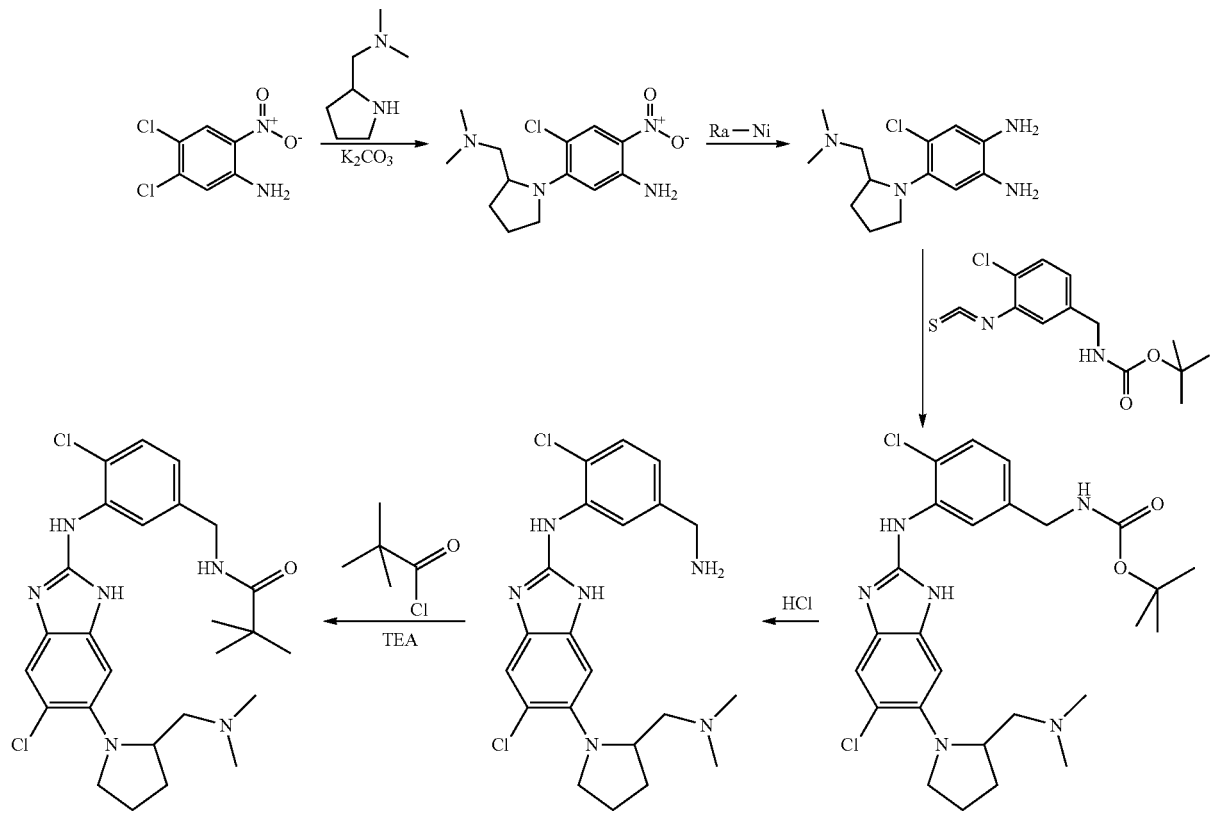

(a) 4-Chloro-5-(2-dimethylaminomethyl-pyrrolidin-1-yl)-2-nitroaniline

The sub-title compound was prepared from 2-dimethylaminomethyl-pyrrolidine (270 mg, 2.1 mmol), 4,5-dichloro-2-nitroaniline (300 mg, 1.5 mmol) and potassium carbonate (300 mg, 2.2 mmol) in DMSO (3 mL) in analogy to the method described in example 3 step (a).

Yield: 220 mg (51%). $R_f$(TLC): 0.05 (silica gel, DCM:EtOH 99:1)

(b) 4-Chloro-5-(2-dimethylaminomethyl-pyrrolidin-1-yl)-benzene-1,2-diamine

A mixture of 4-chloro-5-(2-dimethylaminomethyl-pyrrolidin-1-yl)-2-nitroaniline (150 mg, 0.5 mmol), EtOAc (10 mL) and Ra—Ni (50 mg) was stirred for 19 h at rt under a hydrogen atmosphere (3.0 bar). Further catalyst was added mL). The mixture was stirred at rt for 4 h and then purified by chromatography to give the sub-title compound.

Yield: 20 mg (16%). $R_f$(TLC): 0.30 (silica gel, DCM:EtOH:NH$_4$OH 90:10:1). HPLC-method F: $R_t$=1.01 min. MS m/z: 533 [M+H]$^+$.

(d) 4-Chloro-3-[5-chloro-6-(2-dimethylaminomethyl-pyrrolidin-1-yl)-1H-benzimidazol-2-ylamino]-benzylamine The sub-title compound was prepared from {4-chloro-3-[5-chloro-6-(2-dimethylaminomethyl-pyrrolidin-1-yl)-1H-benzimidazol-2-ylamino]-benzyl}-carbamic acid tert-butyl ester (20 mg, 0.04 mmol) and 6 M aq. HCl-solution (1.0 ml) in THF (2 mL) in analogy to example 3 step (d).

Yield: 30 mg $R_f$(TLC): 0.40 (silica gel, DCM:EtOH:NH$_4$OH 80:20:2).

(e) N-{4-Chloro-3-[5-chloro-6-(2-dimethylaminom-ethyl-pyrrolidin-1-yl)-1H-benzimidazol-2-ylamino]-benzyl}-2,2-dimethyl-propionamide The title compound was prepared analogously to example 3 step (e) from 4-chloro-3-[5-chloro-6-(2-dimethylaminom-ethyl-pyrrolidin-1-yl)-1H-benzimidazol-2-ylamino]-benzy-lamine (30 mg), pivaloyl chloride (10 µL, 0.06 mmol) and TEA (70 µL, 0.54 mmol) in THF (2 mL).

Yield: 20 mg (75%). $R_f$(TLC): 0.90 (silica gel, DCM:EtOH:NH$_4$OH 80:20:2). HPLC-method E: $R_t$=1.42 min. MS m/z: 517 [M+H]$^+$.

Example 8

N-{4-Chloro-3-[5-chloro-6-(3-cyano-pyrrolidin-1-yl)-1H-benzimidazol-2-ylamino]-benzyl}-2,2-dim-ethyl-propionamide

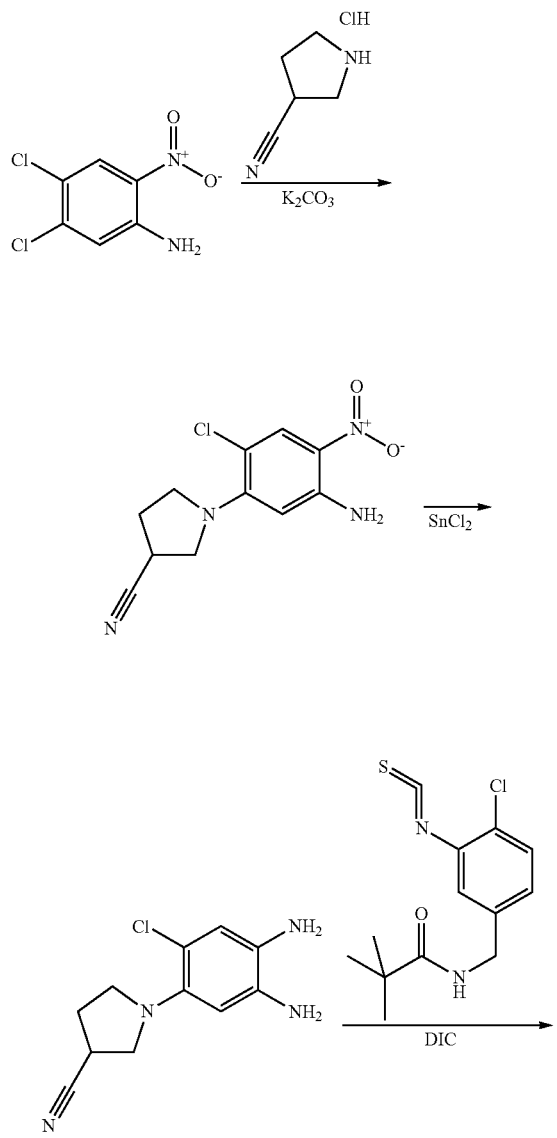

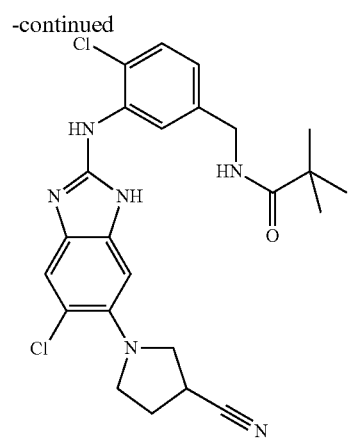

(a) 1-(5-Amino-2-chloro-4-nitro-phenyl)-pyrroli-dine-3-carbonitrile

Potassium carbonate (2.93 g, 21.3 mmol) was added to a mixture of pyrrolidine-3-carbonitrile hydrochloride (1.41 g, 10.6 mmol) and 4,5-dichloro-2-nitroaniline (2.00 g, 9.7 mmol) in DMF (8 mL). The reaction mixture was stirred at 120° C. overnight, diluted with EtOAc and washed with water and brine. The organic layer was dried over Na$_2$SO$_4$, concentrated and the crude was purified by chromatography to give the sub-title compound.

Yield: 1.18 g (78%). $R_f$(TLC): 0.25 (silica gel, DCM). MS m/z: 267 [M+H]$^+$. HPLC-method G: $R_t$=1.33 min.

(b) 1-(4,5-Diamino-2-chloro-phenyl)-pyrrolidine-3-carbonitrile

Tin dichloride dihydrate (410 mg, 1.8 mmol) was added to 1-(5-amino-2-chloro-4-nitro-phenyl)-pyrrolidine-3-carbonitrile (100 mg, 0.4 mmol) in EtOAc (5 mL). The reaction mixture was stirred at reflux for 1.5 h, cooled, diluted with EtOAc and water and basified with conc. ammonia. The mixture was filtered through a pad of celite. The organic layer was dried over Na$_2$SO$_4$ and concentrated to give the sub-title compound.

Yield: 75 mg (42%). $R_f$(TLC): 0.40 (silica gel, DCM:EtOH:NH$_4$OH 90:10:1). MS m/z: 283 [M+H]$^+$. HPLC-method F: $R_t$=0.84 min.

(c) N-{4-Chloro-3-[5-chloro-6-(3-cyano-pyrrolidin-1-yl)-1H-benzimidazol-2-ylamino]-benzyl}2,2-dim-ethyl-propionamide The title compound was prepared from N-(4-chloro-3-isothiocyanatobenzyl)-2,2-dimethyl-propionamide (66 mg, 0.2 mmol), 1-(4,5-diamino-2-chloro-phenyl)-pyrrolidine-3-carbonitrile (55 mg, 0.2 mmol) in DMF (2 mL) and DIC (39 µL, 0.2 mmol) in analogy to example 6 step (c).

Yield: 50 mg (44%). $R_f$(TLC): 0.35 (silica gel, DCM:EtOH 95:5). MS m/z: 485 [M+H]$^+$. HPLC-method G: $R_t$=1.22 min.

Example 9

(R)—N-{4-Chloro-3-[5-chloro-6-(2-hydroxymethyl-pyrrolidin-1-yl)-1H-benzimidazol-2-ylamino]-benzyl}-1-trifluoromethyl-cyclopropanecarboxamide

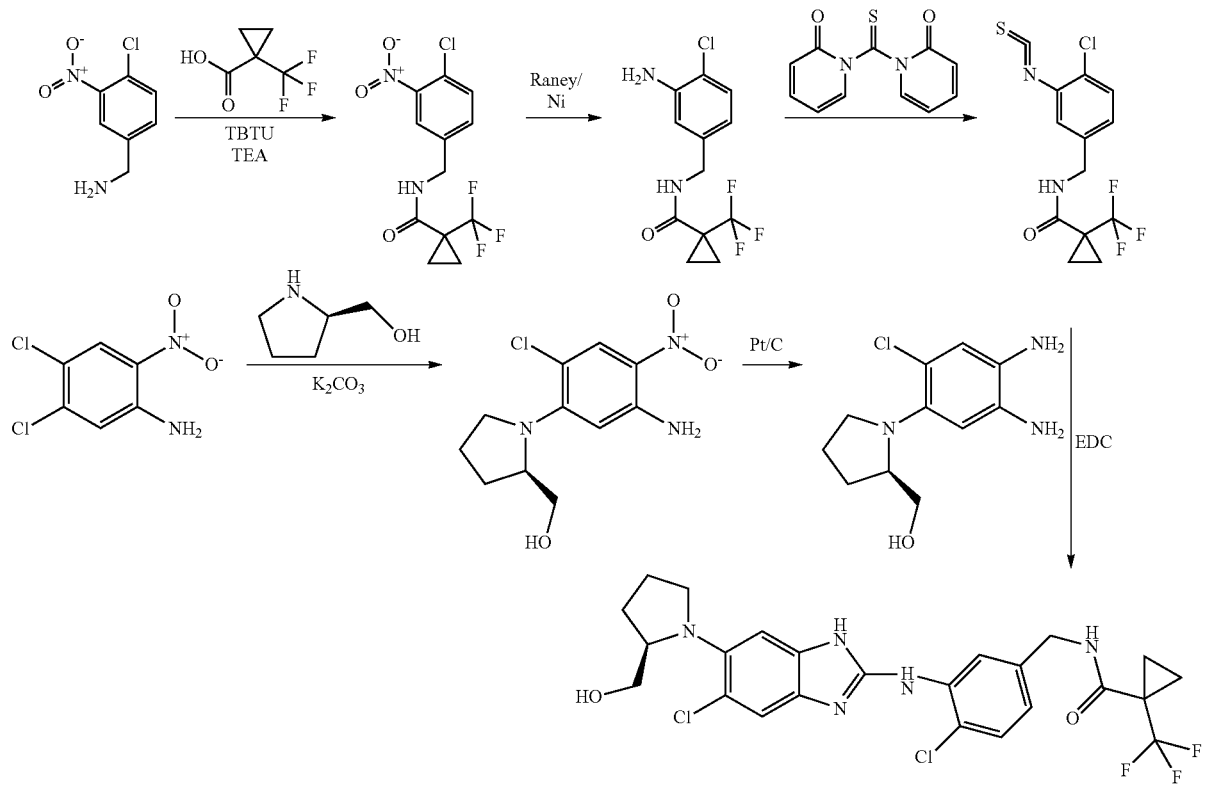

(a) N-(4-Chloro-3-nitro-benzyl)-1-trifluoromethyl-cyclopropanecarboxamide

TBTU (0.44 g, 1.4 mmol) and TEA (0.43 mL, 3.1 mmol) were added to 1-trifluoromethyl-cyclopropanecarboxylic acid (0.19 g, 1.2 mmol) in THF (5 mL). After 10 min at rt 4-chloro-3-nitro-benzylamine (0.23 g, 1.2 mmol) was added to the reaction mixture and stirring was continued overnight. The mixture was concentrated, diluted with EtOAc and washed with sat.aq. NaHCO$_3$-solution, water and brine. The organic layer was dried over Na$_2$SO$_4$ and concentrated to give the subtitle compound.

Yield: 340 mg (86%). MS m/z: 321 [M+H]$^+$. HPLC-method I: R$_t$=2.76 min.

(b) N-(4-Chloro-3-amino-benzyl)-1-trifluoromethyl-cyclopropanecarboxamide

A mixture of N-(4-chloro-3-nitro-benzyl)-1-trifluoromethyl-cyclopropanecarboxamide (340 mg, 1.1 mmol), EtOAc (10 mL) and Ra—Ni (30 mg) was stirred at rt under a hydrogen atmosphere (3 bar). The catalyst was removed by filtration and the filtrate was concentrated to give the sub-title compound.

Yield: 250 mg (81%). R$_f$(TLC): 0.50 (silica gel, DCM:EtOH 95:5). HPLC-method G: R$_t$=1.30 min. MS m/z: 293 [M+H]$^+$.

(c) N-(4-Chloro-3-isothiocyanato-benzyl)-1-trifluoromethyl-cyclopropanecarboxamide A mixture of N-(4-chloro-3-amino-benzyl)-1-trifluoromethyl-cyclopropanecarboxamide (100 mg, 0.3 mmol), N,N-diisopropylcarbodiimide (87 mg, 0.4 mmol) and DCM (5 mL) was stirred at rt overnight. The reaction mixture was filtered through a pad of silica gel and the filtrate was concentrated to give the sub-title compound.

Yield: 95 mg (83%). R$_f$(TLC): 0.75 (silica gel, CH:EtOAc 1:1). MS m/z: 335 [M+H]$^+$.

(d) (R)-1-(5-Amino-2-chloro-4-nitro-phenyl)-2-hydroxymethyl-pyrrolidine (R)-2-Hydroxymethyl-pyrrolidine (202 mg, 2.0 mmol) followed by potassium carbonate (304 mg, 2.2 mmol) were added to a mixture of 4,5-dichloro-2-nitro-phenylamine (414 mg, 2.0 mmol) in DMF (10 mL) and stirred at rt overnight. The reaction mixture was diluted with water, acidified with TFA:H$_2$O 1:1 and filtered. The filtercake was washed with DMF:H$_2$O 1:1 and dried to give the sub-title compound.

Yield: 220 mg (41%). HPLC-method J: R$_t$=1.91 min. MS m/z: 272 [M+H]$^+$.

(e) (R)-1-(4,5-Diamino-2-chloro-phenyl)-2-hydroxymethyl-pyrrolidine

The sub-title compound was prepared from (R)-1-(5-amino-2-chloro-4-nitro-phenyl)-2-hydroxymethyl-pyrrolidine (220 mg, 0.8 mmol) and Pt/C (50 mg) in MeOH (6 mL) and THF (6 mL) in analogy to example 1 step (f).

Yield: 186 mg (95%). HPLC-method C: R$_t$=1.22 min. MS m/z: 242 [M+H]$^+$.

(f) (R)—N-{4-Chloro-3-[5-chloro-6-(2-hydroxymethyl-pyrrolidin-1-yl)-1H-benzimidazol-2-ylamino]-benzyl}-1-trifluoromethyl-cyclopropanecarboxamide The title compound was prepared from N-(4-chloro-3-isothiocyanato-benzyl)-1-trifluoromethyl-cyclopropanecarboxamide (85 mg, 0.3 mmol), (R)-1-(4,5-diamino-2-chlorophenyl)-2-hydroxymethyl-pyrrolidine (62 mg, 0.3 mmol) and EDC (45 μL, 0.3 mmol) in MeCN (5 mL) in analogy with the method described in example 1 step (g).

Yield: 3 mg (2%). HPLC-method J: $R_t$=1.56 min. MS m/z: 542 [M+H]$^+$.

Example 10

N-{4-Chloro-3-[5-chloro-1-methyl-6-morpholin-4-yl)-1H-benzimidazol-2-ylamino]-benzyl}-1-trifluoromethyl-cyclopropanecarboxamide

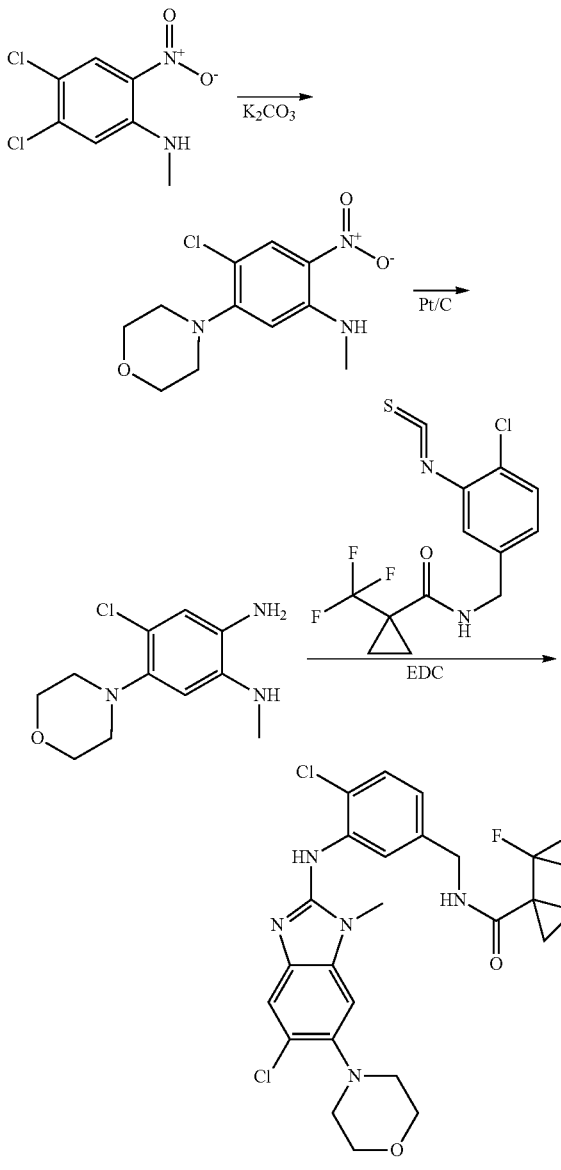

(a) (4-Chloro-5-morpholin-4-yl-2-nitro-N-methyl-aniline

Morpholine (174 mg, 2.0 mmol) followed by potassium carbonate (304 mg, 2.2 mmol) were added to a mixture of 4,5-dichloro-N-methyl-2-nitroaniline (442 mg, 2.0 mmol) in DMF (10 mL) and stirred at rt overnight. The reaction mixture was acidified with TFA:H$_2$O 1:1 and purified by chromatography to give the sub-title compound.

Yield: 260 mg (48%). HPLC-method J: $R_t$=2.18 min. MS m/z: 272 [M+H]$^+$.

(b) 5-Chloro-2-methylamino-4-morpholin-4-yl-aniline

The sub-title compound was prepared from (4-chloro-5-morpholin-4-yl-2-nitro-N-methyl-aniline (260 mg, 1.0 mmol), THF (6 mL), MeOH (6 mL) and Pt/C (50 mg) in analogy to example 1 step (f).

Yield: 219 mg (95%). HPLC-method C: $R_t$=1.57 min. MS m/z: 242 [M+H]$^+$.

(c) N-{4-Chloro-3-[5-chloro-1-methyl-6-morpholin-4-yl)-1H-benzimidazol-2-ylamino]-benzyl}-1-trifluoromethyl-cyclopropanecarboxamide The title compound was prepared from N-(4-chloro-3-isothiocyanato-benzyl)-1-trifluoromethyl-cyclopropanecarboxamide (111 mg, 0.3 mmol), 5-chloro-2-methylamino-4-morpholin-4-yl-aniline (80 mg, 0.3 mmol) and EDC (59 μL, 0.3 mmol) in MeCN (5 mL) in analogy with method described in example 1 step (g).

Yield: 53 mg (30%). HPLC-method J: $R_t$=1.68 min. MS m/z: 542 [M+H]$^+$.

Example 11

N-{4-Chloro-3-[5-chloro-1-methyl-6-(4-methyl-piperazin-1-yl)-1H-benzimidazol-2-ylamino]-benzyl}-1-trifluoromethyl-cyclopropanecarboxamide

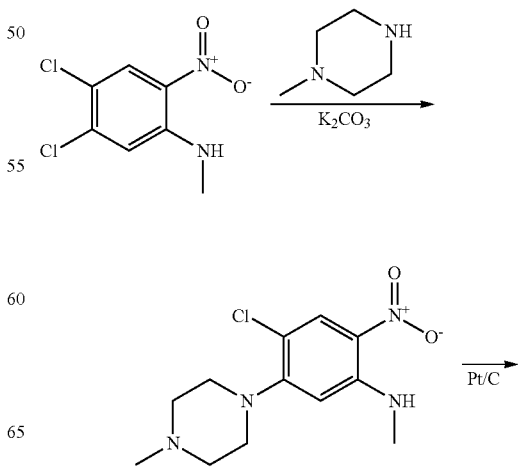

-continued

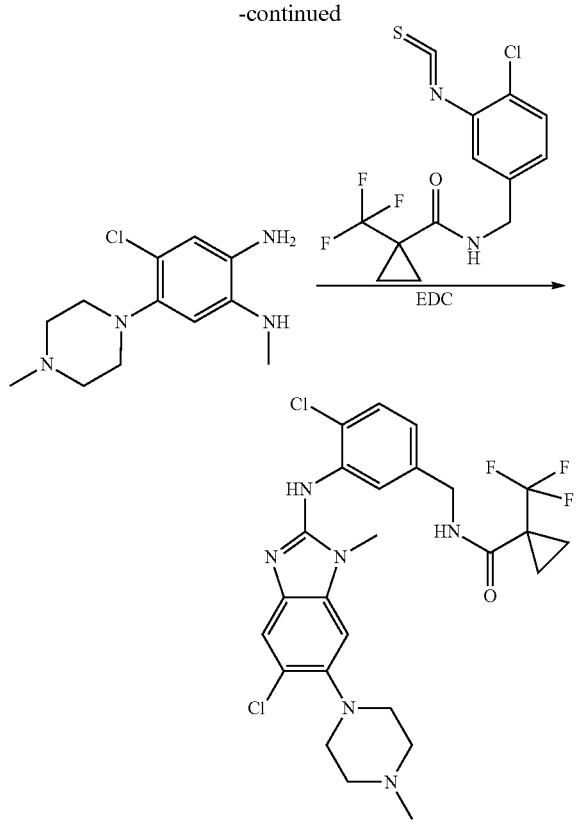

(a) 4-Chloro-5-(4-methyl-piperazin-1-yl)-2-nitro-N-methyl-aniline

The sub-title compound was prepared from N-methylpiperazine (200 mg, 2.0 mmol), 4,5-dichloro-N-methyl-2-nitroaniline (442 mg, 2.0 mmol) and potassium carbonate (304 mg, 2.2 mmol) in DMF (10 mL) in accordance to example 9 step (d).

Yield: 500 mg (88%). HPLC-method J: $R_t$=1.37 min. MS m/z: 285 [M+H]$^+$.

(b) 5-Chloro-2-methylamino-4-(4-methyl-piperazin-1-yl)-aniline

The sub-title compound was prepared from 4-chloro-5-(4-methyl-piperazin-1-yl)-2-nitro-N-methyl-aniline (500 mg, 1.8 mmol), THF (6 mL), MeOH (6 mL) and Pt/C (50 mg) in analogy to example 1 step (f).

Yield: 403 mg (90%). HPLC-method C: $R_t$=1.22 min. MS m/z: 255 [M+H]$^+$.

(c) N-{4-Chloro-3-[5-chloro-1-methyl-6-(4-methyl-piperazin-1-yl)-1H-benzimidazol-2-ylamino]-benzyl}-1-trifluoromethyl-cyclopropanecarboxamide The title compound was prepared from N-(4-chloro-3-isothiocyanato-benzyl)-1-trifluoromethyl-cyclopropanecarboxamide (176 mg, 0.5 mmol), 5-chloro-2-methylamino-4-(4-methyl-piperazin-1-yl)-aniline (134 mg, 0.5 mmol) and EDC (93 μL, 0.5 mmol) in MeCN (5 mL) in analogy to example 1 step (g).

Yield: 84 mg. HPLC-method J: $R_t$=1.40 min. MS m/z: 555 [M+H]$^+$.

Example 12

N-{4-Chloro-3-[3-methyl-6-(4-trifluoromethyl-piperidin-1-yl)-1H-benzimidazol-2-ylamino]-benzyl}-2,2-dimethyl-propionamide

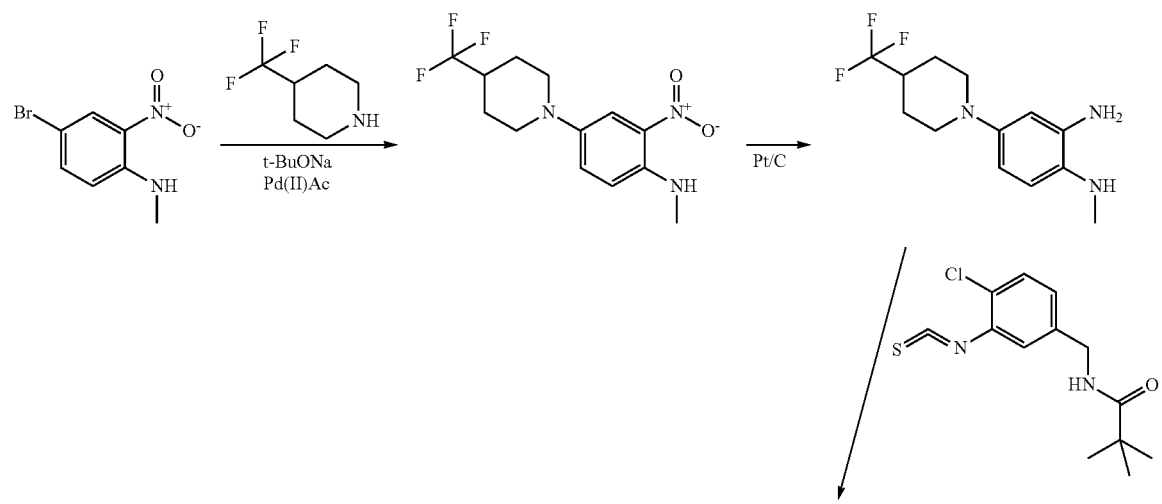

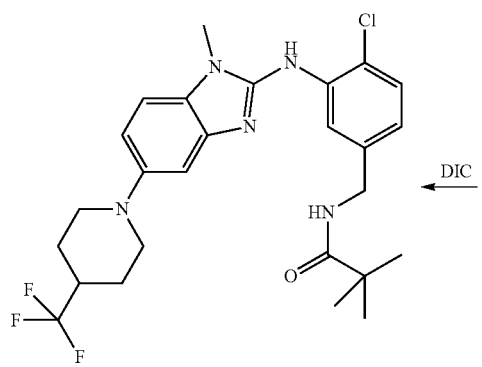 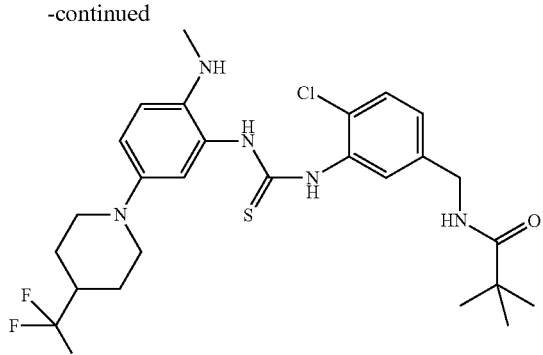

(a) N-Methyl-2-nitro-4-(4-trifluoromethyl-piperidin-1-yl)-aniline

Under argon sodium tert-butoxide (366 mg, 3.8 mmol) followed by palladium(II) acetate (22 mg, 0.1 mmol) and tri-tert-butylphosphine 10% in toluene (450 µL, 0.2 mmol) were added to a mixture of 4-bromo-2-nitro-N-methyl-aniline (440 mg, 1.9 mmol) and 4-(trifluoromethyl)piperidine (660 mg, 2.9 mmol) in toluene (7 mL). The reaction mixture was stirred at 100° C. overnight then allowed to cool and was concentrated. The crude was purified by chromatography to give the sub-title compound.

Yield: 220 mg (38%). $R_f$(TLC): 0.56 (silica gel, DCM:EtOH 98:2). MS m/z: 304 [M+H]$^+$.

(b) 2-Methylamino-5-(4-trifluoromethyl-piperidin-1-yl)aniline

A mixture of N-methyl-2-nitro-4-(4-trifluoromethyl-piperidin-1-yl)-aniline (220 mg, 0.7 mmol), MeOH (7 mL) and Pd/C (30 mg) was stirred for 18 h at rt under a hydrogen atmosphere (3.0 bar). The catalyst was removed by filtration, the filtrate was concentrated and directly used in the next step.

(c) N-(4-Chloro-3-{3-[2-methylamino-5-(4-trifluoromethyl-piperidin-1-yl)-phenyl]-thioureido}-benzyl)-2,2-dimethyl-propionamide A mixture of 2-methylamino-5-(4-trifluoromethyl-piperidin-1-yl)aniline (90 mg, 0.3 mmol) and N-(4-chloro-3-isothiocyanatobenzyl)-2,2-dimethyl-propionamide (93 mg, 0.3 mmol) in THF (10 mL) was stirred at rt for 4 h. The reaction mixture was concentrated and directly used in the next step. Yield: 180 mg (98%). HPLC-method A: $R_t$=2.23 min. MS m/z: 556 [M+H]$^+$.

(d) N-{4-Chloro-3-[3-methyl-6-(4-trifluoromethyl-piperidin-1-yl)-1H-benzimidazol-2-ylamino]-benzyl}-2,2-dimethyl-propionamide DIC (130 µL, 0.8 mmol) was added to N-(4-chloro-3-{3-[2-methylamino-5-(4-trifluoromethyl-piperidin-1-yl)-phenyl]-thioureido}-benzyl)-2,2-dimethyl-propionamide (180 mg, 0.3 mmol) in MeCN. The reaction mixture was heated at 60° C.-80° C. for one week (additional DIC (2.5 ml) was added). The mixture was cooled to rt and concentrated. The residue was treated with MeCN, filtered and washed. The filtercake was diluted with dioxane and HCOOH and lyophilized to give the title compound.

Yield: 33 mg (20%). $R_f$(TLC): 0.65 (silica gel, DCM:EtOH 9:1). MS m/z: 522 [M+H]$^+$.

Example 23

N-{2,4-Dichloro-3-[5-chloro-1-methyl-6-(3-trifluoromethyl-piperidin-1-yl)-1H-benzimidazol-2-ylamino]-benzyl}-1-trifluoromethyl-cyclobutaneamide

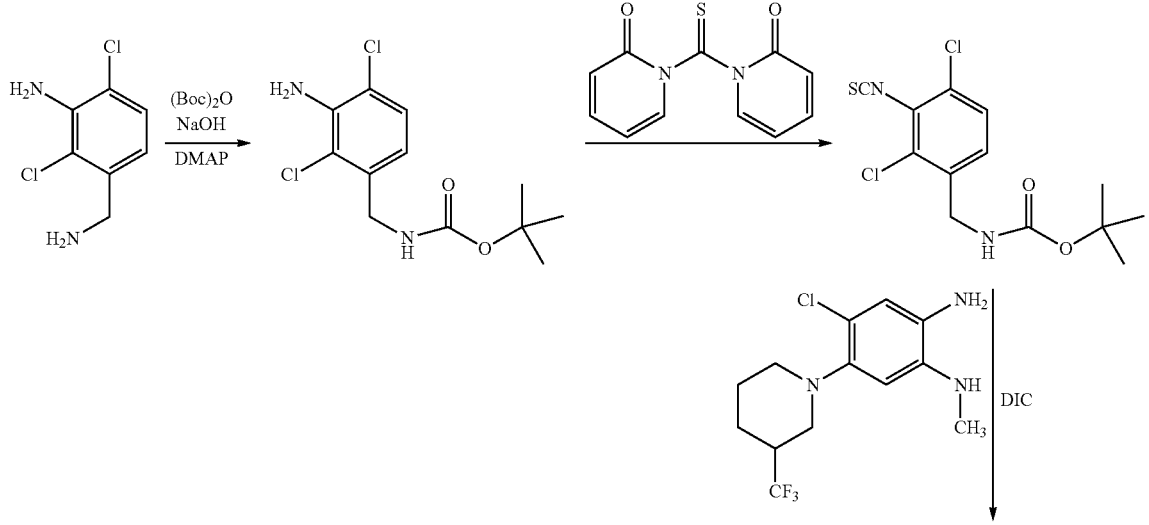

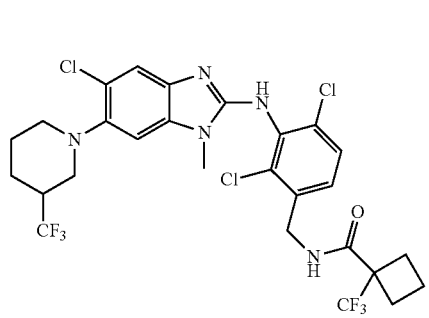 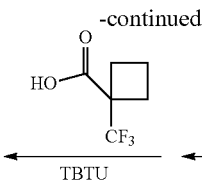 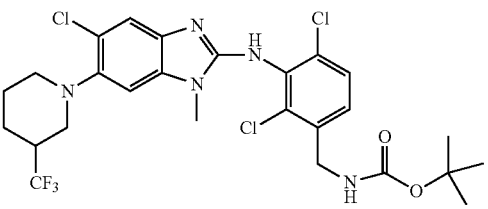

(a) (3-Amino-2,4-dichloro-benzyl)-carbamic acid tert-butyl ester

Boc₂O (1.48 g, 6.68 mmol) in 3.3 mL DCM was added at 0° C. to a mixture of 3-amino-2,4-dichloro-benzylamine (1.16 g, 6.07 mmol), 6.7 mL DCM and 12.1 mL 1 N NaOH-solution. The mixture was stirred vigourously for 2d and diluted with 5% aq NH₃-solution. The organic phase was separated and the aq. phase was washed 2× with DCM. The combined organic phase was washed with brine, dried with Na₂SO₄, filtered and concentrated to give the sub-title compound.

Yield: 1.71 g (97%). $R_f$=0.65 (silica gel, DCM:EtOH 95:5). MS m/z: 291 [M+H]⁺.

b) (2,4-Dichloro-3-isothiocyanato-benzyl)-carbamic acid tert-butyl ester 1,1'-Thiocarbonyldi-2-pyridone (0.42 g, 1.8 mmol) was added to a mixture of (3-amino-2,4-dichloro-benzyl)-carbamic acid tert-butyl ester (0.50 g, 1.7 mmol) and dioxane (25 mL) and stirred at rt for 2 h and at reflux for 2 d. The mixture was concentrated, diluted with DCM and filtered over silica gel. The filtrate was concentrated to give the sub-title compound.

Yield: 0.49 g (86%). $R_f$=0.83 (silica gel, DCM:EtOH 95:5).

(c) N-{2,4-Dichloro-3-[5-chloro-1-methyl-6-(3-(trifluoromethyl)piperidin-1-yl)-1H-benzimidazol-2-ylamino]benzyl}-carbamic acid tert-butyl ester The title compound was prepared from (2,4-dichloro-3-isothiocyanato-benzyl)-carbamic acid tert-butyl ester (5.47 g, 16.4 mmol), 5-chloro-2-methylamino-4-(3-(trifluoromethyl) piperidin-1-yl)aniline (5.05 g, 16.4 mmol) and DIC 4.48 ml, 29 mmol) in MeCN in analogy to example 6 step (c).

HPLC-method A: $R_t$=2.37 min. MS m/z: 606 [M+H]⁺.

(d) 2,4-Dichloro-3-[5-chloro-1-methyl-6-(3-(trifluoromethyl)piperidin-1-yl)-1H-benzimidazol-2-ylamino]benzylamine 4 M HCl in dioxane (38 mL) was added to N-{2,4-dichloro-3-[5-chloro-1-methyl-6-(3-(trifluoromethyl)piperidin-1-yl)-1H-benzimidazol-2-ylamino]benzyl}-carbamic acid tert-butyl ester (5.4 g, 8.9 mmol) in dioxane (300 mL) and stirred at rt overnight. The reaction mixture was concentrated and the resulting residue was diluted with aq. NaHCO₃-solution. The aq. phase was extracted with EtOAc, the organic phase was dried with Na₂SO₄ and concentrated.

Yield: 3.65 g (81%). HPLC-method A: $R_t$=1.33 min. MS m/z: 506 [M+H]⁺.

(e) N-{2,4-Dichloro-3-[5-chloro-1-methyl-6-(3-trifluoromethyl-piperidin-1-yl)-1H-benzimidazol-2-ylamino]-benzyl}-1-trifluoromethyl-cyclobutanecarboxamide The title compound was prepared from TBTU (35 mg, 0.11 mmol), TEA (50 μL, 0.36 mmol), 1-trifluormethyl-cyclobutanecarboxylic acid (57 mg, 0.4 mmol) and 2,4-dichloro-3-[5-chloro-1-methyl-6-(3-(trifluoromethyl)piperidin-1-yl)-1H-benzimidazol-2-ylamino]benzylamine (45.3 mg, 0.1 mmol) in DMF (3 mL) analogy to example 1 step (i).

Yield: 36 mg (55%). HPLC-method Q: $R_t$=1.73 min. MS m/z: 656 [M+H]⁺.

Example 30

N-{4-Chloro-3-[5-(pyrrolidin-1-yl)-1H-benzimidazol-2-ylamino]-benzyl}cyclopropylsulfonamide

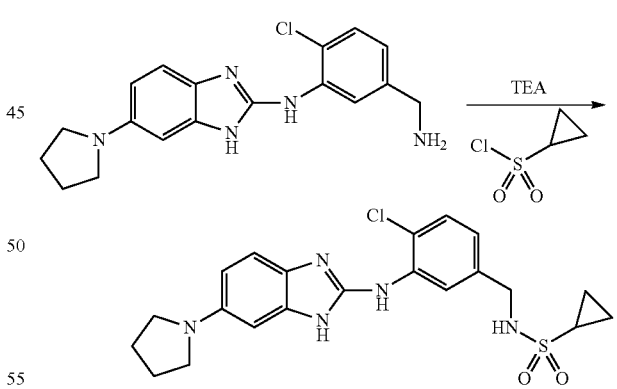

A TEA solution (0.35 M in DMF, 0.1 mL) was added to a 4-Chloro-3-[5-(pyrrolidin-1-yl)-1H-benzimidazol-2-ylamino]-benzylamine solution (0.12 M in MeCN, 0.1 mL, prepared in analogy to example 4d) followed by a cyclopropylsulfonyl chloride solution (0.12 M in MeCN, 0.1 mL). The mixture was stirred overnight and filtered through basic alumina. The solids were washed with DMF/MeOH 9:1 and the combined filtrates were concentrated to give the title compound.

MS m/z: 446 [M+H]⁺. HPLC-method L: $R_t$=1.46 min.

Example 33

N-{2-Fluoro-4-chloro-3-[5-chloro-1-methyl-6-(4-fluoro-piperidin-1-yl)-1H-benzimidazol-2-ylamino]-benzyl}-2,2-dimethyl-propionamide

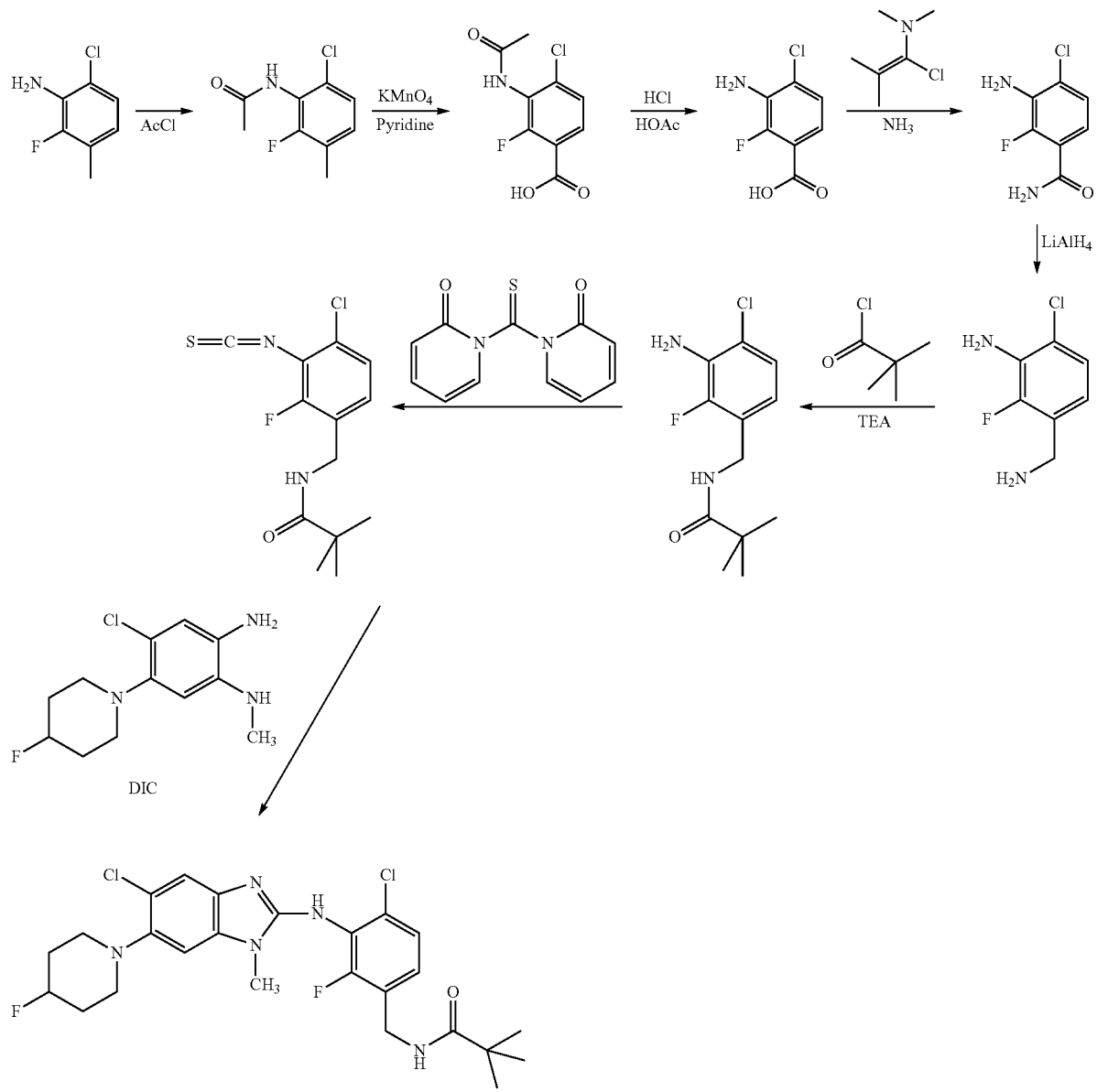

(a) N-(6-Chloro-2-fluoro-3-methyl-phenyl)-acetamide

Acetylchloride (2.56 mL, 36.0 mmol) was added to a mixture of 6-chloro-2-fluoro-3-methyl-aniline (5.00 g, 31.3 mmol) and toluene (200 mL), additional toluene (50 mL) was added and the mixture was heated to reflux for 3 h. The reaction mixture was cooled with an ice bath and the formed precipitate was filtered off, washed with cold toluene and dried.

Yield: 4.75 g (75%). HPLC-method B: $R_t$=1.12 min. MS m/z: 202 [M+H]$^+$.

(b) 3-Acetylamino-4-chloro-2-fluoro-benzoic acid

The sub-title compound was prepared from N-(6-chloro-2-fluoro-3-methyl-phenyl)-acetamide and KMnO$_4$ in pyridine in analogy to step 5a.

Yield: 49%. $R_f$=0.2 (silica gel, DCM/EtOH 4:1). HPLC $R_t$=0.93 min (method B). MS m/z: 232 [M+H]$^+$.

(c) 3-Amino-4-chloro-2-fluoro-benzoic acid

The sub-title compound was prepared from 3-acetylamino-4-chloro-2-fluoro-benzoic acid and 6 M HCl-solution in analogy to step 5b.

Yield: 96%. HPLC $R_t$=1.10 min (method B). MS m/z: 190 [m+Fi]+

(d) 3-Amino-4-chloro-2-fluoro-benzamide

The sub-title compound was prepared from 3-amino-4-chloro-2-fluoro-benzoic acid, (1-chloro-2-methyl-propenyl)-dimethyl-amine and conc. NH$_3$ in analogy to step 5c.

Yield: 69%. R$_f$=0.3 (silica gel, PE:EtOAc 4:6). HPLC-method B: R$_t$=0.97 min. MS m/z: 189 [M+H]$^+$.

(e) 3-Amino-4-chloro-2-fluoro-benzylamine

The crude sub-title compound was prepared from 3-amino-4-chloro-2-fluoro-benzamide and LiAlH$_4$ in analogy to step 5d.

HPLC-method B: R$_t$=0.37 min. MS m/z: 175 [M+H]$^+$.

(f) N-(3-Amino-4-chloro-2-fluoro-benzyl)-2,2-dimethyl-propionamide

The sub-title compound is prepared from crude 3-amino-4-chloro-2-fluoro-benzylamine, 2,2-dimethyl-propionic acid chloride and TEA in analogy to example 5e.

Yield: 36% (side product in 29%: N-(3-Amino-4-chloro-benzyl)-2,2-dimethyl-propionamide).

R$_f$=0.6 (silica gel, PE:EtOAc 6:4). HPLC-method B: R$_t$=1.27 min. MS m/z: 259 [M+H]$^+$.

(g) N-(4-Chloro-2-fluoro-3-isothiocyanato-benzyl)-2,2-dimethyl-propionamide

The title compound is prepared from N-(3-amino-4-chloro-2-fluoro-benzyl)-2,2-dimethyl-propionamide, 1,1'-thiocarbonyldi-2-pyridone in analogy to step 5f.

(h) N-{2-Fluoro-4-chloro-3-[5-chloro-1-methyl-6-(4-fluoro-piperidin-1-yl)-1H-benzimidazol-2-ylamino]-benzyl}-2,2-dimethyl-propionamide The title compound is prepared from N-(4-chloro-2-fluoro-3-isothiocyanato-benzyl)-2,2-dimethyl-propionamide and 5-chloro-2-methylamino-4-(4-fluoropiperidin-1-yl)-aniline and DIC in analogy to example 5l.

Yield: 49%. R$_f$=0.5 (silica gel, PE:EtOAc 1:1). HPLC-method G: R$_t$=1.40 min. MS m/z: 524 [M+H]$^+$.

Example 40

N-{2,4-Dichloro-3-[5-chloro-6-(4-trifluoromethyl-piperidin-1-yl)-1H-benzimidazol-2-ylamino]-benzyl}-2,2-dimethyl-propionamide

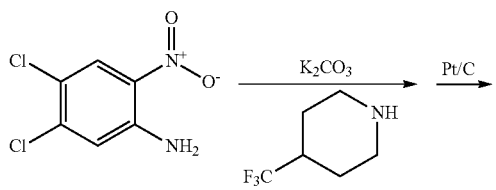

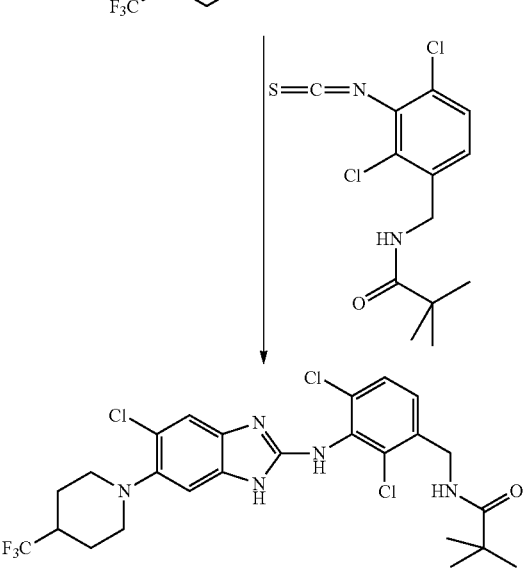

(a) 4-Chloro-2-nitro-5-(4-trifluoromethyl-piperidin-1-yl)aniline

The sub-title compound was prepared from 4,5-dichloro-2-nitro-aniline (500 mg, 2.4 mmol), 4-trifluoromethyl-piperidine hydrochloride (550 mg, 2.9 mmol) and K$_2$CO$_3$ (830 mg, 6.0 mmol) in DMSO (10 mL) in analogy to example 3, step (a).

MS m/z: 324 [M+H]$^+$. HPLC-method G: R$_t$=1.59 min

(b) 4-Chloro-2-amino-5-(4-trifluoromethyl-piperidin-1-yl)aniline

A mixture of 4-chloro-2-nitro-5-(4-trifluoromethyl-piperidin-1-yl)aniline (0.63 g, 1.9 mmol), THF (10 mL), MeOH (20 mL) and 50%-Pt-on-carbon (60 mg) was stirred for 22 h at rt under a hydrogen atmosphere (3 bar). The catalyst was removed by filtration and the mixture was concentrated to give the sub-title compound.

HPLC-method G: R$_t$=1.22 min. MS m/z: 294 [M+H]$^+$.

(c) N-{2,4-Dichloro-3-[5-chloro-6-(4-trifluoromethyl-piperidin-1-yl)-1H-benzimidazol-2-ylamino]-benzyl}-2,2-dimethyl-propionamide The title compound was prepared from N-(2,4-dichloro-3-isothiocyanato-benzyl)-2,2-dimethyl-propionamide (108 mg, 0.34 mmol), 4-chloro-2-amino-5-(4-trifluoromethyl-piperidin-1-yl)aniline (100 mg, 0.34 mmol), DIC (56 μL) in DMF (2 mL) in analogy to example 5, step (i). R$_f$(TLC): 0.35 (silica gel, DCM:EtOH 95:5). MS m/z: 576 [M+H]$^+$. HPLC-method G: R$_t$=1.48 min.

Example 61

N-{2,4-Dichloro-3-[5-trifluoromethyl-6-(4-trifluoromethyl-piperidin-1-yl)-1H-benzimidazol-2-ylamino]benzyl}-2,2-dimethyl-propionamide

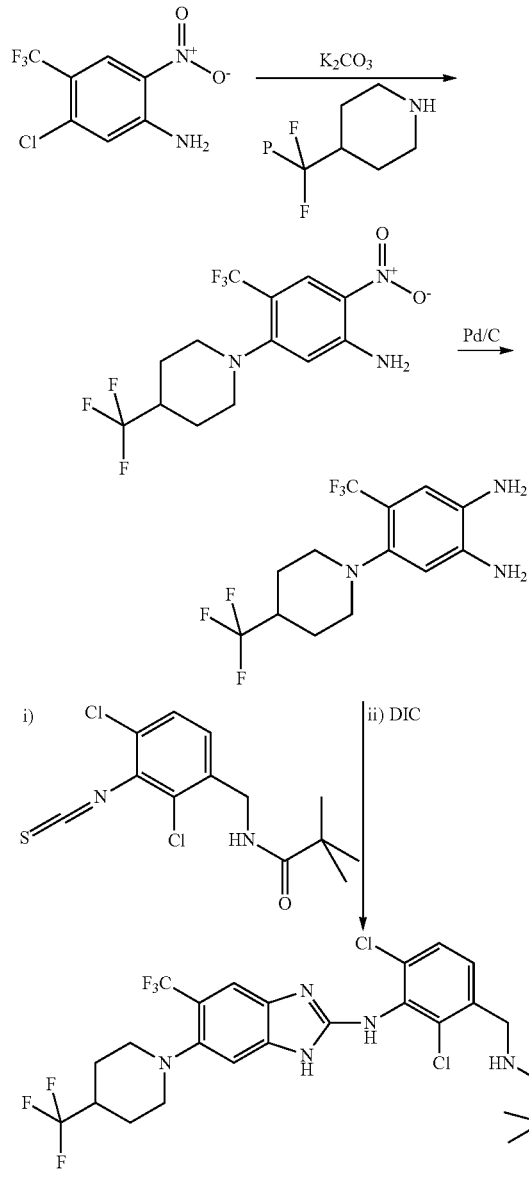

(a) 4-Trifluoromethyl-2-nitro-5-(4-trifluoromethyl-piperidin-1-yl)aniline

The sub-title compound was prepared from 4-trifluoromethyl-5-chloro-2-nitro-aniline (100 mg, 0.42 mmol), 4-trifluoromethyl-piperidine hydrochloride (394 mg, 2.1 mmol) and $K_2CO_3$ (600 mg, 4.4 mmol) in NMP (2 mL) in analogy to example 3, step (a).

MS m/z: 356 [M+H]$^+$. R$_f$(TLC): 0.8 (silica gel, DCM). HPLC-method G: R$_t$=1.62 min (b) 4-Trifluoromethyl-2-amino-5-(4-trifluoromethyl-piperidin-1-yl)aniline A mixture of 4-trifluoromethyl-2-nitro-5-(4-trifluoromethyl-piperidin-1-yl)aniline (0.14 g, 0.39 mmol), THF (10 mL) and Pd/C (15 mg) was stirred for 2 d at rt under a hydrogen atmosphere (3 bar). The catalyst was filtered off and the mixture was concentrated.

MS m/z: 328 [M+H]$^+$. R$_f$(TLC): 0.2 (silica gel, DCM). HPLC-method G: R$_t$=1.42 min.

(c) N-{2,4-Dichloro-3-[5-trifluoromethyl-6-(4-trifluoromethyl-piperidin-1-yl)-1H-benzimidazol-2-ylamino]-benzyl}-2,2-dimethyl-propionamide The compound was prepared from N-(2,4-dichloro-3-isothiocyanato-benzyl)-2,2-dimethyl-propionamide (87 mg, 0.28 mmol), 4-trifluoromethyl-2-amino-5-(4-trifluoromethyl-piperidin-1-yl)aniline (90 mg, 0.28 mmol), DIC (43 µL) in DMF (2 mL) in analogy to example 5, step (i).

Yield: 24%. R$_f$(TLC): 0.30 (silica gel, DCM:EtOH 95:5). MS m/z: 610 [M+H]$^+$. HPLC-method G: R$_t$=1.52 min.

Example 70

N-{2,4-Difluoro-3-[5-chloro-1-methyl-6-(4-trifluoromethyl-piperidin-1-yl)-1H-benzimidazol-2-ylamino]-benzyl}-2,2-dimethyl-propionamide

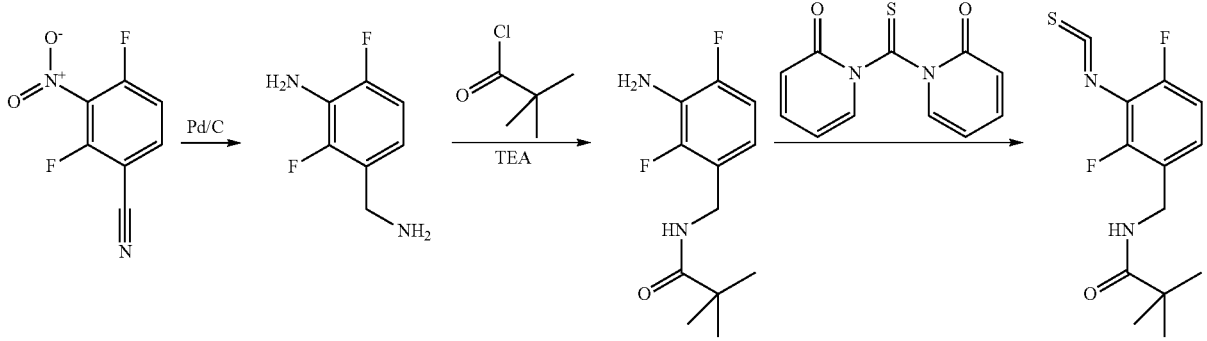

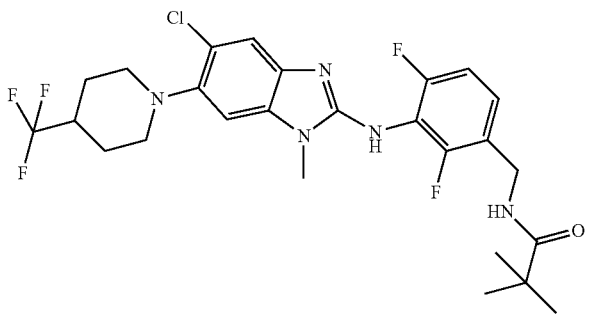
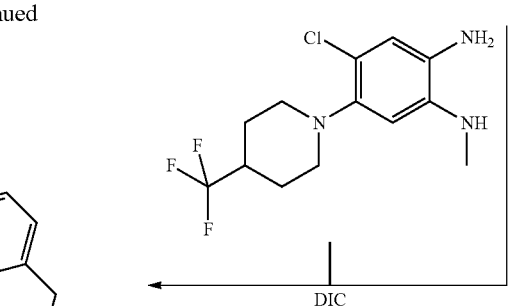

(a) 3-Amino-2,4-difluoro-benzylamine

A mixture of 3-Nitro-2,4-difluoro-benzonitrile (0.50 g, 2.7 mmol), MeOH (25 ml), 37% HCl (1.5 ml) and Pd/C (200 mg) was stirred for 13 h at rt under a hydrogen atmosphere (3 bar). The catalyst was removed by filtration and the filtrate was concentrated.

Yield: 0.58 g. MS m/z: 159 [M+H]$^+$.

(b) N-(3-Amino-2,4-difluoro-benzyl)-2,2-dimethyl-propionamide

TEA (1.92 mL, 13.8 mmol) was added to a mixture of 3-amino-2,4-difluoro-benzylamine (0.58 g, 2.5 mmol) in THF (40 ml) followed by pivaloyl chloride (0.31 mL, 2.5 mmol) and it was stirred overnight. The mixture was diluted with EtOAc, washed successively with satd. NaHCO$_3$ and brine. The organic phase was dried with Na$_2$SO$_4$, filtered and concentrated.

Yield: 0.57 g. HPLC-method G: R$_t$=1.20 min. MS m/z: 243 [M+H]$^+$.

(c) N-(2,4-Difluoro-3-isothiocyanato-benzyl)-2,2-dimethyl-propionamide 1,1'-Thiocarbonyldi-2-pyridone (546 mg, 2.35 mmol) was added to a mixture of N-(3-amino-2,4-difluoro-benzyl)-2,2-dimethyl-propionamide (570 mg, 2.35 mmol) and dioxane (20 mL) and stirred at reflux overnight. The mixture was concentrated, diluted with DCM and filtered over silica gel. The filtrate was concentrated to give the sub-title compound.

Yield: 440 mg R$_f$(TLC): 0.8 (silica gel, DCM:EtOH 95:5).

(d) N-{2,4-Difluoro-3-[5-chloro-1-methyl-6-(4-trifluoromethyl-piperidin-1-yl)-1H-benzimidazol-2-ylamino]-benzyl}-2,2-dimethyl-propionamide The compound was prepared in analogy to example 5 (i) from N-(2,4-difluoro-3-isothiocyanato-benzyl)-2,2-dimethyl-propionamide (68 mg, 0.24 mmol), 5-chloro-2-methylamino-4-(4-trifluoromethyl-piperidin-1-yl)aniline (100 mg, 0.24 mmol), DIC (40 µL, 0.25 mmol) in DMF.

Yield: 50 mg (37%). R$_f$(TLC): 0.4 (silica gel, DCM:EtOH 95:5). MS m/z: 558 [M+H]$^+$. HPLC-method G: R$_t$=1.47 min.

Example 71

N-{4-Chloro-3-[5-chloro-1-methyl-6-(4-trifluoromethyl-piperidin-1-yl)-1H-benzimidazol-2-ylamino]benzyl}-1-trifluoromethyl-cyclopropaneamide

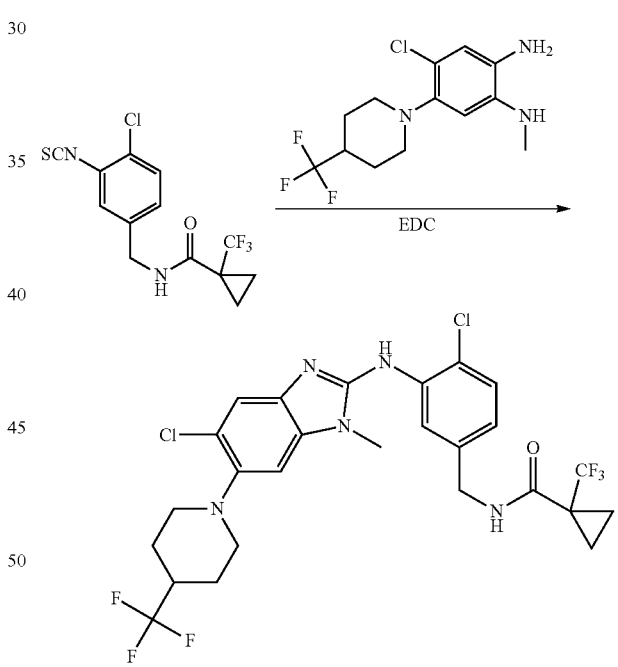

A mixture of N-(4-chloro-3-isothiocyanatobenzyl)-1-(trifluoromethyl)cyclopropane carboxamide (0.15 g; 0.45 mmol) and 5-chloro-2-methylamino-4-(4-trifluoromethyl-piperidin-1-yl)aniline (0.14 g; 0.45 mmol) in DMF (3 mL) was stirred overnight at rt. EDC (0.086 g; 0.45 mmol) was added and the mixture was heated to 90° C. for 1 h. The mixture was poured in water, extracted with DCM and the combined organic layer was washed with brine, dried over Na$_2$SO$_4$, filtered, concentrated and purified by column chromatography.

Yield: 0.079 g (29%). HPLC-method N: R$_t$=13.92 min. MS m/z: 608 [M+H]$^+$.

Example 76

N-{4-Chloro-3-[5-chloro-1-methyl-6-(4-phenyl-piperidin-1-yl)-1H-benzimidazol-2-ylamino]-benzyl}-1-trifluoromethyl-cyclopropanamide

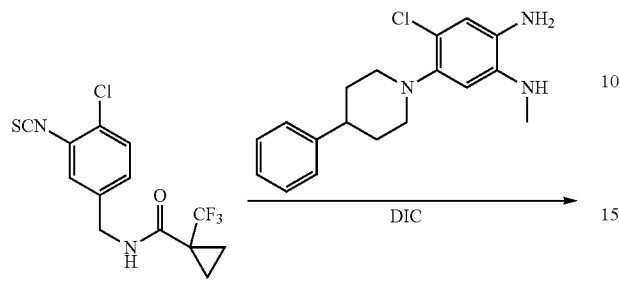

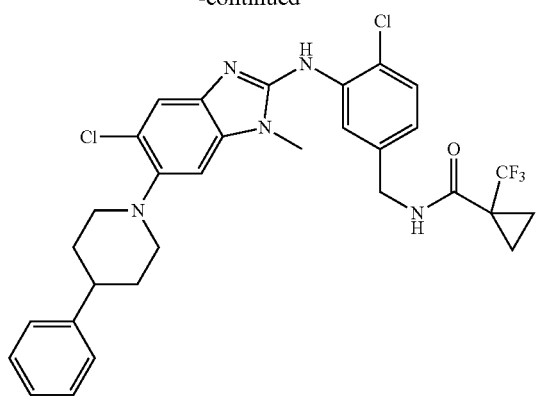

A mixture of N-(4-chloro-3-isothiocyanatobenzyl)-1-(trifluoromethyl)cyclopropane carboxamide (200 mg; 0.60 mmol) and 5-chloro-2-methylamino-4-(4-phenyl-piperidin-1-yl)aniline (190 mg; 0.60 mmol) in DMF (4 mL) was stirred overnight at rt. DIC (76 mg; 0.60 mmol) was added and the mixture was heated at 90° C. for 1.5 h. The mixture was poured in water, extracted with EtOAc and the combined organic layer was dried over Na$_2$SO$_4$, filtered and concentrated and the residue was purified by column chromatography.

Yield: 69 mg (19%). HPLC-method O: R$_t$=11.40 min. MS m/z: 616 [M+H]$^+$.

Example 82

N-{4-Chloro-3-[5-cyano-1-methyl-6-(4-trifluoromethyl-piperidin-1-yl)-1H-benzimidazol-2-ylamino]-benzyl}-1-trifluoromethyl-cyclopropanamide

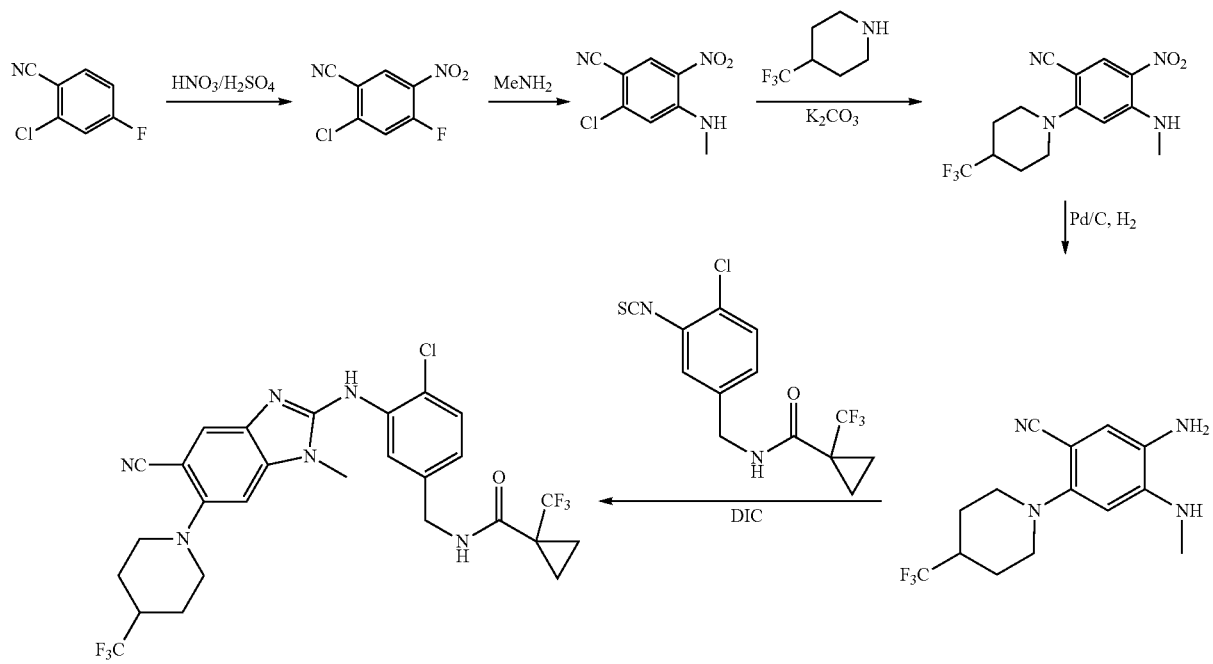

(a) 2-Chloro-4-fluoro-5-nitrobenzonitrile

Fuming HNO$_3$ (2.9 mL, 64 mmol) was added dropwise to a solution of 2-chloro-4-fluorobenzonitrile (5.0 g, 32 mmol) in conc. H$_2$SO$_4$ (5 mL) at 0° C. The mixture was stirred at 0° C. for 15 min and at rt for 30 min whereafter it was poured into ice. The precipitate was filtered off, washed with water and dried under vacuum.

Yield: 6.08 g (95%).

(b) 2-Chloro-4-(methylamino)-5-nitrobenzonitrile

A solution of MeNH$_2$ in THF (14.9 mL, 2 M, 29.8 mmol) was added dropwise to a solution of 2-chloro-4-fluoro-5-nitrobenzonitrile (3.0 g, 15 mmol) in THF (100 mL) at −20° C. The mixture was stirred at −20° C. for 1 h and thereafter concentrated, washed with brine and extracted with EtOAc. The organic layer was dried over Na$_2$SO$_4$, filtered and concentrated. The resulting residue was washed with PE to give the sub-title compound.

Yield: 3.07 g (97%).

(c) 4-(Methylamino)-5-nitro-2-(4-trifluoromethyl-piperidin-1-yl)benzonitrile A mixture of 2-chloro-4-(methylamino)-5-nitrobenzonitrile (3.07 g, 14.5 mmol), 4-trifluoromethylpiperidine (3.33 g, 21.7 mmol), K₂CO₃ (5.01 g, 36.2 mmol) and DMF (16 mL) was heated at 60° C. for 6 h under Ar atmosphere. The mixture was poured into aqueous NH₄OH and extracted with EtOAc. The organic layer was dried over Na₂SO₄, filtered and concentrated. Crystallization from EtOAc/PE gave the sub-title compound.

Yield: 3.65 g (77%).

(d) 5-Amino-4-(methylamino)-2-(4-trifluoromethyl-piperidin-1-yl)benzonitrile H₂ (1 atm) was passed through a mixture of 4-(methylamino)-5-nitro-2-(4-trifluoromethyl-piperidin-1-yl)benzonitrile (204 mg, 0.62 mmol), Pd/C (66 mg, 0.062 mmol), EtOAc (10 mL) and EtOH (10 mL) at rt for 1 h. The mixture was filtered through celite and concentrated. Crystallization from Et₂O/PE gave the sub-title compound.

Yield: 182 mg (98%).

(e) N-{4-Chloro-3-[5-cyano-1-methyl-6-(4-trifluoromethyl-piperidin-1-yl)-1H-benzimidazol-2-ylamino}-benzyl]-1-trifluoromethyl-cyclopropanamide The title compound was prepared in analogy to Example 76 using 5-amino-4-(methylamino)-2-(4-trifluoromethyl-piperidin-1-yl)benzonitrile (179 mg, 0.60 mmol), N-(4-chloro-3-isothiocyanatobenzyl)-1-(trifluoromethyl)cyclopropane carboxamide (200 mg; 0.60 mmol), DIC (76 mg, 0.60 mmol) and DMF (4 mL).

Yield: 142 mg (40%). HPLC-method O: R$_t$=11.23 min. MS m/z: 599 [M+H]⁺.

Example 83

N-{4-Chloro-3-[5-chloro-1-methyl-6-(4-(4-trifluoromethylphenyl)-piperazin-1-yl)-1H-benzimidazol-2-ylamino]-benzyl}-1-trifluoromethyl-cyclopropanamide

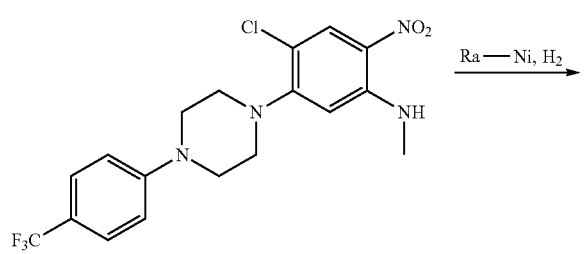

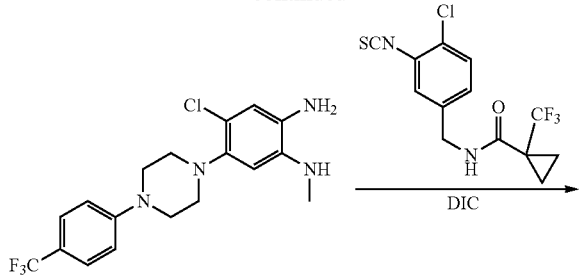

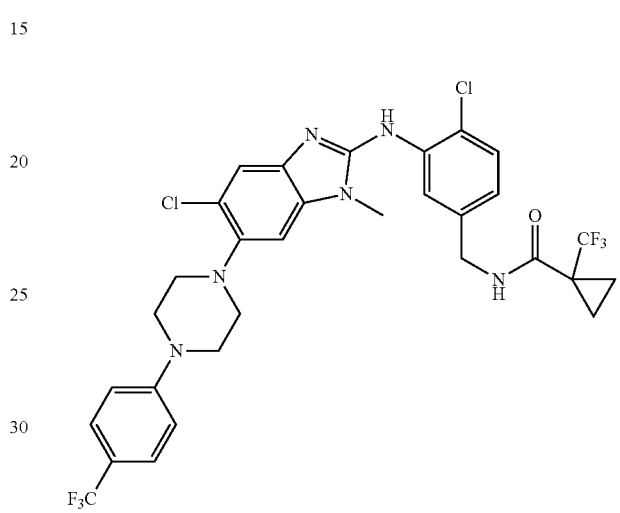

(a) 5-Chloro-2-methylamino-4-(4-(4-trifluoromethylphenyl)piperazin-1-yl)aniline A mixture of 4-chloro-N-methyl-2-nitro-5-(4-(4-trifluoromethylphenyl)-piperazin-1-yl)aniline (200 mg, 0.48 mmol), Ra—Ni (20 mg; 0.34 mmol) and THF (8 mL) was shaken under H₂ atmosphere (1 atm) at rt for 4 h. The mixture was filtered through celite and the resulting solution was used immediately used in the next step.

(b) N-{4-Chloro-3-[5-chloro-1-methyl-6-(4-(4-trifluoromethylphenyl)piperazin-1-yl)-1H-benzimidazol-2-ylamino]-benzyl}-1-trifluoromethyl-cyclopropanamide N-(4-Chloro-3-isothiocyanatobenzyl)-1-trifluoromethyl-cyclopropane carboxamide (161 mg, 0.48 mmol) was added to the THF solution from step (a) above and the mixture was concentrated. DMF (2 mL) was added to the residue, the mixture was stirred at rt for 1 h and DIC (67 mg, 0.53 mmol) was added. The mixture was stirred at rt overnight, another portion of DIC (17 mg, 0.13 mmol) was added and the mixture was stirred at rt overnight. The mixture was concentrated and the residue was purified by column chromatography to give the title compound.

Yield: 91 mg (28%). HPLC-method O: R$_t$=12.37 min. MS m/z: 685 [M+H]⁺.

Example 84

N-{4-Chloro-3-[5,7-difluoro-1-methyl-6-(4-trifluoromethyl-piperidin-1-yl)-1H-benzimidazol-2-ylamino]-benzyl}-1-trifluoromethyl-cyclopropanamide

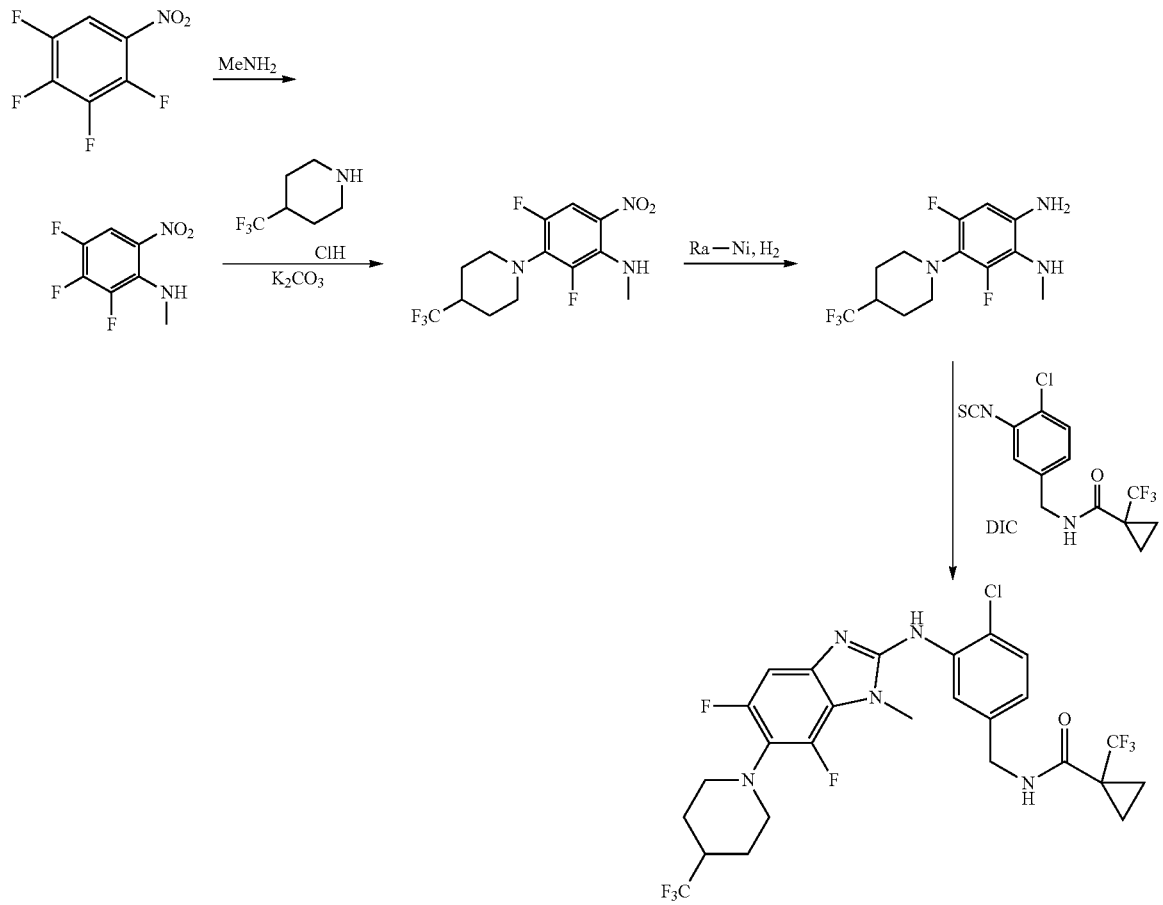

(a) 2,3,4-Trifluoro-N-methyl-6-nitroaniline

A solution of MeNH$_2$ in THF (50.7 mL, 2 M, 101 mmol) was added dropwise to a solution of 1,2,3,4-tetrafluoro-5-nitrobenzene (9.88 g, 50.7 mmol) in THF (200 mL) at −20° C. The mixture was stirred at −20° C. for 1.5 h, concentrated, washed with brine and extracted with EtOAc. The organic layer was dried over Na$_2$SO$_4$, filtered and concentrated. Crystallization from EtOAc/PE gave the sub-title compound. Yield: 8.5 g (81%).

(b) 2,4-Difluoro-N-methyl-6-nitro-3-(4-trifluoromethyl-piperidin-1-yl)aniline A mixture of 2,3,4-trifluoro-N-methyl-6-nitroaniline (1.5 g, 7.3 mmol), 4-trifluoromethyl-piperidine hydrochloride (2.76 g, 14.6 mmol), K$_2$CO$_3$ (2.01 g, 14.6 mmol) and DMF (10 mL) was stirred at rt overnight under Ar atmosphere. The mixture was poured into aqueous ammonia and extracted with EtOAc. The organic layer was dried over Na$_2$SO$_4$, filtered and concentrated. Crystallization from EtOAc/PE gave the sub-title compound. Yield: 2.3 g (93%).

(c) 3,5-Difluoro-2-methylamino-4-(4-trifluoromethyl-piperidin-1-yl)aniline

A mixture of 2,4-difluoro-N-methyl-6-nitro-3-(4-trifluoromethyl-piperidin-1-yl)aniline (210 mg, 0.62 mmol), Ra—Ni (4 mg, 0.062 mmol) and THF (30 mL) was shaken under H$_2$ atmosphere (1 atm) at rt for 1 h. The mixture was filtered through celite and the celite pad was further washed with THF. The resulting solution was concentrated to give the sub-title compound.
Yield: 190 mg (99%).

(d) N-{4-Chloro-3-[5,7-difluoro-1-methyl-6-(4-trifluoromethyl-piperidin-1-yl)-1H-benzimidazol-2-ylamino]-benzyl}-1-trifluoromethyl-cyclopropanamide The title compound was prepared in analogy to Example 76 using 3,5-difluoro-2-methylamino-4-(4-trifluoromethyl-piperidin-1-yl)aniline (186 mg, 0.60 mmol), N-(4-chloro-3-isothiocyanatobenzyl)-1-(trifluoromethyl)cyclopropane carboxamide (200 mg; 0.60 mmol), DIC (76 mg, 0.60 mmol) and DMF (3 mL).
Yield: 119 mg (33%). HPLC-method O: R$_f$=12.25 min. MS m/z: 610 [M+H]$^+$.

Example 86

N-{4-Chloro-3-[5-fluoro-1-methyl-6-(4-trifluoromethyl-piperidin-1-yl)-1H-benzimidazol-2-ylamino]-benzyl}-1-trifluoromethyl-cyclopropanamide

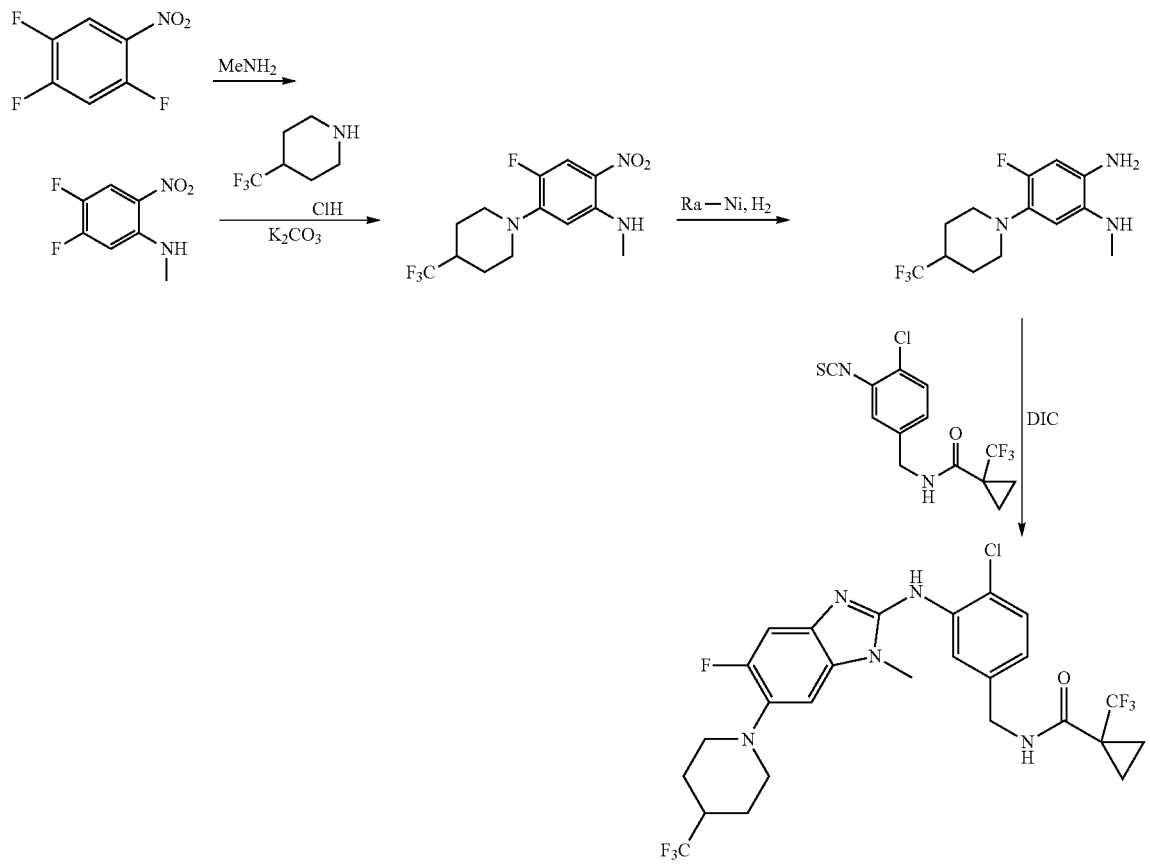

(a) 4,5-Difluoro-N-methyl-2-nitroaniline

A solution of MeNH$_2$ in THF (5.7 mL, 2 M, 11 mmol) was added dropwise to a solution of 1,2,4-trifluoro-5-nitrobenzene (1.0 g, 5.7 mmol) in THF (10 mL) at −20° C. The mixture was stirred at −20° C. for 1 h, concentrated, washed with brine and extracted with EtOAc. The organic layer was dried over Na$_2$SO$_4$, filtered and concentrated. Crystallization from EtOAc/PE gave the sub-title compound. Yield: 1.0 g (81%).

(b) 4-Fluoro-N-methyl-2-nitro-5-(4-trifluoromethyl-piperidin-1-yl)aniline

A mixture of 4,5-difluoro-N-methyl-2-nitroaniline (1.0 g, 5.3 mmol), 4-trifluoromethylpiperidine hydrochloride (2.02 g, 10.6 mmol), K$_2$CO$_3$ (1.47 g, 10.6 mmol) and DMF (7 mL) was stirred at 40° C. overnight under Ar atmosphere. The mixture was poured into aqueous ammonia and extracted with EtOAc. The organic layer was dried over Na$_2$SO$_4$, filtered and concentrated. The residue was washed with Et$_2$O/PE to give the sub-title compound.

Yield: 1.6 g (95%).

(c) 5-Fluoro-2-methylamino-4-(4-trifluoromethyl-piperidin-1-yl)aniline

A mixture of 4-fluoro-N-methyl-2-nitro-5-(4-trifluoromethyl-piperidin-1-yl)aniline (200 mg, 0.62 mmol), Ra—Ni (4 mg, 0.062 mmol) and THF (30 mL) was shaken under H$_2$ atmosphere (1 atm) at rt for 1 h. The mixture was filtered through celite and the celite pad was further washed with THF. Concentration and crystallization from Et$_2$O/PE gave the sub-title compound.

Yield: 176 mg (97%).

(d) N-{4-Chloro-3-[5-fluoro-1-methyl-6-(4-trifluoromethyl-piperidin-1-yl)-1H-benzimidazol-2-ylamino]-benzyl}-1-trifluoromethyl-cyclopropanamide The title compound was prepared in analogy to Example 76 using 5-fluoro-2-methylamino-4-(4-trifluoromethyl-piperidin-1-yl)aniline (175 mg, 0.60 mmol), N-(4-chloro-3-isothiocyanatobenzyl)-1-(trifluoromethyl)cyclopropane carboxamide (200 mg; 0.60 mmol), DIC (76 mg, 0.60 mmol) and DMF (3 mL).

Yield: 155 mg (44%). HPLC-method O: R$_t$=10.62 min. MS m/z: 592 [M+H]$^+$.

Example 93

N-{4-Chloro-3-[4-cyano-5-(3-trifluoromethyl-piperidin-1-yl)-1H-benzimidazol-2-ylamino]-benzyl}-1-trifluoromethyl-cyclopropanamide

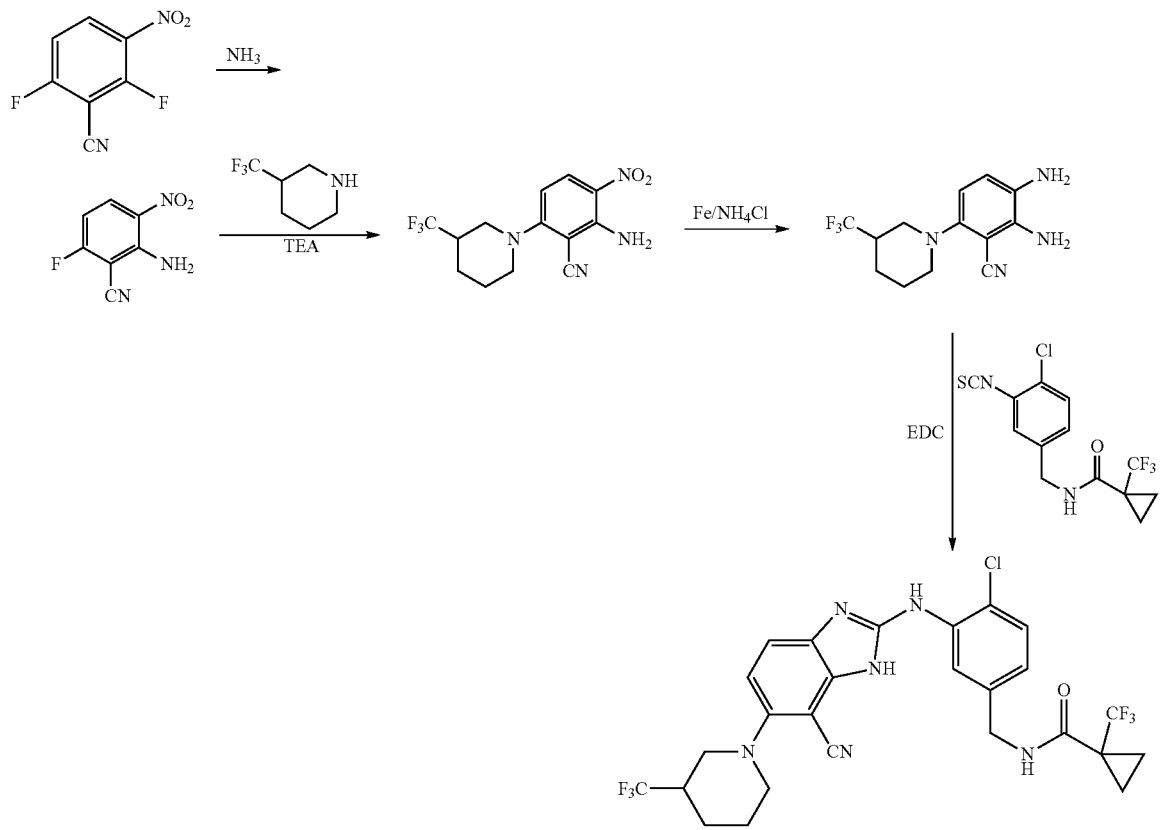

(a) 2-Amino-6-fluoro-3-nitrobenzonitrile

A solution of NH₃ in EtOH (19 mL, 8.6 M, 160 mmol) was added dropwise to a solution of 2,6-difluoro-3-nitrobenzonitrile (10 g, 54 mmol) in THF (50 mL) at 0° C. under Ar and the resulting mixture was stirred at 0° C. for 1 h. The mixture was concentrated and the residue washed with brine and extracted with EtOAc. The organic layer was dried over Na₂SO₄, filtered and concentrated.

Yield: 9.59 g (98%).

(b) 2-Amino-3-nitro-6-(3-trifluoromethyl-piperidin-1-yl)benzonitrile

A mixture of 2-amino-6-fluoro-3-nitrobenzonitrile (3.1 g, 17 mmol), 3-trifluoromethylpiperidine (2.5 g, 19 mmol), TEA (3.4 g, 34 mmol) and THF (110 mL) was stirred under Ar at rt for 3 h. The mixture was concentrated and poured into H₂O and thereafter extracted with EtOAc. The organic layer was dried over Na₂SO₄, filtered and concentrated. Crystallization from EtOAc gave the sub-title compound.

Yield: 2.9 g (54%).

(c) 2,3-Diamino-6-(3-trifluoromethyl-piperidin-1-yl)benzonitrile

A mixture of 2-amino-3-nitro-6-(3-trifluoromethyl-piperidin-1-yl)benzonitrile (200 mg, 0.64 mmol), Fe (178 mg, 3.18 mmol), aqueous NH₄Cl (5 mL) and EtOH (5 mL) was heated under Ar at 90° C. for 2 h. The mixture was thereafter basicified to pH ~9-10 and filtered through celite and the celite pad was washed with EtOH and EtOAc. The organic layer was concentrated and the residue was extracted with EtOAc. The organic layer was dried over Na₂SO₄, filtered and concentrated. The residue was washed with Et₂O to give the sub-title compound.

Yield: 153 mg (84%).

(d) N-{4-Chloro-3-[4-cyano-5-(3-trifluoromethyl-piperidin-1-yl)-1H-benzimidazol-2-ylamino]-benzyl}-1-trifluoromethyl-cyclopropanamide The title compound was prepared in analogy to Example 71 using 2,3-diamino-6-(3-trifluoromethyl-piperidin-1-yl)benzonitrile (115 mg, 0.40 mmol), N-(4-chloro-3-isothiocyanatobenzyl)-1-(trifluoromethyl)cyclopropane carboxamide (135 mg; 0.40 mmol), EDC (77 mg, 0.40 mmol) and DMF (3 mL).

Yield: 69 mg (29%). HPLC-method N: $R_t$=15.50 min. MS m/z: 585 [M+H]⁺.

Example 94

N-{4-Chloro-3-[5-chloro-1-methyl-6-(4-trifluoromethyl-piperidin-1-yl)-1H-benzimidazol-2-ylamino]-benzyl}-2,2-difluoro-propionamide

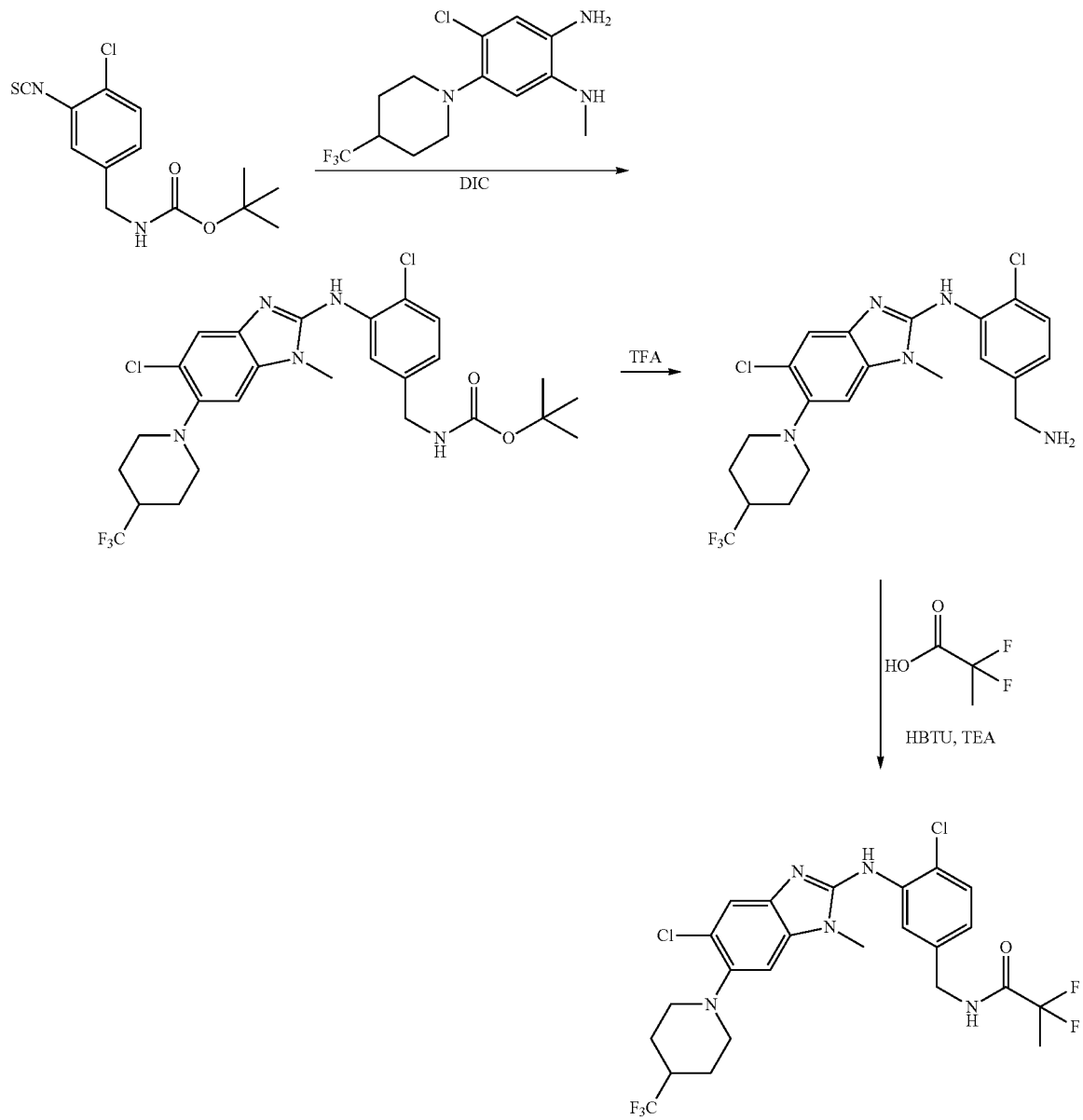

(a) Tert-butyl N-{4-chloro-3-[5-chloro-1-methyl-6-(4-trifluoromethyl-piperidin-1-yl)-1H-benzo[d]imidazol-2-ylamino]benzyl}-carbamate The sub-title compound was prepared in analogy to Example 76 using 5-chloro-2-methylamino-4-(4-trifluoromethyl-piperidin-1-yl)aniline (508 mg, 1.65 mmol), tert-butyl 4-chloro-3-isothiocyanatobenzylcarbamate (493 mg, 1.65 mmol), DIC (208 mg, 1.65 mmol) and DMF (8 mL).

Yield: 701 mg (74%).

(b) 4-Chloro-3-[5-chloro-1-methyl-6-(4-trifluoromethyl-piperidin-1-yl)-1H-benzo[d]imidazol-2-ylamino]benzylamine A mixture of tert-butyl N-{4-chloro-3-[5-chloro-1-methyl-6-(4-trifluoromethyl-piperidin-1-yl)-1H-benzo[d]imidazol-2-ylamino]benzyl}-carbamate (790 mg, 1.38 mmol), TFA (1.54 mL, 20.7 mmol) and DCM (30 mL) was stirred at rt overnight. The mixture was cooled to 0° C., basicified to pH ~10 and extracted with DCM. The organic layer was dried over Na₂SO₄, filtered and concentrated and the residue was washed with Et₂O/PE.

(c) N-{4-Chloro-3-[5-chloro-1-methyl-6-(4-trifluoromethyl-piperidin-1-yl)-1H-benzimidazol-2-ylamino]-benzyl}-2,2-difluoro-propionamide A mixture of 2,2-difluoropropanoic acid (37 mg; 0.34 mmol), HBTU (129 mg; 0.34 mmol) and TEA (69 mg; 0.68 mmol) in DMF (1.5 mL) was stirred for 30 min at rt and added to a solution of 4-chloro-3-[5-chloro-1-methyl-6-(4-trifluoromethyl-piperidin-1-yl)-1H-benzo[d]imidazol-2-ylamino]benzylamine (161 mg; 0.34 mmol) in DMF (1.5 mL). The resulting mixture was stirred overnight at rt, poured into brine and extracted with EtOAc. The organic layer was dried over $Na_2SO_4$, filtered and concentrated and the residue was purified by column chromatography.

Yield: 87 mg (45%). HPLC-method O: $R_t$=10.60 min. MS m/z: 564 [M+H]$^+$.

Example 99

N-(4-Chloro-3-(5-chloro-1-methyl-6-(4-trifluoromethyl-piperidin-1-yl)-1H-benzo[d]imidazol-2-ylamino)benzyl)-2-methylpropane-2-sulfonamide

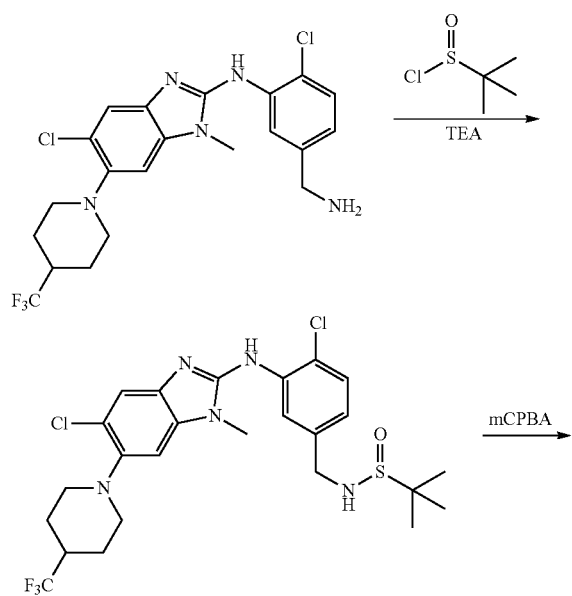

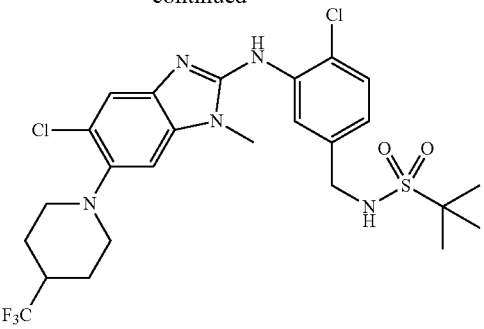

(a) N-(4-Chloro-3-(5-chloro-1-methyl-6-(4-trifluoromethyl-piperidin-1-yl)-1H-benzo[d]imidazol-2-ylamino)benzyl)-2-methylpropane-2-sulfinamide A solution of 2-methylpropane-2-sulfinic acid chloride (83 mg, 0.59 mmol) in DCM (2 mL) was added dropwise to a solution of 4-chloro-3-[5-chloro-1-methyl-6-(4-trifluoromethyl-piperidin-1-yl)-1H-benzo[d]imidazol-2-ylamino]benzylamine (265 mg, 0.56 mmol), TEA (113 mg, 1.12 mmol) and DCM (3 mL) at 0° C. under Ar. The mixture was stirred at rt overnight, poured into $H_2O$ and extracted with DCM. The organic layer was washed with brine, dried over $Na_2SO_4$, filtered and concentrated. Crystallization from DCM/PE gave the sub-title compound.

Yield: 298 mg (92%).

(b) N-(4-Chloro-3-(5-chloro-1-methyl-6-(4-trifluoromethyl-piperidin-1-yl)-1H-benzo[d]imidazol-2-ylamino)benzyl)-2-methylpropane-2-sulfonamide A mixture of N-(4-chloro-3-(5-chloro-1-methyl-6-(4-trifluoromethyl-piperidin-1-yl)-1H-benzo[d]imidazol-2-ylamino)benzyl)-2-methylpropane-2-sulfinamide (298 mg, 0.52 mmol), m-chloroperoxybenzoic acid (127 mg, 0.74 mmol) and DCM (20 mL) was stirred at rt overnight. The mixture was basicified to pH ~8-9 and extracted with EtOAc. The organic layer was dried over $Na_2SO_4$, filtered and concentrated. Crystallization from DCM/$Et_2O$ gave the title compound.

Yield: 39 mg (13%). HPLC-method O: $R_t$=10.84 min. MS m/z: 592 [M+H]$^+$.

Example 101

N-{4-Trifluoromethyl-3-[5-chloro-1-methyl-6-(4-trifluoromethyl-piperidin-1-yl)-1H-benzimidazol-2-ylamino]-benzyl}-1-trifluoromethyl-cyclopropanamide

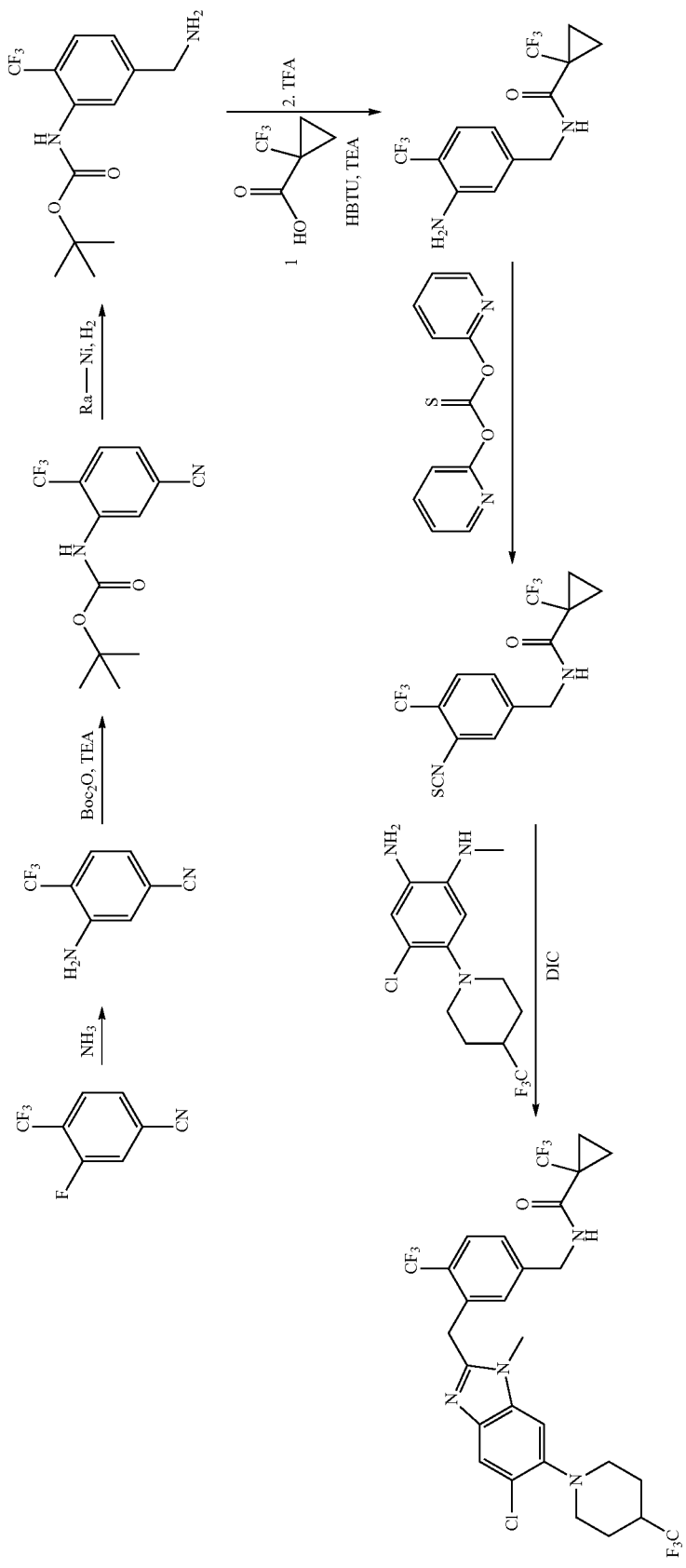

(a) 3-Amino-4-trifluoromethyl-benzonitrile

A closed pressure tube charged with 3-fluoro-4-trifluoromethyl-benzonitrile (10.0 g; 52.9 mmol) and liquid $NH_3$ (60 mL) was heated for 6 days at 90° C. The tube was cooled to −60° C. and opened. The mixture was allowed to stir for 1 h at rt, washed with brine, extracted with EtOAc, dried over $Na_2SO_4$, filtered and concentrated.

Yield: 10.2 g (quantitative; slightly contaminated).

(b) tert-Butyl 5-cyano-2-trifluoromethyl-phenylcarbamate

A mixture of 3-amino-4-trifluoromethyl-benzonitrile (10.0 g; 53.7 mmol), DCM (100 mL) and TEA (8.2 mL; 59 mmol) was treated dropwise with a solution of $Boc_2O$ (12.9 g; 59.1 mmol) in DCM (50 mL) at 0° C. and stirred overnight. Another portion of $Boc_2O$ in DCM and DMAP (656 mg; 5.37 mmol) was added and the mixture was stirred for another 12 h at rt. The mixture was washed with water and brine, dried over $Na_2SO_4$, filtered, concentrated and purified by column chromatography.

Yield: 8.50 g (55%).

(c) tert-Butyl 5-aminomethyl-2-trifluoromethyl-phenylcarbamate

A mixture of tert-butyl 5-cyano-2-trifluoromethyl-phenylcarbamate (8.5 g; 29.7 mmol), Ra—Ni (174 mg; 2.97 mmol) and THF (60 mL) was stirred under $H_2$-atmosphere (5 atm) overnight at rt. The mixture was filtered through celite and the celite pad was washed with THF and EtOAc. Concentration gave the sub-title compound which was used in the next step without further purification. Yield: 8 g (93%).

(d) N-(3-Amino-4-trifluoromethyl-benzyl)-1-trifluoromethyl-cyclopropanecarboxamide The compound was prepared in analogy to the procedures in Example 94, step (c) and Example 94, step (b) using tert-butyl 5-aminomethyl-2-trifluoromethyl-phenylcarbamate (2.09 g; 7.20 mmol), 1-trifluoromethyl-cyclopropanecarboxylic acid (1.11 g; 7.20 mmol), HBTU (2.73 g; 7.20 mmol), TEA (2.19 g; 21.6 mmol), DMF (25 mL), TFA (10 mL) and DCM (50 mL). Yield: 1.8 g (77%).

(e) N-(4-Trifluoromethyl-3-isothiocyanatobenzyl)-1-trifluoromethyl-cyclopropane carboxamide A mixture of N-(3-amino-4-trifluoromethyl-benzyl)-1-trifluoromethyl-cyclopropanecarboxamide (1.60 g; 4.90 mmol), di-(2-pyridyl)thionocarbonate (1.71 g; 7.36 mmol) and THF (40 mL) was stirred in a pressure tube for 2 days at 60° C. The mixture was concentrated and the residue was purified by column chromatography. Yield: 1.29 g (72%).

(f) N-{4-Trifluoromethyl-3-[5-chloro-1-methyl-6-(4-trifluoromethyl-piperidin-1-yl)-1H-benzimidazol-2-ylamino]-benzyl}-1-trifluoromethyl-cyclopropanamide The title compound was prepared in analogy to Example 76 using 5-chloro-2-methylamino-4-(4-trifluoromethyl-piperidin-1-yl)aniline (185 mg, 0.60 mmol), N-(4-trifluoromethyl-3-isothiocyanatobenzyl)-1-(trifluoromethyl)cyclopropane carboxamide (221 mg, 0.60 mmol), DIC (76 mg, 0.60 mmol) and DMF (4 mL).

Yield: 185 mg (48%). HPLC-method O: $R_t$=11.17 min. MS m/z: 642 $[M+H]^+$.

Example 105

N-{4-Trifluoromethyl-3-[5-chloro-1-methyl-6-(4-trifluoromethyl-piperidin-1-yl)-1H-benzimidazol-2-ylamino]-benzyl}-3,3,3-trifluoro-2-methyl-propanamide

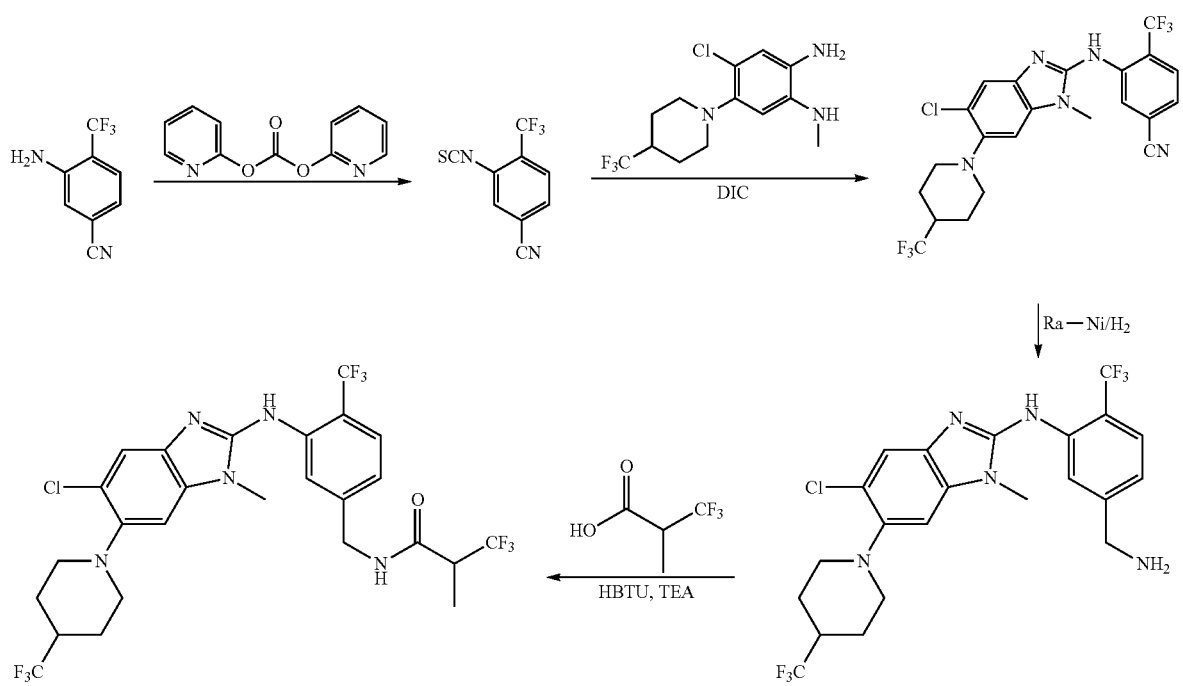

(a) 3-Isothiocyanato-4-trifluoromethyl-benzonitrile

A mixture of 3-amino-4-trifluoromethyl-benzonitrile (1.0 g, 5.4 mmol), di-(2-pyridyl)thionocarbonate (1.87 g, 8.06 mmol) and THF (50 mL) was stirred at rt overnight. The mixture was concentrated and the residue was purified by column chromatography.
Yield: 760 mg (62%).

(b) 3-(5-Chloro-1-methyl-6-(4-trifluoromethyl-piperidin-1-yl)-1H-benzo[d]imidazol-2-ylamino)-4-trifluoromethyl-benzonitrile The sub-title compound was prepared in analogy to Example 76 using 5-chloro-2-methylamino-4-(4-trifluoromethyl-piperidin-1-yl)aniline (998 mg, 3.24 mmol), 3-isothiocyanato-4-(trifluoromethyl)benzonitrile (740 mg, 3.24 mmol), DIC (409 mg, 3.24 mmol) and DMF (7 mL).
Yield: 1.21 g (74%).

(c) 4-Trifluoromethyl-3-[5-chloro-1-methyl-6-(4-trifluoromethyl-piperidin-1-yl)-1H-benzimidazol-2-ylamino]-benzylamine A mixture of 3-(5-chloro-1-methyl-6-(4-trifluoromethyl-piperidin-1-yl)-1H-benzo[d]imidazol-2-ylamino)-4-trifluoromethyl-benzonitrile (1.20 g; 2.39 mmol), Ra—Ni (14 mg; 0.24 mmol) and THF (50 mL) was shaken under H$_2$-atmosphere (5 atm) overnight at rt. The mixture was filtered through celite and the celite pad was washed with THF and EtOAc. Concentration and crystallization from Et$_2$O/PE gave the sub-title compound.
Yield: 1.2 g (99%).

(d) N-{4-Trifluoromethyl-3-[5-chloro-1-methyl-6-(4-trifluoromethyl-piperidin-1-yl)-1H-benzimidazol-2-ylamino]-benzyl}-3,3,3-trifluoro-2-methyl-propanamide The title compound was prepared in analogy to the procedure in Example 94, step (c) using 4-trifluoromethyl-3-[5-chloro-1-methyl-6-(4-trifluoromethyl-piperidin-1-yl)-1H-benzimidazol-2-ylamino]-benzylamine (110 mg; 0.22 mmol), 3,3,3-trifluoro-2-methylpropanoic acid (31 mg; 0.22 mmol), HBTU (83 mg; 0.22 mmol), TEA (45 mg; 0.44 mmol), DMF (2 mL).
Yield: 39 mg (28%). HPLC-method O: R$_t$=11.80 min. MS m/z: 630 [M+H]$^+$.

Example 109

N-(4-Trifluoromethyl-3-(5-chloro-1-methyl-6-(4-trifluoromethyl-piperidin-1-yl)-1H-benzo[d]imidazol-2-ylamino)benzyl)-2-methylpropane-2-sulfinamide

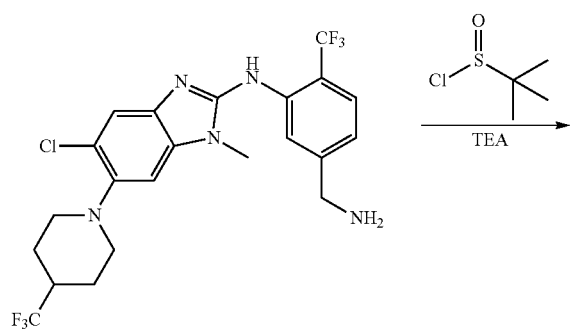

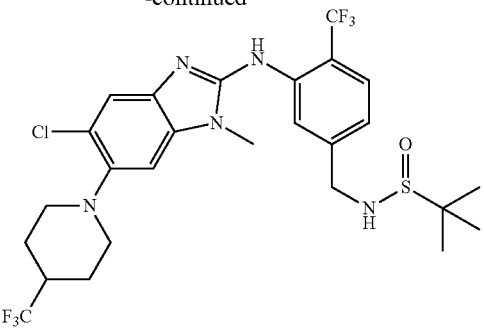

The title compound was prepared in analogy to the procedure in Example 99, step (a) using 2-methylpropane-2-sulfinic chloride (117 mg, 0.83 mmol), 4-trifluoromethyl-3-[5-chloro-1-methyl-6-(4-trifluoromethyl-piperidin-1-yl)-1H-benzimidazol-2-ylamino]-benzylamine (400 mg, 0.79 mmol), TEA (160 mg, 1.58 mmol) and DCM (5 mL).
Yield: 210 mg (44%). HPLC-method O: R$_t$=11.25 min. MS m/z: 610 [M+H]$^+$.

Example 110

N-(4-Trifluoromethyl-3-(5-chloro-1-methyl-6-(4-trifluoromethyl-piperidin-1-yl)-1H-benzo[d]imidazol-2-ylamino)benzyl)-2-methylpropane-2-sulfonamide

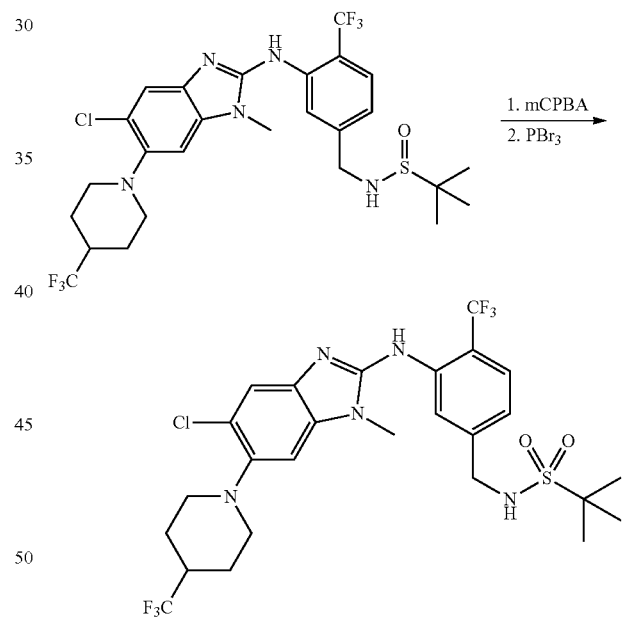

A mixture of N-(4-trifluoromethyl-3-(5-chloro-1-methyl-6-(4-trifluoromethyl-piperidin-1-yl)-1H-benzo[d]imidazol-2-ylamino)benzyl)-2-methylpropane-2-sulfinamide (140 mg, 0.23 mmol), m-chloroperoxybenzoic acid (198 mg, 1.15 mmol) and CHCl$_3$ (7 mL) was stirred at rt for 15 min. The mixture was poured into brine and extracted with DCM. The organic layer was dried over Na$_2$SO$_4$, filtered and concentrated. The residue was mixed with PBr$_3$ (144 mg, 0.50 mmol) and DCM (5 ml) and the mixture was stirred at rt overnight. The mixture was poured into H$_2$O and extracted with DCM. The organic layer was washed with brine, dried over Na$_2$SO$_4$, filtered and concentrated. Purification by column chromatography gave the title compound.
Yield: 33 mg (16%). HPLC-method O: R$_t$=11.44 min. MS m/z: 626 [M+H]$^+$.

Example 111

N-{4-Fluoro-3-[5-chloro-1-methyl-6-(4-trifluoromethyl-piperidin-1-yl)-1H-benzimidazol-2-ylamino]-benzyl}-1-trifluoromethyl-cyclopropanamide

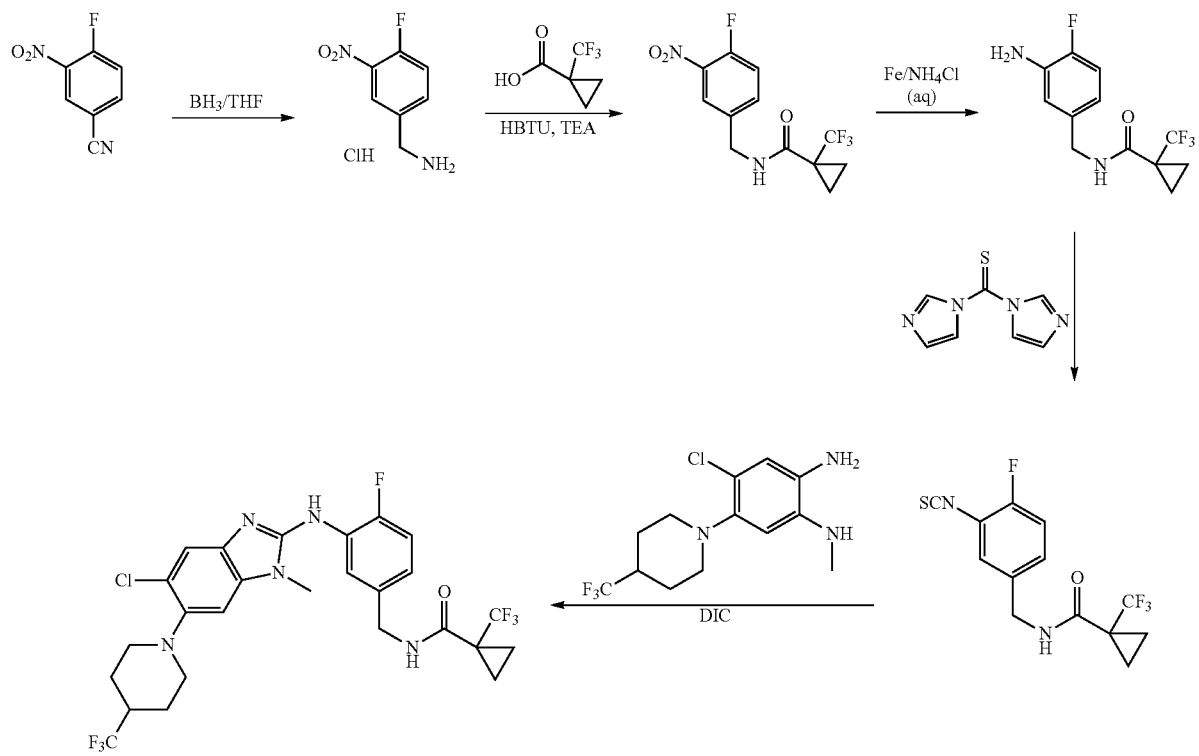

(a) 4-Fluoro-3-nitro-benzylamine hydrochloride

BH$_3$/THF (120 mL; 120 mmol) was added to a solution of 4-fluoro-3-nitro-benzonitrile (10 g; 60 mmol) in THF (50 mL) over 30 min at 0° C. and the resulting mixture was stirred at 0° C. for 1 h and at rt for 3 h. The mixture was acidified to pH ~1 and stirred for 1 h at rt, basicified to pH ~7-8 and extracted with EtOAc. The organic layer was dried over Na$_2$SO$_4$, filtered and concentrated. The residue was dissolved in Et$_2$O and treated with a solution of HCl in 1,4-dioxane to give the sub-title compound.

Yield: 8.7 g (70%).

(b) N-(4-Fluoro-3-nitro-benzyl)-1-(trifluoromethyl) cyclopropanecarboxamide

The sub-title compound was prepared in analogy to the procedure in Example 94, step (c) using 4-fluoro-3-nitro-benzylamine hydrochloride (3.0 g; 14.5 mmol), 1-(trifluoromethyl)-cyclopropanecarboxylic acid (2.5 g; 16.0 mmol), HBTU (6.07 g; 16.0 mmol), TEA (5.88 g; 58.1 mmol) and DMF (50 mL).

Yield: 3.8 g (85%).

(c) N-(3-Amino-4-fluorobenzyl)-1-(trifluoromethyl) cyclopropanecarboxamide

The sub-title compound was prepared in analogy to the procedure in Example 93, step (c) using N-(4-fluoro-3-nitrobenzyl)-1-(trifluoromethyl)-cyclopropanecarboxamide (3.77 g; 12.3 mmol), Fe (3.45 g; 61.6 mmol), NH$_4$Cl (aq, sat, 30 mL) and EtOH (30 mL).

Yield: 3.2 g (76%).

(d) N-(4-Fluoro-3-isothiocyanatobenzyl)-1-(trifluoromethyl)cyclopropane carboxamide A mixture of N-(3-amino-4-fluorobenzyl)-1-(trifluoromethyl)cyclopropanecarboxamide (3.17 g; 11.5 mmol) and TCDI (3.07 g; 17.2 mmol) in DCM (50 mL) was heated overnight at 50° C. The mixture was concentrated and the residue was purified by column chromatography.

Yield: 3 g (82%).

(e) N-{4-Fluoro-3-[5-chloro-1-methyl-6-(4-trifluoromethyl-piperidin-1-yl)-1H-benzimidazol-2-ylamino]-benzyl}-1-trifluoromethyl-cyclopropanamide The title compound was prepared in analogy to the procedure in Example 76 using N-(4-fluoro-3-isothiocyanatobenzyl)-1-(trifluoromethyl)cyclopropane carboxamide (191 mg; 0.60 mmol), 5-chloro-2-methylamino-4-(4-trifluoromethyl-piperidin-1-yl)aniline (185 mg; 0.60 mmol), DIC (76 mg; 0.60 mmol) and DMF (3 mL).

Yield: 111 mg (31%). HPLC-method O: R$_f$=11.07 min. MS m/z: 592 [M+H]$^+$.

Example 114

N-{4-Chloro-2-fluoro-5-[5-chloro-1-methyl-6-(4-trifluoromethyl-piperidin-1-yl)-1H-benzimidazol-2-ylamino]-benzyl}-1-trifluoromethyl-cyclopropanamide

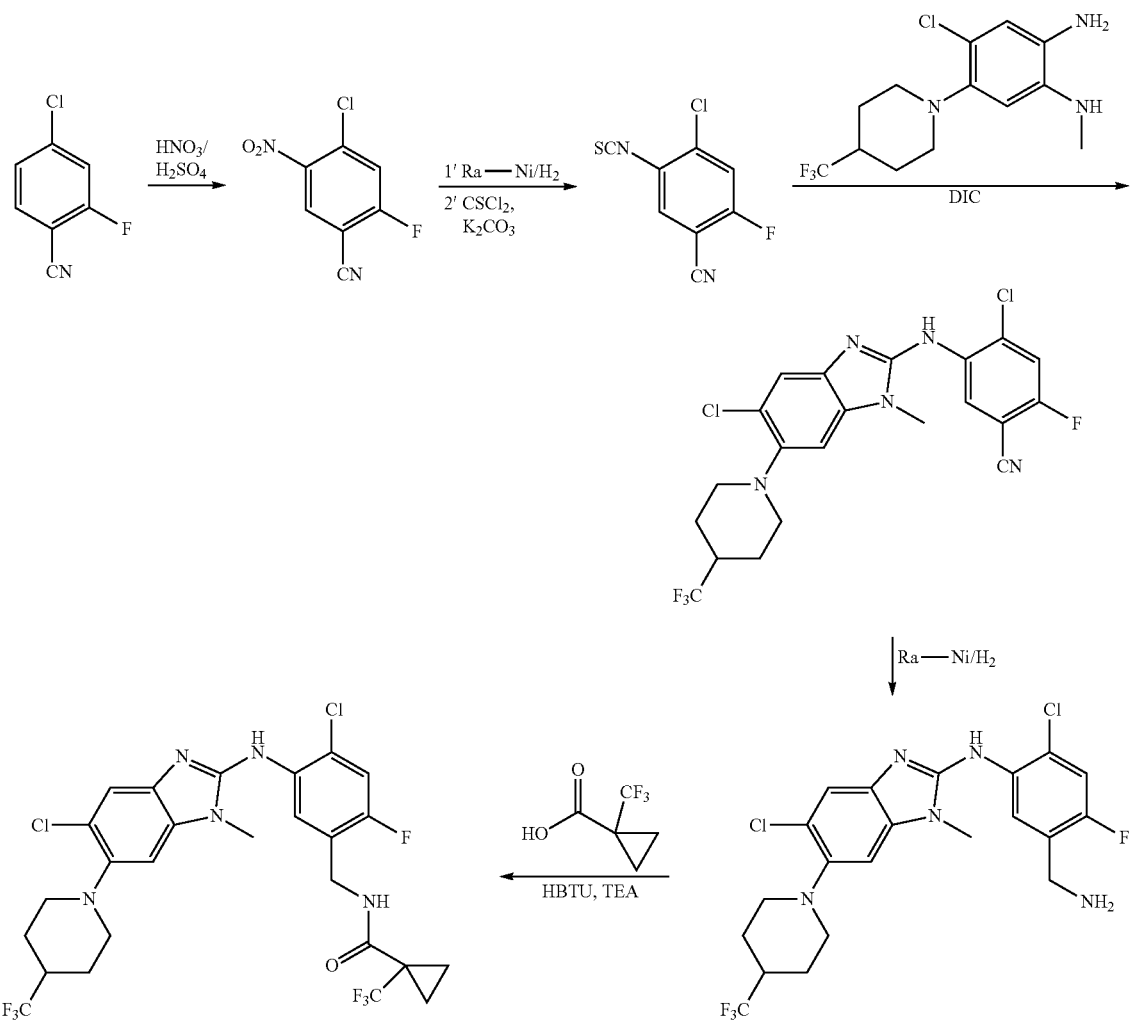

(a) 4-Chloro-2-fluoro-5-nitrobenzonitrile

A mixture of 4-chloro-2-fluorobenzonitrile (4.62 g; 29.7 mmol) in conc. $H_2SO_4$ (42 mL) was treated dropwise with conc. $HNO_3$ (3.9 mL) at 1-2° C. After stirring at 1-2° C. for 2 h the mixture was poured into ice and filtered.

Yield: 5.18 g (87%).

(b) 4-Chloro-2-fluoro-5-isothiocyanatobenzonitrile $H_2$ was passed through a mixture of 4-chloro-2-fluoro-5-nitrobenzonitrile (1.0 g; 5.0 mmol) and Ra—Ni (29 mg, 0.50 mmol) in THF (50 mL) for 6 h. The mixture was filtered through celite. $CSCl_2$ (2.29 g; 19.9 mmol) and $K_2CO_3$ (3.45 g; 25.0 mmol) was added and it was stirred overnight at rt. The residue was concentrated and purified by column chromatography.

Yield: 840 mg (79%).

(c) 4-Chloro-5-[5-chloro-1-methyl-6-(4-(trifluoromethyl)piperidin-1-yl)-1H-benzo[d]imidazol-2-ylamino]-2-fluorobenzonitrile The sub-title compound was prepared in analogy to the procedure in Example 76 using 4-chloro-2-fluoro-5-isothiocyanatobenzonitrile (300 mg; 1.41 mmol), 5-chloro-2-methylamino-4-(4-trifluoromethyl-piperidin-1-yl)aniline (434 mg; 1.41 mmol), DIC (178 mg; 1.41 mmol) and DMF (12 mL).

Yield: 264 mg (39%).

(d) 4-Chloro-2-fluoro-5-[5-chloro-1-methyl-6-(4-trifluoromethyl-piperidin-1-yl)-1H-benzimidazol-2-ylamino]-benzylamine The sub-title compound was prepared in analogy to Example 101, step (c) using 4-chloro-5-[5-chloro-1-methyl-6-(4-(trifluoromethyl)piperidin-1-yl)-1H-benzo[d]imidazol-2-ylamino]-2-fluorobenzonitrile (264 mg; 0.54 mmol), Ra—Ni (3 mg), $H_2$ (5 atm) and THF (30 mL).

(e) N-{4-Chloro-2-fluoro-5-[5-chloro-1-methyl-6-(4-trifluoromethyl-piperidin-1-yl)-1H-benzimidazol-2-ylamino]-benzyl}-1-trifluoromethyl-cyclopropanamide The title compound was prepared in analogy to the procedure in Example 94, step (c) using 4-chloro-2-fluoro-5-[5-chloro-1-methyl-6-(4-trifluoromethyl-piperidin-1-yl)-1H-benzimidazol-2-ylamino]-benzylamine (270 mg; 0.55 mmol), 1-trifluoromethyl-cyclopropanecarboxylic acid (85 mg; 0.55 mmol), HBTU (209 mg; 0.55 mmol), TEA (111 mg; 1.10 mmol) and DMF (5 mL)

Yield: 79 mg (23%). HPLC-method O: $R_t$=11.47 min. MS m/z: 626 [M+H]$^+$.

Example 116

N-{4-Chloro-5-fluoro-3-[5-chloro-1-methyl-6-(4-trifluoromethyl-piperidin-1-yl)-1H-benzimidazol-2-ylamino]-benzyl}-1-trifluoromethyl-cyclopropanamide

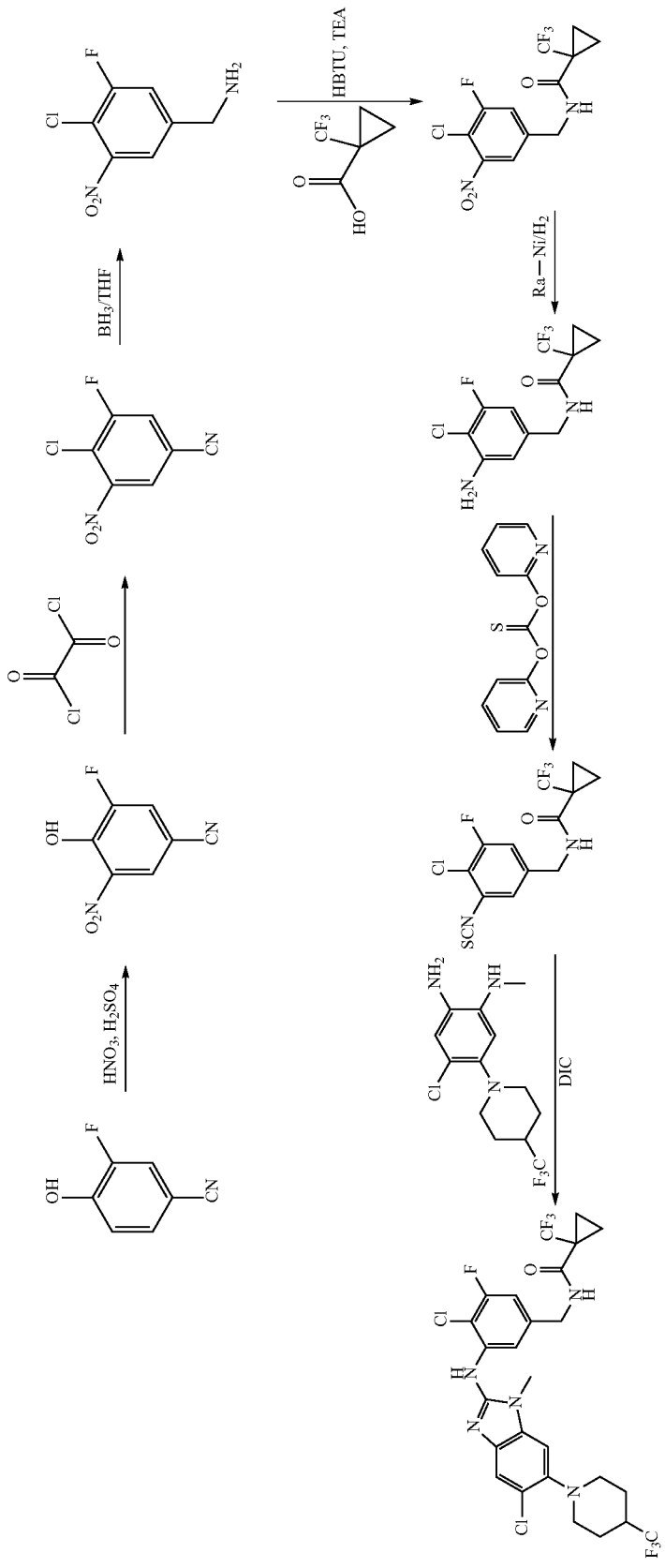

(a) 3-Fluoro-4-hydroxy-5-nitro-benzonitrile

Fuming HNO$_3$ (1.8 mL; 44 mmol) was added dropwise to a solution of 3-fluoro-4-hydroxybenzonitrile (4.0 g; 29 mmol) in conc. H$_2$SO$_4$ (10 mL) at −10° C. The mixture was stirred at −10° C. for 1 h and thereafter slowly poured into ice. The precipitate was filtered off and the filtrate was extracted with EtOAc. The organic layer was dried over Na$_2$SO$_4$, filtered and concentrated. The residue was combined with the precipitate and crystallized from EtOAc/PE to give the sub-title compound.
Yield: 3.9 g (73%).

(b) 4-Chloro-3-fluoro-5-nitro-benzonitrile

Oxalyl chloride (5.44 g; 42.8 mmol) was added dropwise to a solution of 3-fluoro-4-hydroxy-5-nitrobenzonitrile (3.9 g; 21 mmol) in DMF (40 mL) at −25° C. The mixture was stirred at −25° C. for 15 min and thereafter at 80° C. for 2.5 h. The mixture was slowly poured into ice, the precipitate was filtered off and the filtrate was extracted with EtOAc. The organic layer was dried over Na$_2$SO$_4$, filtered and concentrated. The residue was combined with the precipitate and filtered through a plug of silica gel to give the sub-title compound.
Yield: 2.44 g (56%).

(c) 4-Chloro-3-fluoro-5-nitro-benzylamine

A solution of BH$_3$/THF (7.5 mL; 7.5 mmol) was added dropwise to a solution of 4-chloro-3-fluoro-5-nitrobenzonitrile (750 mg; 3.74 mmol) in THF (5 mL) at 0° C. The mixture was stirred at 0° C. for 3 h, it was acidified to pH ~1 and stirred at rt for 1 h and then basicified to pH ~8 and extracted with EtOAc. The organic layer was dried over Na$_2$SO$_4$, filtered and concentrated. The residue was dissolved in Et$_2$O and precipitated with PE to give the sub-title compound.
Yield: 761 mg (99%).

(d) N-(4-Chloro-3-fluoro-5-nitro-benzyl)-1-trifluoromethyl-cyclopropanecarboxamide The sub-title compound was prepared in analogy to the procedure in Example 94, step (c) using 4-chloro-3-fluoro-5-nitro-benzylamine (761 mg; 3.72 mmol), 1-trifluoromethyl-cyclopropanecarboxylic acid (573 mg; 3.72 mmol), HBTU (1.41 g; 3.72 mmol), TEA (753 mg; 7.44 mmol) and DMF (10 mL).
Yield: 980 mg (77%).

(e) N-(3-Amino-4-chloro-5-fluoro-benzyl)-1-trifluoromethyl-cyclopropanecarboxamide H$_2$ was passed through a shaken mixture of N-(4-chloro-3-fluoro-5-nitrobenzyl)-1-trifluoromethyl-cyclopropanecarboxamide (980 mg, 2.88 mmol), Ra—Ni (17 mg, 0.29 mmol) and THF (50 mL) at rt for 1.5 h. The mixture was filtered through celite and concentrated.
Yield: 800 mg (89%).

(f) N-(4-Chloro-5-fluoro-3-isothiocyanatobenzyl)-1-trifluoromethyl-cyclopropane carboxamide The sub-title compound was prepared in analogy to Example 105, step (a) using N-(3-amino-4-chloro-5-fluorobenzyl)-1-trifluoromethyl-cyclopropanecarboxamide (800 mg, 2.57 mmol), di-(2-pyridyl)thionocarbonate (897 mg, 3.86 mmol) and THF (20 mL).
Yield: 211 mg (23%).

(g) N-{4-Chloro-5-fluoro-3-[5-chloro-1-methyl-6-(4-trifluoromethyl-piperidin-1-yl)-1H-benzimidazol-2-ylamino]-benzyl}-1-trifluoromethyl-cyclopropanamide The title compound was prepared in analogy to the procedure in Example 76 using N-(4-chloro-5-fluoro-3-isothiocyanatobenzyl)-1-trifluoromethyl-cyclopropane carboxamide (211 mg; 0.60 mmol), 5-chloro-2-methylamino-4-(4-trifluoromethyl-piperidin-1-yl)aniline (184 mg; 0.60 mmol), DIC (78 mg; 0.60 mmol) and DMF (4 mL).
Yield: 75 mg (20%). HPLC-method O: R$_t$=11.80 min. MS m/z: 626 [M+H]$^+$.

Example 117

N-{3-(5-Cyano-6-[3-trifluoromethyl-piperidin-1-yl)-1H-benzo[d]imidazol-2-ylamino]-4-trifluoromethoxy-benzyl}-2,2-dimethyl-propionamide

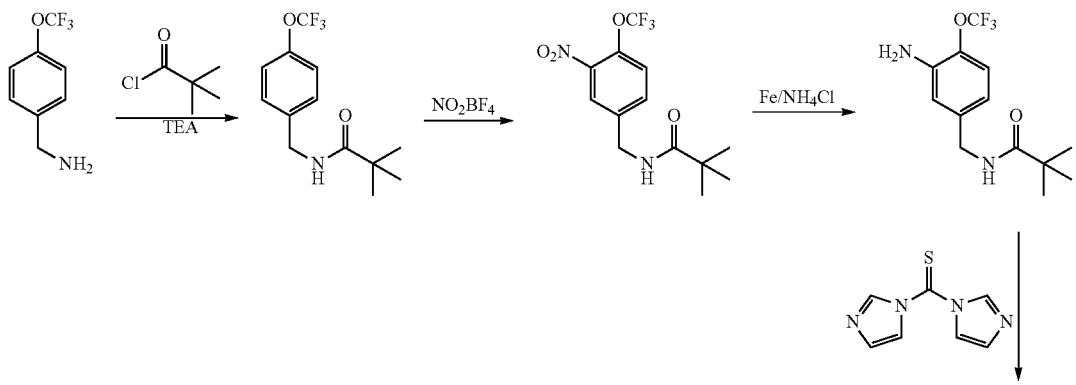

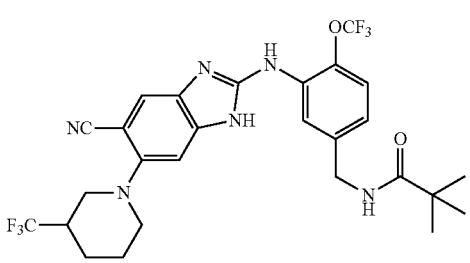 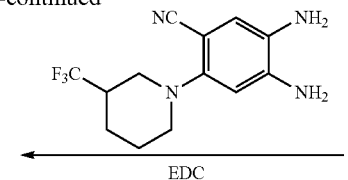 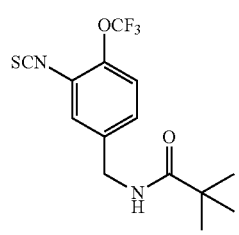

(a) N-(4-Trifluoromethoxy-benzyl)-2,2-dimethyl-propionamide

A solution of pivaloyl chloride (2.1 mL, 17 mmol) in MeCN (10 mL) was added dropwise over 10 min to a solution of 4-trifluoromethoxy-benzylamine (2.6 mL, 17 mmol) and TEA (4.0 mL, 29 mmol) in MeCN (20 mL) at 0° C. The mixture was stirred for 30 min, filtered and concentrated. The residue was treated with water and filtration gave the sub-title compound.

Yield: 4.12 g (88%).

(b) N-(3-Nitro-4-trifluoromethoxy-benzyl)-2,2-dimethyl-propionamide

Nitronium tetrafluoroborate (3.97 g, 29.9 mmol) was added in portions over 5 min to N-(4-trifluoromethoxy-benzyl)-2,2-dimethyl-propionamide (4.1 g, 15 mmol) in MeNO$_2$ (35 mL) and the mixture was stirred at rt for 1 h. The mixture was treated with ice and Et$_2$O was added. The organic layer was dried over Na$_2$SO$_4$, filtered and concentrated. The residue was treated with PE and the sub-title compound was filtered off.

Yield: 3.40 g (71%).

(c) N-(3-Amino-4-trifluoromethoxy-benzyl)-2,2-dimethyl-propionamide

A mixture of N-(3-nitro-4-trifluoromethoxy-benzyl)-2,2-dimethyl-propionamide (3.4 g, 11 mmol), Fe (3.7 g, 66 mmol), saturated aqueous NH$_4$Cl-solution (35 mL) and EtOH (170 mL) was refluxed for 30 min. The mixture was concentrated, treated with water and the pH was adjusted to ~8. The mixture was extracted with EtOAc and the organic layer was dried over Na$_2$SO$_4$, filtered and concentrated. The residue was treated with PE and the sub-title compound was filtered off. Yield: 2.7 g (88%).

(d) N-(3-Isothiocyanato-4-trifluoromethoxy-benzyl)-2,2-dimethyl-propionamide A mixture of N-(3-amino-4-trifluoromethoxy-benzyl)-2,2-dimethyl-propionamide (200 mg, 0.69 mmol), TCDI (133 mg, 0.746 mmol) and MeCN (3 mL) was refluxed for 1 h. Concentration and purification by column chromatography gave the sub-title compound.

Yield: 135 mg (59%).

N-{3-[5-Cyano-6-(3-trifluoromethyl-piperidin-1-yl)-1H-benzo[d]imidazol-2-ylamino]-4-trifluoromethoxy-benzyl}-2,2-dimethyl-propionamide A mixture of N-(3-isothiocyanato-4-trifluoromethoxy-benzyl)-2,2-dimethyl-propionamide (135 mg, 0.406 mmol), 4,5-diamino-2-(3-trifluoromethyl-piperidin-1-yl)benzonitrile (115 mg, 0.406 mmol) and DMF (2 mL) was stirred at rt for 4 h. EDC (101 mg, 0.527 mmol) was added and mixture was stirred at rt overnight. The mixture was treated with water and extracted with Et$_2$O. Concentration and purification by column chromatography gave an oil. The oil was treated with CHCl$_3$ and the precipitate was collected by filtration.

Yield: 52 mg (22%). HPLC-method N: R$_t$=14.60 min. MS m/z: 583 [M+H]$^+$.

Example 133

(S)—N-{4-Chloro-3-[5-chloro-6-(2-methoxymethyl-pyrrolidin-1-yl)-1H-benzo[d]imidazol-2-ylamino] benzyl}-1-trifluoromethyl-cyclopropanecarboxamide

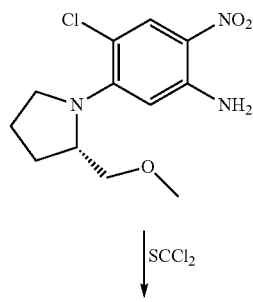

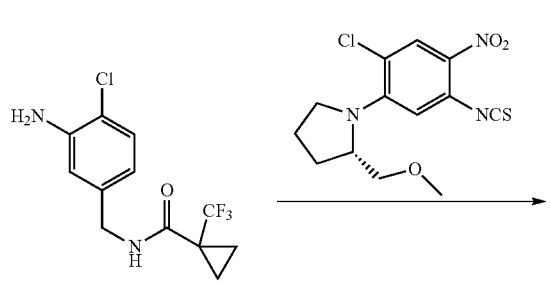
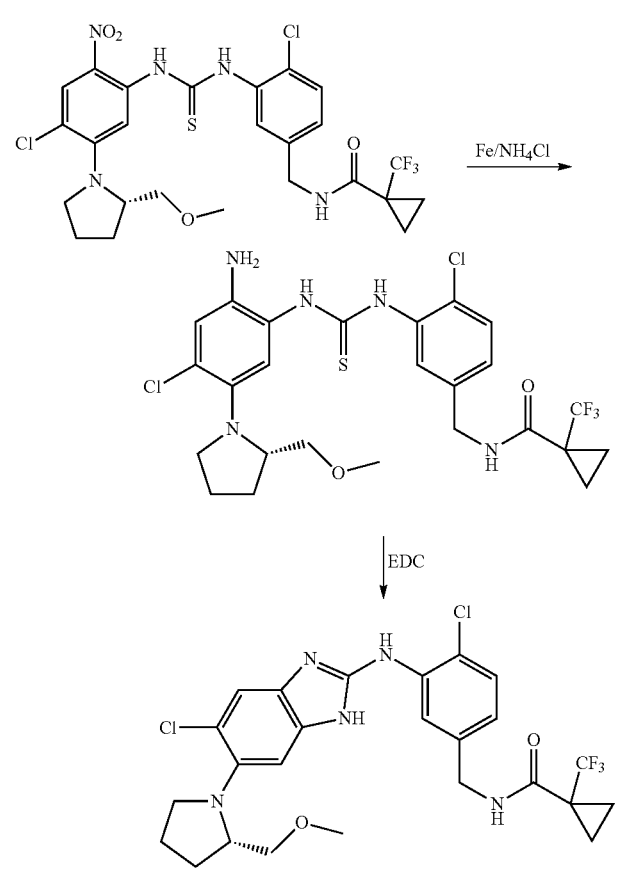

(a) (S)-5-Chloro-2-isothiocyanato-4-(2-(methoxymethyl)pyrrolidin-1-yl)-nitrobenzene A mixture of (S)-4-chloro-5-(2-(methoxymethyl)pyrrolidin-1-yl)-2-nitroaniline (200 mg; 0.70 mmol), NaHCO$_3$ (588 mg; 7.00 mmol), CH$_2$Cl$_2$ (7 mL) and SCCl$_2$ (402 mg; 3.50 mmol) was stirred at rt overnight and concentrated and the residue was purified by column chromatography. Yield: 170 mg (74%).

(b) (S)—N-(4-Chloro-3-(3-(4-chloro-5-(2-(methoxymethyl)pyrrolidin-1-yl)-2-nitrophenyl)thioureido)benzyl)-1-(trifluoromethyl)cyclopropanecarboxamide A mixture of N-(3-amino-4-chlorobenzyl)-1-(trifluoromethyl)cyclopropanecarboxamide (150 mg; 0.51 mmol), (S)-5-chloro-2-isothiocyanato-4-(2-(methoxymethyl)pyrrolidin-1-yl)-nitrobenzene (169 mg; 0.51 mmol) and DMF (3 mL) was stirred at rt overnight. The mixture was poured into brine and extracted with CH$_2$Cl$_2$. The organic layer was dried over Na$_2$SO$_4$, filtered and concentrated. The residue was washed with Et$_2$O to give the sub-title compound.
Yield: 145 mg (46%).

(c) (S)—N-(3-(3-(2-Amino-4-chloro-5-(2-(methoxymethyl)pyrrolidin-1-yl)phenyl)thioureido)-4-chlorobenzyl)-1-(trifluoromethyl)cyclopropanecarboxamide A mixture of (S)—N-(4-chloro-3-(3-(4-chloro-5-(2-(methoxymethyl)pyrrolidin-1-yl)-2-nitrophenyl)thioureido)benzyl)-1-(trifluoromethyl)cyclopropanecarboxamide (145 mg; 0.23 mmol), Fe (65 mg; 1.2 mmol), saturated aqueous NH$_4$Cl-solution (3 mL) and EtOH (3 mL) was stirred at 90° C. for 2 h. The mixture was basicified to pH-9-10 and filtered through celite. The celite pad was washed with EtOH and EtOAc. The mixture was concentrated and the residue was extracted with EtOAc. The organic layer was dried over Na$_2$SO$_4$, filtered and concentrated. The residue was washed with Et$_2$O to give the sub-title compound.
Yield: 110 mg (81%).

(d) (S)—N-(4-Chloro-3-(5-chloro-6-(2-(methoxymethyl)pyrrolidin-1-yl)-1H-benzo[d]imidazol-2-ylamino)benzyl)-1-(trifluoromethyl)cyclopropanecarboxamide A mixture of (S)—N-(3-(3-(2-amino-4-chloro-5-(2-(methoxymethyl)pyrrolidin-1-yl)phenyl)thioureido)-4-chlorobenzyl)-1-(trifluoromethyl)cyclopropanecarboxamide (110 mg; 0.19 mmol), EDC (36 mg; 0.19 mmol) and DMF (4 mL) was stirred at 90° C. overnight. The mixture was poured into brine and extracted with CH$_2$Cl$_2$. The organic layer was dried over Na$_2$SO$_4$, filtered and concentrated and the residue was purified by column chromatography.
Yield: 29 mg (27%). HPLC-method N: R$_t$=12.10 min. MS m/z: 556 [M+H]$^+$.

The following examples were prepared in analogy to the indicated methods described above using the appropriate building blocks.

| Ex. | Structure | Formula/Mw. | MS* m/z [M + H]+ | Rf (TLC) or Rt [min] (HPLC-method) | Prepared in analogy to example |
|---|---|---|---|---|---|
| 13 | 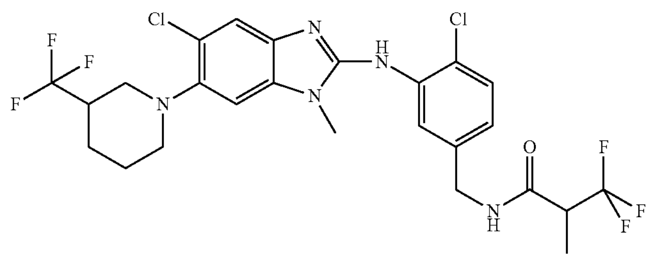 [SMILES: CC(C(=O)NCc1ccc(Cl)c(Nc2nc3cc(Cl)c(N4CCCC(C(F)(F)F)C4)cc3n2C)c1)C(F)(F)F] | C25H25Cl2F6N5O 596.39 | 596 | Rt = 2.31 (method C) | 12 |
| 14 | 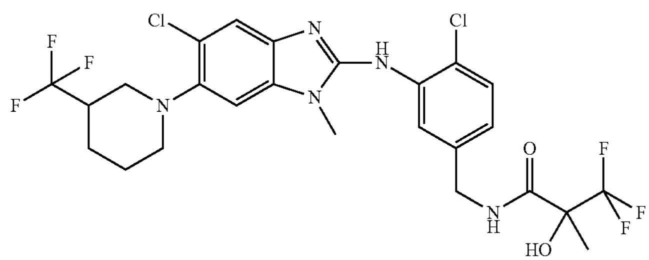 [SMILES: Cn1c(Nc2cc(CNC(=O)C(C)(O)C(F)(F)F)ccc2Cl)nc2cc(Cl)c(N3CCCC(C(F)(F)F)C3)cc21] | C25H25Cl2F6N5O2 612.39 | 612 | Rt: 2.56 (method K) | 12 |
| 15 | 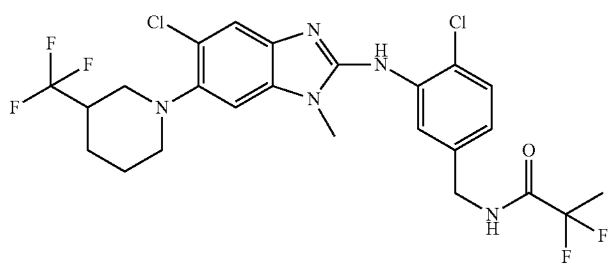 [SMILES: Cn1c(Nc2cc(CNC(=O)C(C)(F)F)ccc2Cl)nc2cc(Cl)c(N3CCCC(C(F)(F)F)C3)cc21] | C24H24Cl2F5N5O 564.38 | 564 | Rt: 2.78 (method D) | 12 |
| 16 | 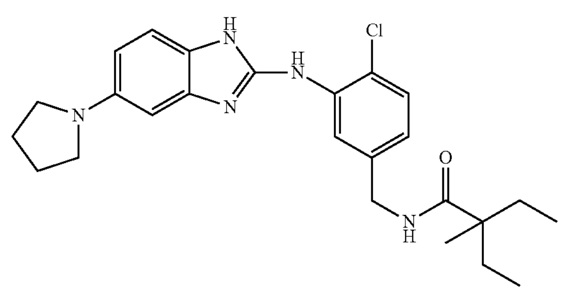 [SMILES: CCC(C)(CC)C(=O)NCc1ccc(Cl)c(Nc2nc3cc(N4CCCC4)ccc3[nH]2)c1] | C25H32ClN5O 454.02 | 454 | Rt: 1.66 (method L) | 1(i) |
| 17 | 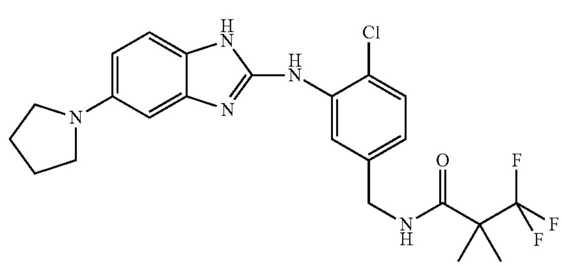 [SMILES: CC(C)(C(=O)NCc1ccc(Cl)c(Nc2nc3cc(N4CCCC4)ccc3[nH]2)c1)C(F)(F)F] | C25H25ClF3N5O 479.93 | 480 | Rt: 1.62 (method L) | 1(i) |

-continued

| Ex. | Structure | Formula/Mw. | MS* m/z [M + H]+ | Rf (TLC) or Rt [min] (HPLC- method) | Prepared in analogy to example |
|---|---|---|---|---|---|
| 18 | 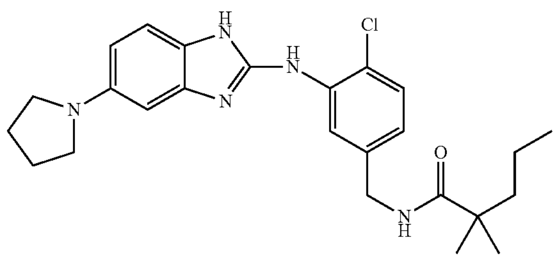 [SMILES: CCCC(C)(C)C(=O)NCc1ccc(Cl)c(Nc2nc3cc(N4CCCC4)ccc3[nH]2)c1] | C25H32ClN5O 454.02 | 454 | Rt: 1.69 (method L) | 1(i) |
| 19 | 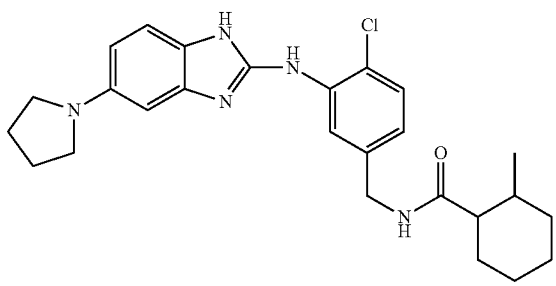 [SMILES: CC1CCCCC1C(=O)NCc1ccc(Cl)c(Nc2nc3cc(N4CCCC4)ccc3[nH]2)c1] | C26H32ClN5O 466.03 | 466 | Rt: 1.67 (method L) | 1(i) |
| 20 | 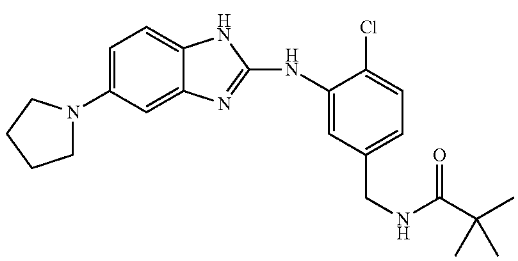 [SMILES: CC(C)(C)C(=O)NCc1ccc(Cl)c(Nc2nc3cc(N4CCCC4)ccc3[nH]2)c1] | C23H28ClN5O 425.96 | 426 | Rt: 1.51 (method L) | 1(i) |
| 21 | 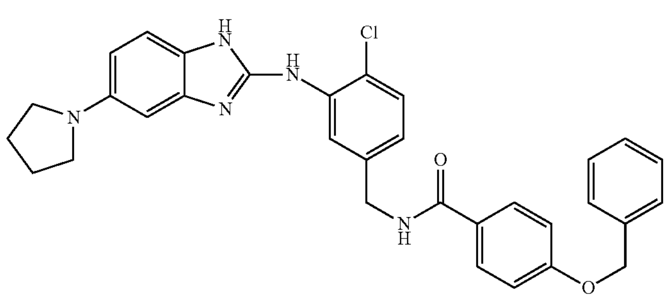 [SMILES: O=C(NCc1ccc(Cl)c(Nc2nc3cc(N4CCCC4)ccc3[nH]2)c1)c1ccc(OCc2ccccc2)cc1] | C32H30ClN5O2 552.08 | 552 | Rt: 1.78 (method L) | 1(i) |
| 22 | 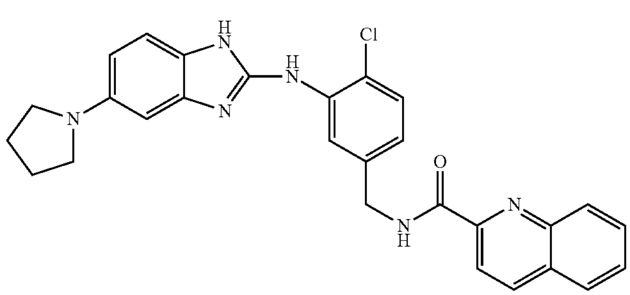 [SMILES: O=C(NCc1ccc(Cl)c(Nc2nc3cc(N4CCCC4)ccc3[nH]2)c1)c1ccc2ccccc2n1] | C28H25ClN6O 497.00 | 497 | Rt: 1.66 (method L) | 1(i) |

-continued

| Ex. | Structure | Formula/Mw. | MS* m/z [M + H]+ | Rf (TLC) or Rt [min] (HPLC-method) | Prepared in analogy to example |
|---|---|---|---|---|---|
| 24 | 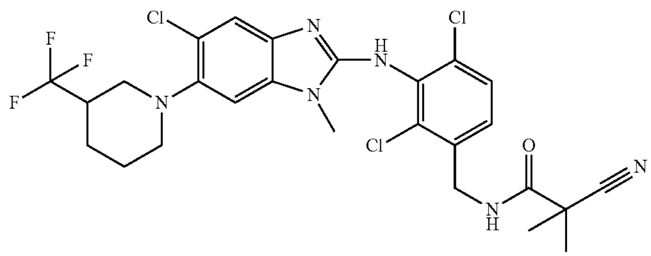 [SMILES: Cn1c(Nc2c(Cl)ccc(CNC(=O)C(C)(C)C#N)c2Cl)nc2cc(Cl)c(N3CCCC(C(F)(F)F)C3)cc21] | $C_{27}H_{27}Cl_3F_3N_5O$ 600.9 | 600 | Rt: 1.68 (method Q) | 23 |
| 25 | 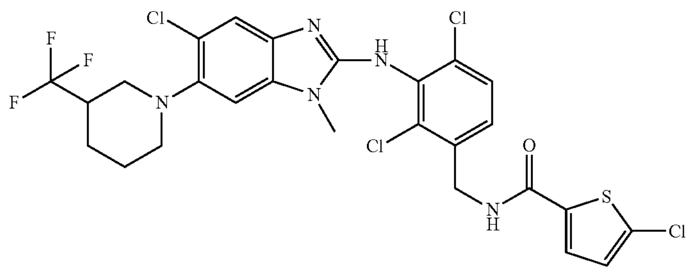 [SMILES: Cn1c(Nc2c(Cl)ccc(CNC(=O)c3ccc(Cl)s3)c2Cl)nc2cc(Cl)c(N3CCCC(C(F)(F)F)C3)cc21] | $C_{26}H_{22}Cl_4F_3N_5OS$ 651.37 | 650 | Rt: 1.77 (method Q) | 23 |
| 26 | 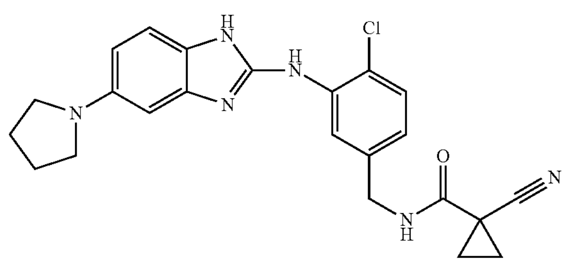 [SMILES: N#CC1(C(=O)NCc2ccc(Cl)c(Nc3nc4cc(N5CCCC5)ccc4[nH]3)c2)CC1] | $C_{23}H_{23}ClN_6O$ 434.93 | 435 | Rt: 1.46 (method L) | 1(i) |
| 27 | 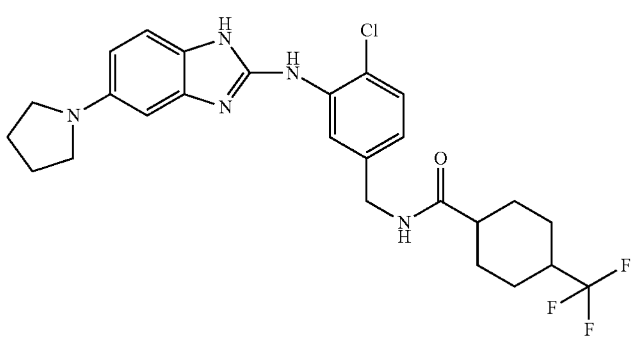 [SMILES: O=C(NCc1ccc(Cl)c(Nc2nc3cc(N4CCCC4)ccc3[nH]2)c1)C1CCC(C(F)(F)F)CC1] | $C_{26}H_{29}ClF_3N_5O$ 520.00 | 520 | Rt: 1.68 (method L) | 1(i) |
| 28 | 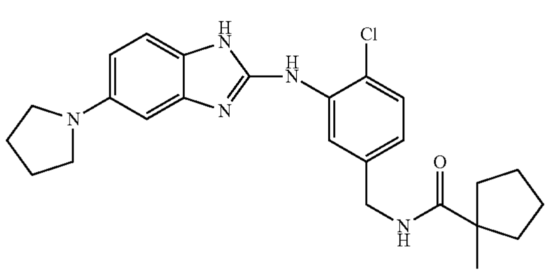 [SMILES: CC1(C(=O)NCc2ccc(Cl)c(Nc3nc4cc(N5CCCC5)ccc4[nH]3)c2)CCCC1] | $C_{25}H_{30}ClN_5O$ 452.00 | 452 | Rt: 1.62 (method L) | 1(i) |

-continued

| Ex. | Structure | Formula/Mw. | MS* m/z [M + H]+ | Rf (TLC) or Rt [min] (HPLC-method) | Prepared in analogy to example |
|---|---|---|---|---|---|
| 29 | 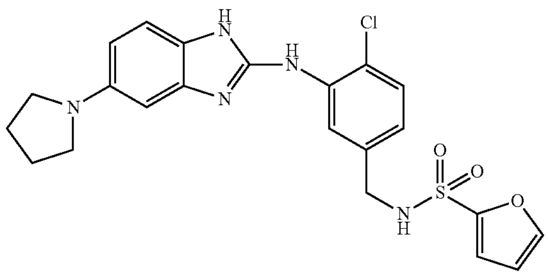 [SMILES: O=S(=O)(NCc1ccc(Cl)c(Nc2nc3cc(N4CCCC4)ccc3[nH]2)c1)c1ccco1] | $C_{22}H_{22}ClN_5O_3S$ 471.97 | 472 | Rt: 1.54 (method L) | 30 |
| 31 | 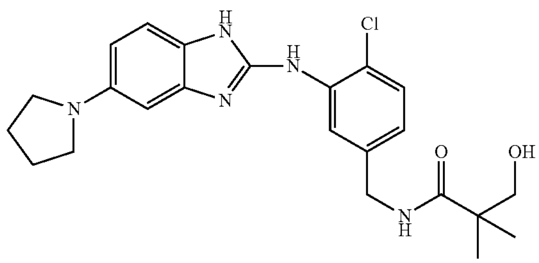 [SMILES: CC(C)(CO)C(=O)NCc1ccc(Cl)c(Nc2nc3cc(N4CCCC4)ccc3[nH]2)c1] | $C_{23}H_{28}ClN_5O_2$ 441.96 | 442 | Rt: 1.40 (method L) | 1(i) |
| 32 | 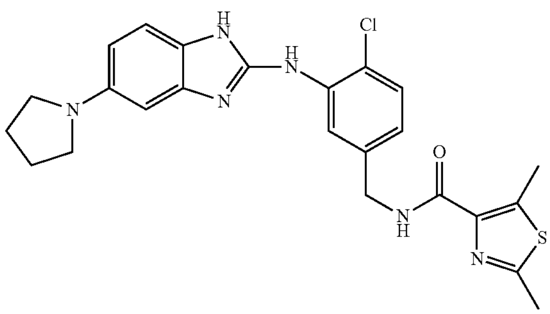 [SMILES: Cc1nc(C(=O)NCc2ccc(Cl)c(Nc3nc4cc(N5CCCC5)ccc4[nH]3)c2)c(C)s1] | $C_{24}H_{25}ClN_6OS$ 481.02 | 481 | Rt: 1.47 (method L) | 1(i) |
| 34 | 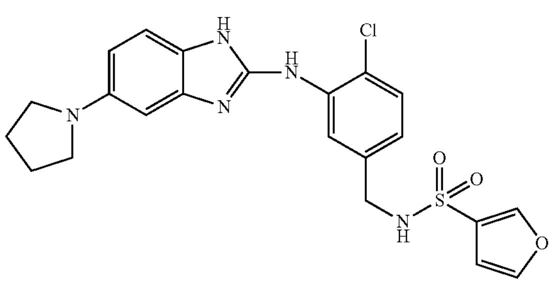 [SMILES: O=S(=O)(NCc1ccc(Cl)c(Nc2nc3cc(N4CCCC4)ccc3[nH]2)c1)c1ccoc1] | $C_{22}H_{22}ClN_5O_3S$ 471.97 | 472 | Rt: 1.53 (method L) | 30 |
| 35 | 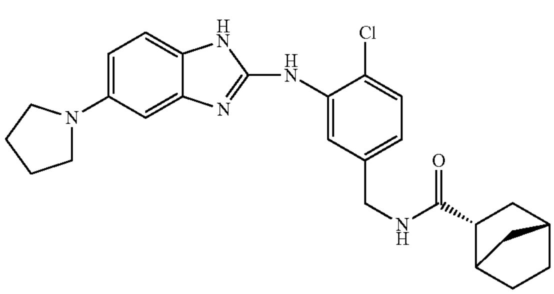 [SMILES: O=C(NCc1ccc(Cl)c(Nc2nc3cc(N4CCCC4)ccc3[nH]2)c1)[C@@H]1C[C@@H]2CCC1C2] | $C_{26}H_{30}ClN_5O$ 464.01 | 464 | Rt: 1.64 (method L) | 1(i) |

-continued

| Ex. | Structure | Formula/Mw. | MS* m/z [M + H]+ | Rf (TLC) or Rt [min] (HPLC-method) | Prepared in analogy to example |
|---|---|---|---|---|---|
| 36 | 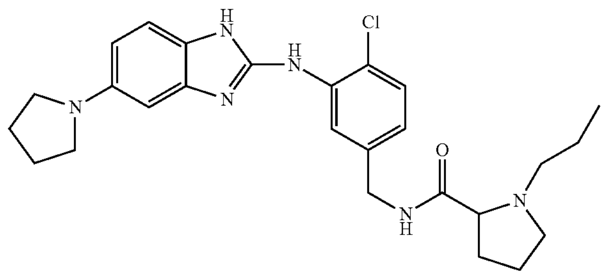 [SMILES: CCCN1CCCC1C(=O)NCc1ccc(Cl)c(Nc2nc3cc(N4CCCC4)ccc3[nH]2)c1] | C26H33ClN6O 481.04 | 480 | Rt: 1.33 (method L) | 1(i) |
| 37 | 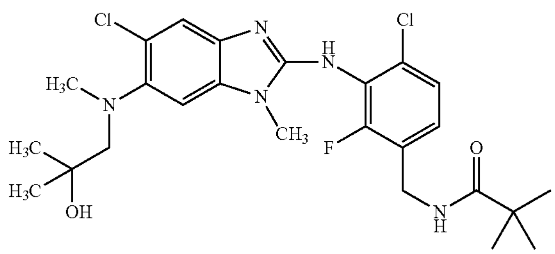 [SMILES: CN(CC(C)(C)O)c1cc2c(cc1Cl)nc(Nc1c(Cl)ccc(CNC(=O)C(C)(C)C)c1F)n2C] | C25H32Cl2FN5O2 524.46 | 524 | Rf: 0.3 (silica; DCM: EtOH 95:5) | 33 |
| 38 | 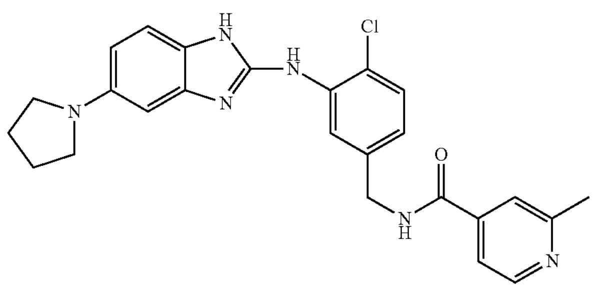 [SMILES: Cc1cc(C(=O)NCc2ccc(Cl)c(Nc3nc4cc(N5CCCC5)ccc4[nH]3)c2)ccn1] | C25H25ClN6O 460.97 | 460 | Rt: 1.31 (method L) | 1(i) |
| 39 | 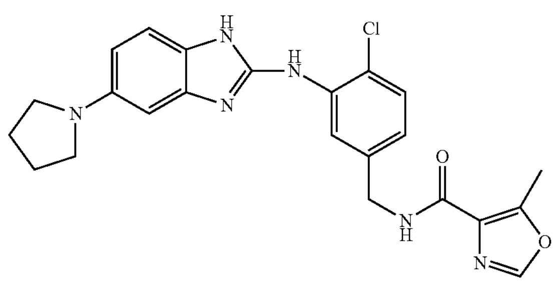 [SMILES: Cc1ocnc1C(=O)NCc1ccc(Cl)c(Nc2nc3cc(N4CCCC4)ccc3[nH]2)c1] | C23H23ClN6O2 450.93 | 451 | Rt: 1.48 (method L) | 1(i) |
| 41 | 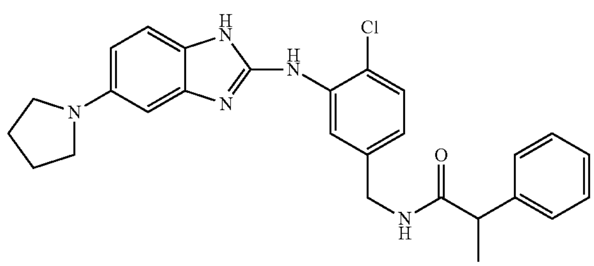 [SMILES: CC(C(=O)NCc1ccc(Cl)c(Nc2nc3cc(N4CCCC4)ccc3[nH]2)c1)c1ccccc1] | C27H28ClN5O 474.01 | 474 | Rt: 1.62 (method L) | 1(i) |

-continued

| Ex. | Structure | Formula/Mw. | MS* m/z [M + H]+ | Rf (TLC) or Rt [min] (HPLC-method) | Prepared in analogy to example |
|---|---|---|---|---|---|
| 42 | 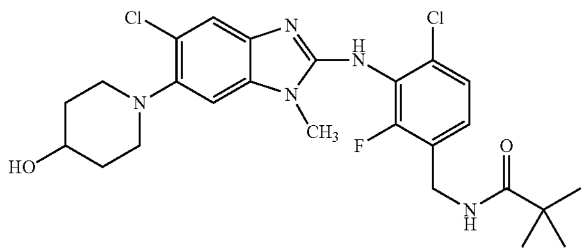 [SMILES: Cn1c(Nc2c(Cl)ccc(CNC(=O)C(C)(C)C)c2F)nc2cc(Cl)c(N3CCC(O)CC3)cc21] | C25H30Cl2FN5O2 522.442 | 522 | Rt: 1.20 (method G) | 33 |
| 43 | 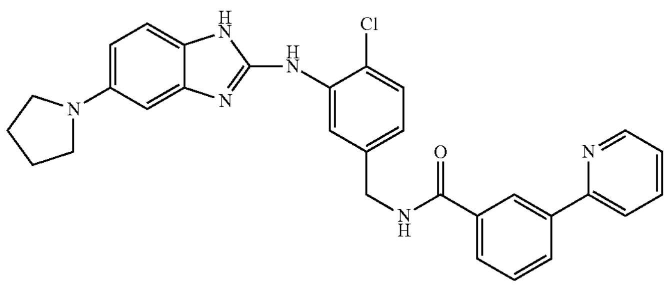 [SMILES: O=C(NCc1ccc(Cl)c(Nc2nc3cc(N4CCCC4)ccc3[nH]2)c1)c1cccc(-c2ccccn2)c1] | C30H27ClN6O 523.04 | 523 | Rt: 1.40 (method L) | 1(i) |
| 44 | 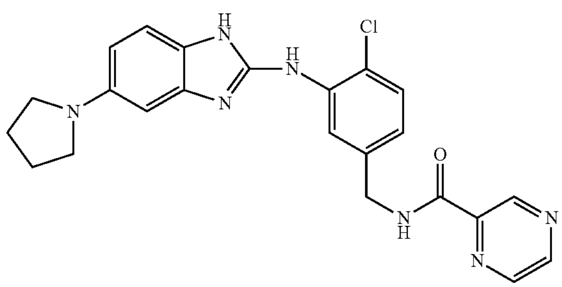 [SMILES: O=C(NCc1ccc(Cl)c(Nc2nc3cc(N4CCCC4)ccc3[nH]2)c1)c1cnccn1] | C23H22ClN7O 447.93 | 448 | Rt: 1.40 (method L) | 1(i) |
| 45 | 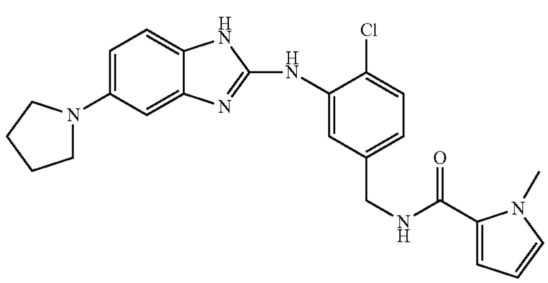 [SMILES: Cn1cccc1C(=O)NCc1ccc(Cl)c(Nc2nc3cc(N4CCCC4)ccc3[nH]2)c1] | C24H25ClN6O 448.96 | 449 | Rt: 1.54 (method L) | 1(i) |
| 46 | 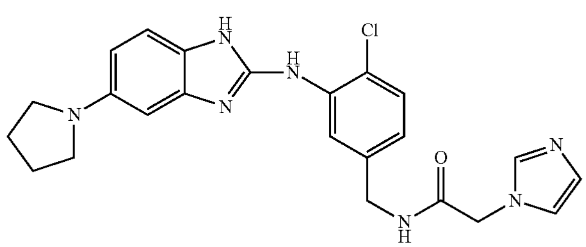 [SMILES: O=C(Cn1ccnc1)NCc1ccc(Cl)c(Nc2nc3cc(N4CCCC4)ccc3[nH]2)c1] | C23H24ClN7O 449.94 | 448 | Rt: 0.32 (method L) | 1(i) |

-continued

| Ex. | Structure | Formula/Mw. | MS* m/z [M + H]+ | Rf (TLC) or Rt [min] (HPLC-method) | Prepared in analogy to example |
|---|---|---|---|---|---|
| 47 | 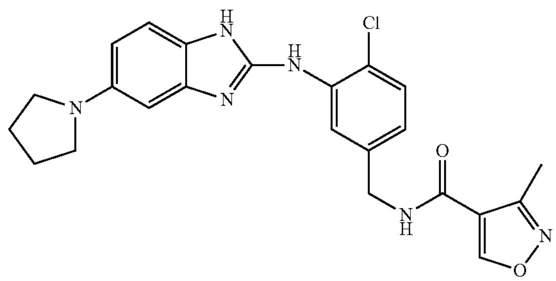 [SMILES: Cc1nocc1C(=O)NCc1ccc(Cl)c(Nc2nc3cc(N4CCCC4)ccc3[nH]2)c1] | C23H23ClN6O2 450.93 | 451 | Rt: 0.60 (method L) | 1(i) |
| 48 | 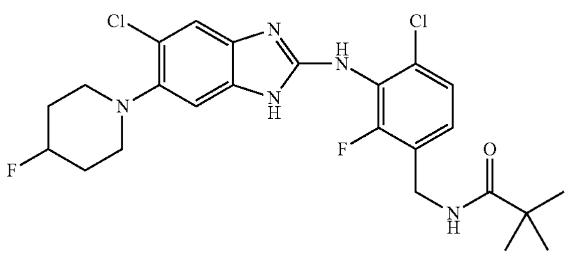 [SMILES: CC(C)(C)C(=O)NCc1ccc(Cl)c(Nc2nc3cc(Cl)c(N4CCC(F)CC4)cc3[nH]2)c1F] | C24H27Cl2F2N5O 510.408 | 510 | Rt: 1.41 (method G) | 33 |
| 49 | 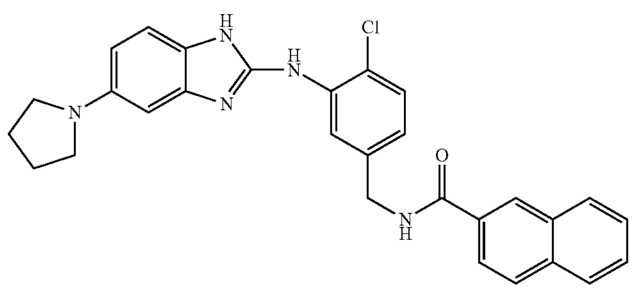 [SMILES: O=C(NCc1ccc(Cl)c(Nc2nc3cc(N4CCCC4)ccc3[nH]2)c1)c1ccc2ccccc2c1] | C29H26ClN5O 496.01 | 496 | $R_r$: 1.74 (method L) | 1(i) |
| 50 | 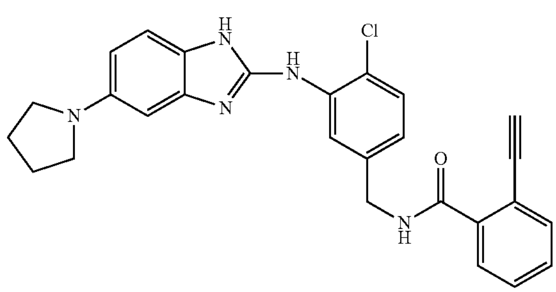 [SMILES: C#Cc1ccccc1C(=O)NCc1ccc(Cl)c(Nc2nc3cc(N4CCCC4)ccc3[nH]2)c1] | C27H24ClN5O 469.97 | 470 | $R_r$: 0.68 (method L) | 1(i) |
| 51 | 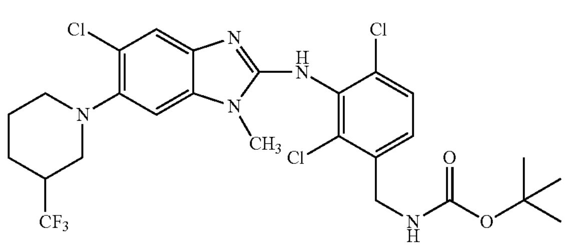 [SMILES: Cn1c(Nc2c(Cl)ccc(CNC(=O)OC(C)(C)C)c2Cl)nc2cc(Cl)c(N3CCCC(C(F)(F)F)C3)cc21] | C26H29Cl3F3N5O2 606.894 | 606 | $R_r$: 2.37 (method A) | 1 |

-continued

| Ex. | Structure | Formula/Mw. | MS* m/z [M + H]+ | Rf (TLC) or Rt [min] (HPLC-method) | Prepared in analogy to example |
|---|---|---|---|---|---|
| 52 | 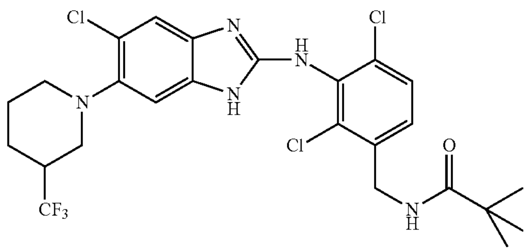 [SMILES: CC(C)(C)C(=O)NCc1ccc(Cl)c(Nc2nc3cc(Cl)c(N4CCCC(C(F)(F)F)C4)cc3[nH]2)c1Cl] | C25H27Cl3F3N5O 576.87 | 576 | | 5 |
| 53 | 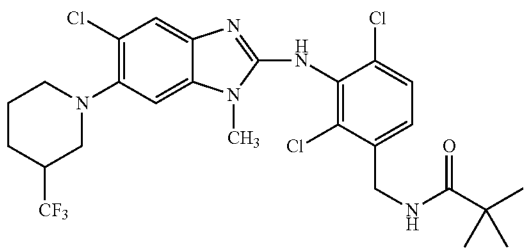 [SMILES: Cn1c(Nc2c(Cl)ccc(CNC(=O)C(C)(C)C)c2Cl)nc2cc(Cl)c(N3CCCC(C(F)(F)F)C3)cc21] | C26H29Cl3F3N5O 590.90 | 590 | Rt: 1.51 (method G) | 5 |
| 54 | 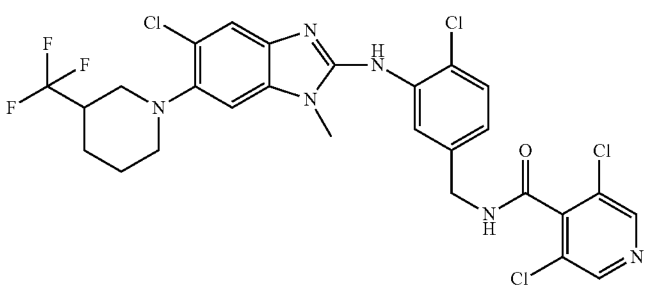 [SMILES: Cn1c(Nc2cc(CNC(=O)c3c(Cl)cncc3Cl)ccc2Cl)nc2cc(Cl)c(N3CCCC(C(F)(F)F)C3)cc21] | C27H23Cl4F3N6O 646.33 | 645 | Rt: 1.52 (method M) | 1(i) |
| 55 | 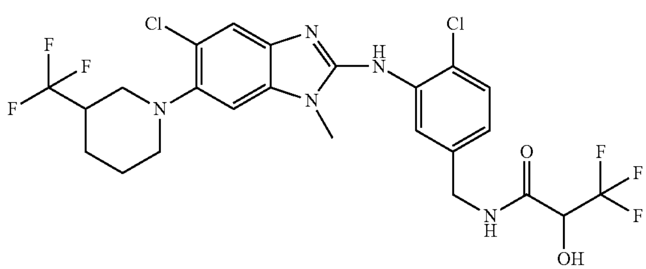 [SMILES: Cn1c(Nc2cc(CNC(=O)C(O)C(F)(F)F)ccc2Cl)nc2cc(Cl)c(N3CCCC(C(F)(F)F)C3)cc21] | C24H23Cl2F6N5O2 598.37 | 596 | Rt: 1.43 (method M) | 1(i) |
| 56 | 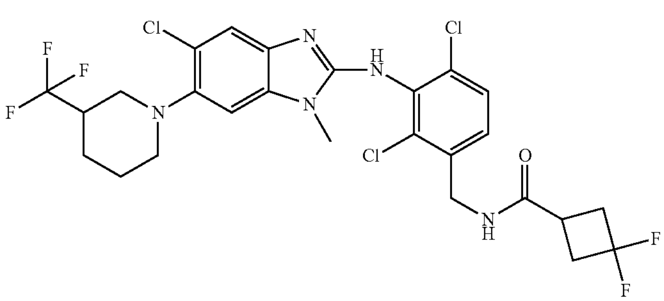 [SMILES: Cn1c(Nc2c(Cl)ccc(CNC(=O)C3CC(F)(F)C3)c2Cl)nc2cc(Cl)c(N3CCCC(C(F)(F)F)C3)cc21] | C26H25Cl3F5N5O 624.87 | 624 | Rt: 1.97 (method Q) | 1(i) |

-continued

| Ex. | Structure | Formula/Mw. | MS* m/z [M + H]+ | Rf (TLC) or Rt [min] (HPLC-method) | Prepared in analogy to example |
|---|---|---|---|---|---|
| 57 | 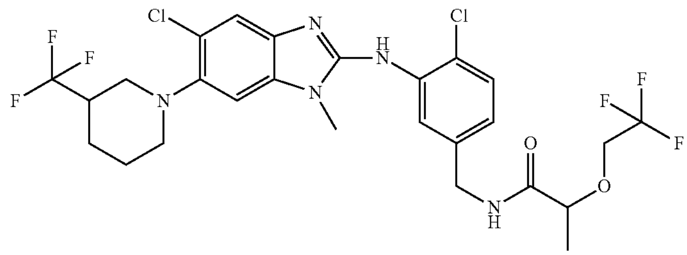 [SMILES: CC(OCC(F)(F)F)C(=O)NCc1ccc(Cl)c(Nc2nc3cc(Cl)c(N4CCCC(C(F)(F)F)C4)cc3n2C)c1] | $C_{26}H_{27}Cl_2F_6N_5O_2$ 626.43 | 626 | $R_t$: 1.93 (method L) | 1(i) |
| 58 | 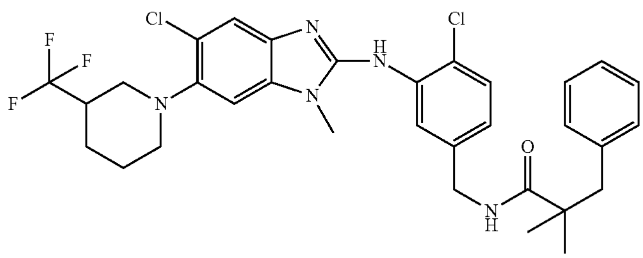 [SMILES: Cn1c(Nc2cc(CNC(=O)C(C)(C)Cc3ccccc3)ccc2Cl)nc2cc(Cl)c(N3CCCC(C(F)(F)F)C3)cc21] | $C_{32}H_{34}Cl_2F_3N_5O$ 632.56 | 632 | $R_t$: 2.03 (method L) | 1(i) |
| 59 | 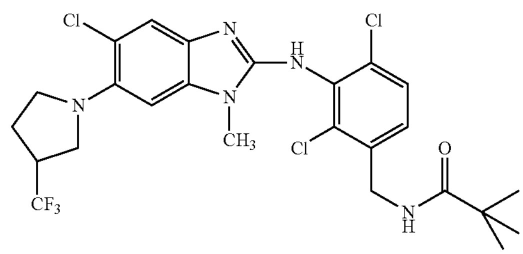 [SMILES: Cn1c(Nc2c(Cl)ccc(CNC(=O)C(C)(C)C)c2Cl)nc2cc(Cl)c(N3CCC(C(F)(F)F)C3)cc21] | $C_{25}H_{27}Cl_3F_3N_5O$ 576.87 | 576 | $R_t$: 1.50 (method G) | 5 |
| 60 | 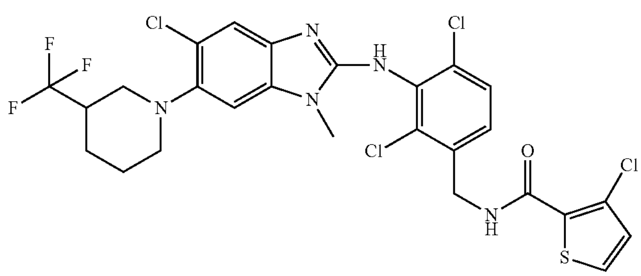 [SMILES: Cn1c(Nc2c(Cl)ccc(CNC(=O)c3sccc3Cl)c2Cl)nc2cc(Cl)c(N3CCCC(C(F)(F)F)C3)cc21] | $C_{26}H_{22}Cl_4F_3N_5OS$ 651.37 | 650 | $R_t$: 1.69 (method Q) | 23 |
| 62 | 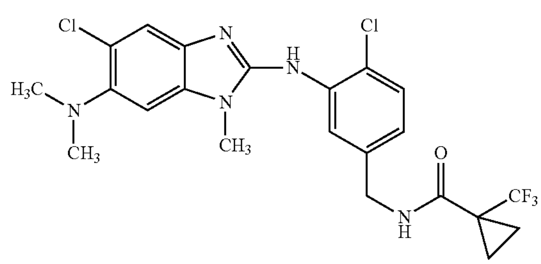 [SMILES: CN(C)c1cc2c(cc1Cl)nc(Nc1cc(CNC(=O)C3(C(F)(F)F)CC3)ccc1Cl)n2C] | $C_{22}H_{22}Cl_2F_3N_5O$ 500.34 | 500 | $R_t$: 1.54 (method J) | 71 |

-continued

| Ex. | Structure | Formula/Mw. | MS* m/z [M + H]+ | Rf (TLC) or Rt [min] (HPLC-method) | Prepared in analogy to example |
|---|---|---|---|---|---|
| 63 | 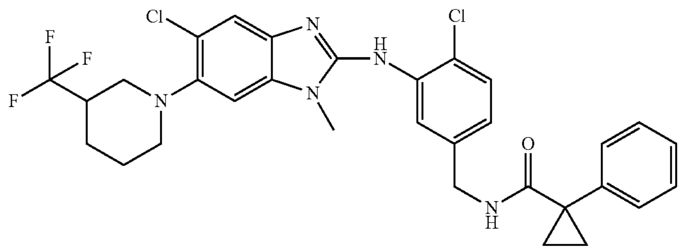 [SMILES: Cn1c(Nc2cc(CNC(=O)C3(c4ccccc4)CC3)ccc2Cl)nc2cc(Cl)c(N3CCCC(C(F)(F)F)C3)cc21] | C₃₁H₃₀Cl₂F₃N₅O 616.51 | 616 | R_t: 2.00 (method L) | 1(i) |
| 64 | 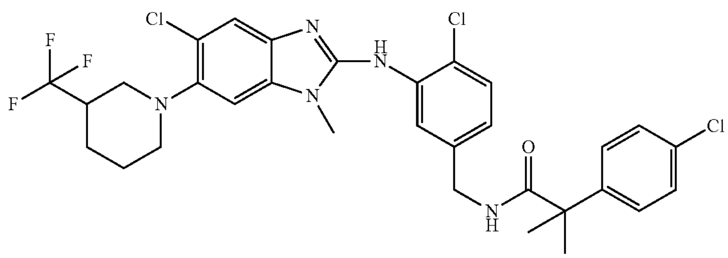 [SMILES: Cn1c(Nc2cc(CNC(=O)C(C)(C)c3ccc(Cl)cc3)ccc2Cl)nc2cc(Cl)c(N3CCCC(C(F)(F)F)C3)cc21] | C₃₁H₃₁Cl₃F₃N₅O 652.97 | 652 | R_t: 2.05 (method L) | 1(i) |
| 65 | 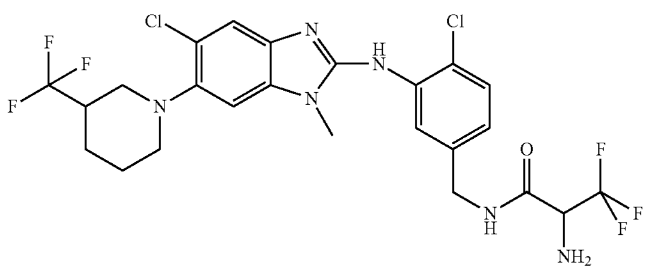 [SMILES: Cn1c(Nc2cc(CNC(=O)C(N)C(F)(F)F)ccc2Cl)nc2cc(Cl)c(N3CCCC(C(F)(F)F)C3)cc21] | C₂₄H₂₄Cl₂F₆N₆O 597.39 | 597 | R_t: 1.69 (method L) | 1(i) |
| 66 | 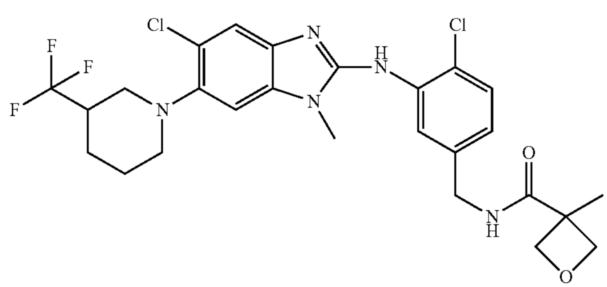 [SMILES: Cn1c(Nc2cc(CNC(=O)C3(C)COC3)ccc2Cl)nc2cc(Cl)c(N3CCCC(C(F)(F)F)C3)cc21] | C₂₆H₂₈Cl₂F₃N₅O₂ 570.44 | 570 | R_t: 1.81 (method L) | 1(i) |
| 67 | 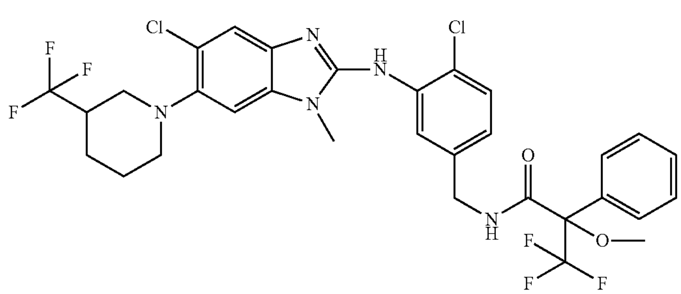 [SMILES: COC(C(=O)NCc1ccc(Cl)c(Nc2nc3cc(Cl)c(N4CCCC(C(F)(F)F)C4)cc3n2C)c1)(c1ccccc1)C(F)(F)F] | C₃₁H₂₉Cl₂F₆N₅O₂ 688.50 | 688 | R_t: 2.04 (method L) | 1(i) |

-continued

| Ex. | Structure | Formula/Mw. | MS* m/z [M + H]+ | Rf (TLC) or Rt [min] (HPLC-method) | Prepared in analogy to example |
|---|---|---|---|---|---|
| 68 | 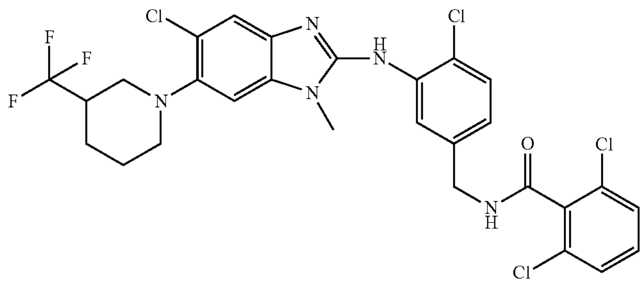 [SMILES: Cn1c(Nc2cc(CNC(=O)c3c(Cl)cccc3Cl)ccc2Cl)nc2cc(Cl)c(N3CCCC(C(F)(F)F)C3)cc21] | C28H24Cl4F3N5O 645.34 | 644 | Rt: 1.96 (method L) | 1(i) |
| 69 | 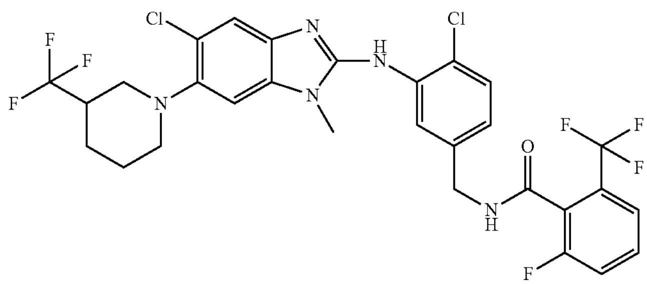 [SMILES: Cn1c(Nc2cc(CNC(=O)c3c(F)cccc3C(F)(F)F)ccc2Cl)nc2cc(Cl)c(N3CCCC(C(F)(F)F)C3)cc21] | C29H24Cl2F7N5O 662.44 | 662 | Rt: 1.96 (method L) | 1(i) |
| 72 | 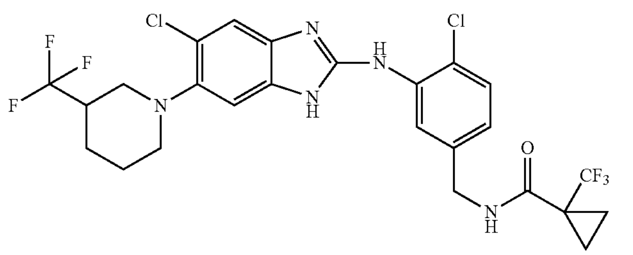 [SMILES: O=C(NCc1ccc(Cl)c(Nc2nc3cc(Cl)c(N4CCCC(C(F)(F)F)C4)cc3[nH]2)c1)C1(C(F)(F)F)CC1] | C25H23Cl2F6N5O 594.38 | 594 | Rt: 13.74 (method N) | 71 |
| 73 | 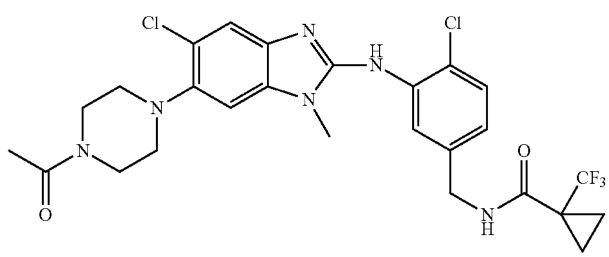 [SMILES: CC(=O)N1CCN(c2cc3c(cc2Cl)nc(Nc2cc(CNC(=O)C4(C(F)(F)F)CC4)ccc2Cl)n3C)CC1] | C26H27Cl2F3N6O2 583.43 | 583 | Rt: 11.03 (method N) | 71 |
| 74 | 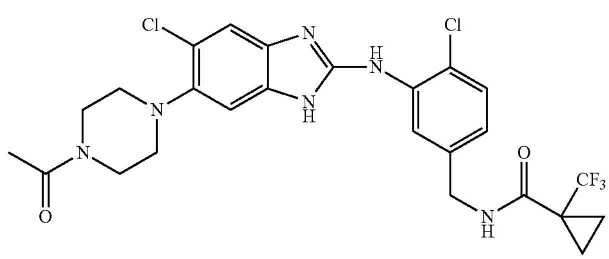 [SMILES: CC(=O)N1CCN(c2cc3[nH]c(Nc4cc(CNC(=O)C5(C(F)(F)F)CC5)ccc4Cl)nc3cc2Cl)CC1] | C25H25Cl2F3N6O2 569.41 | 569 | Rt: 10.87 (method N) | 71 |

-continued

| Ex. | Structure | Formula/Mw. | MS* m/z [M+H]+ | Rf (TLC) or Rt [min] (HPLC-method) | Prepared in analogy to example |
|---|---|---|---|---|---|
| 75 | 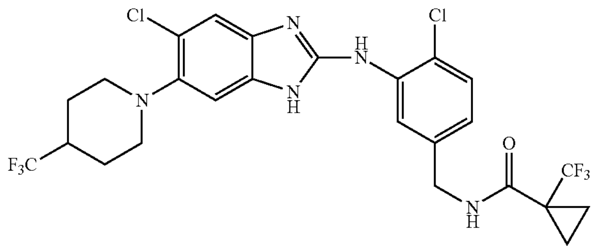 [SMILES: O=C(NCc1ccc(Cl)c(Nc2nc3cc(Cl)c(N4CCC(C(F)(F)F)CC4)cc3[nH]2)c1)C1(C(F)(F)F)CC1] | C25H23Cl2F6N5O 594.38 | 594 | Rt: 13.70 (method N) | 71 |
| 77 | 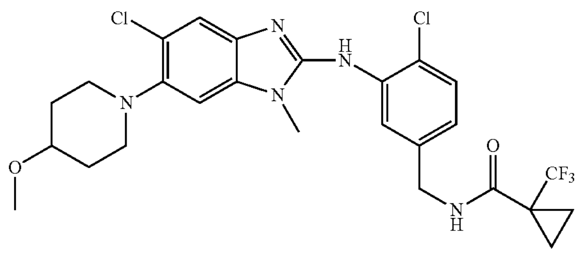 [SMILES: COC1CCN(c2cc3c(cc2Cl)nc(Nc2cc(CNC(=O)C4(C(F)(F)F)CC4)ccc2Cl)n3C)CC1] | C26H28Cl2F3N5O2 570.43 | 570 | Rt: 9.55 (method O) | 76 |
| 78 | 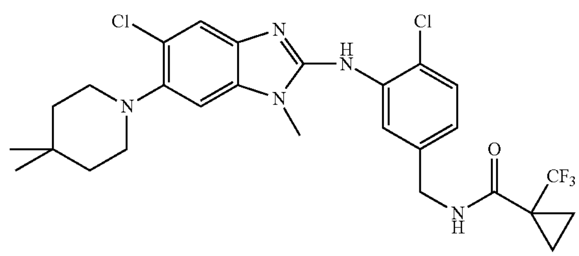 | C27H30Cl2F3N5O 568.46 | 568 | Rt: 11.39 (method O) | 76 |
| 79 | 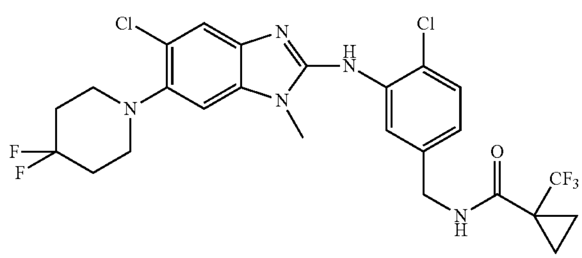 [SMILES: Cn1c(Nc2cc(CNC(=O)C3(C(F)(F)F)CC3)ccc2Cl)nc2cc(Cl)c(N3CCC(F)(F)CC3)cc21] | C25H24Cl2F5N5O 576.39 | 576 | Rt: 10.59 (method O) | 76 |
| 80 | 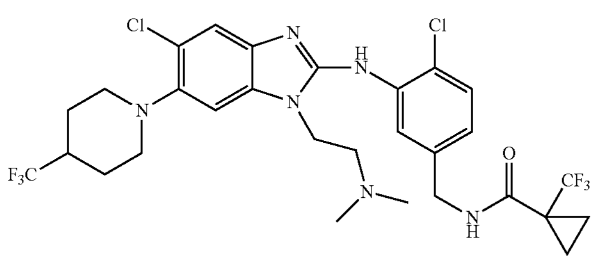 [SMILES: CN(C)CCn1c(Nc2cc(CNC(=O)C3(C(F)(F)F)CC3)ccc2Cl)nc2cc(Cl)c(N3CCC(C(F)(F)F)CC3)cc21] | C29H32Cl2F6N6O 665.50 | 665 | Rt: 10.67 (method O) | 76 |

-continued

| Ex. | Structure | Formula/Mw. | MS* m/z [M + H]+ | Rf (TLC) or Rt [min] (HPLC-method) | Prepared in analogy to example |
|---|---|---|---|---|---|
| 81 | 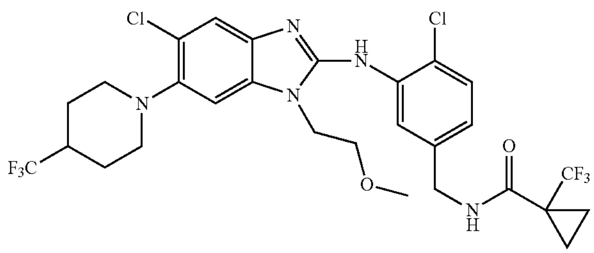 [SMILES: COCCn1c(Nc2cc(CNC(=O)C3(C(F)(F)F)CC3)ccc2Cl)nc2cc(Cl)c(N3CCC(C(F)(F)F)CC3)cc21] | $C_{26}H_{29}Cl_2F_6N_5O_2$ 652.46 | 652 | Rt: 12.90 (method O) | 76 |
| 85 | 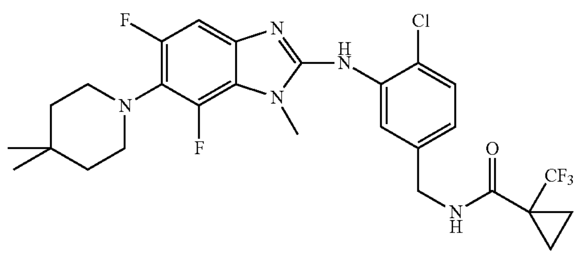 | $C_{27}H_{29}ClF_5N_5O$ 570.00 | 570 | Rt: 12.64 (method O) | 84 |
| 87 | 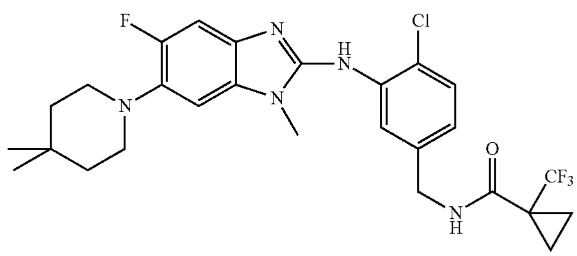 [SMILES: Cn1c(Nc2cc(CNC(=O)C3(C(F)(F)F)CC3)ccc2Cl)nc2cc(F)c(N3CCC(C)(C)CC3)cc21] | $C_{27}H_{30}ClF_4N_5O$ 552.01 | 552 | Rt: 10.65 (method O) | 86 |
| 88 | 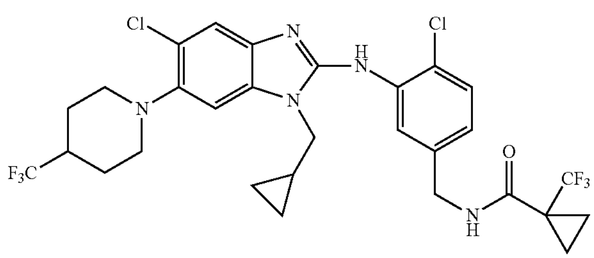 [SMILES: O=C(NCc1ccc(Cl)c(Nc2nc3cc(Cl)c(N4CCC(C(F)(F)F)CC4)cc3n2CC2CC2)c1)C1(C(F)(F)F)CC1] | $C_{29}H_{29}Cl_2F_6N_5O$ 648.47 | 648 | Rt: 11.70 (method O) | 76 |
| 89 | 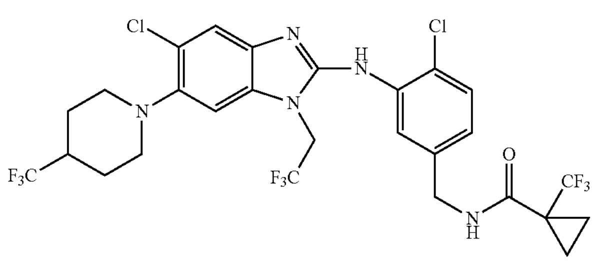 [SMILES: O=C(NCc1ccc(Cl)c(Nc2nc3cc(Cl)c(N4CCC(C(F)(F)F)CC4)cc3n2CC(F)(F)F)c1)C1(C(F)(F)F)CC1] | $C_{27}H_{24}Cl_2F_9N_5O$ 676.40 | 676 | Rt: 13.07 (method O) | 76 |

-continued

| Ex. | Structure | Formula/Mw. | MS* m/z [M + H]+ | Rf (TLC) or Rt [min] (HPLC-method) | Prepared in analogy to example |
|---|---|---|---|---|---|
| 90 | 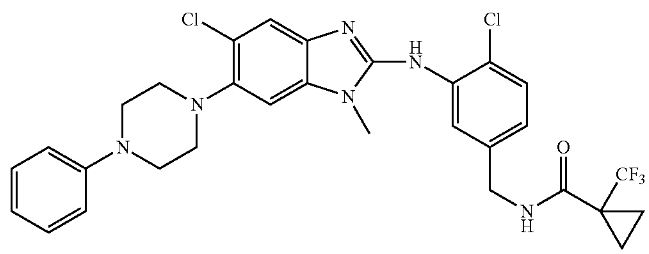 [SMILES: Cn1c(Nc2cc(CNC(=O)C3(C(F)(F)F)CC3)ccc2Cl)nc2cc(Cl)c(N3CCN(c4ccccc4)CC3)cc21] | C₃₀H₂₉Cl₂F₃N₆O 617.49 | 617 | Rt: 11.23 (method O) | 76 |
| 91 | 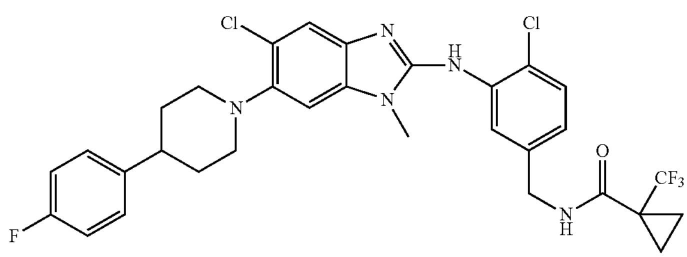 [SMILES: Cn1c(Nc2cc(CNC(=O)C3(C(F)(F)F)CC3)ccc2Cl)nc2cc(Cl)c(N3CCC(c4ccc(F)cc4)CC3)cc21] | C₃₁H₂₉Cl₂F₄N₅O 634.49 | 634 | Rt: 11.88 (method O) | 76 |
| 92 | 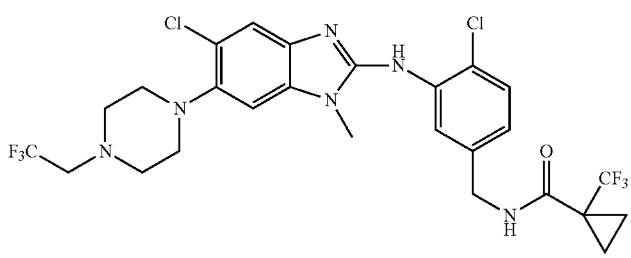 [SMILES: Cn1c(Nc2cc(CNC(=O)C3(C(F)(F)F)CC3)ccc2Cl)nc2cc(Cl)c(N3CCN(CC(F)(F)F)CC3)cc21] | C₂₆H₂₆Cl₂F₆N₆O 623.42 | 623 | Rt: 10.85 (method O) | 76 |
| 95 | 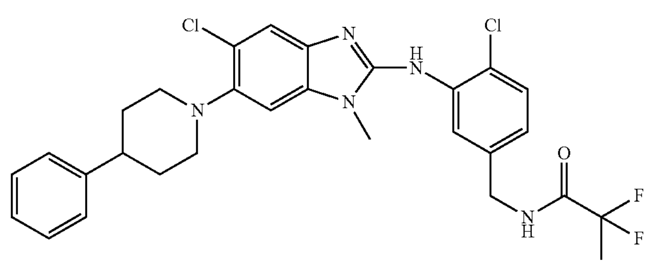 [SMILES: Cn1c(Nc2cc(CNC(=O)C(C)(F)F)ccc2Cl)nc2cc(Cl)c(N3CCC(c4ccccc4)CC3)cc21] | C₂₉H₂₉Cl₂F₂N₅O 572.48 | 572 | Rt: 11.20 (method O) | 94 |
| 96 | 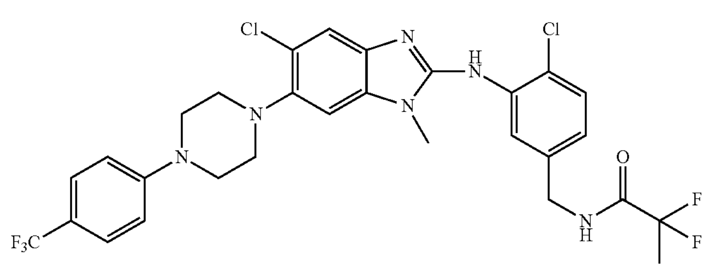 [SMILES: Cn1c(Nc2cc(CNC(=O)C(C)(F)F)ccc2Cl)nc2cc(Cl)c(N3CCN(c4ccc(C(F)(F)F)cc4)CC3)cc21] | C₂₉H₂₇Cl₂F₅N₆O 641.46 | 641 | Rt: 12.00 (method O) | 94 |

-continued

| Ex. | Structure | Formula/Mw. | MS* m/z [M + H]+ | Rf (TLC) or Rt [min] (HPLC-method) | Prepared in analogy to example |
|---|---|---|---|---|---|
| 97 | 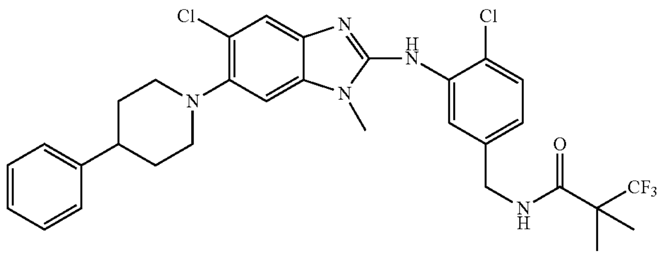 [SMILES: Cn1c(Nc2cc(CNC(=O)C(C)(C)C(F)(F)F)ccc2Cl)nc2cc(Cl)c(N3CCC(c4ccccc4)CC3)cc21] | C31H32Cl2F3N5O 618.52 | 618 | Rt: 12.02 (method O) | 94 |
| 98 | 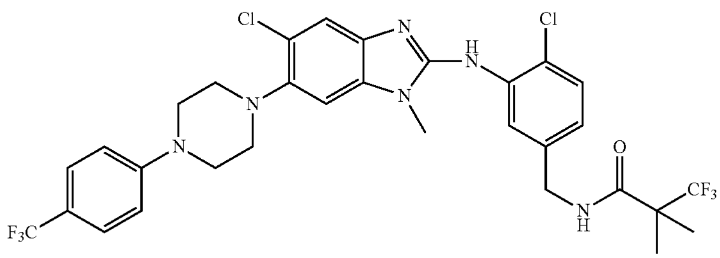 [SMILES: Cn1c(Nc2cc(CNC(=O)C(C)(C)C(F)(F)F)ccc2Cl)nc2cc(Cl)c(N3CCN(c4ccc(C(F)(F)F)cc4)CC3)cc21] | C31H30Cl2F6N6O 687.51 | 687 | Rt: 12.19 (method O) | 94 |
| 100 | 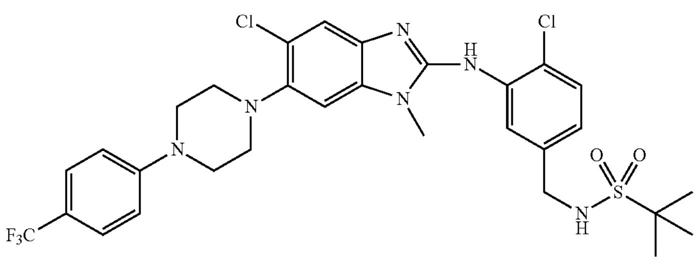 [SMILES: Cn1c(Nc2cc(CNS(=O)(=O)C(C)(C)C)ccc2Cl)nc2cc(Cl)c(N3CCN(c4ccc(C(F)(F)F)cc4)CC3)cc21] | C30H33Cl2F3N6O2S 669.59 | 669 | Rt: 12.12 (method O) | 99 |
| 102 | 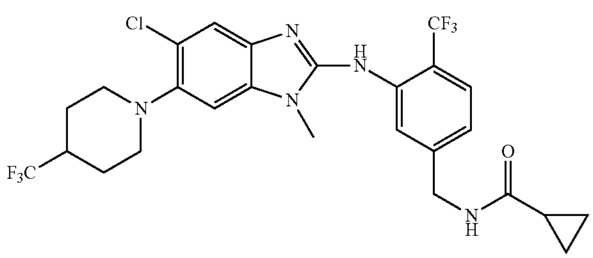 [SMILES: Cn1c(Nc2cc(CNC(=O)C3CC3)ccc2C(F)(F)F)nc2cc(Cl)c(N3CCC(C(F)(F)F)CC3)cc21] | C26H26ClF6N5O 573.96 | 574 | Rt: 10.53 (method O) | 101 |
| 103 | 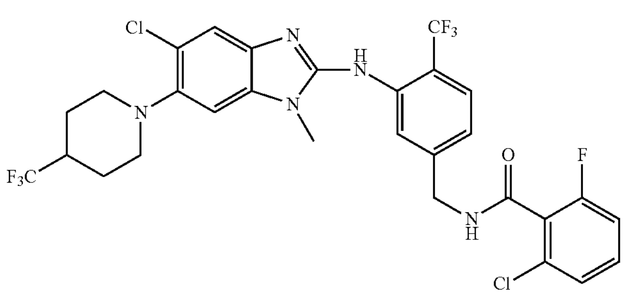 [SMILES: Cn1c(Nc2cc(CNC(=O)c3c(F)cccc3Cl)ccc2C(F)(F)F)nc2cc(Cl)c(N3CCC(C(F)(F)F)CC3)cc21] | C29H24Cl2F7N5O 662.43 | 662 | Rt: 11.10 (method O) | 101 |

-continued

| Ex. | Structure | Formula/Mw. | MS* m/z [M + H]+ | Rf (TLC) or Rt [min] (HPLC-method) | Prepared in analogy to example |
|---|---|---|---|---|---|
| 104 | 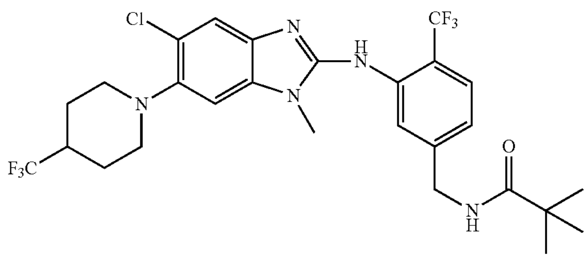 [SMILES: Cn1c(Nc2cc(CNC(=O)C(C)(C)C)ccc2C(F)(F)F)nc2cc(Cl)c(N3CCC(C(F)(F)F)CC3)cc21] | C27H30ClF6N5O 590.00 | 590 | Rt: 11.03 (method O) | 101 |
| 106 | 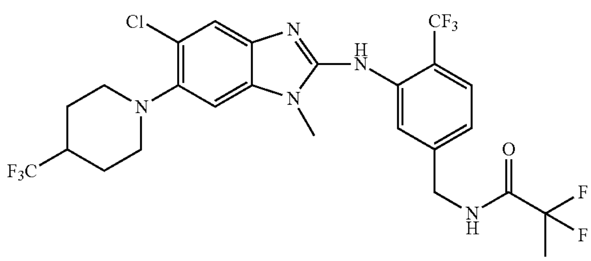 [SMILES: Cn1c(Nc2cc(CNC(=O)C(C)(F)F)ccc2C(F)(F)F)nc2cc(Cl)c(N3CCC(C(F)(F)F)CC3)cc21] | C25H24ClF8N5O 597.93 | 598 | Rt: 11.23 (method O) | 105 |
| 107 | 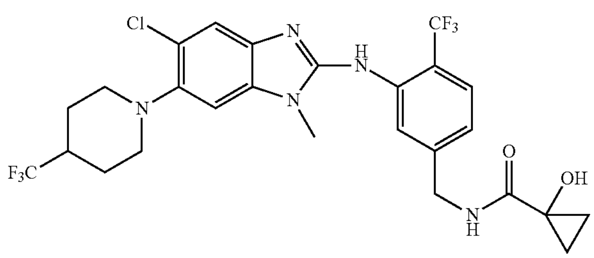 [SMILES: Cn1c(Nc2cc(CNC(=O)C3(O)CC3)ccc2C(F)(F)F)nc2cc(Cl)c(N3CCC(C(F)(F)F)CC3)cc21] | C26H26ClF6N5O2 589.96 | 590 | Rt: 10.50 (method O) | 105 |
| 108 | 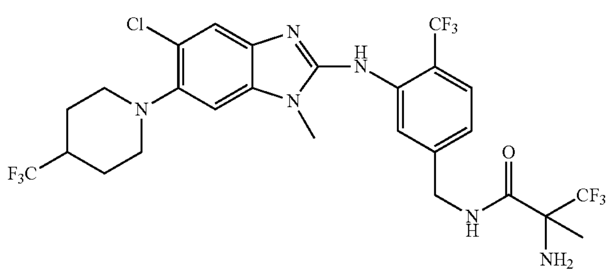 [SMILES: Cn1c(Nc2cc(CNC(=O)C(C)(N)C(F)(F)F)ccc2C(F)(F)F)nc2cc(Cl)c(N3CCC(C(F)(F)F)CC3)cc21] | C26H26ClF6N6O 644.96 | 645 | Rt: 11.27 (method O) | 105 |
| 112 | 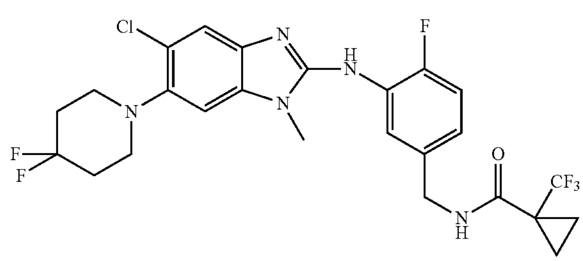 | C25H24ClF6N5O 559.93 | 560 | Rt: 10.48 (method O) | 111 |

-continued

| Ex. | Structure | Formula/Mw. | MS* m/z [M+H]+ | Rf (TLC) or Rt [min] (HPLC-method) | Prepared in analogy to example |
|---|---|---|---|---|---|
| 113 | 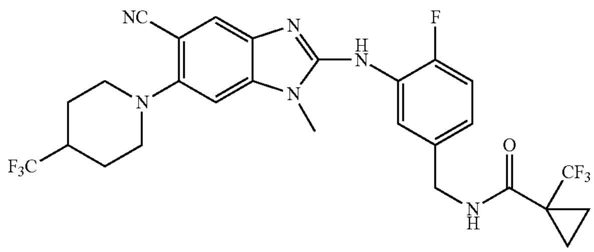 [SMILES: Cn1c(Nc2cc(CNC(=O)C3(C(F)(F)F)CC3)ccc2F)nc2cc(C#N)c(N3CCC(C(F)(F)F)CC3)cc21] | C27H25F7N6O 582.52 | 583 | Rt: 10.82 (method O) | 111 |
| 115 | 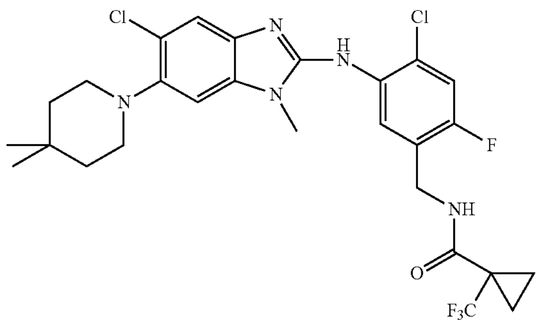 [SMILES: Cn1c(Nc2cc(CNC(=O)C3(C(F)(F)F)CC3)c(F)cc2Cl)nc2cc(Cl)c(N3CCC(C)(C)CC3)cc21] | C27H29Cl2F4N5O 586.45 | 586 | Rt: 11.60 (method O) | 114 |
| 118 | 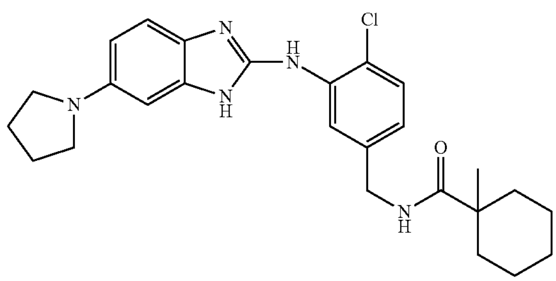 [SMILES: CC1(C(=O)NCc2ccc(Cl)c(Nc3nc4ccc(N5CCCC5)cc4[nH]3)c2)CCCCC1] | C26H32ClN5O 466.02 | 466 | Rt: 6.10 (method P) | 71 |
| 119 | 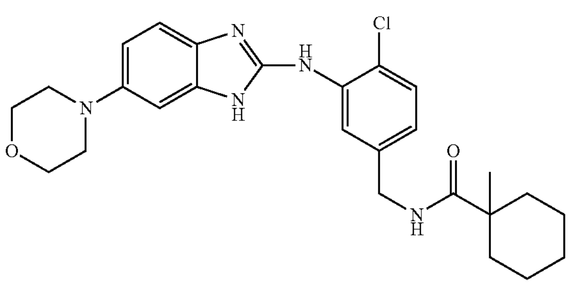 [SMILES: CC1(C(=O)NCc2ccc(Cl)c(Nc3nc4ccc(N5CCOCC5)cc4[nH]3)c2)CCCCC1] | C26H32ClN5O2 482.02 | 482 | Rt: 4.79 (method P) | 71 |
| 120 | 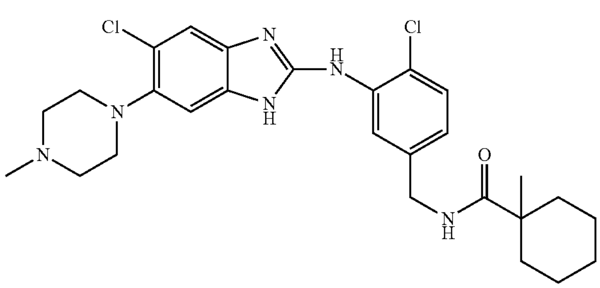 [SMILES: CN1CCN(c2cc3[nH]c(Nc4cc(CNC(=O)C5(C)CCCCC5)ccc4Cl)nc3cc2Cl)CC1] | C27H34Cl2N6O 529.50 | 529 | Rt: 3.82 (method P) | 71 |

-continued

| Ex. | Structure | Formula/Mw. | MS* m/z [M + H]+ | Rf (TLC) or Rt [min] (HPLC-method) | Prepared in analogy to example |
|---|---|---|---|---|---|
| 121 | 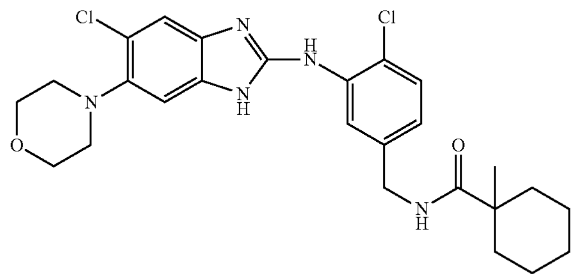 [SMILES: CC1(C(=O)NCc2ccc(Cl)c(Nc3nc4cc(Cl)c(N5CCOCC5)cc4[nH]3)c2)CCCCC1] | C26H31Cl2N5O2 516.46 | 516 | Rt: 11.62 (method N) | 71 |
| 122 | 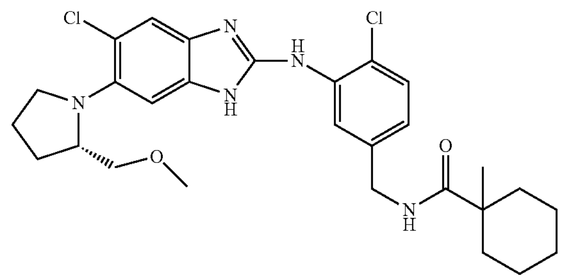 [SMILES: COC[C@@H]1CCCN1c1cc2[nH]c(Nc3cc(CNC(=O)C4(C)CCCCC4)ccc3Cl)nc2cc1Cl] | C28H35Cl2N5O2 544.52 | 544 | Rt: 12.50 (method N) | 71 |
| 123 | 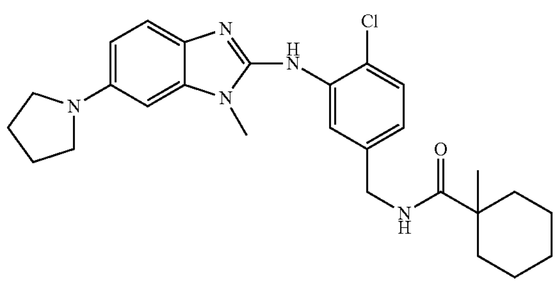 [SMILES: Cn1c(Nc2cc(CNC(=O)C3(C)CCCCC3)ccc2Cl)nc2ccc(N3CCCC3)cc21] | C27H34ClN5O 480.04 | 480 | Rt: 12.25 (method N) | 71 |
| 124 | 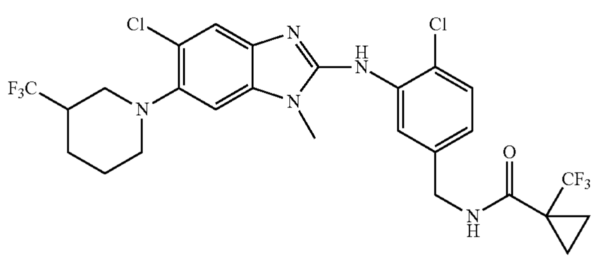 [SMILES: Cn1c(Nc2cc(CNC(=O)C3(C(F)(F)F)CC3)ccc2Cl)nc2cc(Cl)c(N3CCCC(C(F)(F)F)C3)cc21] | C26H25Cl2F6N5O 608.41 | 608 | Rt: 14.02 (method N) | 71 |
| 125 | 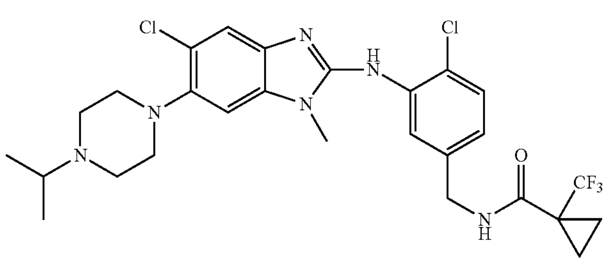 [SMILES: CC(C)N1CCN(c2cc3c(cc2Cl)nc(Nc2cc(CNC(=O)C4(C(F)(F)F)CC4)ccc2Cl)n3C)CC1] | C27H31Cl2F3N6O 583.48 | 583 | Rt: 9.35 (method N) | 71 |

-continued

| Ex. | Structure | Formula/Mw. | MS* m/z [M + H]+ | Rf (TLC) or Rt [min] (HPLC-method) | Prepared in analogy to example |
|---|---|---|---|---|---|
| 126 | 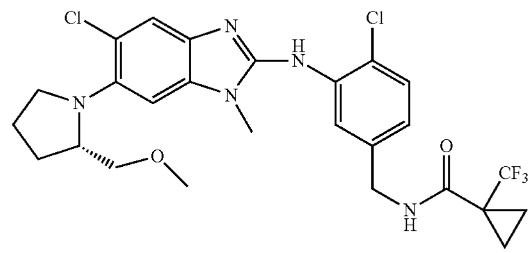 [SMILES: COC[C@@H]1CCCN1c1cc2c(cc1Cl)nc(Nc1cc(CNC(=O)C3(C(F)(F)F)CC3)ccc1Cl)n2C] | C$_{26}$H$_{28}$Cl$_2$F$_3$N$_5$O$_2$ 570.43 | 570 | Rt: 12.52 (method N) | 71 |
| 127 | 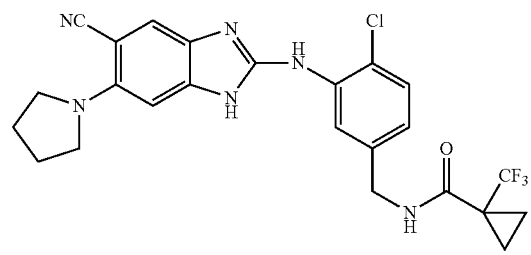 [SMILES: N#Cc1cc2nc(Nc3cc(CNC(=O)C4(C(F)(F)F)CC4)ccc3Cl)[nH]c2cc1N1CCCC1] | C$_{24}$H$_{22}$ClF$_3$N$_6$O 502.92 | 503 | Rt: 11.84 (method N) | 71 |
| 128 | 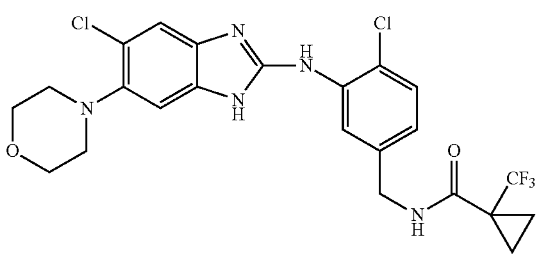 [SMILES: O=C(NCc1ccc(Cl)c(Nc2nc3cc(Cl)c(N4CCOCC4)cc3[nH]2)c1)C1(C(F)(F)F)CC1] | C$_{23}$H$_{22}$Cl$_2$F$_3$N$_5$O$_2$ 528.35 | 528 | Rt: 11.28 (method N) | 71 |
| 129 | 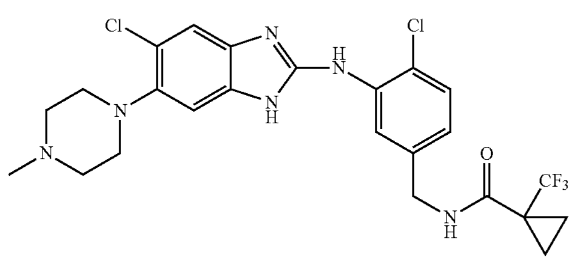 [SMILES: CN1CCN(c2cc3[nH]c(Nc4cc(CNC(=O)C5(C(F)(F)F)CC5)ccc4Cl)nc3cc2Cl)CC1] | C$_{24}$H$_{25}$Cl$_2$F$_3$N$_6$O 541.40 | 541 | Rt: 8.90 (method N) | 71 |
| 130 | 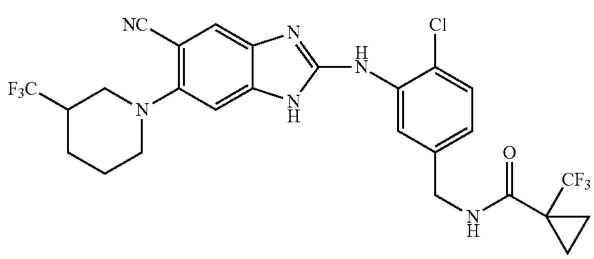 [SMILES: N#Cc1cc2nc(Nc3cc(CNC(=O)C4(C(F)(F)F)CC4)ccc3Cl)[nH]c2cc1N1CCCC(C(F)(F)F)C1] | C$_{26}$H$_{23}$ClF$_6$N$_6$O 584.94 | 585 | Rt: 13.92 (method N) | 82 |

-continued

| Ex. | Structure | Formula/Mw. | MS* m/z [M + H]+ | Rf (TLC) or Rt [min] (HPLC-method) | Prepared in analogy to example |
|---|---|---|---|---|---|
| 131 | 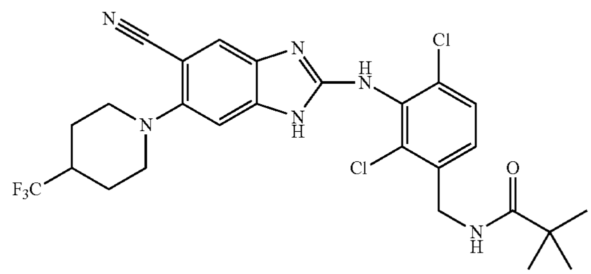 [SMILES: CC(C)(C)C(=O)NCc1ccc(Cl)c(Nc2nc3cc(C#N)c(N4CCC(C(F)(F)F)CC4)cc3[nH]2)c1Cl] | C26H27Cl2F3N6O 567.433 | 567 | Rt: 1.39 (method G) | 82 |
| 132 | 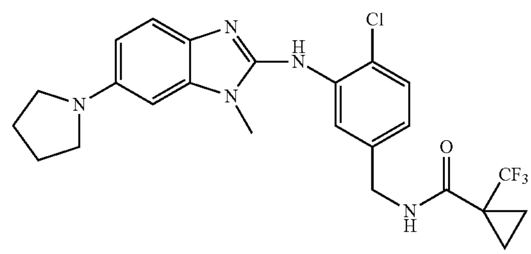 [SMILES: Cn1c(Nc2cc(CNC(=O)C3(C(F)(F)F)CC3)ccc2Cl)nc2ccc(N3CCCC3)cc21] | C24H25ClF3N5O 491.94 | 492 | Rt: 12.00 (method N) | 9(f) |
| 134 | 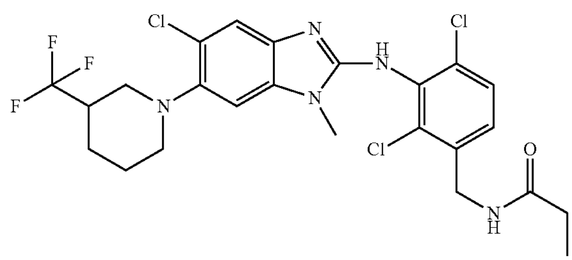 [SMILES: CCC(=O)NCc1ccc(Cl)c(Nc2nc3cc(Cl)c(N4CCCC(C(F)(F)F)C4)cc3n2C)c1Cl] | C24H25Cl3F3N5O 562.85 | 562 | Rt: 1.62 (method Q) | 23 |
| 135 | 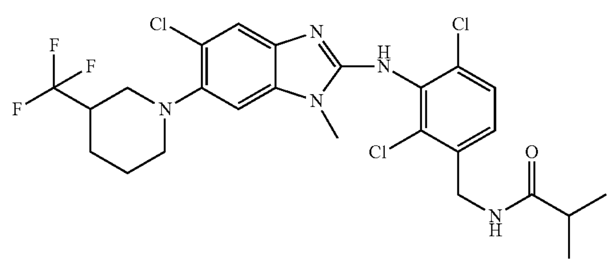 [SMILES: CC(C)C(=O)NCc1ccc(Cl)c(Nc2nc3cc(Cl)c(N4CCCC(C(F)(F)F)C4)cc3n2C)c1Cl] | C25H27Cl3F3N5O 576.88 | 576 | Rt: 1.66 (method Q) | 23 |
| 136 | 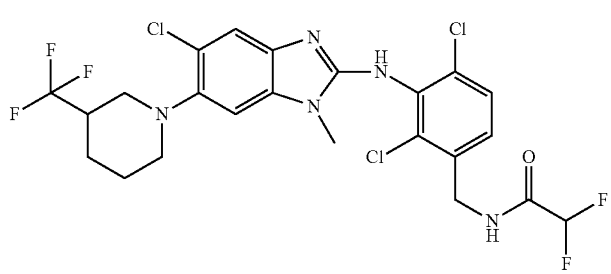 [SMILES: Cn1c(Nc2c(Cl)ccc(CNC(=O)C(F)F)c2Cl)nc2cc(Cl)c(N3CCCC(C(F)(F)F)C3)cc21] | C23H21Cl3F5N5O 584.8 | 584 | Rt: 1.61 (method Q) | 23 |

-continued

| Ex. | Structure | Formula/Mw. | MS* m/z [M + H]+ | Rf (TLC) or Rt [min] (HPLC-method) | Prepared in analogy to example |
|---|---|---|---|---|---|
| 137 | 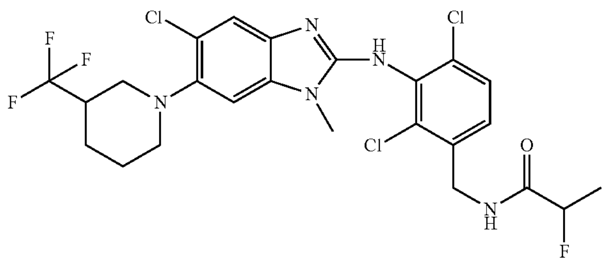 [SMILES: CC(F)C(=O)NCc1ccc(Cl)c(Nc2nc3cc(Cl)c(N4CCCC(C(F)(F)F)C4)cc3n2C)c1Cl] | C24H24Cl3F4N5O 580.84 | 580 | Rt: 1.62 (method Q)) | 23 |
| 138 | 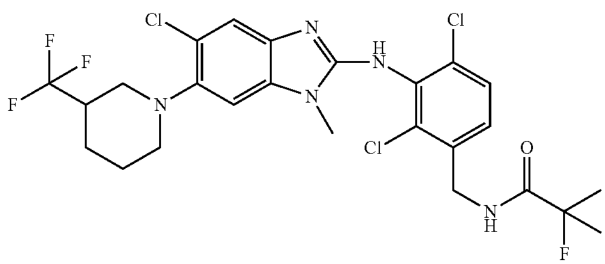 [SMILES: Cn1c(Nc2c(Cl)ccc(CNC(=O)C(C)(C)F)c2Cl)nc2cc(Cl)c(N3CCCC(C(F)(F)F)C3)cc21] | C25H26Cl3F4N5O 594.87 | 594 | Rt: 1.65 (method Q) | 23 |
| 139 | 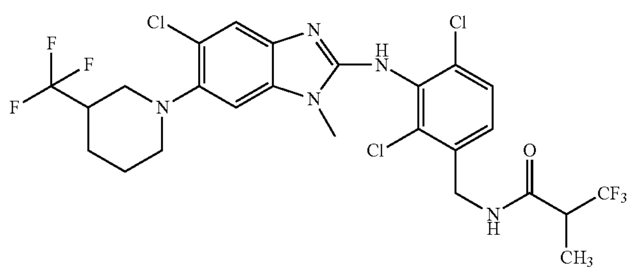 [SMILES: CC(C(=O)NCc1ccc(Cl)c(Nc2nc3cc(Cl)c(N4CCCC(C(F)(F)F)C4)cc3n2C)c1Cl)C(F)(F)F] | C25H24Cl3F6N5O 630.85 | 630 | Rt: 1.69 (method Q) | 23 |
| 140 | 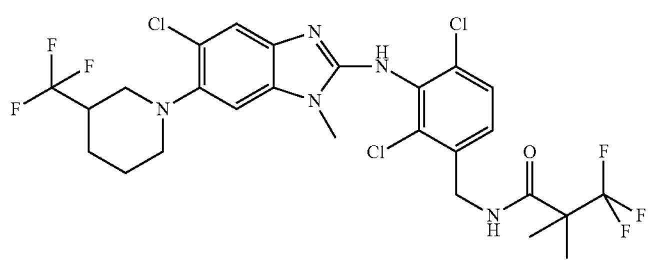 [SMILES: Cn1c(Nc2c(Cl)ccc(CNC(=O)C(C)(C)C(F)(F)F)c2Cl)nc2cc(Cl)c(N3CCCC(C(F)(F)F)C3)cc21] | C26H26Cl3F6N5O 644.87 | 644 | Rt: 1.72 (method Q) | 23 |
| 141 | 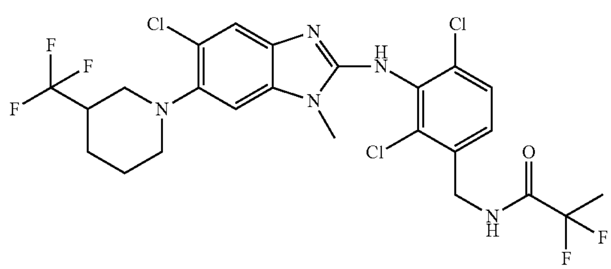 [SMILES: Cn1c(Nc2c(Cl)ccc(CNC(=O)C(C)(F)F)c2Cl)nc2cc(Cl)c(N3CCCC(C(F)(F)F)C3)cc21] | C24H23Cl3F5N5O 598.83 | 598 | Rt: 1.64 (method Q) | 23 |

-continued

| Ex. | Structure | Formula/Mw. | MS* m/z [M + H]+ | Rf (TLC) or Rt [min] (HPLC-method) | Prepared in analogy to example |
|---|---|---|---|---|---|
| 142 | 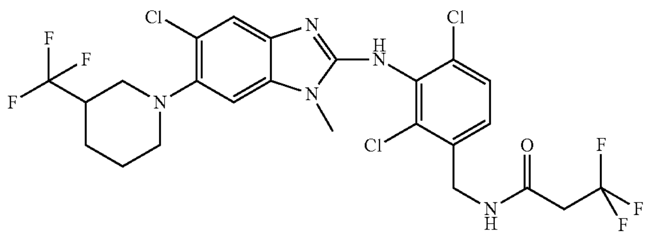 [SMILES: Cn1c(Nc2c(Cl)ccc(CNC(=O)CC(F)(F)F)c2Cl)nc2cc(Cl)c(N3CCCC(C(F)(F)F)C3)cc21] | C₂₄H₂₂Cl₃F₆N₅O 616.82 | 616 | Rt: 1.65 (method Q) | 23 |
| 143 | 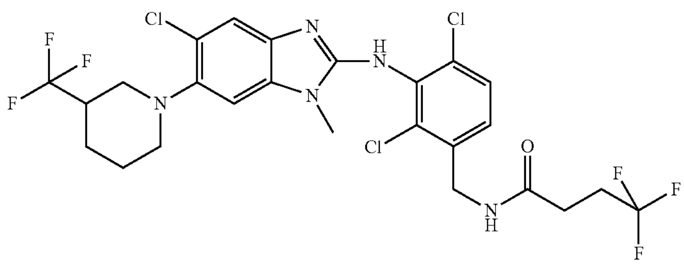 [SMILES: Cn1c(Nc2c(Cl)ccc(CNC(=O)CCC(F)(F)F)c2Cl)nc2cc(Cl)c(N3CCCC(C(F)(F)F)C3)cc21] | C₂₅H₂₄Cl₃F₆N₅O 630.85 | 630 | Rt: 1.68 (method Q) | 23 |
| 144 | 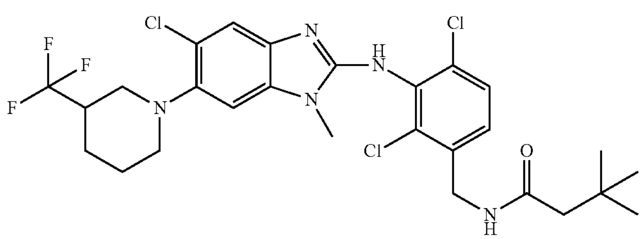 [SMILES: Cn1c(Nc2c(Cl)ccc(CNC(=O)CC(C)(C)C)c2Cl)nc2cc(Cl)c(N3CCCC(C(F)(F)F)C3)cc21] | C₂₇H₃₁Cl₃F₃N₅O 604.93 | 604 | Rt: 1.73 (method Q) | 23 |
| 145 | 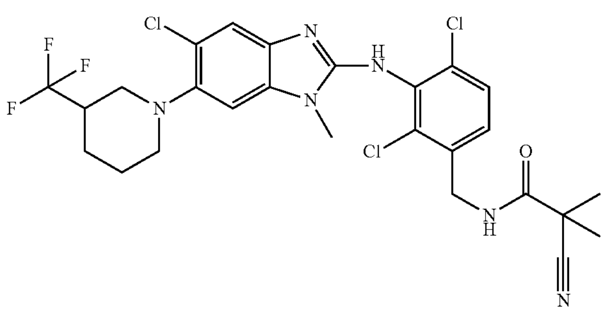 [SMILES: Cn1c(Nc2c(Cl)ccc(CNC(=O)C(C)(C)C#N)c2Cl)nc2cc(Cl)c(N3CCCC(C(F)(F)F)C3)cc21] | C₂₆H₂₆Cl₃F₃N₆O 601.89 | 601 | Rt: 1.63 (method Q) | 23 |
| 146 | 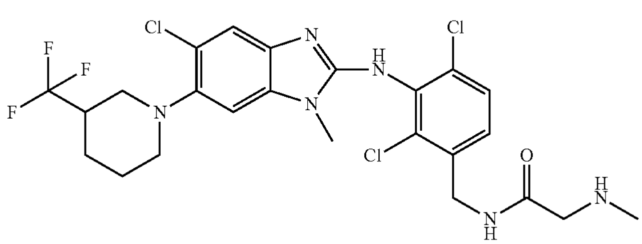 [SMILES: CNCC(=O)NCc1ccc(Cl)c(Nc2nc3cc(Cl)c(N4CCCC(C(F)(F)F)C4)cc3n2C)c1Cl] | C₂₄H₂₆Cl₃F₃N₆O 577.86 | 577 | Rt: 1.40 (method Q) | 23 |

-continued

| Ex. | Structure | Formula/Mw. | MS* m/z [M + H]+ | Rf (TLC) or Rt [min] (HPLC-method) | Prepared in analogy to example |
|---|---|---|---|---|---|
| 147 | 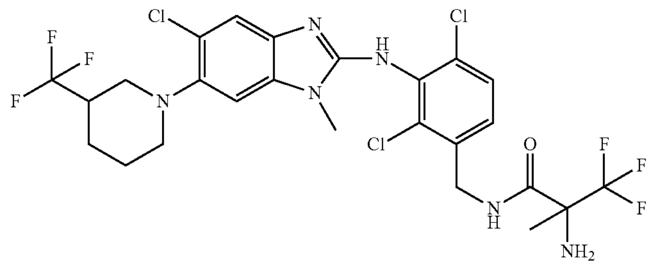 [SMILES: Cn1c(Nc2c(Cl)ccc(CNC(=O)C(C)(N)C(F)(F)F)c2Cl)nc2cc(Cl)c(N3CCCC(C(F)(F)F)C3)cc21] | C25H25Cl3F6N6O 645.86 | 645 | Rt: 1.57 (method Q) | 23 |
| 148 | 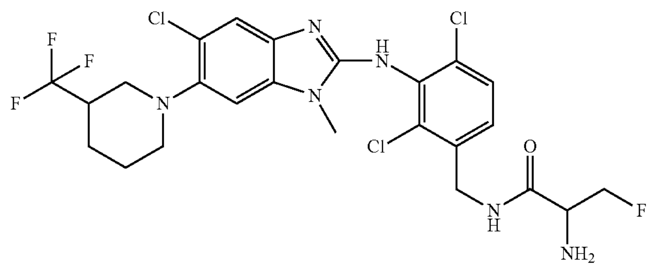 [SMILES: Cn1c(Nc2c(Cl)ccc(CNC(=O)C(N)CF)c2Cl)nc2cc(Cl)c(N3CCCC(C(F)(F)F)C3)cc21] | C24H25Cl3F4N6O 595.85 | 595 | Rt: 1.41 (method Q) | 23 |
| 149 | 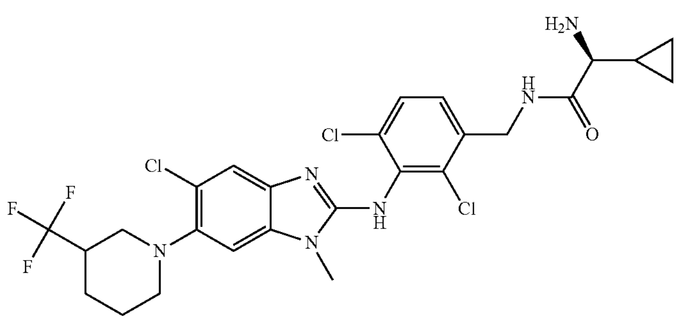 [SMILES: Cn1c(Nc2c(Cl)ccc(CNC(=O)[C@@H](N)C3CC3)c2Cl)nc2cc(Cl)c(N3CCCC(C(F)(F)F)C3)cc21] | C26H28Cl3F3N6O 603.9 | 603 | Rt: 1.42 (method Q) | 23 |
| 150 | 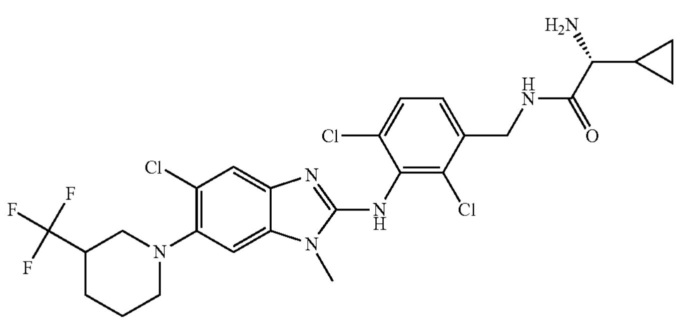 [SMILES: Cn1c(Nc2c(Cl)ccc(CNC(=O)[C@H](N)C3CC3)c2Cl)nc2cc(Cl)c(N3CCCC(C(F)(F)F)C3)cc21] | C26H28Cl3F3N6O 603.9 | 603 | Rt: 1.42 (method Q) | 23 |
| 151 | 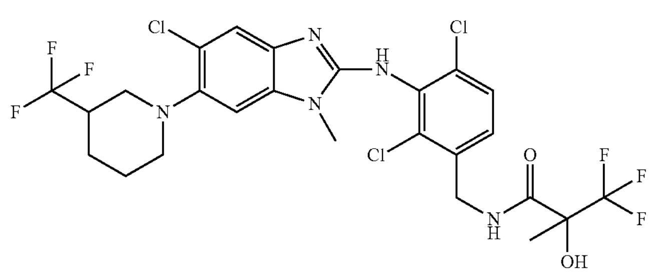 [SMILES: Cn1c(Nc2c(Cl)ccc(CNC(=O)C(C)(O)C(F)(F)F)c2Cl)nc2cc(Cl)c(N3CCCC(C(F)(F)F)C3)cc21] | C25H24Cl3F6N5O2 646.84 | 646 | Rt: 1.66 (method Q) | 23 |

-continued

| Ex. | Structure | Formula/Mw. | MS* m/z [M + H]+ | Rf (TLC) or Rt [min] (HPLC-method) | Prepared in analogy to example |
|---|---|---|---|---|---|
| 152 | 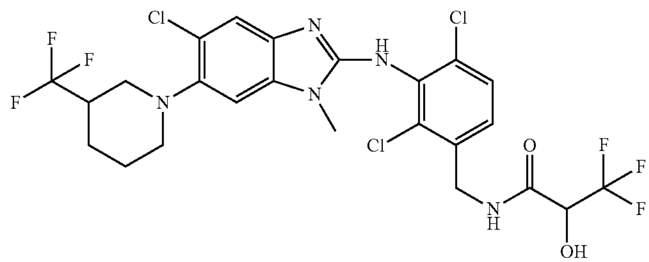 [SMILES: Cn1c(Nc2c(Cl)ccc(CNC(=O)C(O)C(F)(F)F)c2Cl)nc2cc(Cl)c(N3CCCC(C(F)(F)F)C3)cc21] | $C_{24}H_{22}Cl_3F_6N_5O_2$ 632.82 | 632 | Rt: 1.63 (method Q) | 23 |
| 153 | 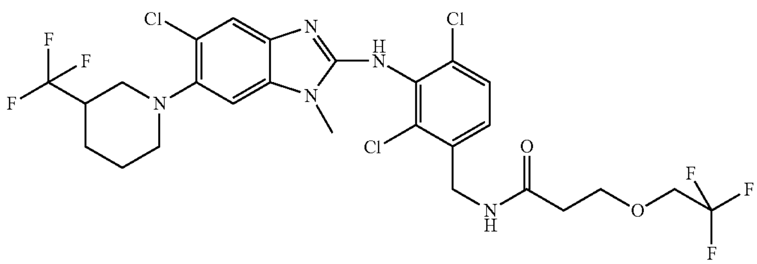 [SMILES: Cn1c(Nc2c(Cl)ccc(CNC(=O)CCOCC(F)(F)F)c2Cl)nc2cc(Cl)c(N3CCCC(C(F)(F)F)C3)cc21] | $C_{26}H_{26}Cl_3F_6N_5O_2$ 660.87 | 660 | Rt: 1.67 (method Q) | 23 |
| 154 | 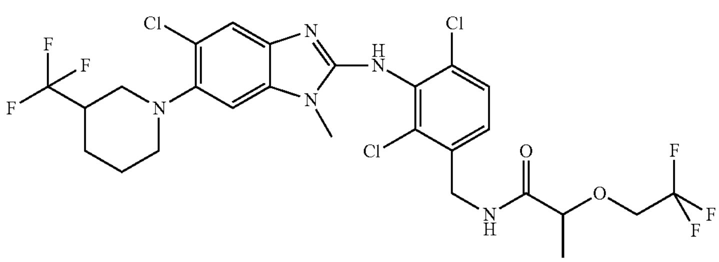 [SMILES: CC(OCC(F)(F)F)C(=O)NCc1ccc(Cl)c(Nc2nc3cc(Cl)c(N4CCCC(C(F)(F)F)C4)cc3n2C)c1Cl] | $C_{26}H_{26}Cl_3F_6N_5O_2$ 660.87 | 660 | Rt: 1.68 (method Q) | 23 |
| 155 | 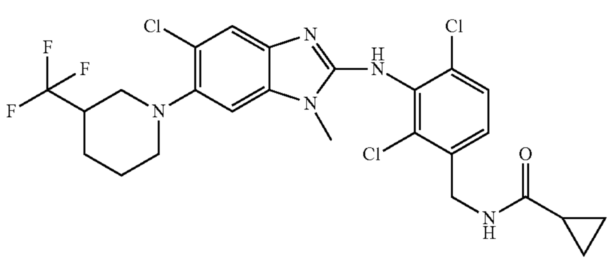 [SMILES: Cn1c(Nc2c(Cl)ccc(CNC(=O)C3CC3)c2Cl)nc2cc(Cl)c(N3CCCC(C(F)(F)F)C3)cc21] | $C_{25}H_{25}Cl_3F_3N_5O$ 574.86 | 574 | Rt: 1.64 (method Q) | 23 |
| 156 | 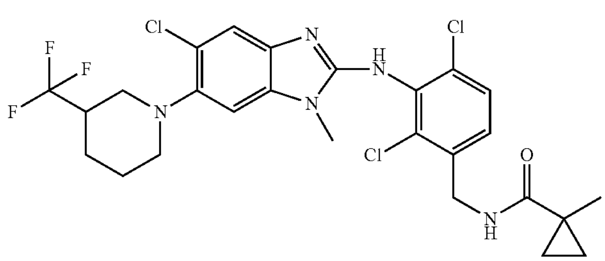 [SMILES: Cn1c(Nc2c(Cl)ccc(CNC(=O)C3(C)CC3)c2Cl)nc2cc(Cl)c(N3CCCC(C(F)(F)F)C3)cc21] | $C_{26}H_{27}Cl_3F_3N_5O$ 588.89 | 588 | Rt: 1.68 (method Q) | 23 |

-continued

| Ex. | Structure | Formula/Mw. | MS* m/z [M + H]+ | Rf (TLC) or Rt [min] (HPLC-method) | Prepared in analogy to example |
|---|---|---|---|---|---|
| 157 | 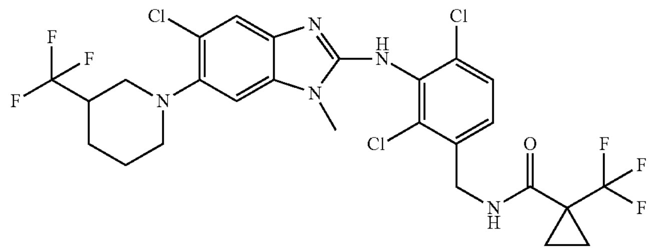 [SMILES: Cn1c(Nc2c(Cl)ccc(CNC(=O)C3(C(F)(F)F)CC3)c2Cl)nc2cc(Cl)c(N3CCCC(C(F)(F)F)C3)cc21] | C25H24Cl3F6N5O 642.86 | 642 | Rt: 1.70 (method Q) | 23 |
| 158 | 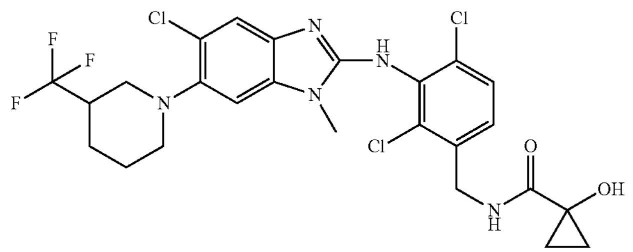 [SMILES: Cn1c(Nc2c(Cl)ccc(CNC(=O)C3(O)CC3)c2Cl)nc2cc(Cl)c(N3CCCC(C(F)(F)F)C3)cc21] | C25H25Cl3F3N5O2 590.86 | 590 | Rt: 1.61 (method Q) | 23 |
| 159 | 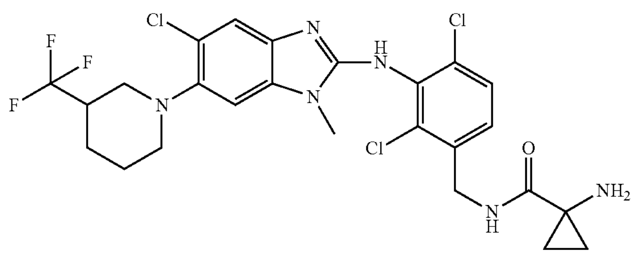 [SMILES: Cn1c(Nc2c(Cl)ccc(CNC(=O)C3(N)CC3)c2Cl)nc2cc(Cl)c(N3CCCC(C(F)(F)F)C3)cc21] | C25H26Cl3F3N6O 589.87 | 589 | Rt: 1.40 (method Q) | 23 |
| 160 | 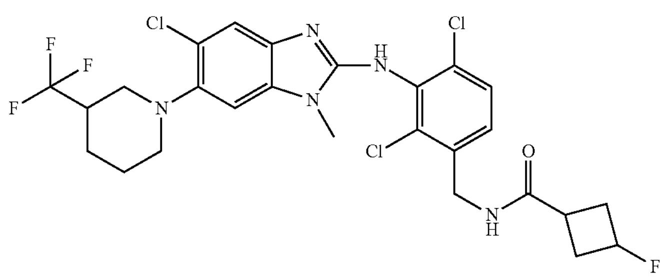 [SMILES: Cn1c(Nc2c(Cl)ccc(CNC(=O)C3CC(F)C3)c2Cl)nc2cc(Cl)c(N3CCCC(C(F)(F)F)C3)cc21] | C26H26Cl3F4N5O 606.88 | 606 | Rt: 1.66 (method Q) | 23 |
| 161 | 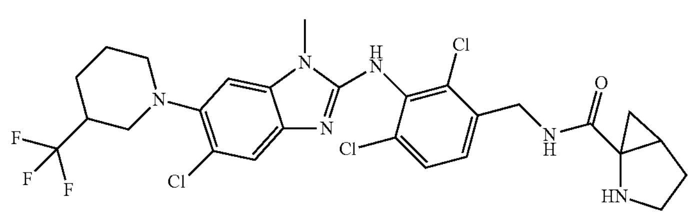 [SMILES: Cn1c(Nc2c(Cl)ccc(CNC(=O)C34CC3CCN4)c2Cl)nc2cc(Cl)c(N3CCCC(C(F)(F)F)C3)cc21] | C27H28Cl3F3N6O 615.91 | 615 | Rt: 1.41 (method Q) | 23 |
| 162 | 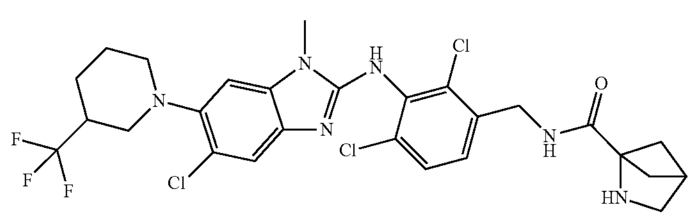 [SMILES: Cn1c(Nc2c(Cl)ccc(CNC(=O)C34CC(CN3)C4)c2Cl)nc2cc(Cl)c(N3CCCC(C(F)(F)F)C3)cc21] | C27H28Cl3F3N6O 615.91 | 615 | Rt: 1.41 (method Q) | 23 |

-continued

| Ex. | Structure | Formula/Mw. | MS* m/z [M + H]+ | Rf (TLC) or Rt [min] (HPLC-method) | Prepared in analogy to example |
|---|---|---|---|---|---|
| 163 | 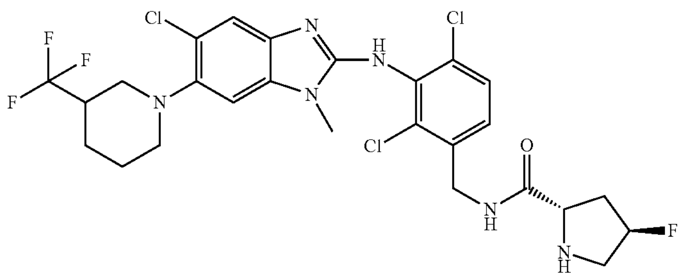 [SMILES: Cn1c(Nc2c(Cl)ccc(CNC(=O)[C@@H]3C[C@@H](F)CN3)c2Cl)nc2cc(Cl)c(N3CCCC(C(F)(F)F)C3)cc21] | C26H27Cl3F4N6O 621.89 | 621 | Rt: 1.40 (method Q) | 23 |
| 164 | 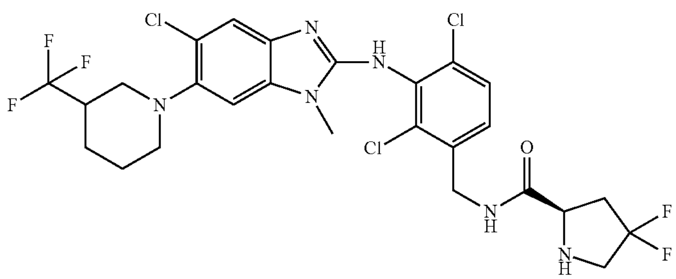 [SMILES: Cn1c(Nc2c(Cl)ccc(CNC(=O)[C@H]3CC(F)(F)CN3)c2Cl)nc2cc(Cl)c(N3CCCC(C(F)(F)F)C3)cc21] | C26H26Cl3F5N6O 639.88 | 639 | Rt: 1.46 (method Q) | 23 |
| 165 | 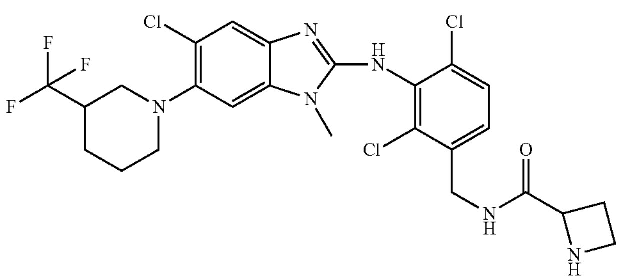 [SMILES: Cn1c(Nc2c(Cl)ccc(CNC(=O)C3CCN3)c2Cl)nc2cc(Cl)c(N3CCCC(C(F)(F)F)C3)cc21] | C25H26Cl3F3N6O 589.87 | 589 | Rt: 1.40 (method Q) | 23 |
| 166 | 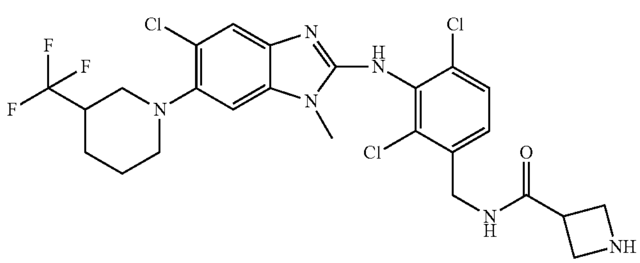 [SMILES: Cn1c(Nc2c(Cl)ccc(CNC(=O)C3CNC3)c2Cl)nc2cc(Cl)c(N3CCCC(C(F)(F)F)C3)cc21] | C25H26Cl3F3N6O 589.87 | 589 | Rt: 1.40 (method Q) | 23 |
| 167 | 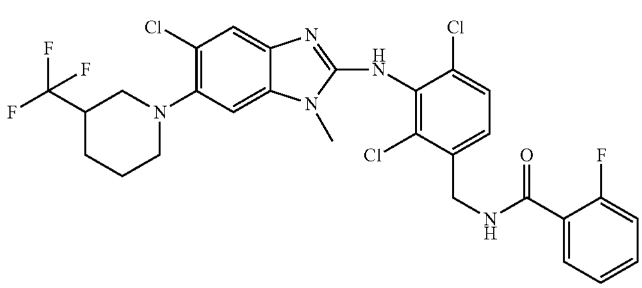 | C28H24Cl3F4N5O 628.88 | 628 | Rt: 1.67 (method Q) | 23 |

-continued

| Ex. | Structure | Formula/Mw. | MS* m/z [M+H]+ | Rf (TLC) or Rt [min] (HPLC-method) | Prepared in analogy to example |
|---|---|---|---|---|---|
| 168 | 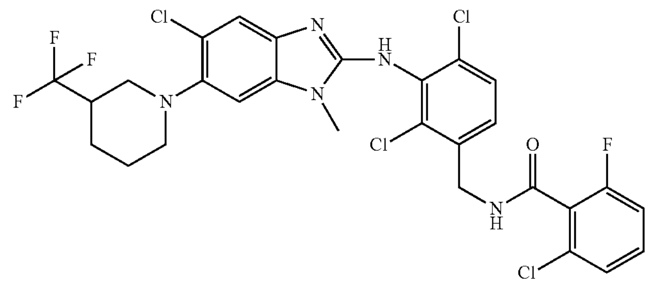 [SMILES: Cn1c(Nc2c(Cl)ccc(CNC(=O)c3c(F)cccc3Cl)c2Cl)nc2cc(Cl)c(N3CCCC(C(F)(F)F)C3)cc21] | C28H23Cl4F4N5O 663.33 | 662 | Rt: 1.67 (method Q) | 23 |
| 169 | 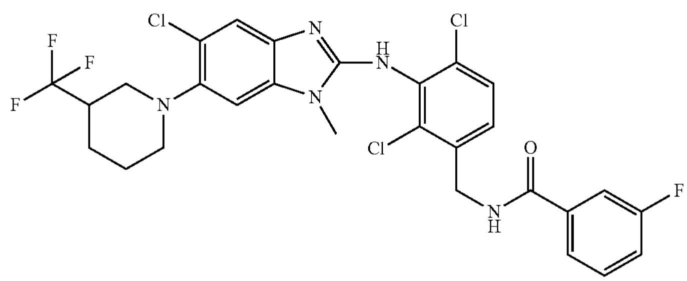 [SMILES: Cn1c(Nc2c(Cl)ccc(CNC(=O)c3cccc(F)c3)c2Cl)nc2cc(Cl)c(N3CCCC(C(F)(F)F)C3)cc21] | C28H24Cl3F4N5O 628.88 | 628 | Rt: 1.71 (method Q) | 23 |
| 170 | 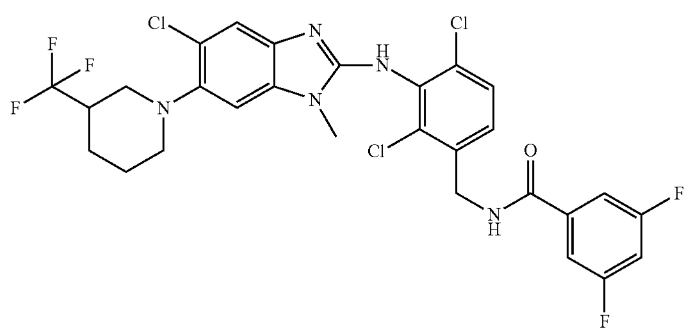 [SMILES: Cn1c(Nc2c(Cl)ccc(CNC(=O)c3cc(F)cc(F)c3)c2Cl)nc2cc(Cl)c(N3CCCC(C(F)(F)F)C3)cc21] | C28H23Cl3F5N5O 646.87 | 646 | Rt: 1.74 (method Q) | 23 |
| 171 | 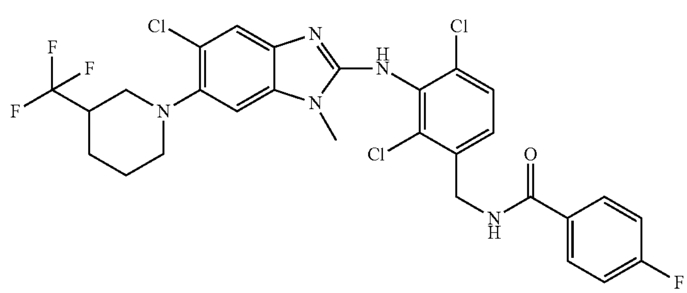 [SMILES: Cn1c(Nc2c(Cl)ccc(CNC(=O)c3ccc(F)cc3)c2Cl)nc2cc(Cl)c(N3CCCC(C(F)(F)F)C3)cc21] | C28H24Cl3F4N5O 628.88 | 628 | Rt: 1.71 (method Q) | 23 |
| 172 | 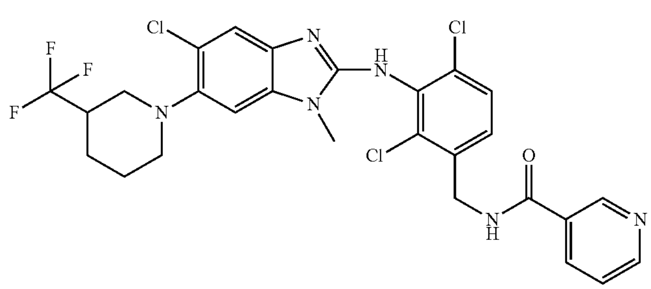 [SMILES: Cn1c(Nc2c(Cl)ccc(CNC(=O)c3cccnc3)c2Cl)nc2cc(Cl)c(N3CCCC(C(F)(F)F)C3)cc21] | C27H24Cl3F3N6O 611.88 | 611 | Rt: 1.60 (method Q) | 23 |

-continued

| Ex. | Structure | Formula/Mw. | MS* m/z [M + H]+ | Rf (TLC) or Rt [min] (HPLC-method) | Prepared in analogy to example |
|---|---|---|---|---|---|
| 173 | 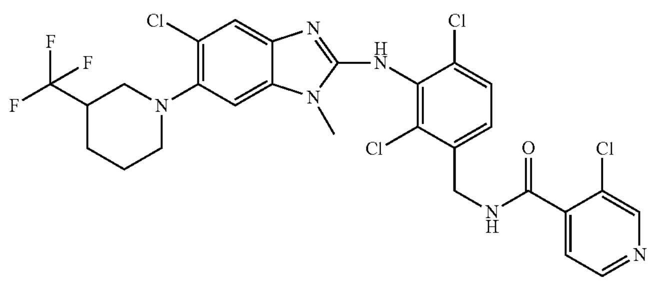 [SMILES: Cn1c(Nc2c(Cl)ccc(CNC(=O)c3ccncc3Cl)c2Cl)nc2cc(Cl)c(N3CCCC(C(F)(F)F)C3)cc21] | C27H23Cl4F3N6O 646.33 | 645 | Rt: 1.63 (method Q) | 23 |
| 174 | 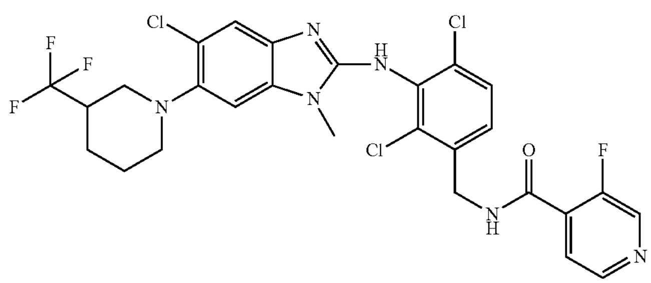 | C27H23Cl3F4N6O 629.87 | 629 | Rt: 1.62 (method Q) | 23 |
| 175 | 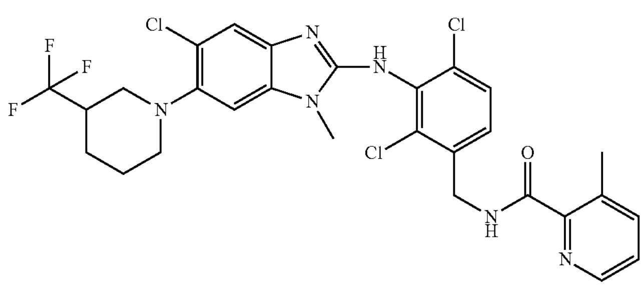 | C28H26Cl3F3N6O 625.91 | 625 | Rt: 1.67 (method Q) | 23 |
| 176 | 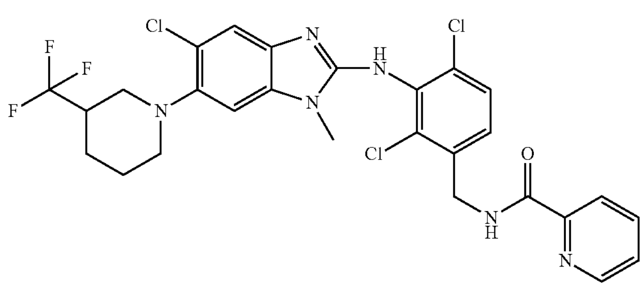 [SMILES: Cn1c(Nc2c(Cl)ccc(CNC(=O)c3ccccn3)c2Cl)nc2cc(Cl)c(N3CCCC(C(F)(F)F)C3)cc21] | C27H24Cl3F3N6O 611.88 | 611 | Rt: 1.65 (method Q) | 23 |
| 177 | 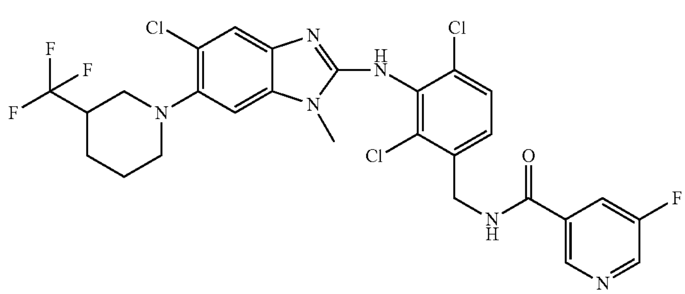 [SMILES: Cn1c(Nc2c(Cl)ccc(CNC(=O)c3cncc(F)c3)c2Cl)nc2cc(Cl)c(N3CCCC(C(F)(F)F)C3)cc21] | C27H23Cl3F4N6O 629.87 | 629 | Rt: 1.66 (method Q) | 23 |

-continued

| Ex. | Structure | Formula/Mw. | MS* m/z [M + H]+ | Rf (TLC) or Rt [min] (HPLC-method) | Prepared in analogy to example |
|---|---|---|---|---|---|
| 178 | 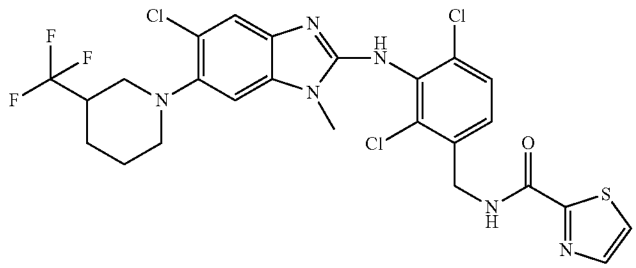 [SMILES: Cn1c(Nc2c(Cl)ccc(CNC(=O)c3nccs3)c2Cl)nc2cc(Cl)c(N3CCCC(C(F)(F)F)C3)cc21] | C25H22Cl3F3N6OS 617.91 | 617 | Rt: 1.64 (method Q) | 23 |
| 179 | 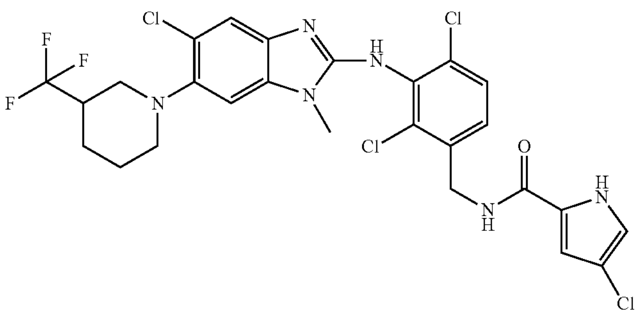 | C26H23Cl4F3N6O 634.31 | 633 | Rt: 1.69 (method Q) | 23 |
| 180 | 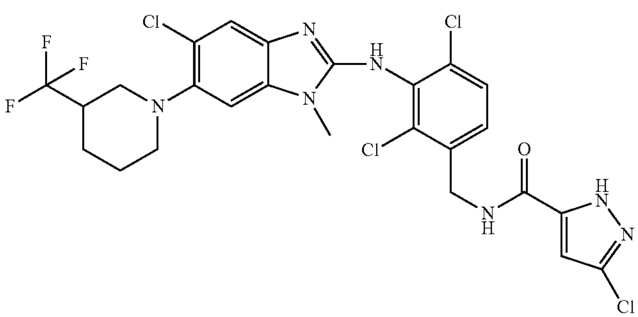 [SMILES: Cn1c(Nc2c(Cl)ccc(CNC(=O)c3cc(Cl)n[nH]3)c2Cl)nc2cc(Cl)c(N3CCCC(C(F)(F)F)C3)cc21] | C25H22Cl4F3N7O 635.3 | 634 | Rt: 1.66 (method Q) | 23 |

The invention claimed is:
1. A compound of formula (I)

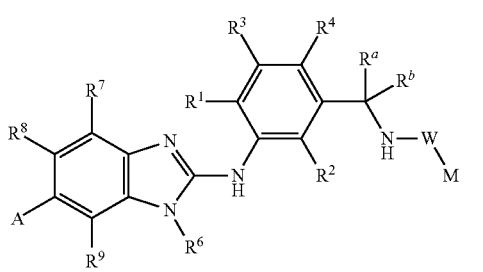

in which
R¹ represents halo, —OH, —CN, C$_{1-3}$ alkyl, C$_{2-6}$ alkynyl, or —OC$_{1-3}$ alkyl which latter three groups are optionally substituted by one or more substituents selected from fluoro, —CN, =O, —OH, —OCH$_3$, or —OCF$_3$;

R², R³ and R⁴ independently represent hydrogen, halo, —CN, C$_{1-3}$ alkyl, or —OC$_{1-3}$ alkyl which latter two alkyl groups are optionally substituted by one or more substituents selected from fluoro, —CN, =O, —OH, —OCH$_3$, or —OCF$_3$;

R$^a$ and R$^b$ independently represent hydrogen, or C$_{1-3}$ alkyl which is optionally substituted by one or more fluorine atoms,
or both together with the carbon atom which they are bound to, form a C$_{3-7}$ cycloalkyl ring, or a 4-6 membered heterocycloalkyl ring which latter two groups are optionally substituted by one or more fluorine atoms;

W represents —C(O)—, —S(O)—, —S(O)$_2$—, —C(O)O—, or —C(O)NR$^d$— which groups are bound to the nitrogen of the —NH— moiety via carbon or sulfur atom;

R$^d$ represents hydrogen, or C$_{1-3}$ alkyl;

M represents C$_{1-8}$ alkyl, C$_{2-8}$ alkynyl, C$_{3-8}$ cycloalkyl-C$_{0-4}$ alkyl-, or 4-10 membered heterocycloalkyl-C$_{0-4}$ alkyl- which latter four groups are optionally substituted by one or more groups selected from fluoro, —OH, =O, —CN, —NH$_2$, C$_{1-3}$ alkyl, —NH(C$_{1-3}$ alkyl), —N(C$_{1-3}$ alkyl)$_2$, azetidinyl, pyrrolidinyl, piperidinyl,
—OC$_{1-3}$ alkyl, [which latter seven alkyl groups can be substituted by one or more substituents selected from fluoro, —OH, —CN, —OC$_{1-2}$ alkyl (which latter alkyl group is optionally substituted by one or more fluorine atoms)],
aryl, or heteroaryl [which latter two groups are optionally substituted by one or more substituents selected from halo, —OH, —CN, C$_{1-3}$ alkyl, —OC$_{1-3}$ alkyl (which latter two alkyl groups are optionally substituted by one or more fluorine atoms)], or
aryl, or heteroaryl which latter two groups are optionally substituted by one or more substituents selected from
halo, —OH, —CN, —NH$_2$, aryl, heteroaryl [which latter two groups are optionally substituted by one or more substituents selected from halo, —OH, —CN, C$_{1-3}$ alkyl, —OC$_{1-3}$ alkyl (which latter two alkyl groups are optionally substituted by one or more fluorine atoms)],
C$_{1-7}$alkyl, C$_{2-7}$ alkynyl, C$_{3-7}$ cycloalkyl, 4-7 membered heterocycloalkyl, —NH$_2$, —NH(C$_{1-3}$ alkyl), —N(C$_{1-3}$ alkyl)$_2$, —OC$_{1-3}$ alkyl, —O—C$_{0-2}$alkyl-aryl, or —SC$_{1-3}$ alkyl, (which latter alkyl, alkynyl, heterocycloalkyl, aryl or cycloalkyl groups are optionally substituted by one or more substituents selected from fluoro, —CN, =O, —NH$_2$, —NH(C$_{1-3}$ alkyl), —N(C$_{1-3}$ alkyl)$_2$, —OH, or —OC$_{1-3}$alkyl)];
R$^6$ represents hydrogen, C$_{1-5}$ alkyl, C$_{3-6}$ alkynyl, 4-7 membered hetero-cycloalkyl-C$_{0-2}$alkyl or C$_{3-7}$cycloalkyl-C$_{0-2}$alkyl (which latter four groups are optionally substituted by one or more substituents selected from fluoro, —CN, =O, C$_{1-3}$ alkyl, —OH, —NH$_2$, —OC$_{1-3}$ alkyl, —NH(C$_{1-3}$ alkyl), or —N(C$_{1-3}$ alkyl)$_2$);
R$^7$, R$^8$ and R$^9$ independently represent hydrogen, halo, —CN, C$_{1-5}$ alkyl, C$_{3-5}$ cycloalkyl-C$_{0-2}$alkyl-, C$_{1-5}$ alkyl-O—, or C$_{3-5}$cycloalkyl-C$_{0-2}$alkyl-O— (in which latter four groups the alkyl and cycloalkyl fragments are optionally substituted by one or more substituents selected from fluoro, —CN, —OH, —OC$_{1-3}$ alkyl or by one or more C$_{1-3}$ alkyl groups which are optionally substituted by one or more fluorine atoms);
A represents —NHR$^{10}$, —NR$^{10}$R$^{11}$, or a
4-10-membered heterocycloalkyl group which is bound to the benzimidazole through a nitrogen atom, and which is optionally substituted by one or more substituents R$^{12}$;
R$^{10}$ and R$^{11}$ independently represent C$_{1-7}$ alkyl, C$_{3-7}$ cycloalkyl-C$_{0-4}$ alkyl- or C$_{4-7}$ heterocycloalkyl-C$_{0-4}$ alkyl- [which latter three groups are optionally substituted by one or more groups selected from fluoro, —OH, NH$_2$, —CN, C$_{1-3}$ alkyl, —NH(C$_{1-3}$ alkyl), —N(C$_{1-3}$ alkyl)$_2$, —OC$_{1-5}$ alkyl,
—OC$_{3-6}$ cycloalkyl, or —OC$_{4-6}$ heterocycloalkyl (which latter six groups are optionally substituted by one or more substituents selected from fluoro, —CF$_3$, —CHF$_2$, —CH$_2$F, or —CH$_3$)],
or
aryl-C$_{0-4}$ alkyl-, or heteroaryl-C$_{0-4}$ alkyl-[which latter two groups are optionally substituted by one or more substituents selected from halo, —OH, —CN, C$_{1-3}$ alkyl, C$_{3-5}$ cycloalkyl, C$_{1-3}$ alkyl-O—, or
C$_{3-5}$ cycloalkyl-O— (which latter four groups are optionally substituted by one or more fluorine atoms)];
each R$^{12}$ independently represents halo, —OH, —NH$_2$, =O, —CN, C$_{1-4}$ alkyl, C$_{3-5}$ cycloalkyl-C$_{0-2}$ alkyl-, C$_{4-5}$ heterocycloalkyl-C$_{0-2}$ alkyl-, C$_{1-4}$ alkyl-O—, C$_{1-3}$ alkyl-C(=O)—, —C(=O)—NH(C$_{1-3}$ alkyl), or —C(=O)—N(C$_{1-3}$ alkyl)$_2$ [which latter six groups are optionally substituted by one or more groups selected from fluoro, —OH, oxo, —NH$_2$, —CN, C$_{1-3}$ alkyl, —NH(C$_{1-3}$ alkyl), —N(C$_{1-3}$ alkyl)$_2$, —OC$_{1-3}$ alkyl, or —OC$_{3-5}$ cycloalkyl [which latter five groups are optionally substituted by one or more substituents selected from fluoro, —CF$_3$, —CHF$_2$, or —CH$_2$F],
or
aryl-C$_{0-4}$ alkyl-, or heteroaryl-C$_{0-4}$ alkyl-[which latter two groups are optionally substituted by one or more substituents selected from halo, —OH, —CN, C$_{1-3}$ alkyl, C$_{3-5}$ cycloalkyl, C$_{1-3}$ alkyl-O—, or
C$_{3-5}$ cycloalkyl-O— (which latter four groups are optionally substituted by one or more fluorine atoms)];
or a salt thereof.

2. A compound according to claim 1, wherein
R$^1$ represents halo, C$_{1-3}$ alkyl, or —OC$_{1-3}$ alkyl which latter two groups are
optionally substituted by one or more fluorine atoms;
or a pharmaceutically acceptable salt thereof.

3. A compound according to claim 1, wherein
R$^3$ and R$^4$ independently represent hydrogen, or halo;
or a pharmaceutically acceptable salt thereof.

4. A compound according to claim 1, wherein
M represents C$_{1-6}$ alkyl, C$_{2-6}$ alkynyl, C$_{3-8}$ cycloalkyl-C$_{0-1}$ alkyl-, oxetanyl-, tetrahydrofuranyl-, azetidinyl-, pyrrolidinyl-, or piperidinyl- or one of the following heterocyclic groups all of which groups are optionally substituted by one or more groups selected from
fluoro, —OH, —CN, —NH$_2$, C$_{1-3}$ alkyl, —NH(C$_{1-2}$ alkyl), —N(C$_{1-2}$ alkyl)$_2$, or —OC$_{1-2}$ alkyl [which latter four alkyl groups are optionally substituted by one or more substituents selected from fluoro],
phenyl, or imidazolyl-[which latter two groups are optionally substituted by one or more substituents selected from halo, C$_{1-2}$ alkyl, or OC$_{1-2}$alkyl (which latter two alkyl groups are optionally substituted by one or more fluorine atoms)],
or
phenyl, naphthyl, furanyl, thienyl, oxazolyl, isoxazolyl, thiazolyl, pyrrolyl, pyrazolyl, pyridinyl, pyrazinyl, or quinolynyl which latter twelve groups are optionally substituted by one or more substituents selected from halo, aryl, heteroaryl [which latter two groups are optionally substituted by one or more substituents selected from halo, —CH$_3$, —CH$_2$F, —CHF$_2$, or —CF$_3$],
C$_{1-2}$ alkyl, —OC$_{1-2}$ alkyl [which latter two groups are optionally substituted by one or more fluorine atoms],
C$_{2-3}$ alkynyl, or —O—C$_{0-2}$alkyl-phenyl [in which latter group the phenyl is optionally substituted by one or more substituents selected from halo, —CH$_3$, —CH$_2$F, —CHF$_2$, or —CF$_3$];
or a pharmaceutically acceptable salt thereof.

5. A compound according to claim 1, wherein
$R^7$ and $R^9$ independently represent hydrogen, halo, —CN, or $C_{1-3}$ alkyl optionally substituted by one or more fluorine atoms;
or a pharmaceutically acceptable salt thereof.

6. A compound according to claim 1, wherein
A represents —$NHR^{10}$, —$NR^{10}R^{11}$, or
azetidinyl-, pyrrolidinyl-, piperidinyl-, morpholinyl-, piperazinyl- or all of which heterocyclic groups are optionally substituted by one or more substituents $R^{12}$ and annulated to a phenyl or a 5- or 6-membered heteroaryl ring, while the above mentioned groups are bonded to the benzimidazole core through a nitrogen atom;
$R^{10}$ and $R^{11}$ independently represent $C_{1-5}$ alkyl, or $C_{3-6}$ cycloalkyl-$C_{0-1}$ alkyl-[which latter two groups are optionally substituted by one or more groups selected from fluoro, —OH, or $C_{1-3}$ alkyl],
or
aryl-$C_{0-1}$ alkyl- optionally substituted by one or more substituents selected from halo, —OH, —CN, $C_{1-3}$ alkyl, or $C_{1-3}$ alkyl-O—[which latter two groups are optionally substituted by one or more fluorine atoms];
each $R^{12}$ independently represents halo, —OH, —CN, $C_{1-4}$ alkyl, $C_{1-2}$ alkyl-O—, $C_{1-2}$ alkyl-C(=O)—, —C(=O)—NH($C_{1-2}$ alkyl), or —C(=O)—N($C_{1-2}$ alkyl)$_2$ [which latter five groups are optionally substituted by one or more groups selected from fluoro, —OH, $C_{1-3}$ alkyl, —NH($C_{1-2}$ alkyl), —N($C_{1-2}$ alkyl)$_2$, or —O$C_{1-2}$ alkyl (which latter four groups are optionally substituted by one or more substituents selected from fluoro, $CF_3$, $CHF_2$ or $CH_2F$)],
or
phenyl optionally substituted by one or more substituents selected from halo or $C_{1-3}$ alkyl which is optionally substituted by one or more fluorine atoms;
or a pharmaceutically acceptable salt thereof.

7. A compound according to claim 1, namely a compound of formula Ia (Ia)

in which
$R^1$ represents halo, $C_{1-3}$ alkyl, or —O$C_{1-3}$ alkyl which latter two groups are optionally substituted by one or more fluorine atoms;
$R^2$ represents hydrogen, halo, or $C_{1-3}$ alkyl optionally substituted by one or more fluorine atoms;

$R^3$ and $R^4$ independently represent hydrogen, or halo;
W represents —C(O)—, —S(O)$_2$—, or —C(O)O— which groups are bound to the nitrogen of the —NH— moiety via carbon or sulfur atom;
M represents $C_{1-6}$ alkyl, $C_{2-6}$ alkynyl, $C_{3-8}$ cycloalkyl-$C_{0-1}$ alkyl-, oxetanyl-, tetrahydrofuranyl-, azetidinyl-, pyrrolidinyl-, or piperidinyl- or one of the following heterocyclic groups all of which groups are optionally substituted by one or more groups selected from
fluoro, —OH, —CN, —$NH_2$, $C_{1-3}$ alkyl, —NH($C_{1-2}$ alkyl), —N($C_{1-2}$ alkyl)$_2$, or —O$C_{1-2}$ alkyl, [which latter four alkyl groups are optionally substituted by one or more fluorine atoms], phenyl, imidazolyl-[which latter two groups are optionally substituted by one or more substituents selected from halo, $C_{1-2}$ alkyl, or O$C_{1-2}$alkyl (which latter two alkyl groups are optionally substituted by one or more fluorine atoms)],
or
phenyl, naphthyl, furanyl, thienyl, oxazolyl, isoxazolyl, thiazolyl, pyrrolyl, pyrazolyl, pyridinyl, pyrazinyl, or quinolynyl which latter twelve groups are optionally substituted by one or more substituents selected from
halo, aryl, heteroaryl [which latter two groups are optionally substituted by one or more substituents selected from halo, —$CH_3$, —$CH_2F$, —$CHF_2$, —$CF_3$],
$C_{1-2}$ alkyl, —O$C_{1-2}$ alkyl [which latter two groups are optionally substituted by one or more fluorine atoms],
$C_{2-3}$ alkynyl, or —O—$C_{0-2}$alkyl-phenyl [in which latter group the phenyl is optionally substituted by one or more substituents selected from halo, —$CH_3$, —$CH_2F$, —$CHF_2$, or —$CF_3$];
$R^6$ represents hydrogen, $C_{1-5}$ alkyl or $C_{3-7}$cycloalkyl-$C_{0-2}$alkyl [which latter two groups are optionally substituted by one or more substituents selected from fluoro, $C_{1-3}$ alkyl, —O$C_{1-3}$ alkyl, —NH($C_{1-3}$ alkyl), or —N($C_{1-3}$ alkyl)$_2$];
$R^8$ represents hydrogen, halo, —CN, $C_{1-5}$ alkyl, or $C_{3-5}$ cycloalkyl-$C_{0-2}$ alkyl-(in which latter two groups the alkyl and cycloalkyl fragments are optionally substituted by one or more fluorine atoms, or by one or more $C_{1-3}$ alkyl groups which are optionally substituted by one or more fluorine atoms)
$R^9$ represents hydrogen, halo, —CN, or $C_{1-3}$ alkyl optionally substituted by one or more substituents selected from fluorine atoms;
A represents —$NHR^{10}$, —$NR^{10}R^{11}$, or
azetidinyl-, pyrrolidinyl-, piperidinyl-, morpholinyl-, piperazinyl- or all of which heterocyclic groups can optionally be substituted by one or more substituents R$^{12}$ and optionally annulated to a phenyl or a 5- or 6-membered heteroaryl ring, whereby the above mentioned groups are bonded to the benzimidazole core through a nitrogen atom;

R$^{10}$ and R$^{11}$ independently represent C$_{1-5}$ alkyl or C$_{3-6}$ cycloalkyl-C$_{0-1}$ alkyl-[which latter two groups are optionally substituted by one or more groups selected from: fluoro, —OH, C$_{1-3}$ alkyl],
or
aryl-C$_{0-1}$ alkyl- which can be substituted by one or more substituents selected from halo, —OH, —CN, C$_{1-3}$ alkyl, or C$_{1-3}$ alkyl-O—[which latter two groups are optionally substituted by one or more fluorine atoms];

each R$^{12}$ independently represents halo, —OH, —CN, C$_{1-4}$ alkyl, C$_{1-2}$ alkyl-O—, C$_{1-2}$ alkyl-C(=O)—, —C(=O)—NH(C$_{1-2}$ alkyl), or —C(=O)—N(C$_{1-2}$ alkyl)$_2$ [which latter five groups are optionally substituted by one or more groups selected from fluoro, —OH, C$_{1-3}$ alkyl, —NH(C$_{1-2}$ alkyl), —N(C$_{1-2}$ alkyl)$_2$, or —OC$_{1-2}$ alkyl, (which latter four groups are optionally substituted by one or more substituents selected from fluoro, CF$_3$, CHF$_2$ or CH$_2$F)],
or
phenyl optionally substituted by one or more substituents selected from halo or C$_{1-3}$ alkyl which is optionally substituted by one or more fluorine atoms;
or a pharmaceutically acceptable salt thereof.

8. A compound according to claim 1, wherein R$^8$ represents hydrogen, fluoro, chloro, CF$_3$, or —CN; or a pharmaceutically acceptable salt thereof.

9. A compound according to claim 1, wherein A represents a group selected from

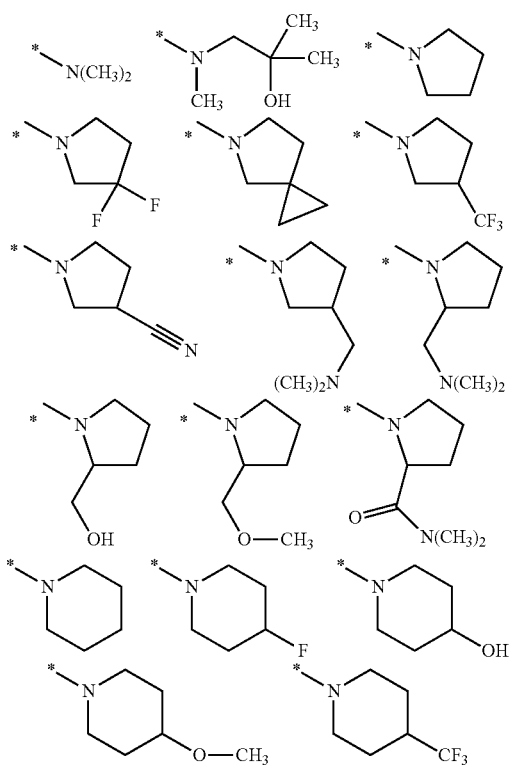

or a pharmaceutically acceptable salt thereof.

10. A compound according to claim 1, wherein M represents a group selected from

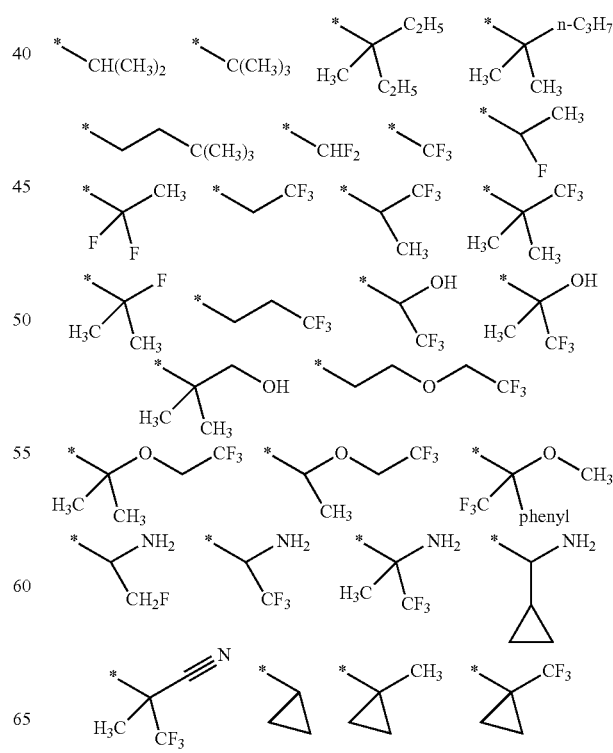

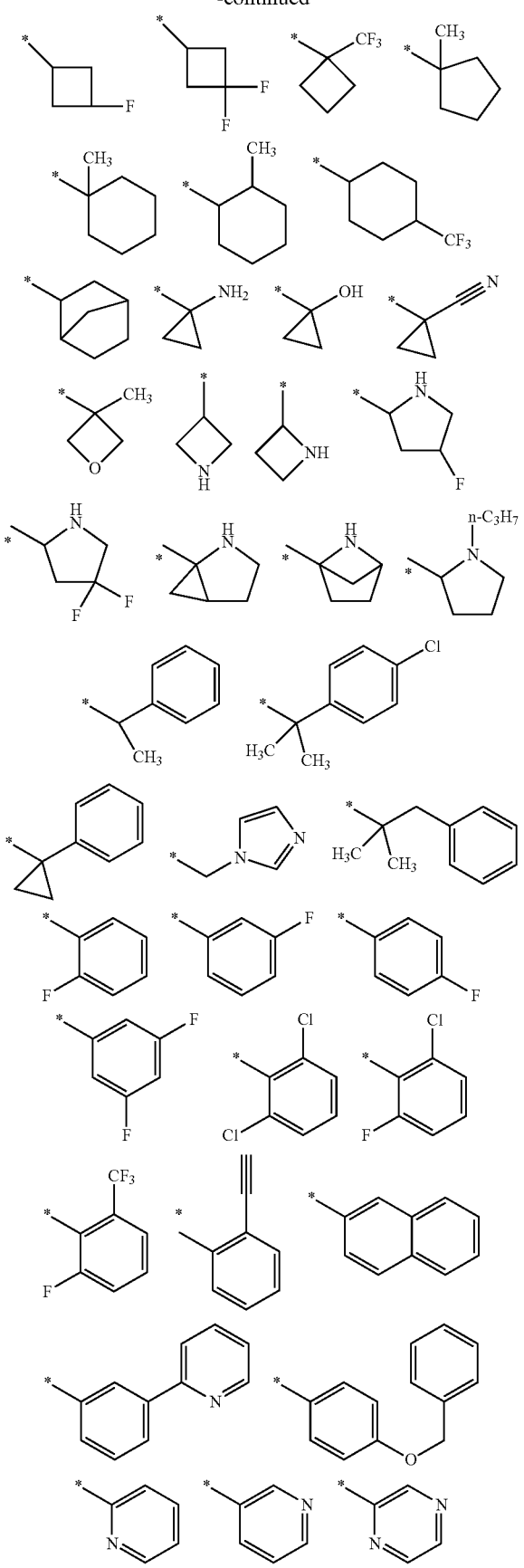

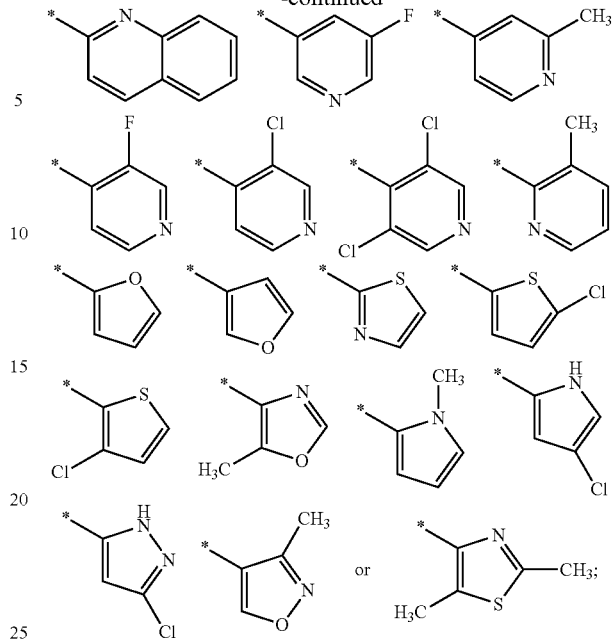

or a pharmaceutically acceptable salt thereof.

11. A compound according to claim 1, namely a compound of formula (Ia)

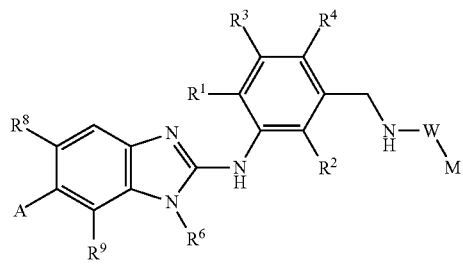

in which
$R^1$ represents fluoro, chloro, $CH_3$, $CHF_2$, $CH_2F$, $CF_3$ or —$OCF_3$;
$R^2$ represents hydrogen, fluoro or chloro;
$R^3$ and $R^4$ independently represent hydrogen, or fluoro;
$R^6$ represents hydrogen, —$CH_3$, —$CH_2CF_3$, cyclopropyl-methyl-, —$CH_2CH_2$—O—$CH_3$, or —$CH_2CH_2$—N$(CH_3)_2$;
$R^8$ represents hydrogen, fluoro, chloro, $CF_3$, or —CN;
$R^9$ represents hydrogen, or fluoro;
A represents a group selected from

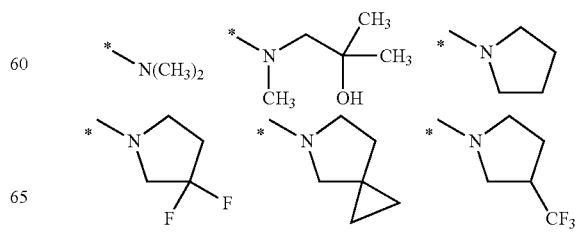

183
-continued
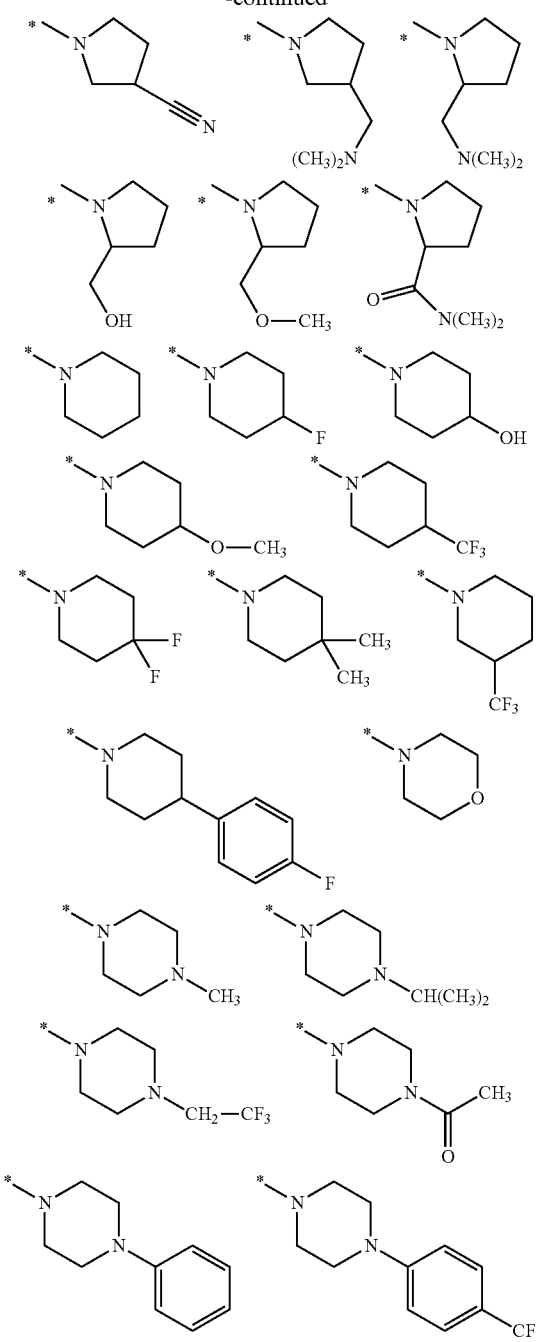
W represents —C(O)—, or —S(O)₂— which groups are bound to the nitrogen of the —NH— moiety via carbon or sulfur atom;
M represents a group selected from
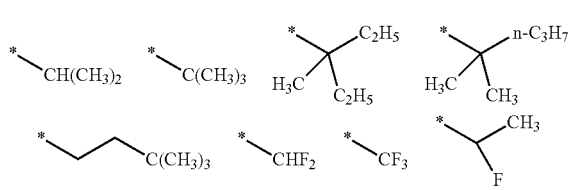
184
-continued
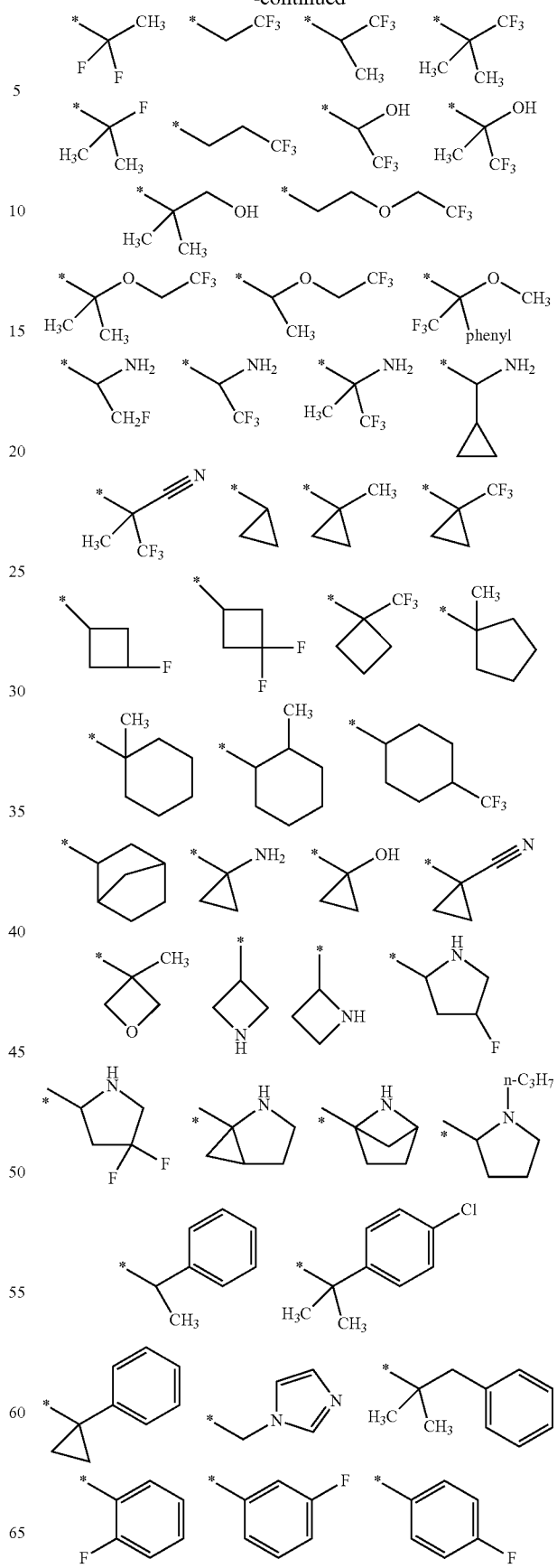

-continued
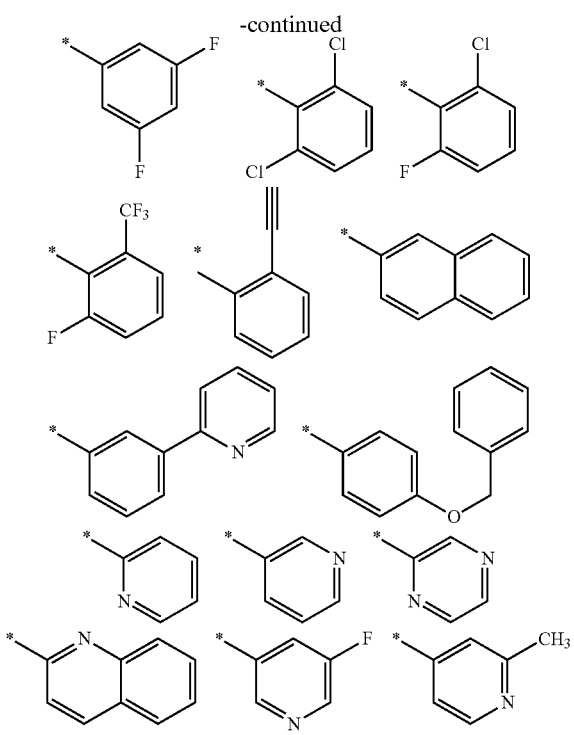
-continued
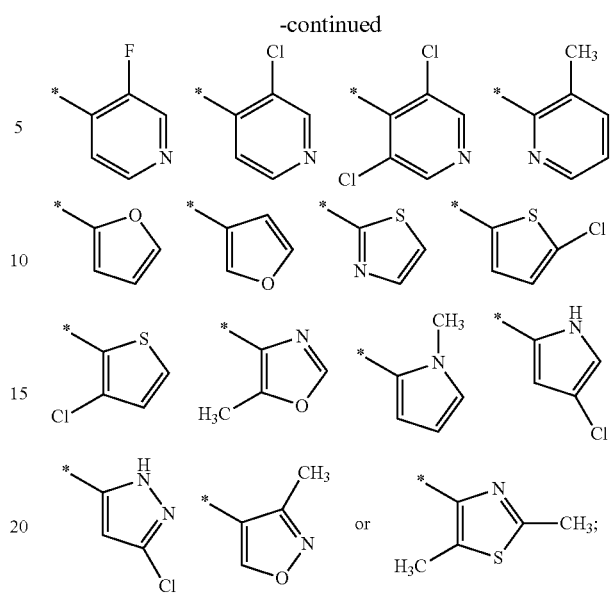
or a pharmaceutically acceptable salt thereof.
12. A compound according to claim 1 selected from the compounds below:
| | Structure |
|---|---|
| 1 | 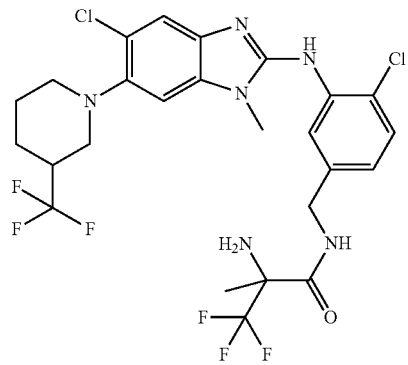 [SMILES: Cn1c(Nc2cc(CNC(=O)C(C)(N)C(F)(F)F)ccc2Cl)nc2cc(Cl)c(N3CCCC(C(F)(F)F)C3)cc21] |
| 2 | 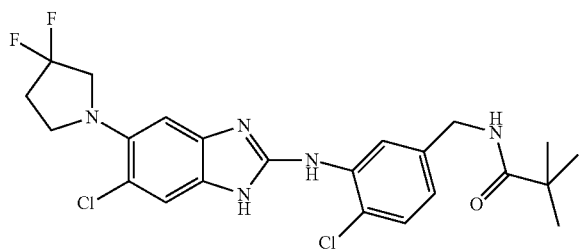 [SMILES: CC(C)(C)C(=O)NCc1ccc(Cl)c(Nc2nc3cc(N4CCC(F)(F)C4)c(Cl)cc3[nH]2)c1] |

-continued
| | Structure |
|---|---|
| 3 | 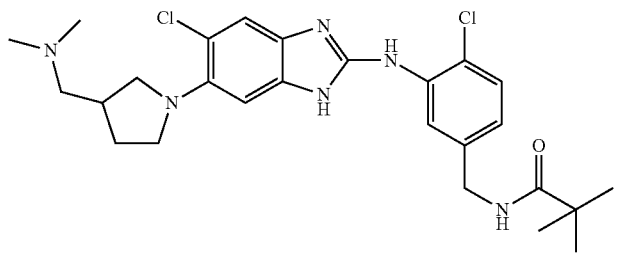 [SMILES: CN(C)CC1CCN(c2cc3[nH]c(Nc4cc(CNC(=O)C(C)(C)C)ccc4Cl)nc3cc2Cl)C1] |
| 4 | 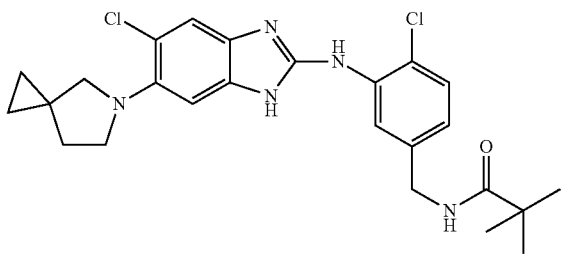 [SMILES: CC(C)(C)C(=O)NCc1ccc(Cl)c(Nc2nc3cc(Cl)c(N4CCC5(CC5)C4)cc3[nH]2)c1] |
| 5 | 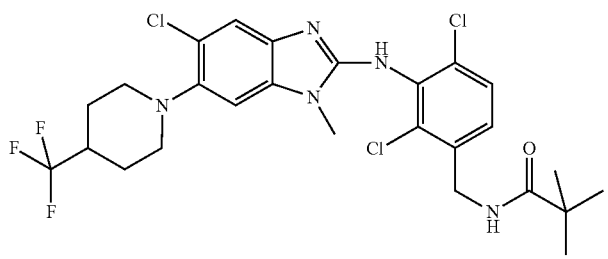 [SMILES: Cn1c(Nc2c(Cl)ccc(CNC(=O)C(C)(C)C)c2Cl)nc2cc(Cl)c(N3CCC(C(F)(F)F)CC3)cc21] |
| 6 | 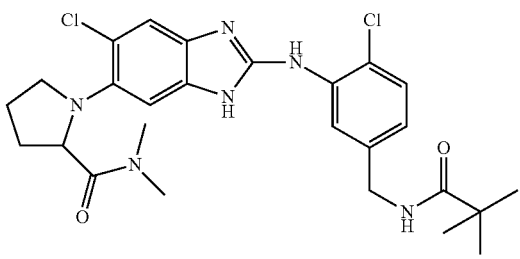 [SMILES: CN(C)C(=O)C1CCCN1c1cc2[nH]c(Nc3cc(CNC(=O)C(C)(C)C)ccc3Cl)nc2cc1Cl] |
| 7 | 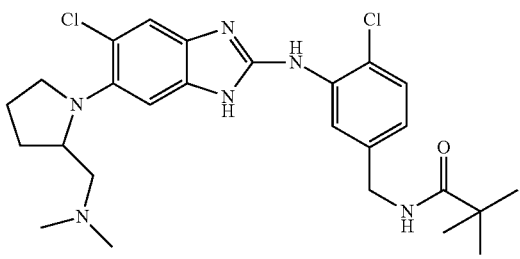 [SMILES: CN(C)CC1CCCN1c1cc2[nH]c(Nc3cc(CNC(=O)C(C)(C)C)ccc3Cl)nc2cc1Cl] |
| 8 | 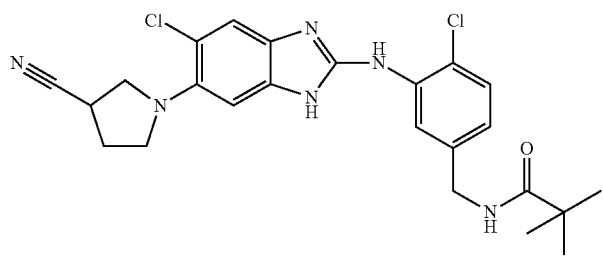 [SMILES: CC(C)(C)C(=O)NCc1ccc(Cl)c(Nc2nc3cc(Cl)c(N4CCC(C#N)C4)cc3[nH]2)c1] |

| | Structure |
|---|---|
| 9 | 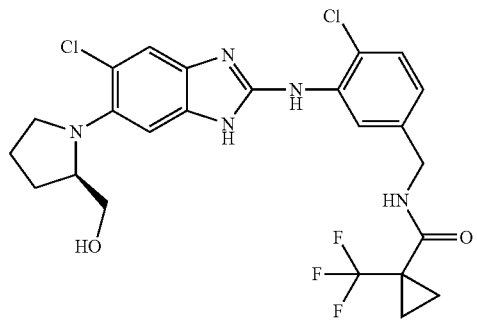 [SMILES: O=C(NCc1ccc(Cl)c(Nc2nc3cc(Cl)c(N4CCC[C@@H]4CO)cc3[nH]2)c1)C1(C(F)(F)F)CC1] |
| 10 | 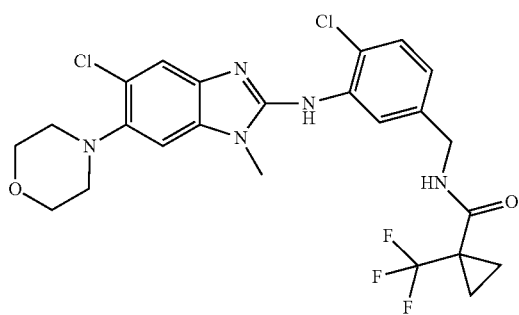 [SMILES: Cn1c(Nc2cc(CNC(=O)C3(C(F)(F)F)CC3)ccc2Cl)nc2cc(Cl)c(N3CCOCC3)cc21] |
| 11 | 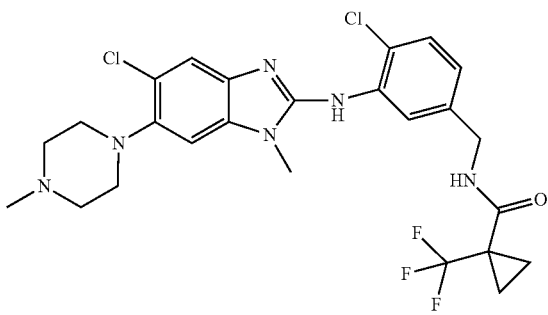 [SMILES: CN1CCN(c2cc3c(cc2Cl)nc(Nc2cc(CNC(=O)C4(C(F)(F)F)CC4)ccc2Cl)n3C)CC1] |
| 12 | 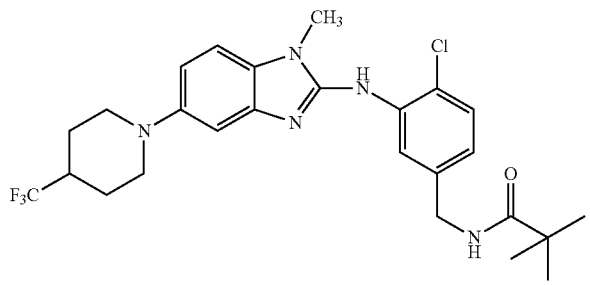 [SMILES: Cn1c(Nc2cc(CNC(=O)C(C)(C)C)ccc2Cl)nc2cc(N3CCC(C(F)(F)F)CC3)ccc21] |
| 13 | 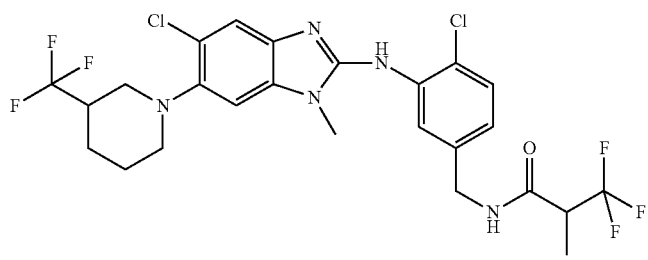 [SMILES: CC(C(=O)NCc1ccc(Cl)c(Nc2nc3cc(Cl)c(N4CCCC(C(F)(F)F)C4)cc3n2C)c1)C(F)(F)F] |

-continued
| | Structure |
|---|---|
| 14 | 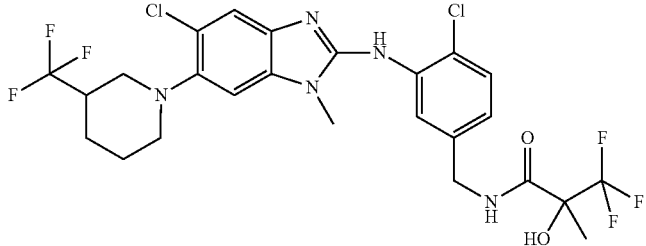 [SMILES: Cn1c(Nc2cc(CNC(=O)C(C)(O)C(F)(F)F)ccc2Cl)nc2cc(Cl)c(N3CCCC(C(F)(F)F)C3)cc21] |
| 15 | 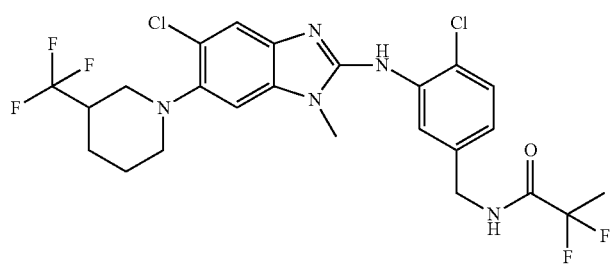 [SMILES: Cn1c(Nc2cc(CNC(=O)C(C)(F)F)ccc2Cl)nc2cc(Cl)c(N3CCCC(C(F)(F)F)C3)cc21] |
| 16 | 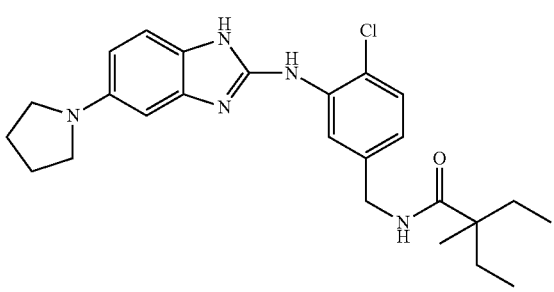 [SMILES: CCC(C)(CC)C(=O)NCc1ccc(Cl)c(Nc2nc3cc(N4CCCC4)ccc3[nH]2)c1] |
| 17 | 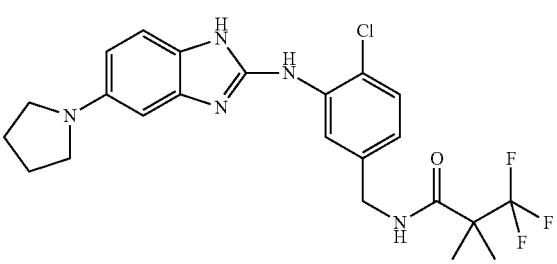 [SMILES: CC(C)(C(=O)NCc1ccc(Cl)c(Nc2nc3cc(N4CCCC4)ccc3[nH]2)c1)C(F)(F)F] |
| 18 | 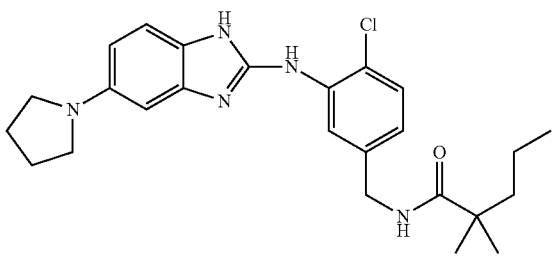 [SMILES: CCCC(C)(C)C(=O)NCc1ccc(Cl)c(Nc2nc3cc(N4CCCC4)ccc3[nH]2)c1] |
| 19 | 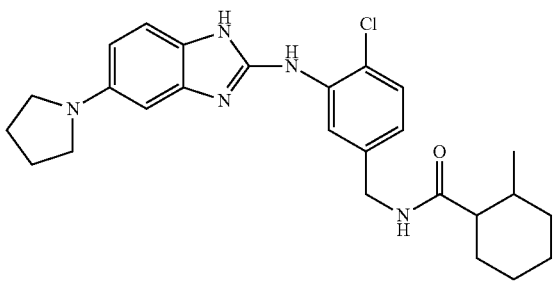 [SMILES: CC1CCCCC1C(=O)NCc1ccc(Cl)c(Nc2nc3cc(N4CCCC4)ccc3[nH]2)c1] |

-continued
| | Structure |
|---|---|
| 20 | 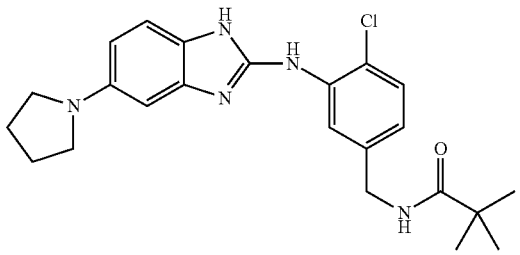 [SMILES: CC(C)(C)C(=O)NCc1ccc(Cl)c(Nc2nc3cc(N4CCCC4)ccc3[nH]2)c1] |
| 21 | 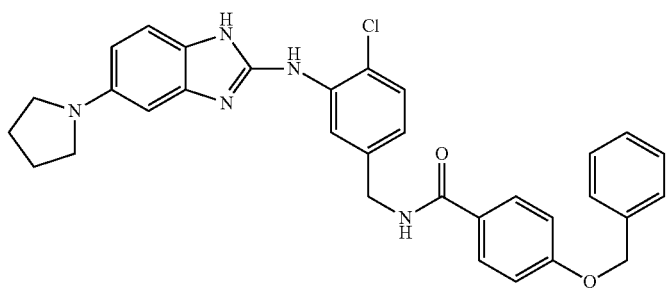 [SMILES: O=C(NCc1ccc(Cl)c(Nc2nc3cc(N4CCCC4)ccc3[nH]2)c1)c1ccc(OCc2ccccc2)cc1] |
| 22 | 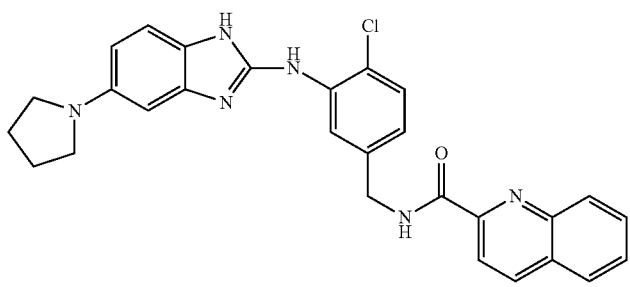 [SMILES: O=C(NCc1ccc(Cl)c(Nc2nc3cc(N4CCCC4)ccc3[nH]2)c1)c1ccc2ccccc2n1] |
| 23 | 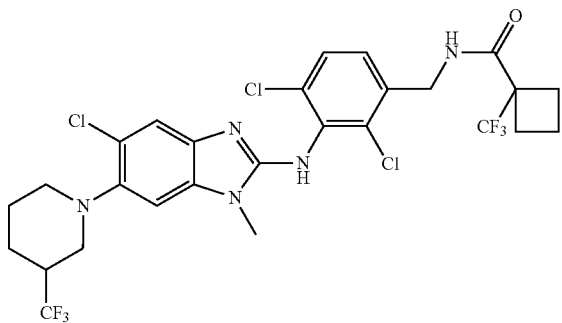 [SMILES: Cn1c(Nc2c(Cl)ccc(CNC(=O)C3(C(F)(F)F)CCC3)c2Cl)nc2cc(Cl)c(N3CCCC(C(F)(F)F)C3)cc21] |
| 24 | 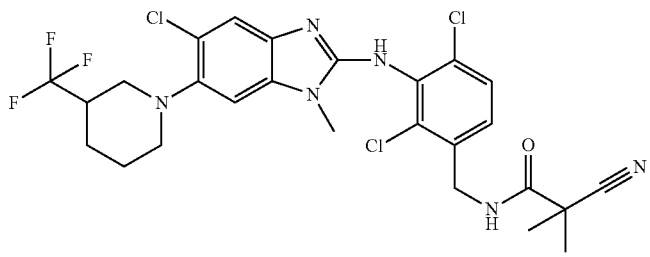 [SMILES: Cn1c(Nc2c(Cl)ccc(CNC(=O)C(C)(C)C#N)c2Cl)nc2cc(Cl)c(N3CCCC(C(F)(F)F)C3)cc21] |

-continued
| | Structure |
|---|---|
| 25 | 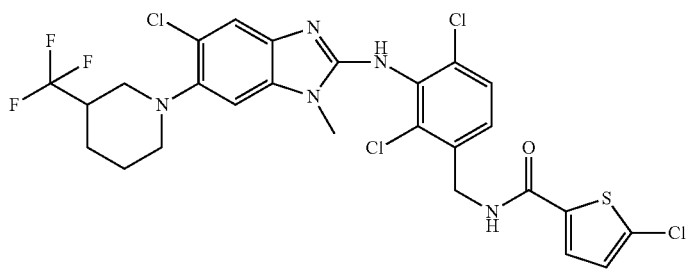 [SMILES: Cn1c(Nc2c(Cl)ccc(CNC(=O)c3ccc(Cl)s3)c2Cl)nc2cc(Cl)c(N3CCCC(C(F)(F)F)C3)cc21] |
| 26 | 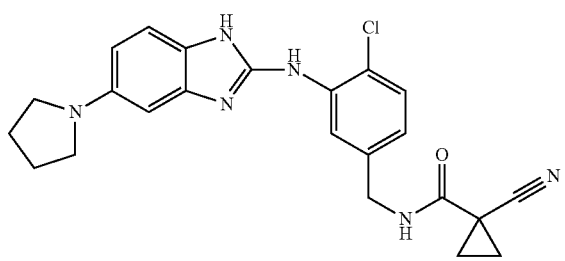 [SMILES: N#CC1(C(=O)NCc2ccc(Cl)c(Nc3nc4cc(N5CCCC5)ccc4[nH]3)c2)CC1] |
| 27 | 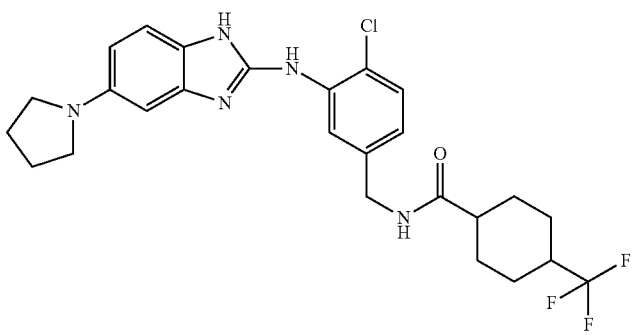 [SMILES: O=C(NCc1ccc(Cl)c(Nc2nc3cc(N4CCCC4)ccc3[nH]2)c1)C1CCC(C(F)(F)F)CC1] |
| 28 | 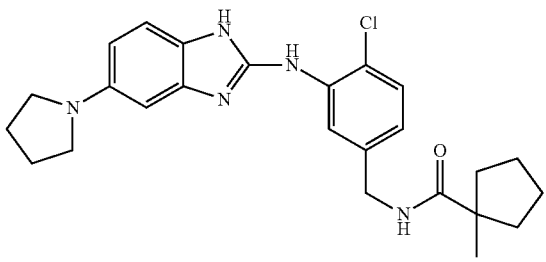 [SMILES: CC1(C(=O)NCc2ccc(Cl)c(Nc3nc4cc(N5CCCC5)ccc4[nH]3)c2)CCCC1] |
| 29 | 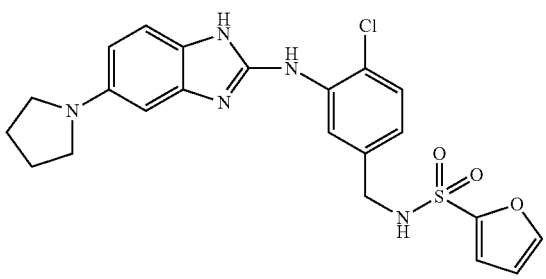 [SMILES: O=S(=O)(NCc1ccc(Cl)c(Nc2nc3cc(N4CCCC4)ccc3[nH]2)c1)c1ccco1] |

| | Structure |
|---|---|
| 30 | 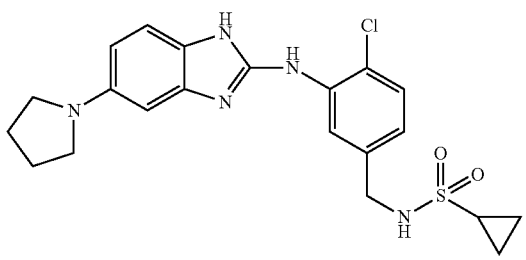 [SMILES: O=S(=O)(NCc1ccc(Cl)c(Nc2nc3cc(N4CCCC4)ccc3[nH]2)c1)C1CC1] |
| 31 | 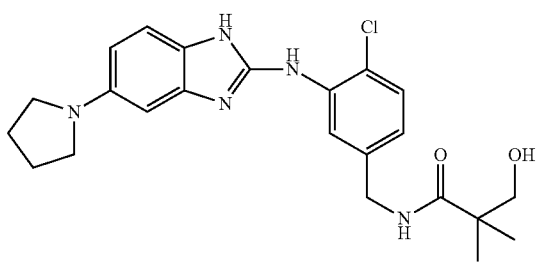 [SMILES: CC(C)(CO)C(=O)NCc1ccc(Cl)c(Nc2nc3cc(N4CCCC4)ccc3[nH]2)c1] |
| 32 | 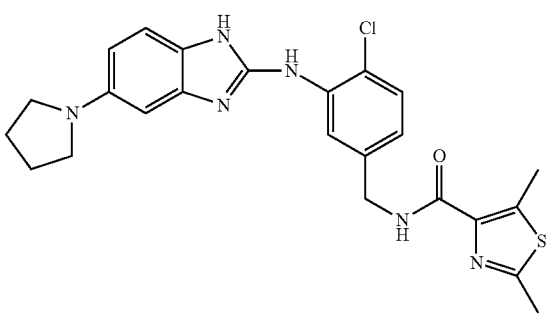 [SMILES: Cc1nc(C(=O)NCc2ccc(Cl)c(Nc3nc4cc(N5CCCC5)ccc4[nH]3)c2)c(C)s1] |
| 33 | 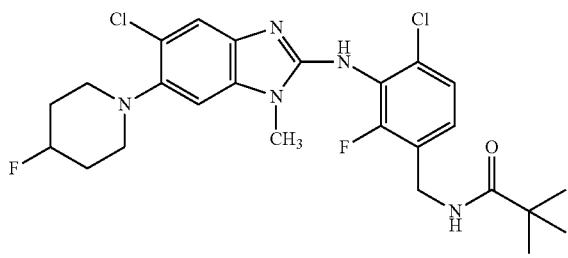 [SMILES: Cn1c(Nc2c(Cl)ccc(CNC(=O)C(C)(C)C)c2F)nc2cc(Cl)c(N3CCC(F)CC3)cc21] |
| 34 | 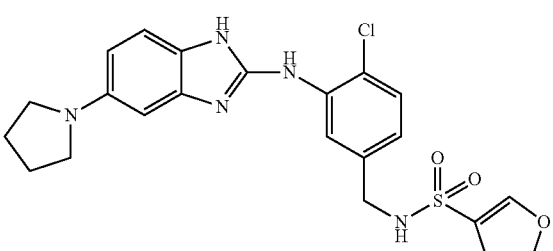 |

| | Structure |
|---|---|
| 35 | 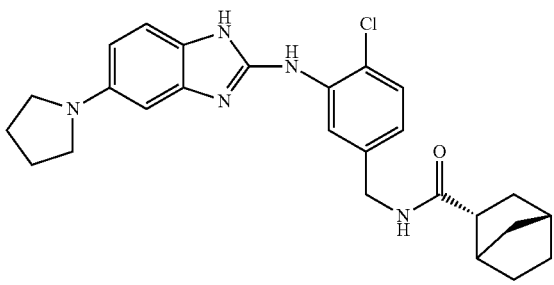 [SMILES: O=C(NCc1ccc(Cl)c(Nc2nc3cc(N4CCCC4)ccc3[nH]2)c1)[C@@H]1C[C@@H]2CCC1C2] |
| 36 | 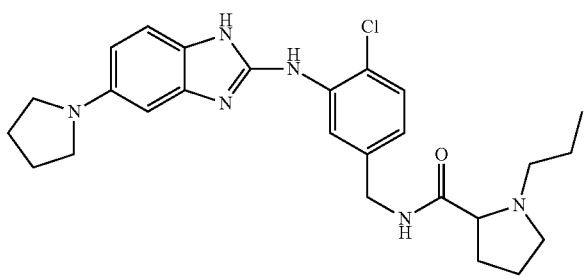 [SMILES: CCCN1CCCC1C(=O)NCc1ccc(Cl)c(Nc2nc3cc(N4CCCC4)ccc3[nH]2)c1] |
| 37 | 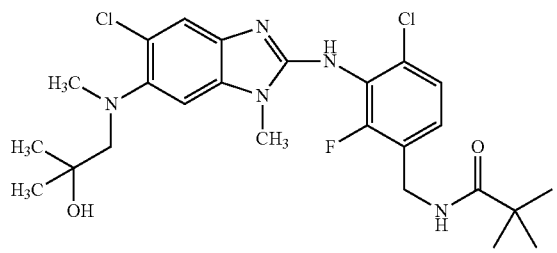 [SMILES: CN(CC(C)(C)O)c1cc2c(cc1Cl)nc(Nc1c(Cl)ccc(CNC(=O)C(C)(C)C)c1F)n2C] |
| 38 | 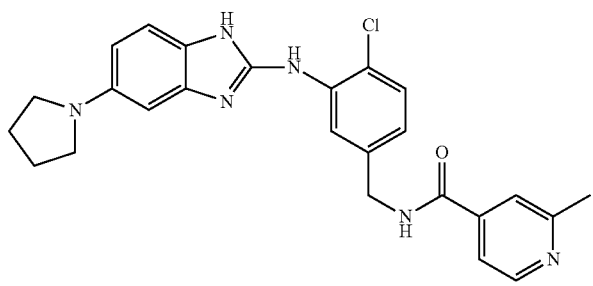 [SMILES: Cc1cc(C(=O)NCc2ccc(Cl)c(Nc3nc4cc(N5CCCC5)ccc4[nH]3)c2)ccn1] |
| 39 | 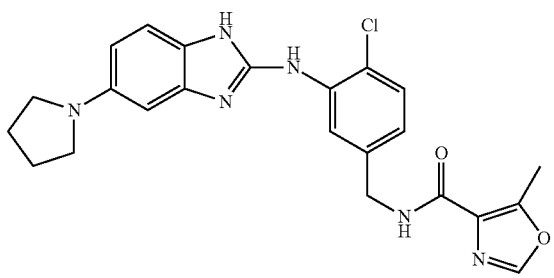 [SMILES: Cc1ocnc1C(=O)NCc1ccc(Cl)c(Nc2nc3cc(N4CCCC4)ccc3[nH]2)c1] |

| | Structure |
|---|---|
| 40 | 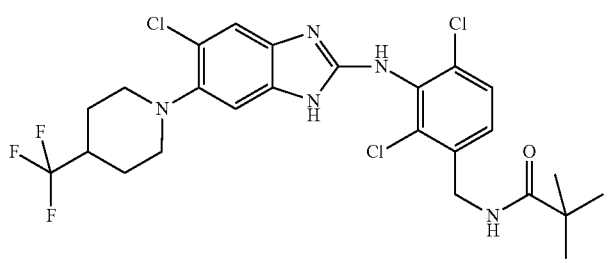 [SMILES: CC(C)(C)C(=O)NCc1ccc(Cl)c(Nc2nc3cc(Cl)c(N4CCC(C(F)(F)F)CC4)cc3[nH]2)c1Cl] |
| 41 | 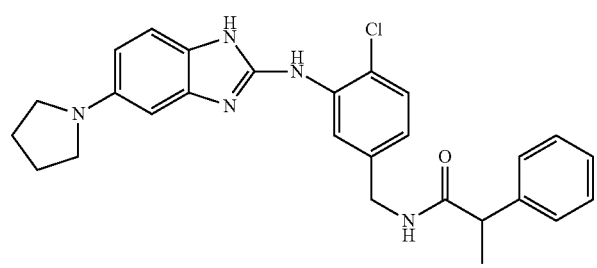 [SMILES: CC(C(=O)NCc1ccc(Cl)c(Nc2nc3cc(N4CCCC4)ccc3[nH]2)c1)c1ccccc1] |
| 42 | 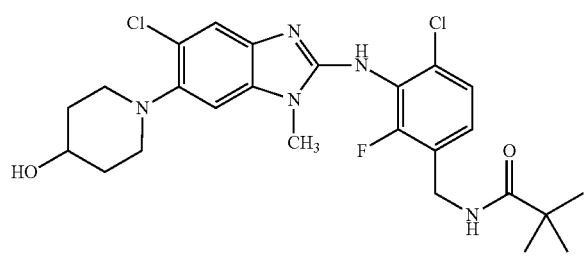 [SMILES: Cn1c(Nc2c(Cl)ccc(CNC(=O)C(C)(C)C)c2F)nc2cc(Cl)c(N3CCC(O)CC3)cc21] |
| 43 | 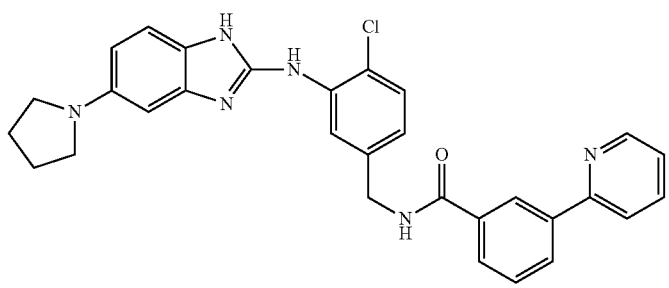 [SMILES: O=C(NCc1ccc(Cl)c(Nc2nc3cc(N4CCCC4)ccc3[nH]2)c1)c1cccc(-c2ccccn2)c1] |
| 44 | 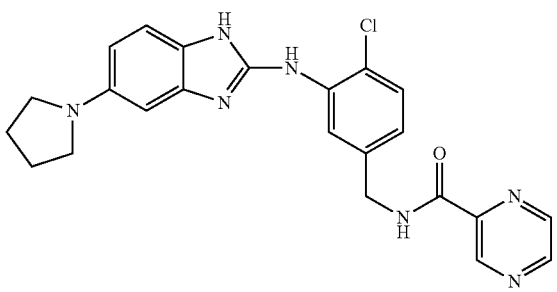 [SMILES: O=C(NCc1ccc(Cl)c(Nc2nc3cc(N4CCCC4)ccc3[nH]2)c1)c1cnccn1] |

-continued
| | Structure |
|---|---|
| 45 | 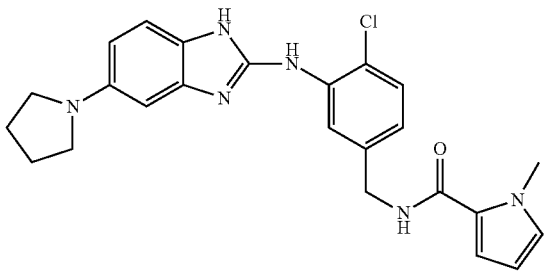 [SMILES: Cn1cccc1C(=O)NCc1ccc(Cl)c(Nc2nc3cc(N4CCCC4)ccc3[nH]2)c1] |
| 46 | 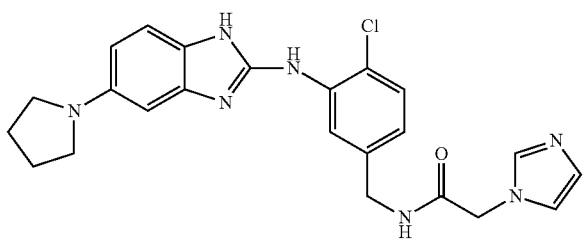 [SMILES: O=C(Cn1ccnc1)NCc1ccc(Cl)c(Nc2nc3cc(N4CCCC4)ccc3[nH]2)c1] |
| 47 | 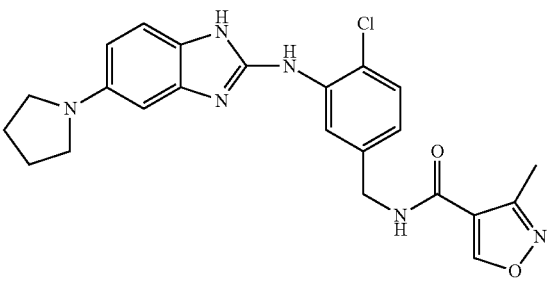 [SMILES: Cc1nocc1C(=O)NCc1ccc(Cl)c(Nc2nc3cc(N4CCCC4)ccc3[nH]2)c1] |
| 48 | 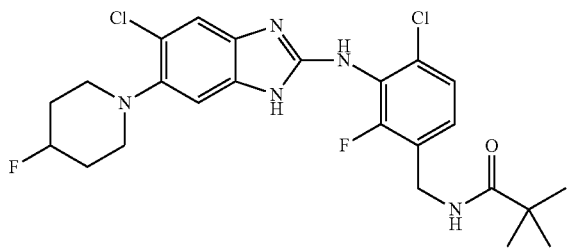 [SMILES: CC(C)(C)C(=O)NCc1ccc(Cl)c(Nc2nc3cc(Cl)c(N4CCC(F)CC4)cc3[nH]2)c1F] |
| 49 | 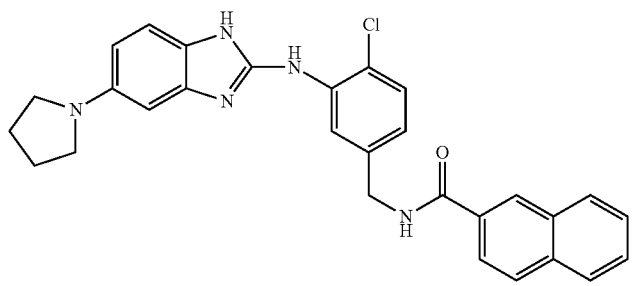 |

-continued
| | Structure |
|---|---|
| 50 | 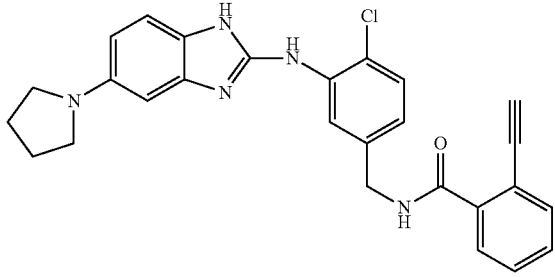 [SMILES: C#Cc1ccccc1C(=O)NCc1ccc(Cl)c(Nc2nc3cc(N4CCCC4)ccc3[nH]2)c1] |
| 51 | 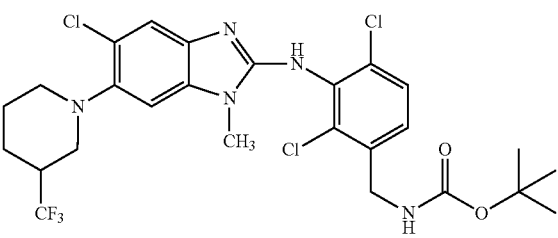 [SMILES: Cn1c(Nc2c(Cl)ccc(CNC(=O)OC(C)(C)C)c2Cl)nc2cc(Cl)c(N3CCCC(C(F)(F)F)C3)cc21] |
| 52 | 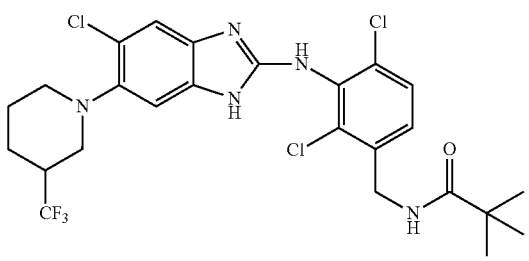 [SMILES: CC(C)(C)C(=O)NCc1ccc(Cl)c(Nc2nc3cc(Cl)c(N4CCCC(C(F)(F)F)C4)cc3[nH]2)c1Cl] |
| 53 | 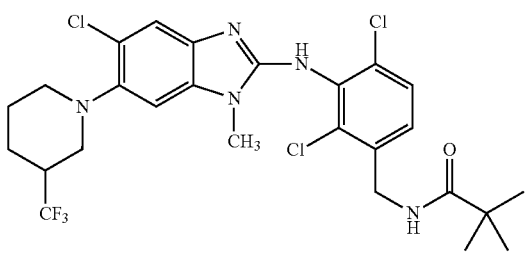 [SMILES: Cn1c(Nc2c(Cl)ccc(CNC(=O)C(C)(C)C)c2Cl)nc2cc(Cl)c(N3CCCC(C(F)(F)F)C3)cc21] |
| 54 | 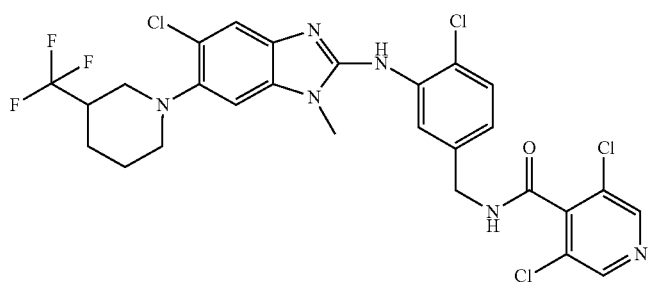 [SMILES: Cn1c(Nc2cc(CNC(=O)c3c(Cl)cncc3Cl)ccc2Cl)nc2cc(Cl)c(N3CCCC(C(F)(F)F)C3)cc21] |
| 55 | 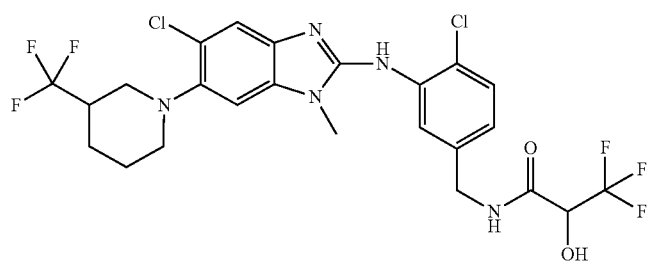 [SMILES: Cn1c(Nc2cc(CNC(=O)C(O)C(F)(F)F)ccc2Cl)nc2cc(Cl)c(N3CCCC(C(F)(F)F)C3)cc21] |

-continued
| | Structure |
|---|---|
| 56 | 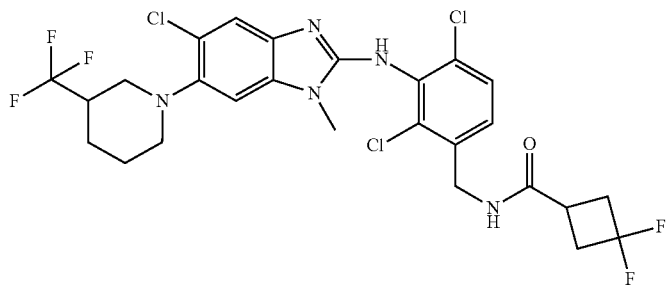 [SMILES: Cn1c(Nc2c(Cl)ccc(CNC(=O)C3CC(F)(F)C3)c2Cl)nc2cc(Cl)c(N3CCCC(C(F)(F)F)C3)cc21] |
| 57 | 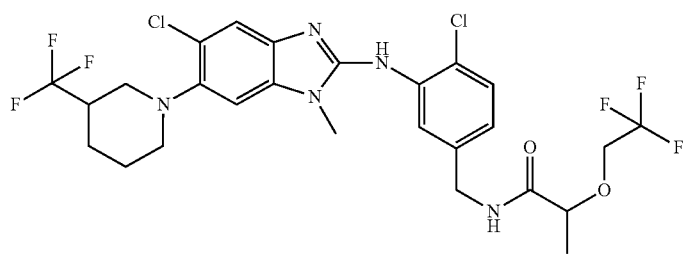 [SMILES: CC(OCC(F)(F)F)C(=O)NCc1ccc(Cl)c(Nc2nc3cc(Cl)c(N4CCCC(C(F)(F)F)C4)cc3n2C)c1] |
| 58 | 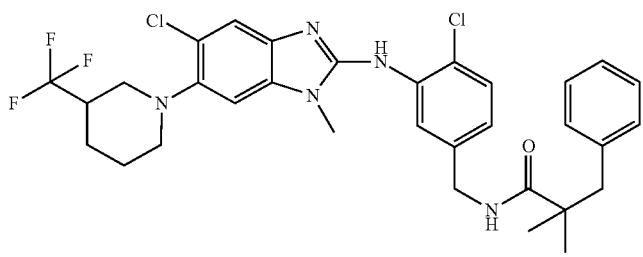 [SMILES: Cn1c(Nc2cc(CNC(=O)C(C)(C)Cc3ccccc3)ccc2Cl)nc2cc(Cl)c(N3CCCC(C(F)(F)F)C3)cc21] |
| 59 | 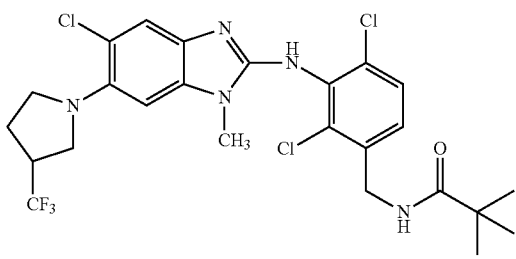 [SMILES: Cn1c(Nc2c(Cl)ccc(CNC(=O)C(C)(C)C)c2Cl)nc2cc(Cl)c(N3CCC(C(F)(F)F)C3)cc21] |
| 60 | 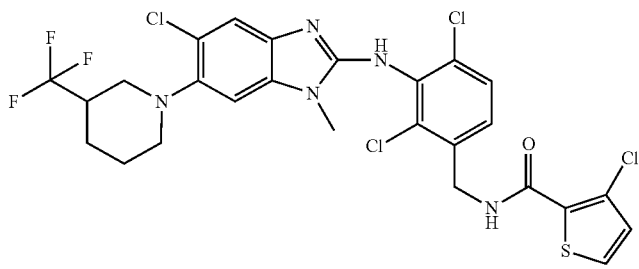 [SMILES: Cn1c(Nc2c(Cl)ccc(CNC(=O)c3sccc3Cl)c2Cl)nc2cc(Cl)c(N3CCCC(C(F)(F)F)C3)cc21] |

-continued
| | Structure |
|---|---|
| 61 | 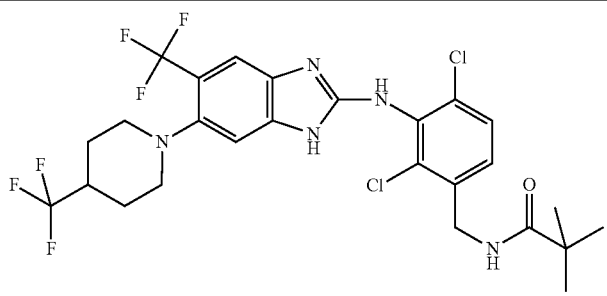 |
| 62 | 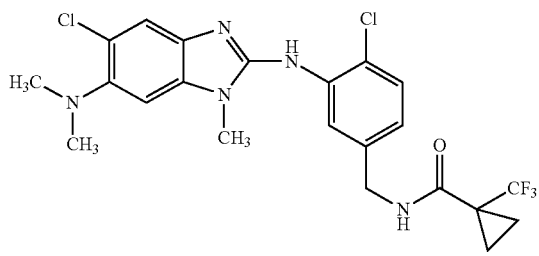 [SMILES: CN(C)c1cc2c(cc1Cl)nc(Nc1cc(CNC(=O)C3(C(F)(F)F)CC3)ccc1Cl)n2C] |
| 63 | 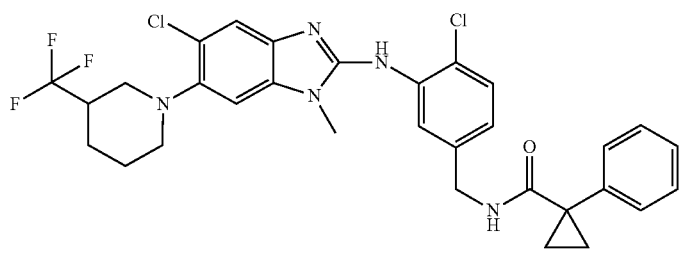 [SMILES: Cn1c(Nc2cc(CNC(=O)C3(c4ccccc4)CC3)ccc2Cl)nc2cc(Cl)c(N3CCCC(C(F)(F)F)C3)cc21] |
| 64 | 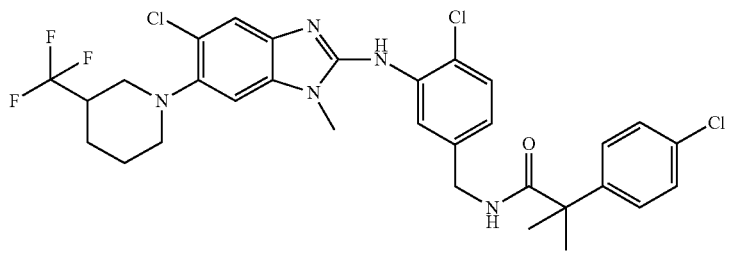 [SMILES: Cn1c(Nc2cc(CNC(=O)C(C)(C)c3ccc(Cl)cc3)ccc2Cl)nc2cc(Cl)c(N3CCCC(C(F)(F)F)C3)cc21] |
| 65 | 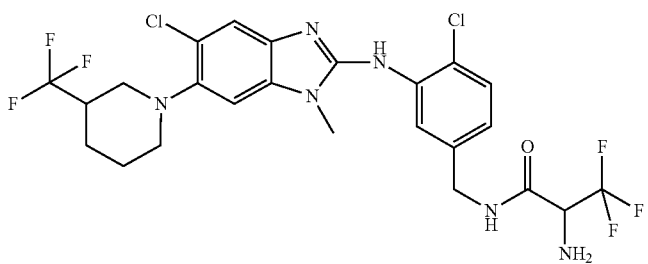 [SMILES: Cn1c(Nc2cc(CNC(=O)C(N)C(F)(F)F)ccc2Cl)nc2cc(Cl)c(N3CCCC(C(F)(F)F)C3)cc21] |
| 66 | 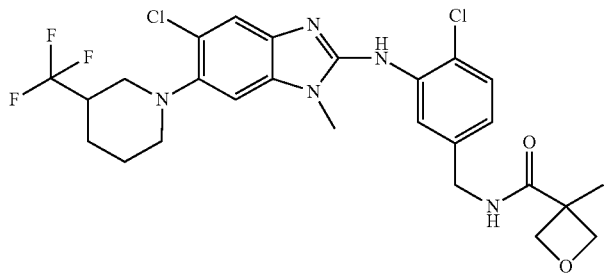 [SMILES: Cn1c(Nc2cc(CNC(=O)C3(C)COC3)ccc2Cl)nc2cc(Cl)c(N3CCCC(C(F)(F)F)C3)cc21] |

-continued
| | Structure |
|---|---|
| 67 | 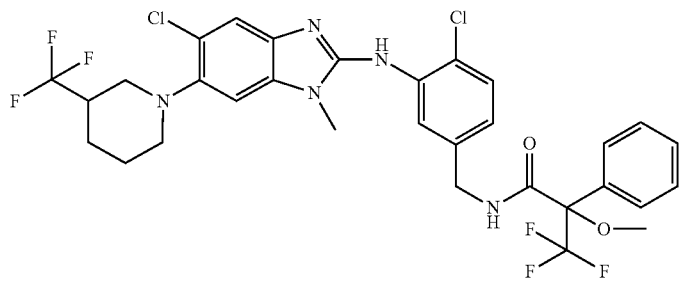 [SMILES: COC(C(=O)NCc1ccc(Cl)c(Nc2nc3cc(Cl)c(N4CCCC(C(F)(F)F)C4)cc3n2C)c1)(c1ccccc1)C(F)(F)F] |
| 68 | 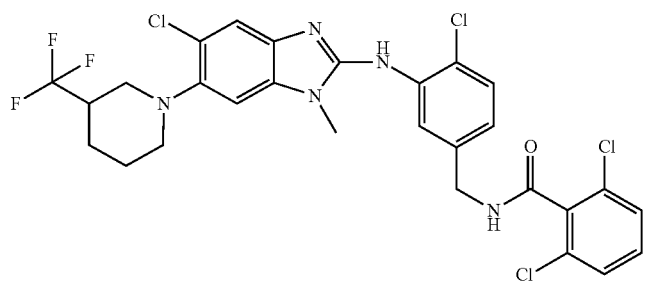 [SMILES: Cn1c(Nc2cc(CNC(=O)c3c(Cl)cccc3Cl)ccc2Cl)nc2cc(Cl)c(N3CCCC(C(F)(F)F)C3)cc21] |
| 69 | 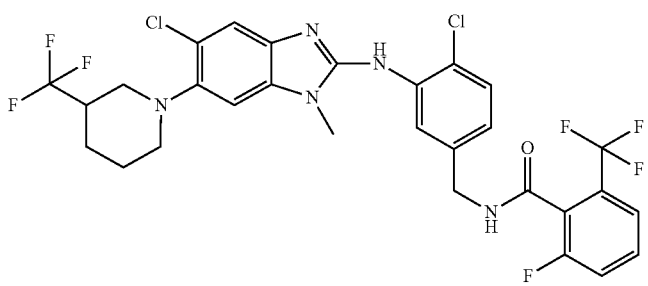 [SMILES: Cn1c(Nc2cc(CNC(=O)c3c(F)cccc3C(F)(F)F)ccc2Cl)nc2cc(Cl)c(N3CCCC(C(F)(F)F)C3)cc21] |
| 70 | 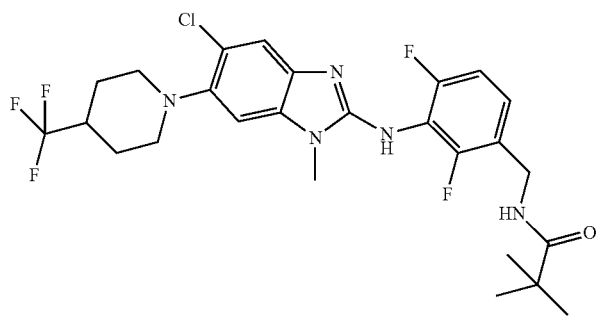 [SMILES: Cn1c(Nc2c(F)ccc(CNC(=O)C(C)(C)C)c2F)nc2cc(Cl)c(N3CCC(C(F)(F)F)CC3)cc21] |
| 71 | 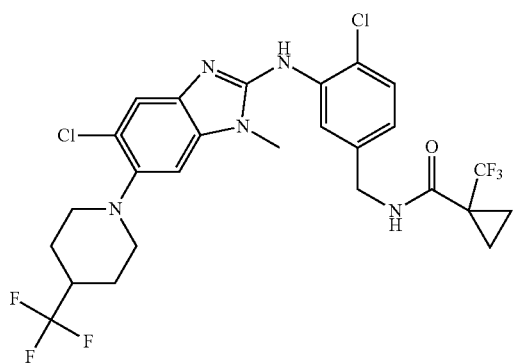 |

-continued
| | Structure |
|---|---|
| 72 | 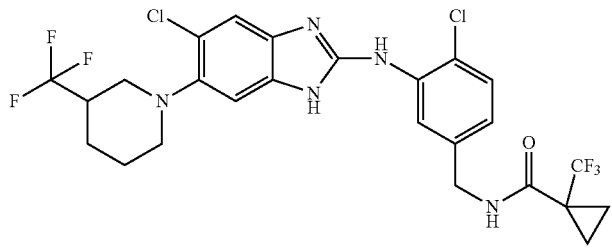 [SMILES: O=C(NCc1ccc(Cl)c(Nc2nc3cc(Cl)c(N4CCCC(C(F)(F)F)C4)cc3[nH]2)c1)C1(C(F)(F)F)CC1] |
| 73 | 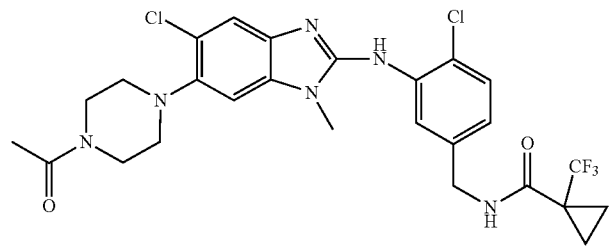 [SMILES: CC(=O)N1CCN(c2cc3c(cc2Cl)nc(Nc2cc(CNC(=O)C4(C(F)(F)F)CC4)ccc2Cl)n3C)CC1] |
| 74 | 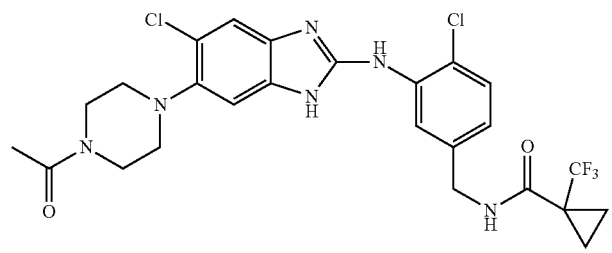 [SMILES: CC(=O)N1CCN(c2cc3[nH]c(Nc4cc(CNC(=O)C5(C(F)(F)F)CC5)ccc4Cl)nc3cc2Cl)CC1] |
| 75 | 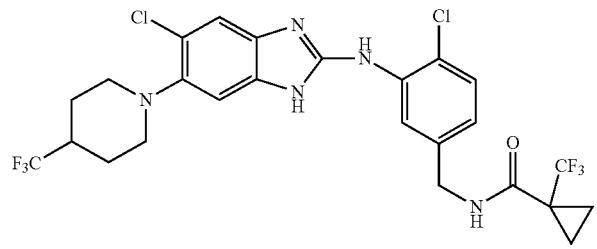 [SMILES: O=C(NCc1ccc(Cl)c(Nc2nc3cc(Cl)c(N4CCC(C(F)(F)F)CC4)cc3[nH]2)c1)C1(C(F)(F)F)CC1] |
| 76 | 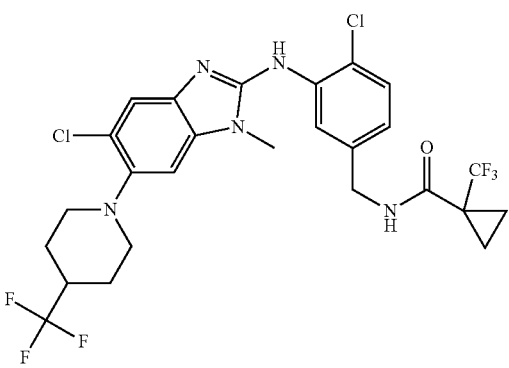 |

-continued
| | Structure |
|---|---|
| 77 | 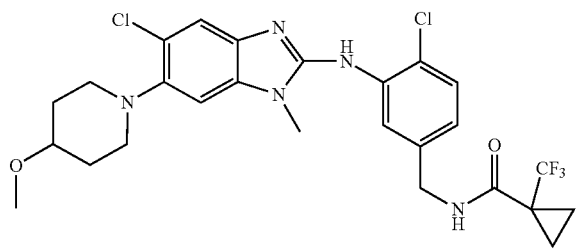 [SMILES: COC1CCN(c2cc3c(cc2Cl)nc(Nc2cc(CNC(=O)C4(C(F)(F)F)CC4)ccc2Cl)n3C)CC1] |
| 78 | 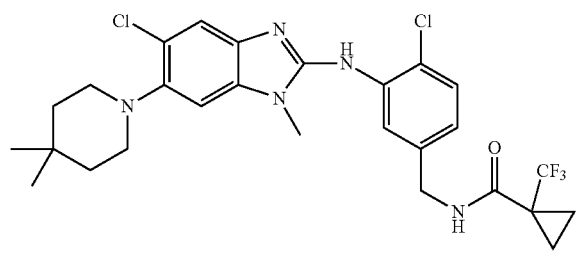 [SMILES: Cn1c(Nc2cc(CNC(=O)C3(C(F)(F)F)CC3)ccc2Cl)nc2cc(Cl)c(N3CCC(C)(C)CC3)cc21] |
| 79 | 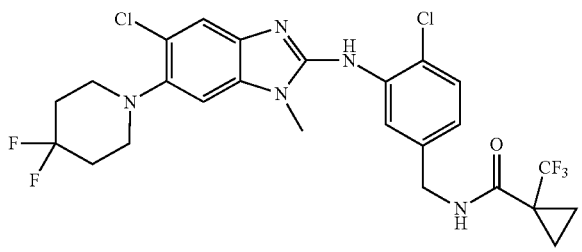 [SMILES: Cn1c(Nc2cc(CNC(=O)C3(C(F)(F)F)CC3)ccc2Cl)nc2cc(Cl)c(N3CCC(F)(F)CC3)cc21] |
| 80 | 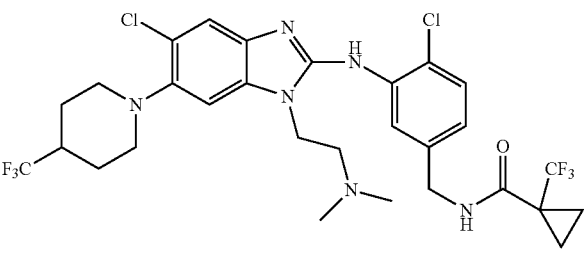 [SMILES: CN(C)CCn1c(Nc2cc(CNC(=O)C3(C(F)(F)F)CC3)ccc2Cl)nc2cc(Cl)c(N3CCC(C(F)(F)F)CC3)cc21] |
| 81 | 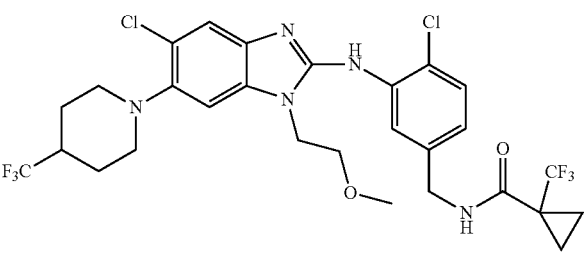 [SMILES: COCCn1c(Nc2cc(CNC(=O)C3(C(F)(F)F)CC3)ccc2Cl)nc2cc(Cl)c(N3CCC(C(F)(F)F)CC3)cc21] |

-continued
| | Structure |
|---|---|
| 82 | 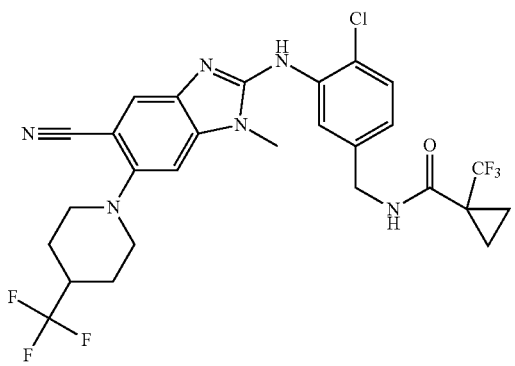 [SMILES: Cn1c(Nc2cc(CNC(=O)C3(C(F)(F)F)CC3)ccc2Cl)nc2cc(C#N)c(N3CCC(C(F)(F)F)CC3)cc21] |
| 83 | 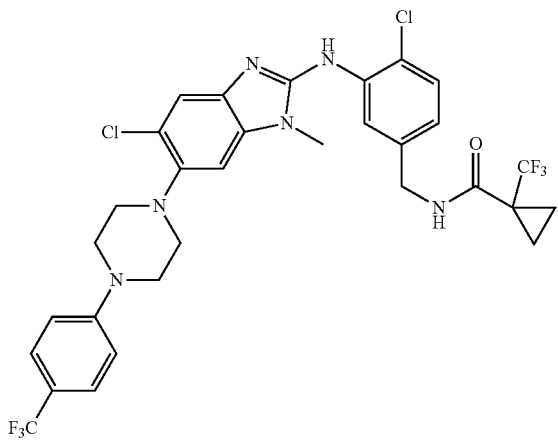 [SMILES: Cn1c(Nc2cc(CNC(=O)C3(C(F)(F)F)CC3)ccc2Cl)nc2cc(Cl)c(N3CCN(c4ccc(C(F)(F)F)cc4)CC3)cc21] |
| 84 | 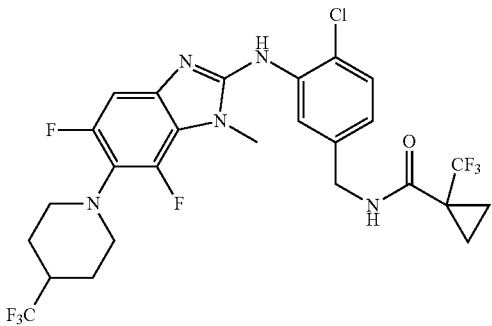 [SMILES: Cn1c(Nc2cc(CNC(=O)C3(C(F)(F)F)CC3)ccc2Cl)nc2cc(F)c(N3CCC(C(F)(F)F)CC3)c(F)c21] |
| 85 | 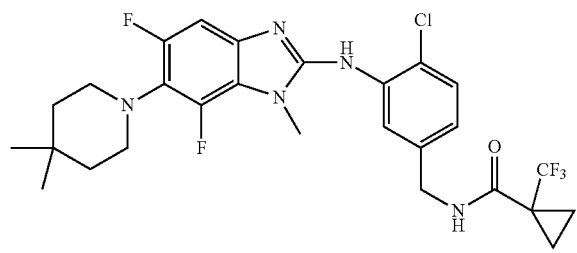 [SMILES: Cn1c(Nc2cc(CNC(=O)C3(C(F)(F)F)CC3)ccc2Cl)nc2cc(F)c(N3CCC(C)(C)CC3)c(F)c21] |

-continued
| | Structure |
|---|---|
| 86 | 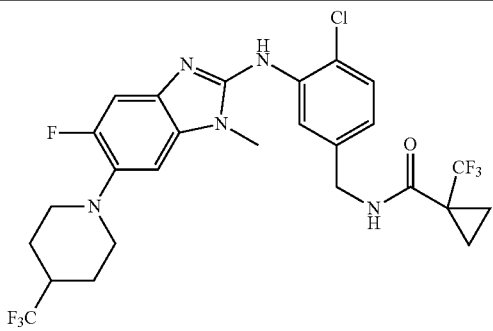 |
| 87 | 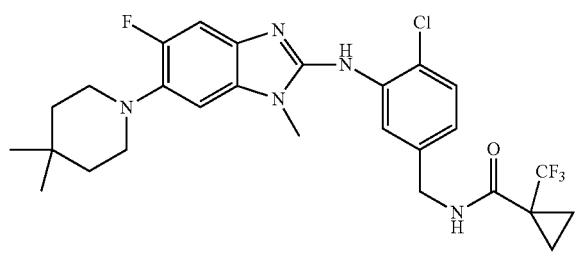 [SMILES: Cn1c(Nc2cc(CNC(=O)C3(C(F)(F)F)CC3)ccc2Cl)nc2cc(F)c(N3CCC(C)(C)CC3)cc21] |
| 88 | 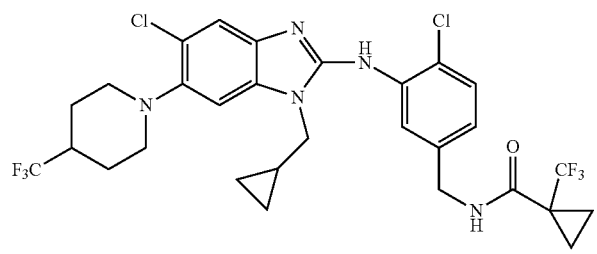 [SMILES: O=C(NCc1ccc(Cl)c(Nc2nc3cc(Cl)c(N4CCC(C(F)(F)F)CC4)cc3n2CC2CC2)c1)C1(C(F)(F)F)CC1] |
| 89 | 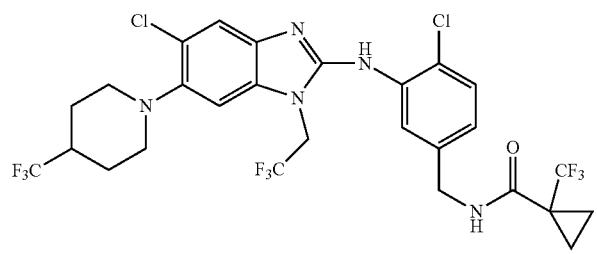 [SMILES: O=C(NCc1ccc(Cl)c(Nc2nc3cc(Cl)c(N4CCC(C(F)(F)F)CC4)cc3n2CC(F)(F)F)c1)C1(C(F)(F)F)CC1] |
| 90 | 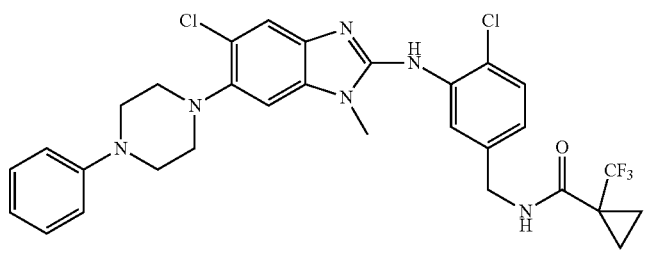 [SMILES: Cn1c(Nc2cc(CNC(=O)C3(C(F)(F)F)CC3)ccc2Cl)nc2cc(Cl)c(N3CCN(c4ccccc4)CC3)cc21] |
| 91 | 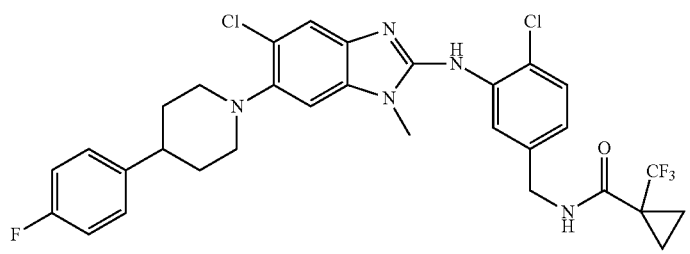 [SMILES: Cn1c(Nc2cc(CNC(=O)C3(C(F)(F)F)CC3)ccc2Cl)nc2cc(Cl)c(N3CCC(c4ccc(F)cc4)CC3)cc21] |

-continued
| | Structure |
|---|---|
| 92 | 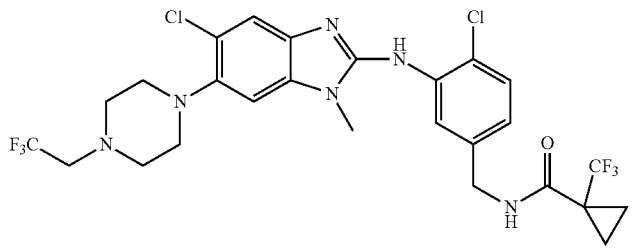 [SMILES: Cn1c(Nc2cc(CNC(=O)C3(C(F)(F)F)CC3)ccc2Cl)nc2cc(Cl)c(N3CCN(CC(F)(F)F)CC3)cc21] |
| 93 | 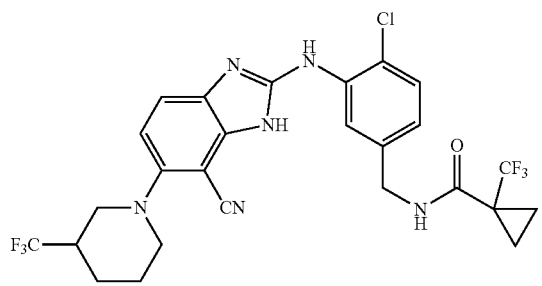 [SMILES: N#Cc1c(N2CCCC(C(F)(F)F)C2)ccc2nc(Nc3cc(CNC(=O)C4(C(F)(F)F)CC4)ccc3Cl)[nH]c12] |
| 94 | 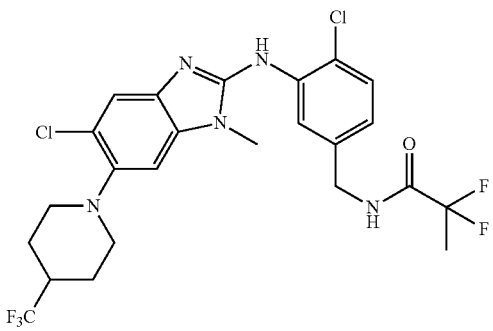 [SMILES: Cn1c(Nc2cc(CNC(=O)C(C)(F)F)ccc2Cl)nc2cc(Cl)c(N3CCC(C(F)(F)F)CC3)cc21] |
| 95 | 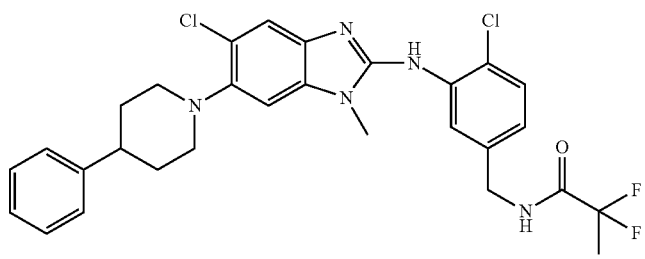 [SMILES: Cn1c(Nc2cc(CNC(=O)C(C)(F)F)ccc2Cl)nc2cc(Cl)c(N3CCC(c4ccccc4)CC3)cc21] |
| 96 | 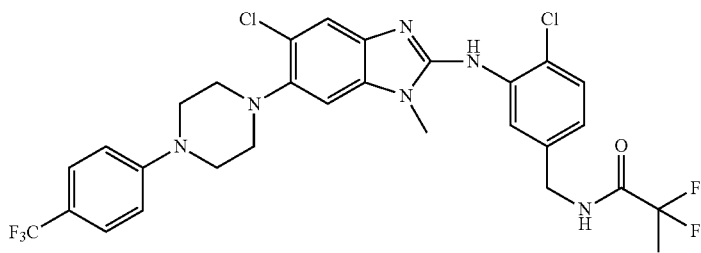 [SMILES: Cn1c(Nc2cc(CNC(=O)C(C)(F)F)ccc2Cl)nc2cc(Cl)c(N3CCN(c4ccc(C(F)(F)F)cc4)CC3)cc21] |

| | Structure |
|---|---|
| 97 | 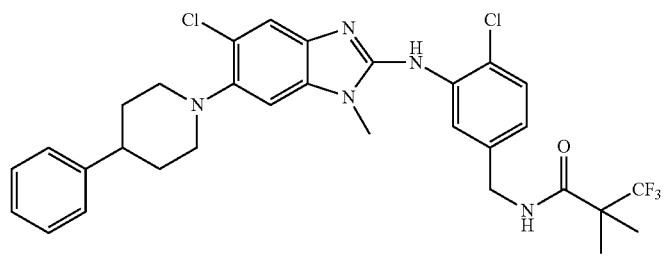 [SMILES: Cn1c(Nc2cc(CNC(=O)C(C)(C)C(F)(F)F)ccc2Cl)nc2cc(Cl)c(N3CCC(c4ccccc4)CC3)cc21] |
| 98 | 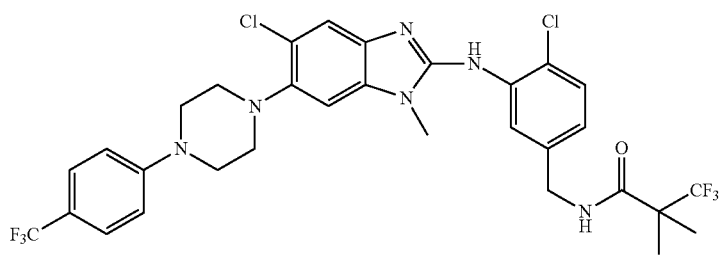 [SMILES: Cn1c(Nc2cc(CNC(=O)C(C)(C)C(F)(F)F)ccc2Cl)nc2cc(Cl)c(N3CCN(c4ccc(C(F)(F)F)cc4)CC3)cc21] |
| 99 | 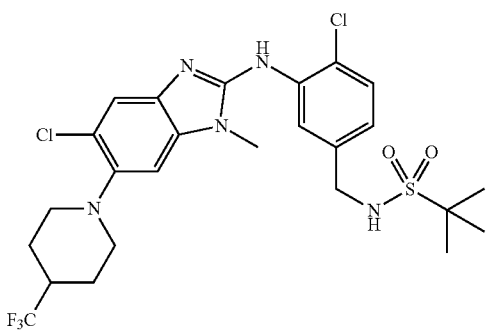 [SMILES: Cn1c(Nc2cc(CNS(=O)(=O)C(C)(C)C)ccc2Cl)nc2cc(Cl)c(N3CCC(C(F)(F)F)CC3)cc21] |
| 100 | 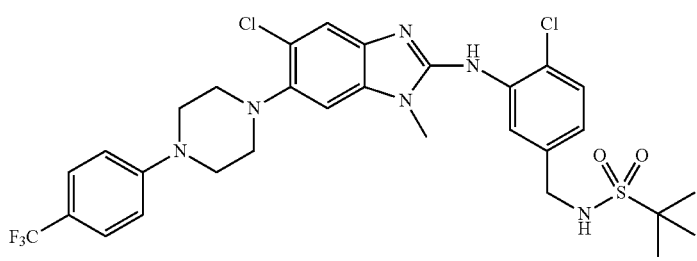 [SMILES: Cn1c(Nc2cc(CNS(=O)(=O)C(C)(C)C)ccc2Cl)nc2cc(Cl)c(N3CCN(c4ccc(C(F)(F)F)cc4)CC3)cc21] |
| 101 | 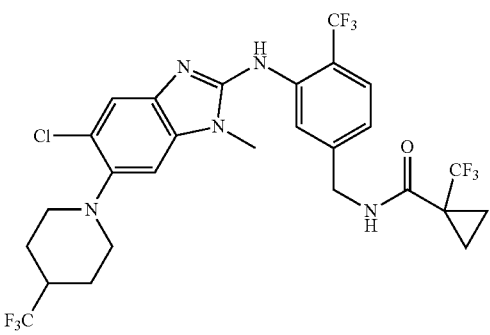 [SMILES: Cn1c(Nc2cc(CNC(=O)C3(C(F)(F)F)CC3)ccc2C(F)(F)F)nc2cc(Cl)c(N3CCC(C(F)(F)F)CC3)cc21] |

|   | Structure |
|---|---|
| 102 | 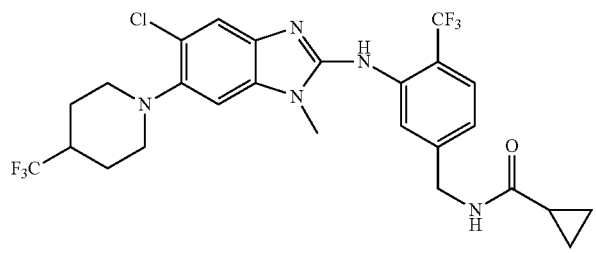 [SMILES: Cn1c(Nc2cc(CNC(=O)C3CC3)ccc2C(F)(F)F)nc2cc(Cl)c(N3CCC(C(F)(F)F)CC3)cc21] |
| 103 | 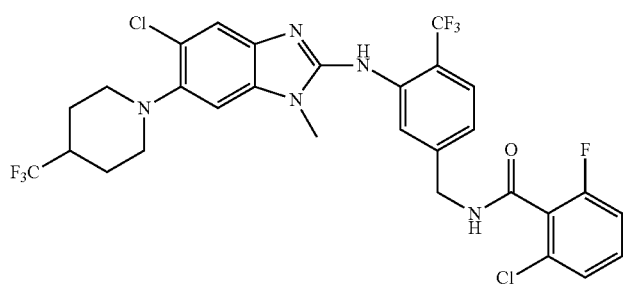 [SMILES: Cn1c(Nc2cc(CNC(=O)c3c(F)cccc3Cl)ccc2C(F)(F)F)nc2cc(Cl)c(N3CCC(C(F)(F)F)CC3)cc21] |
| 104 | 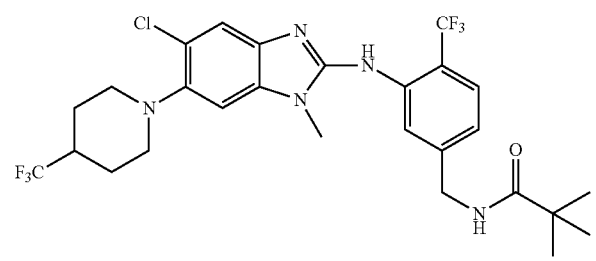 [SMILES: Cn1c(Nc2cc(CNC(=O)C(C)(C)C)ccc2C(F)(F)F)nc2cc(Cl)c(N3CCC(C(F)(F)F)CC3)cc21] |
| 105 | 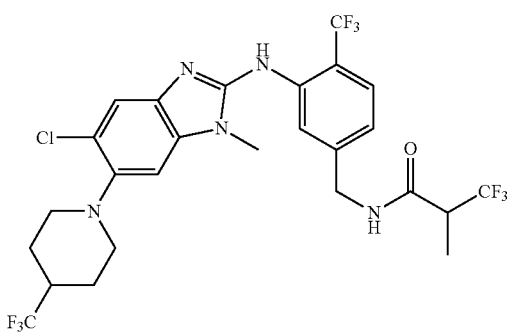 [SMILES: CC(C(=O)NCc1ccc(C(F)(F)F)c(Nc2nc3cc(Cl)c(N4CCC(C(F)(F)F)CC4)cc3n2C)c1)C(F)(F)F] |
| 106 | 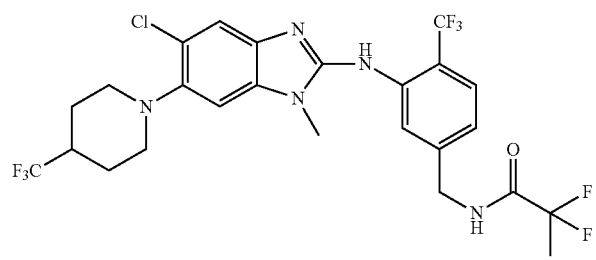 [SMILES: Cn1c(Nc2cc(CNC(=O)C(C)(F)F)ccc2C(F)(F)F)nc2cc(Cl)c(N3CCC(C(F)(F)F)CC3)cc21] |

-continued
| | Structure |
|---|---|
| 107 | 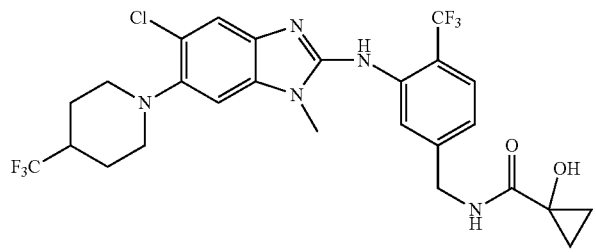 [SMILES: Cn1c(Nc2cc(CNC(=O)C3(O)CC3)ccc2C(F)(F)F)nc2cc(Cl)c(N3CCC(C(F)(F)F)CC3)cc21] |
| 108 | 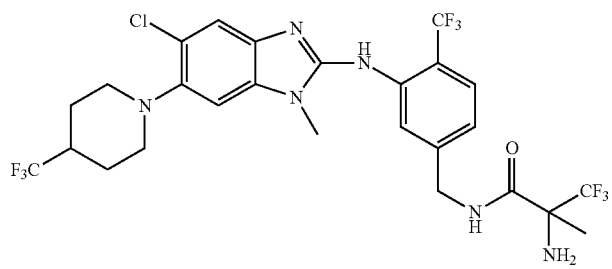 [SMILES: Cn1c(Nc2cc(CNC(=O)C(C)(N)C(F)(F)F)ccc2C(F)(F)F)nc2cc(Cl)c(N3CCC(C(F)(F)F)CC3)cc21] |
| 109 | 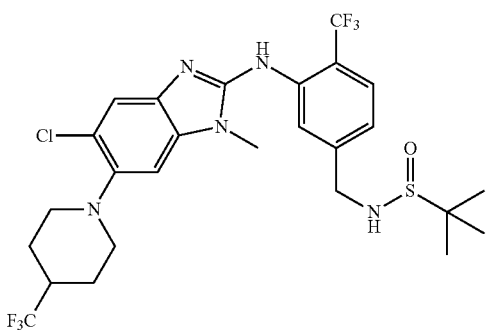 [SMILES: Cn1c(Nc2cc(CNS(=O)C(C)(C)C)ccc2C(F)(F)F)nc2cc(Cl)c(N3CCC(C(F)(F)F)CC3)cc21] |
| 110 | 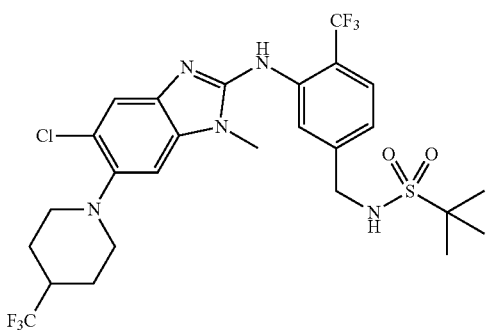 [SMILES: Cn1c(Nc2cc(CNS(=O)(=O)C(C)(C)C)ccc2C(F)(F)F)nc2cc(Cl)c(N3CCC(C(F)(F)F)CC3)cc21] |
| 111 | 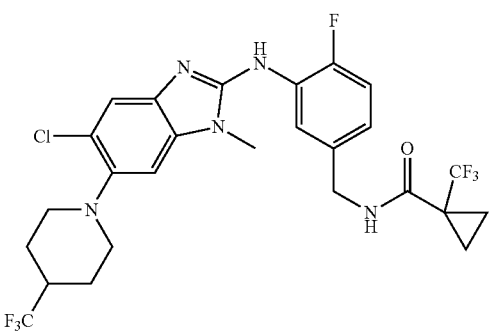 [SMILES: Cn1c(Nc2cc(CNC(=O)C3(C(F)(F)F)CC3)ccc2F)nc2cc(Cl)c(N3CCC(C(F)(F)F)CC3)cc21] |

| | Structure |
|---|---|
| 112 | 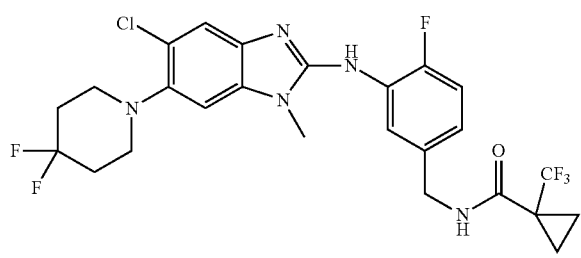 [SMILES: Cn1c(Nc2cc(CNC(=O)C3(C(F)(F)F)CC3)ccc2F)nc2cc(Cl)c(N3CCC(F)(F)CC3)cc21] |
| 113 | 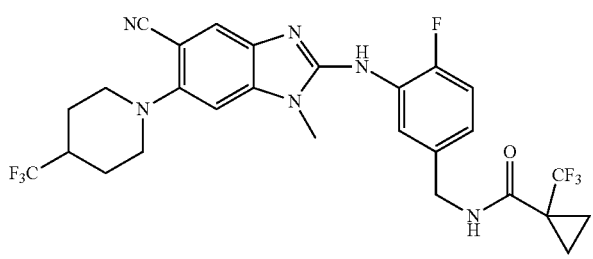 [SMILES: Cn1c(Nc2cc(CNC(=O)C3(C(F)(F)F)CC3)ccc2F)nc2cc(C#N)c(N3CCC(C(F)(F)F)CC3)cc21] |
| 114 | 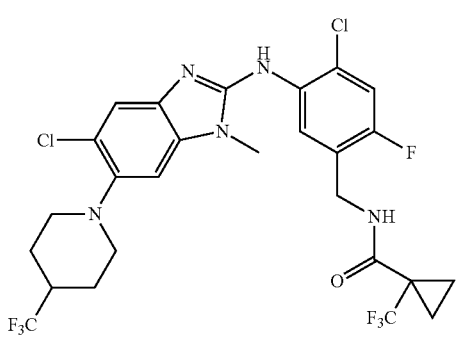 [SMILES: Cn1c(Nc2cc(CNC(=O)C3(C(F)(F)F)CC3)c(F)cc2Cl)nc2cc(Cl)c(N3CCC(C(F)(F)F)CC3)cc21] |
| 115 | 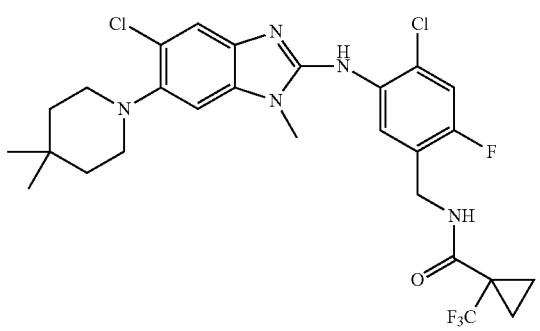 [SMILES: Cn1c(Nc2cc(CNC(=O)C3(C(F)(F)F)CC3)c(F)cc2Cl)nc2cc(Cl)c(N3CCC(C)(C)CC3)cc21] |
| 116 | 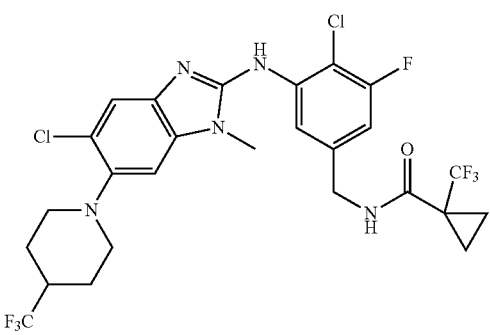 [SMILES: Cn1c(Nc2cc(CNC(=O)C3(C(F)(F)F)CC3)cc(F)c2Cl)nc2cc(Cl)c(N3CCC(C(F)(F)F)CC3)cc21] |

| Structure |
|---|
| 117 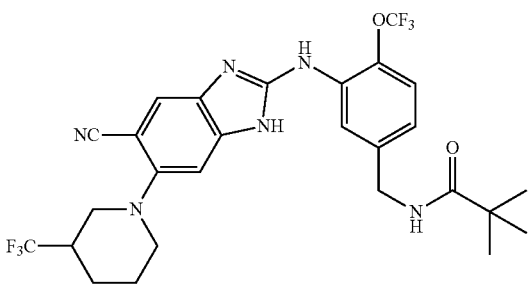 [SMILES: CC(C)(C)C(=O)NCc1ccc(OC(F)(F)F)c(Nc2nc3cc(C#N)c(N4CCCC(C(F)(F)F)C4)cc3[nH]2)c1] |
| 118 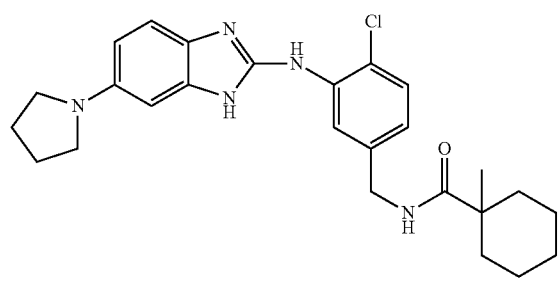 [SMILES: CC1(C(=O)NCc2ccc(Cl)c(Nc3nc4ccc(N5CCCC5)cc4[nH]3)c2)CCCCC1] |
| 119 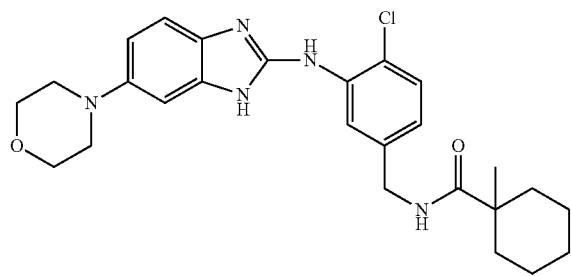 [SMILES: CC1(C(=O)NCc2ccc(Cl)c(Nc3nc4ccc(N5CCOCC5)cc4[nH]3)c2)CCCCC1] |
| 120 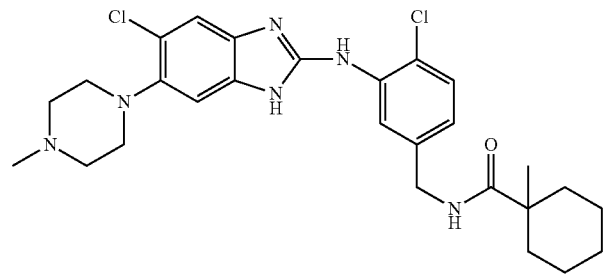 [SMILES: CN1CCN(c2cc3[nH]c(Nc4cc(CNC(=O)C5(C)CCCCC5)ccc4Cl)nc3cc2Cl)CC1] |
| 121 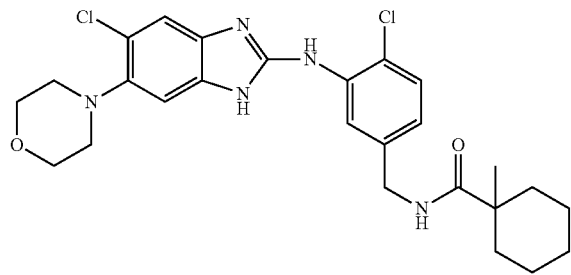 [SMILES: CC1(C(=O)NCc2ccc(Cl)c(Nc3nc4cc(Cl)c(N5CCOCC5)cc4[nH]3)c2)CCCCC1] |

US 8,466,186 B2
233                                                                 234
-continued
| | Structure |
|---|---|
| 122 | 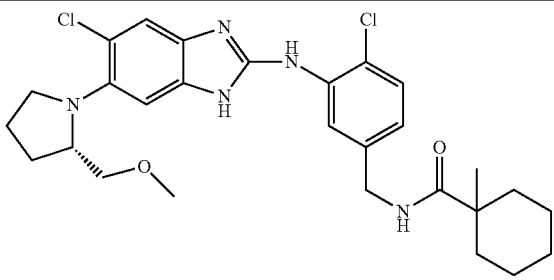 |
| 123 | 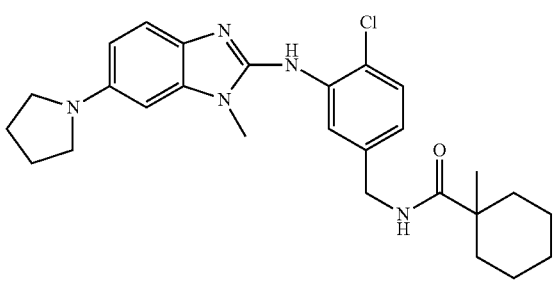 [SMILES: Cn1c(Nc2cc(CNC(=O)C3(C)CCCCC3)ccc2Cl)nc2ccc(N3CCCC3)cc21] |
| 124 | 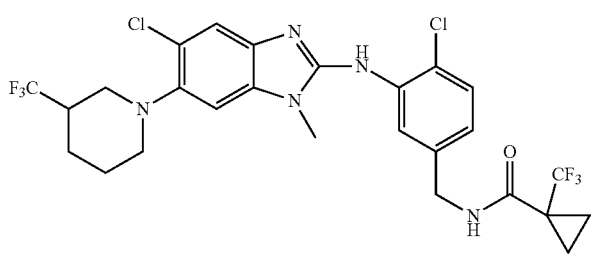 [SMILES: Cn1c(Nc2cc(CNC(=O)C3(C(F)(F)F)CC3)ccc2Cl)nc2cc(Cl)c(N3CCCC(C(F)(F)F)C3)cc21] |
| 125 | 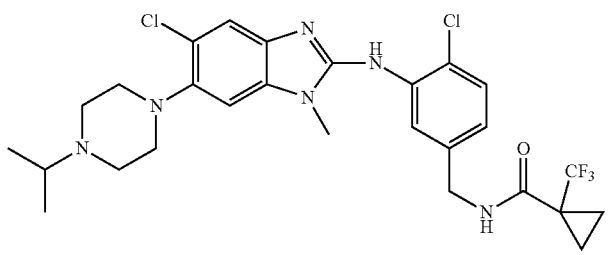 [SMILES: CC(C)N1CCN(c2cc3c(cc2Cl)nc(Nc2cc(CNC(=O)C4(C(F)(F)F)CC4)ccc2Cl)n3C)CC1] |
| 126 | 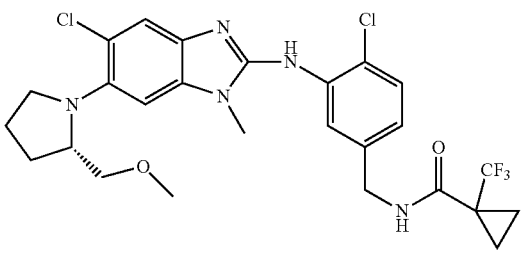 [SMILES: COC[C@@H]1CCCN1c1cc2c(cc1Cl)nc(Nc1cc(CNC(=O)C3(C(F)(F)F)CC3)ccc1Cl)n2C] |
| 127 | 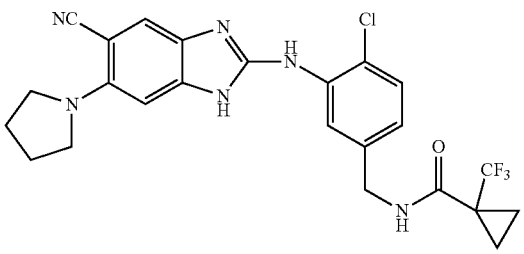 [SMILES: N#Cc1cc2nc(Nc3cc(CNC(=O)C4(C(F)(F)F)CC4)ccc3Cl)[nH]c2cc1N1CCCC1] |

-continued
| | Structure |
|---|---|
| 128 | 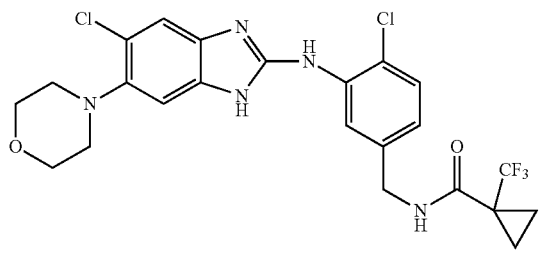 [SMILES: O=C(NCc1ccc(Cl)c(Nc2nc3cc(Cl)c(N4CCOCC4)cc3[nH]2)c1)C1(C(F)(F)F)CC1] |
| 129 | 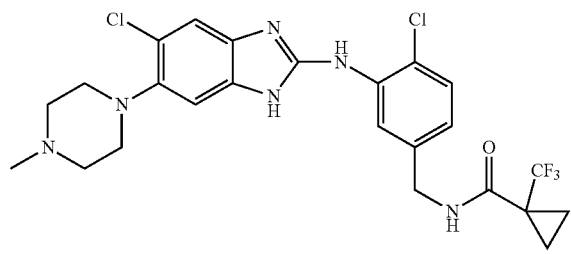 [SMILES: CN1CCN(c2cc3[nH]c(Nc4cc(CNC(=O)C5(C(F)(F)F)CC5)ccc4Cl)nc3cc2Cl)CC1] |
| 130 | 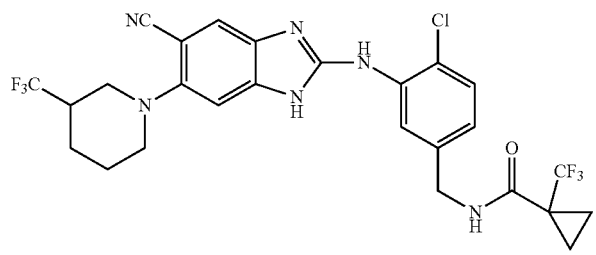 [SMILES: N#Cc1cc2nc(Nc3cc(CNC(=O)C4(C(F)(F)F)CC4)ccc3Cl)[nH]c2cc1N1CCCC(C(F)(F)F)C1] |
| 131 | 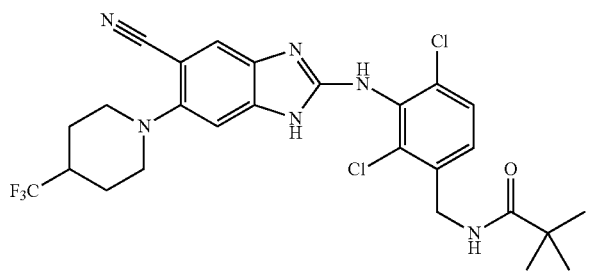 [SMILES: CC(C)(C)C(=O)NCc1ccc(Cl)c(Nc2nc3cc(C#N)c(N4CCC(C(F)(F)F)CC4)cc3[nH]2)c1Cl] |
| 132 | 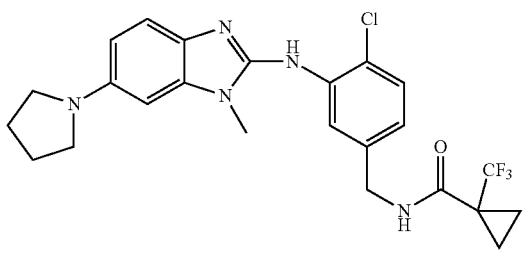 [SMILES: Cn1c(Nc2cc(CNC(=O)C3(C(F)(F)F)CC3)ccc2Cl)nc2ccc(N3CCCC3)cc21] |
| 133 | 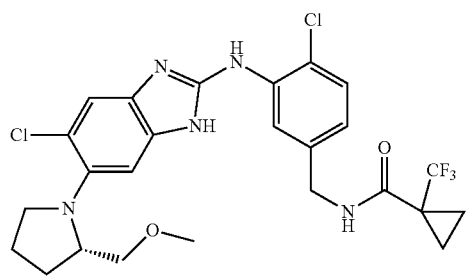 [SMILES: COC[C@@H]1CCCN1c1cc2[nH]c(Nc3cc(CNC(=O)C4(C(F)(F)F)CC4)ccc3Cl)nc2cc1Cl] |

US 8,466,186 B2
| | Structure |
|---|---|
| 134 | 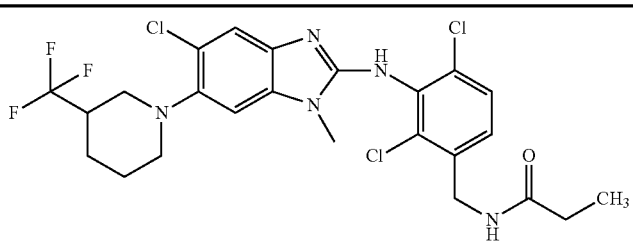 |
| 135 | 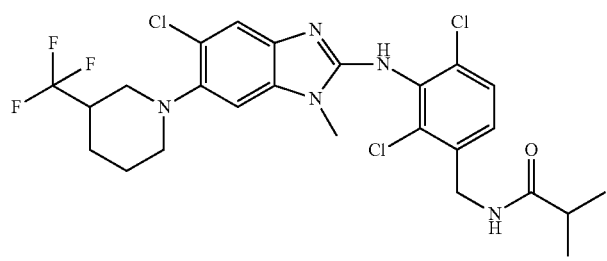 |
| 136 | 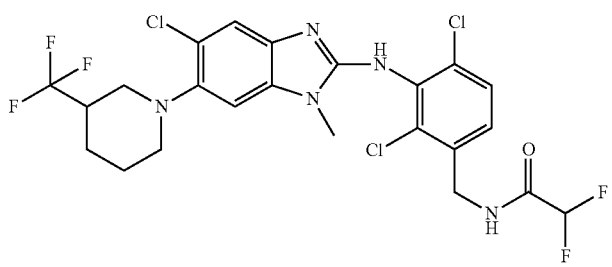 [SMILES: Cn1c(Nc2c(Cl)ccc(CNC(=O)C(F)F)c2Cl)nc2cc(Cl)c(N3CCCC(C(F)(F)F)C3)cc21] |
| 137 | 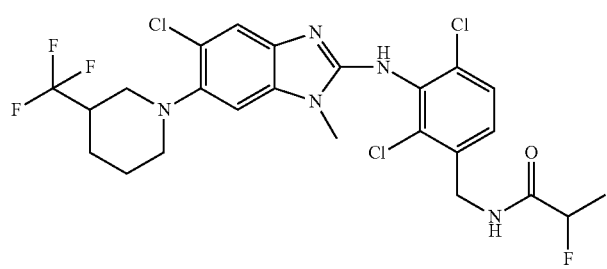 [SMILES: CC(F)C(=O)NCc1ccc(Cl)c(Nc2nc3cc(Cl)c(N4CCCC(C(F)(F)F)C4)cc3n2C)c1Cl] |
| 138 | 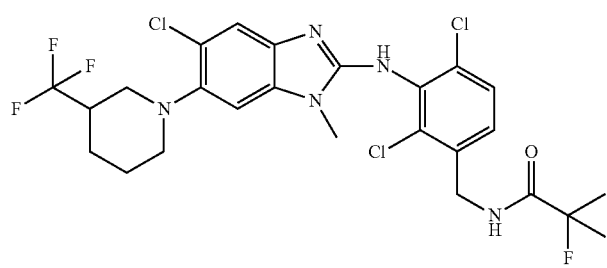 [SMILES: Cn1c(Nc2c(Cl)ccc(CNC(=O)C(C)(C)F)c2Cl)nc2cc(Cl)c(N3CCCC(C(F)(F)F)C3)cc21] |
| 139 | 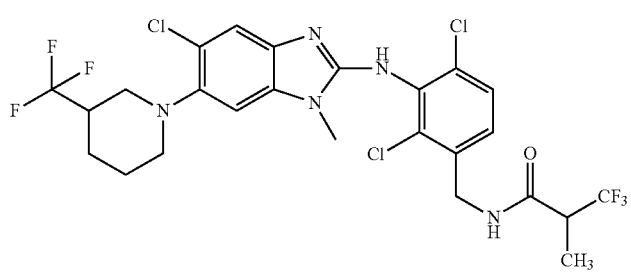 [SMILES: CC(C(=O)NCc1ccc(Cl)c(Nc2nc3cc(Cl)c(N4CCCC(C(F)(F)F)C4)cc3n2C)c1Cl)C(F)(F)F] |

-continued
| | Structure |
|---|---|
| 140 | 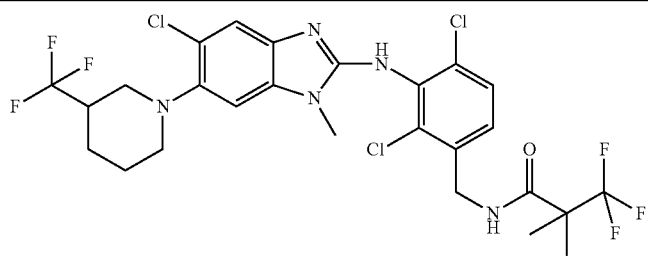 |
| 141 | 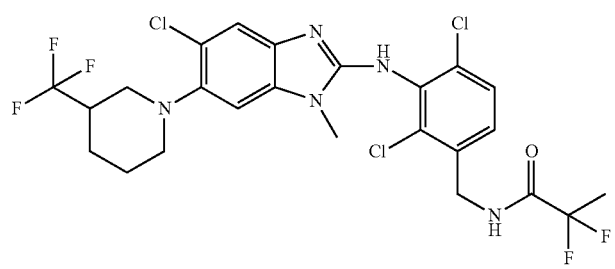 [SMILES: Cn1c(Nc2c(Cl)ccc(CNC(=O)C(C)(F)F)c2Cl)nc2cc(Cl)c(N3CCCC(C(F)(F)F)C3)cc21] |
| 142 | 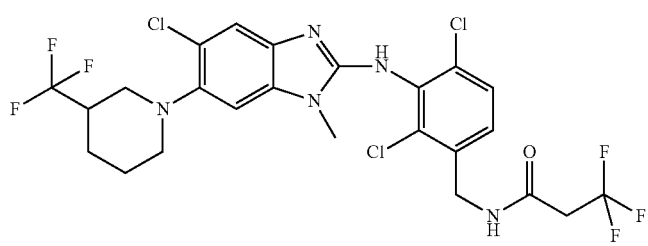 [SMILES: Cn1c(Nc2c(Cl)ccc(CNC(=O)CC(F)(F)F)c2Cl)nc2cc(Cl)c(N3CCCC(C(F)(F)F)C3)cc21] |
| 143 | 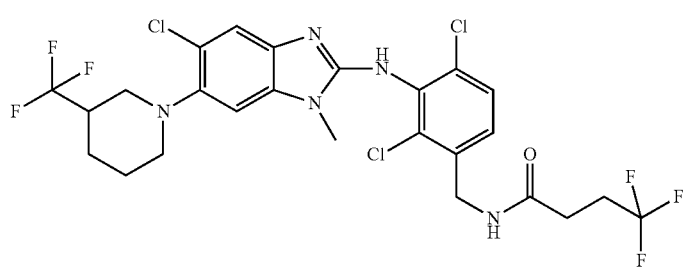 [SMILES: Cn1c(Nc2c(Cl)ccc(CNC(=O)CCC(F)(F)F)c2Cl)nc2cc(Cl)c(N3CCCC(C(F)(F)F)C3)cc21] |
| 144 | 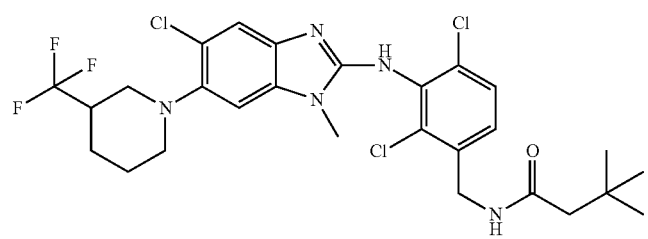 [SMILES: Cn1c(Nc2c(Cl)ccc(CNC(=O)CC(C)(C)C)c2Cl)nc2cc(Cl)c(N3CCCC(C(F)(F)F)C3)cc21] |
| 145 | 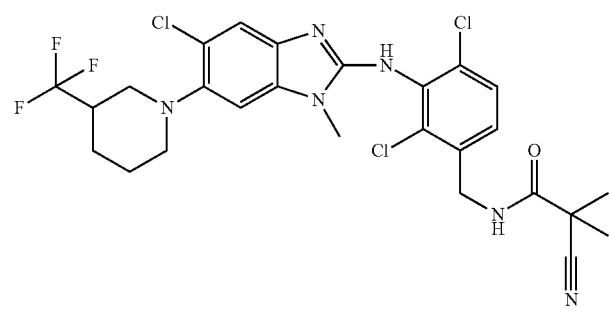 |

-continued
| | Structure |
|---|---|
| 146 | 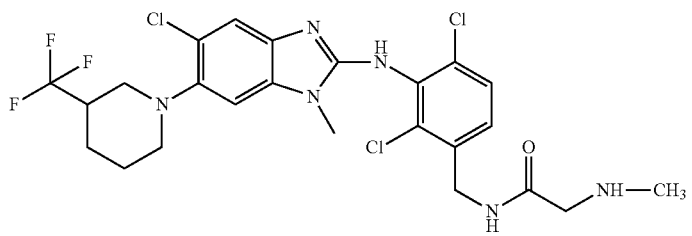 [SMILES: CNCC(=O)NCc1ccc(Cl)c(Nc2nc3cc(Cl)c(N4CCCC(C(F)(F)F)C4)cc3n2C)c1Cl] |
| 147 | 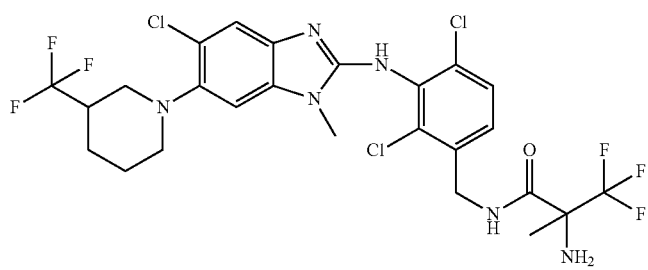 [SMILES: Cn1c(Nc2c(Cl)ccc(CNC(=O)C(C)(N)C(F)(F)F)c2Cl)nc2cc(Cl)c(N3CCCC(C(F)(F)F)C3)cc21] |
| 148 | 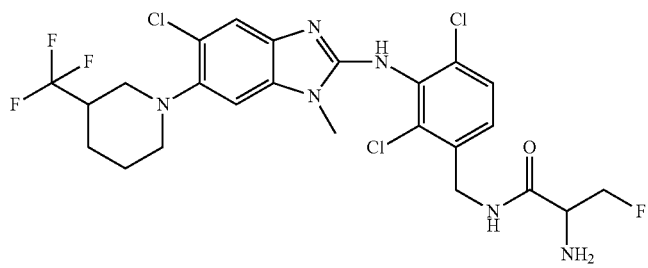 [SMILES: Cn1c(Nc2c(Cl)ccc(CNC(=O)C(N)CF)c2Cl)nc2cc(Cl)c(N3CCCC(C(F)(F)F)C3)cc21] |
| 149 | 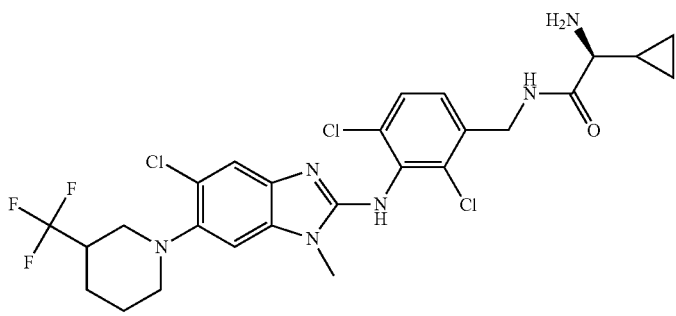 [SMILES: Cn1c(Nc2c(Cl)ccc(CNC(=O)[C@@H](N)C3CC3)c2Cl)nc2cc(Cl)c(N3CCCC(C(F)(F)F)C3)cc21] |
| 150 | 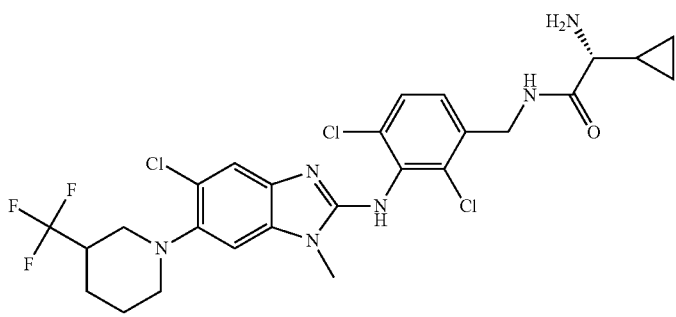 [SMILES: Cn1c(Nc2c(Cl)ccc(CNC(=O)[C@H](N)C3CC3)c2Cl)nc2cc(Cl)c(N3CCCC(C(F)(F)F)C3)cc21] |

-continued
| | Structure |
|---|---|
| 151 | 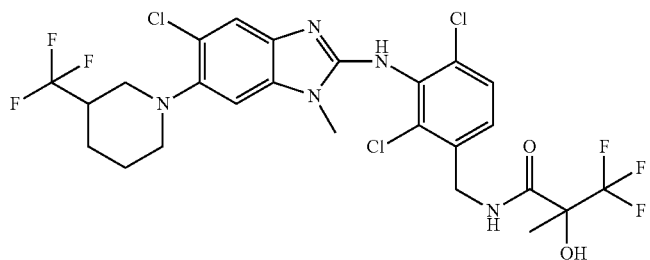 [SMILES: Cn1c(Nc2c(Cl)ccc(CNC(=O)C(C)(O)C(F)(F)F)c2Cl)nc2cc(Cl)c(N3CCCC(C(F)(F)F)C3)cc21] |
| 152 | 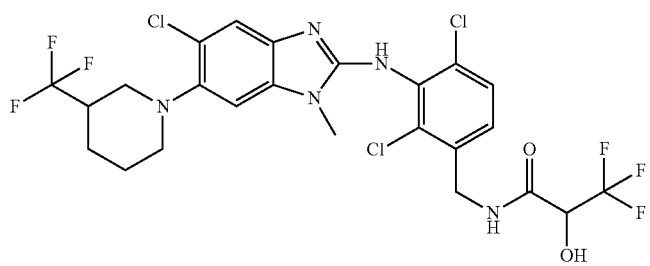 [SMILES: Cn1c(Nc2c(Cl)ccc(CNC(=O)C(O)C(F)(F)F)c2Cl)nc2cc(Cl)c(N3CCCC(C(F)(F)F)C3)cc21] |
| 153 | 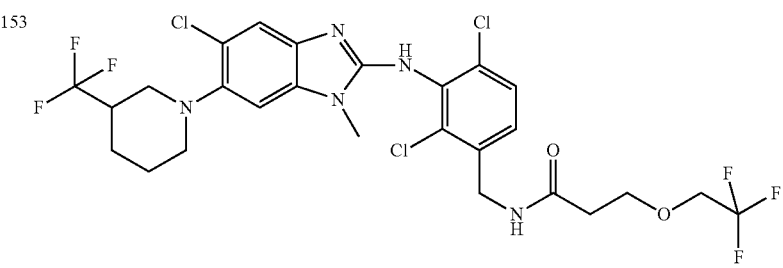 |
| 154 | 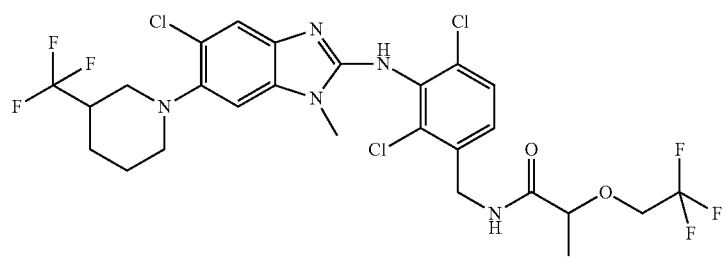 [SMILES: CC(OCC(F)(F)F)C(=O)NCc1ccc(Cl)c(Nc2nc3cc(Cl)c(N4CCCC(C(F)(F)F)C4)cc3n2C)c1Cl] |
| 155 | 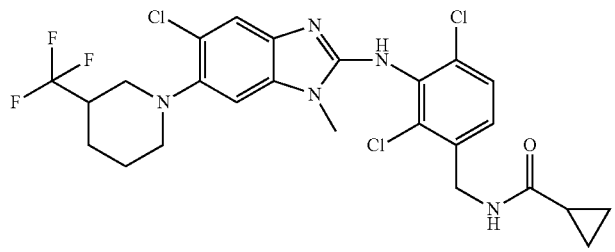 [SMILES: Cn1c(Nc2c(Cl)ccc(CNC(=O)C3CC3)c2Cl)nc2cc(Cl)c(N3CCCC(C(F)(F)F)C3)cc21] |
| 156 | 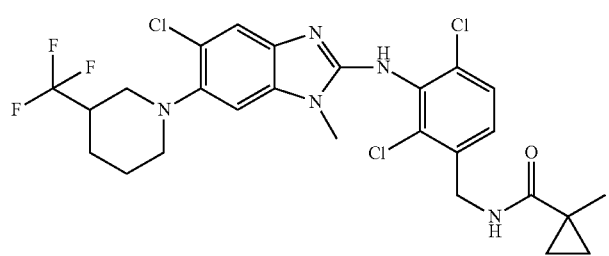 |

-continued
| | Structure |
|---|---|
| 157 | 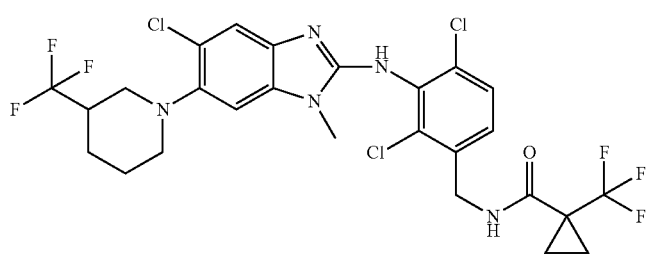 [SMILES: Cn1c(Nc2c(Cl)ccc(CNC(=O)C3(C(F)(F)F)CC3)c2Cl)nc2cc(Cl)c(N3CCCC(C(F)(F)F)C3)cc21] |
| 158 | 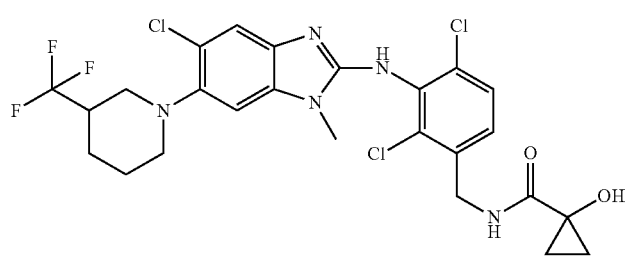 [SMILES: Cn1c(Nc2c(Cl)ccc(CNC(=O)C3(O)CC3)c2Cl)nc2cc(Cl)c(N3CCCC(C(F)(F)F)C3)cc21] |
| 159 | 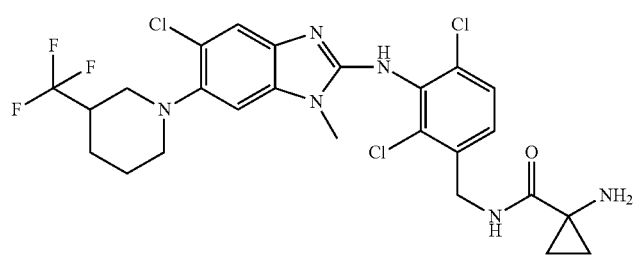 |
| 160 | 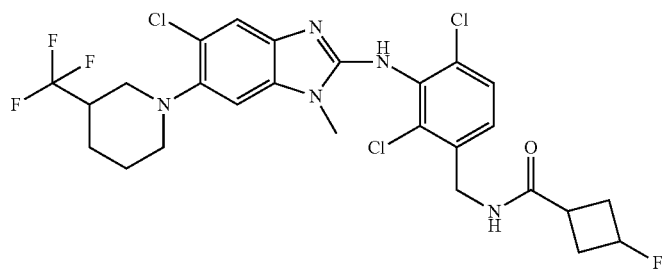 [SMILES: Cn1c(Nc2c(Cl)ccc(CNC(=O)C3CC(F)C3)c2Cl)nc2cc(Cl)c(N3CCCC(C(F)(F)F)C3)cc21] |
| 161 | 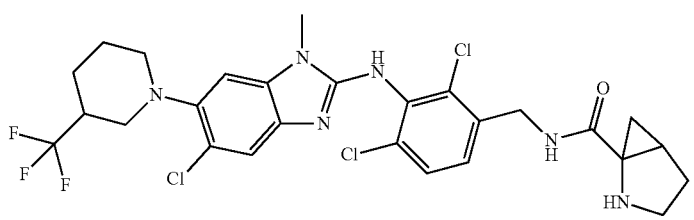 [SMILES: Cn1c(Nc2c(Cl)ccc(CNC(=O)C34CC3CCN4)c2Cl)nc2cc(Cl)c(N3CCCC(C(F)(F)F)C3)cc21] |
| 162 | 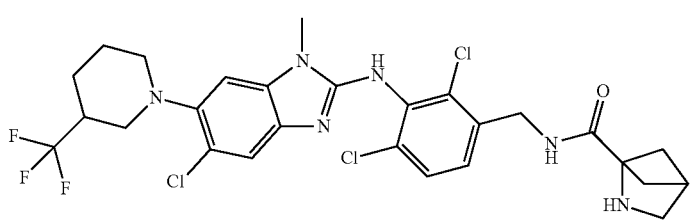 [SMILES: Cn1c(Nc2c(Cl)ccc(CNC(=O)C34CC(CN3)C4)c2Cl)nc2cc(Cl)c(N3CCCC(C(F)(F)F)C3)cc21] |

-continued
| | Structure |
|---|---|
| 163 | 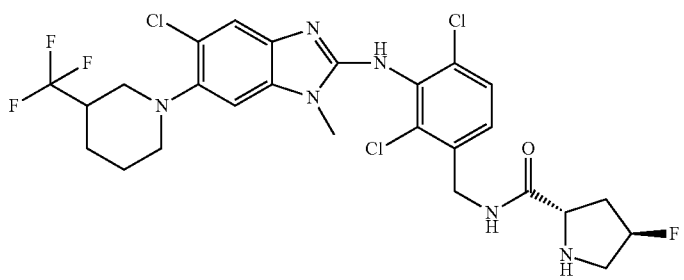 [SMILES: Cn1c(Nc2c(Cl)ccc(CNC(=O)[C@@H]3C[C@@H](F)CN3)c2Cl)nc2cc(Cl)c(N3CCCC(C(F)(F)F)C3)cc21] |
| 164 | 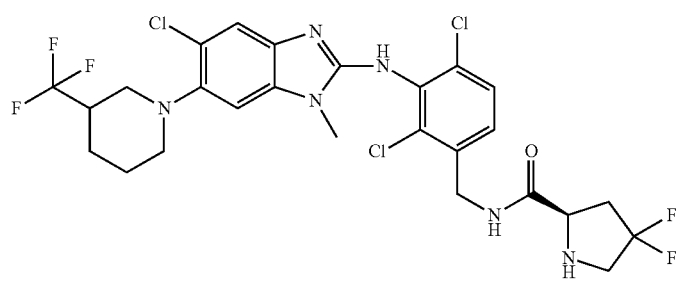 [SMILES: Cn1c(Nc2c(Cl)ccc(CNC(=O)[C@H]3CC(F)(F)CN3)c2Cl)nc2cc(Cl)c(N3CCCC(C(F)(F)F)C3)cc21] |
| 165 | 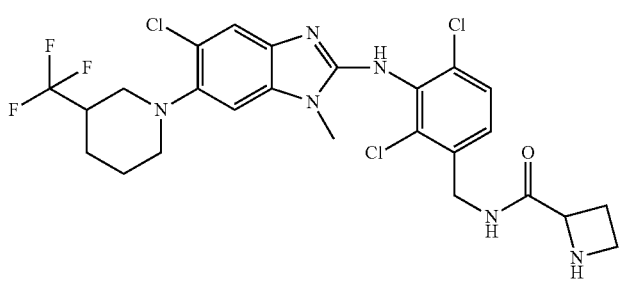 [SMILES: Cn1c(Nc2c(Cl)ccc(CNC(=O)C3CCN3)c2Cl)nc2cc(Cl)c(N3CCCC(C(F)(F)F)C3)cc21] |
| 166 | 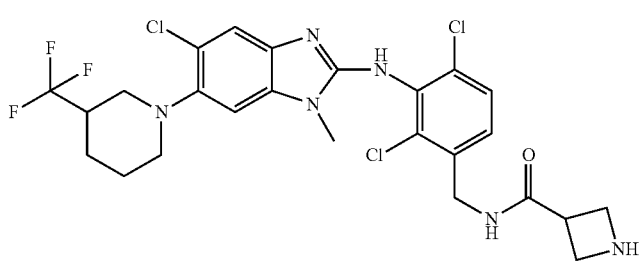 |
| 167 | 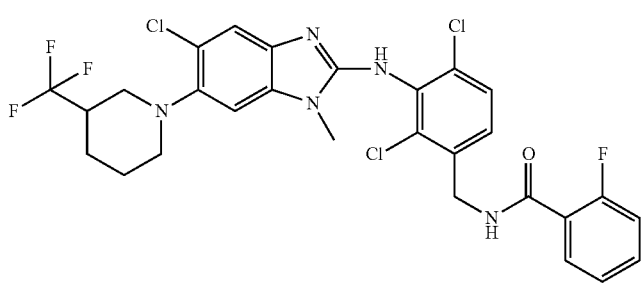 [SMILES: Cn1c(Nc2c(Cl)ccc(CNC(=O)c3ccccc3F)c2Cl)nc2cc(Cl)c(N3CCCC(C(F)(F)F)C3)cc21] |

| | Structure |
|---|---|
| 168 | 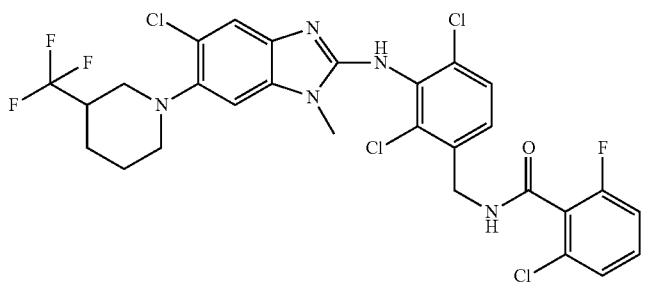 [SMILES: Cn1c(Nc2c(Cl)ccc(CNC(=O)c3c(F)cccc3Cl)c2Cl)nc2cc(Cl)c(N3CCCC(C(F)(F)F)C3)cc21] |
| 169 | 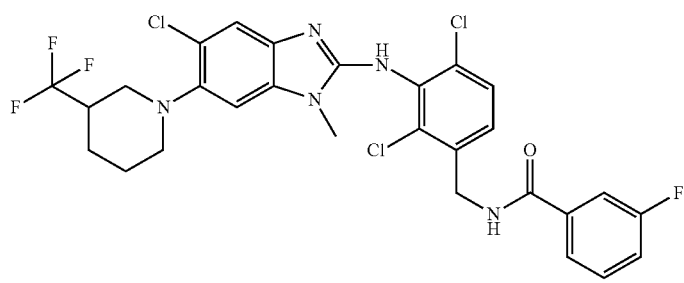 [SMILES: Cn1c(Nc2c(Cl)ccc(CNC(=O)c3cccc(F)c3)c2Cl)nc2cc(Cl)c(N3CCCC(C(F)(F)F)C3)cc21] |
| 170 | 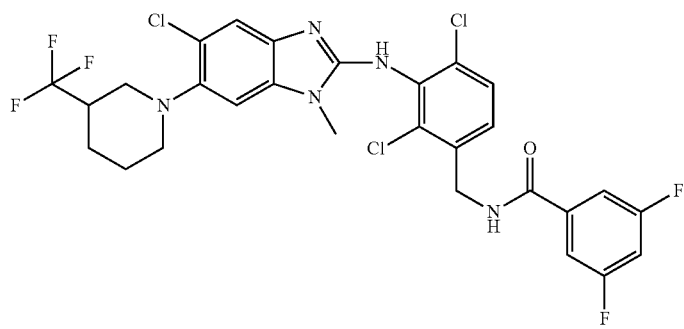 [SMILES: Cn1c(Nc2c(Cl)ccc(CNC(=O)c3cc(F)cc(F)c3)c2Cl)nc2cc(Cl)c(N3CCCC(C(F)(F)F)C3)cc21] |
| 171 | 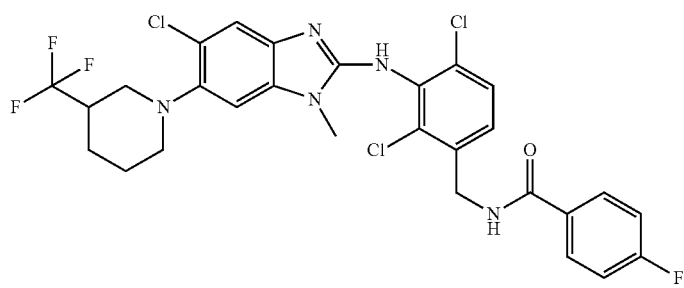 [SMILES: Cn1c(Nc2c(Cl)ccc(CNC(=O)c3ccc(F)cc3)c2Cl)nc2cc(Cl)c(N3CCCC(C(F)(F)F)C3)cc21] |
| 172 | 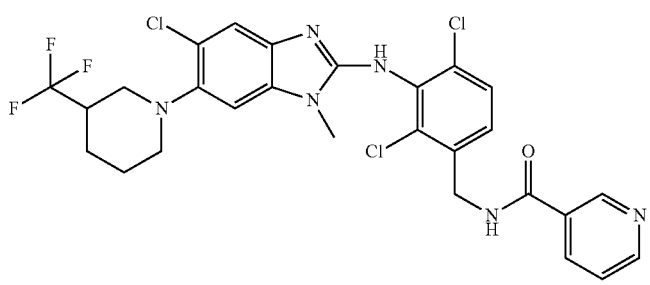 [SMILES: Cn1c(Nc2c(Cl)ccc(CNC(=O)c3cccnc3)c2Cl)nc2cc(Cl)c(N3CCCC(C(F)(F)F)C3)cc21] |

| | Structure |
|---|---|
| 173 | 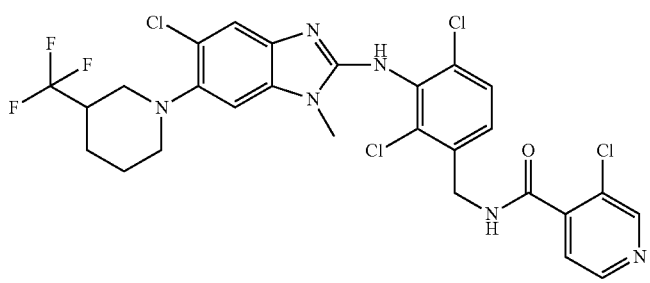 |
| 174 | 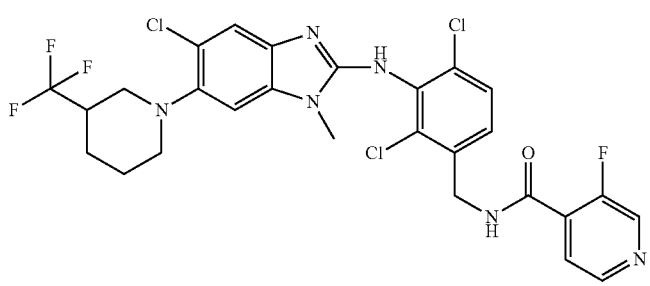 [SMILES: Cn1c(Nc2c(Cl)ccc(CNC(=O)c3ccncc3F)c2Cl)nc2cc(Cl)c(N3CCCC(C(F)(F)F)C3)cc21] |
| 175 | 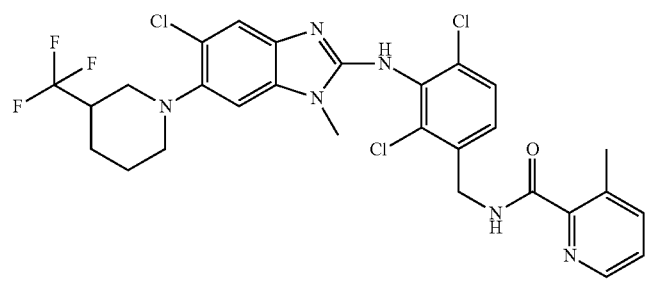 |
| 176 | 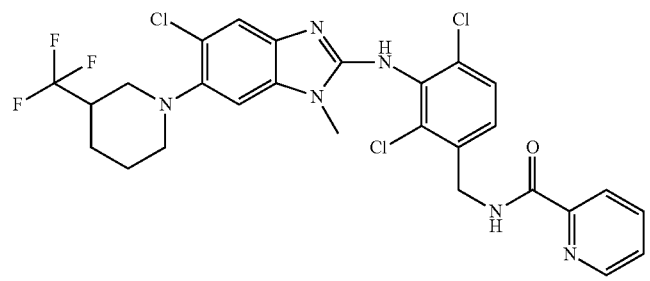 [SMILES: Cn1c(Nc2c(Cl)ccc(CNC(=O)c3ccccn3)c2Cl)nc2cc(Cl)c(N3CCCC(C(F)(F)F)C3)cc21] |
| 177 | 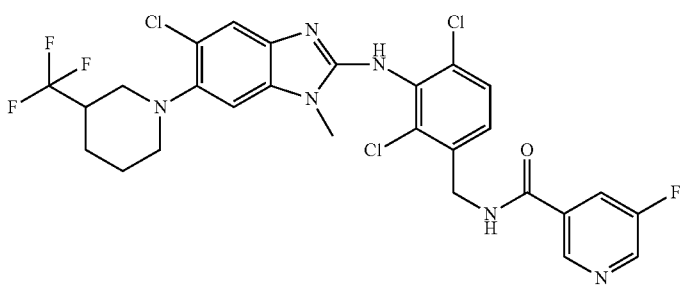 [SMILES: Cn1c(Nc2c(Cl)ccc(CNC(=O)c3cncc(F)c3)c2Cl)nc2cc(Cl)c(N3CCCC(C(F)(F)F)C3)cc21] |

| | Structure |
|---|---|
| 178 | 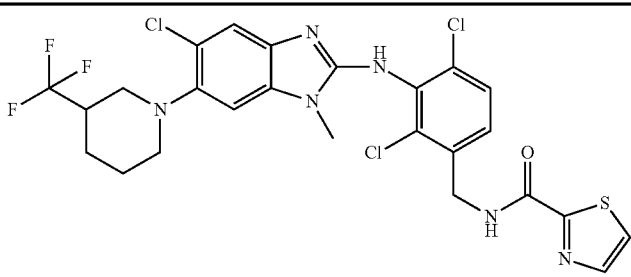 |
| 179 | 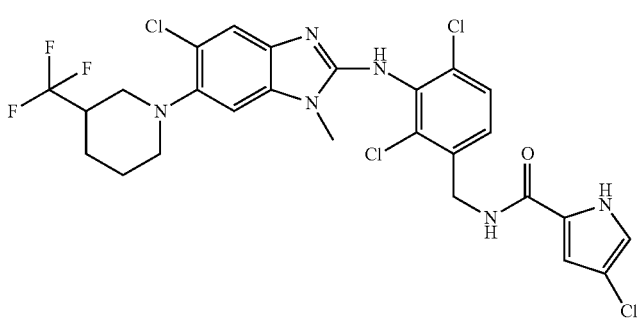 |
| 180 | 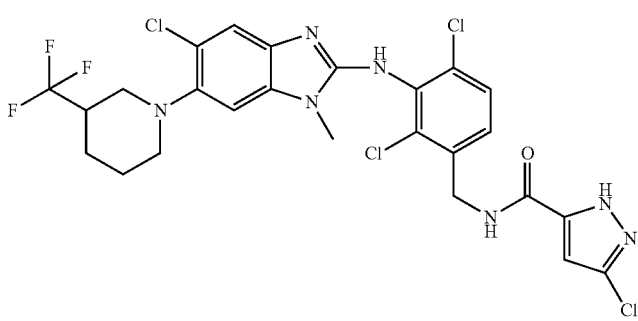 [SMILES: Cn1c(Nc2c(Cl)ccc(CNC(=O)c3cc(Cl)n[nH]3)c2Cl)nc2cc(Cl)c(N3CCCC(C(F)(F)F)C3)cc21] | and pharmaceutically acceptable salts thereof.

13. A pharmaceutical composition comprising at least one compound according to claim 1, or a pharmaceutically acceptable salt thereof, in a mixture with a pharmaceutically acceptable adjuvant, diluent and/or carrier.

14. A method for the treatment or prevention of an inflammatory disease in a patient comprising administering to said patient a therapeutically effective amount of a compound according to claim 1, or a pharmaceutically acceptable salt thereof.

* * * * *